(12) United States Patent
Si et al.

(10) Patent No.: US 11,214,561 B2
(45) Date of Patent: Jan. 4, 2022

(54) HISTONE METHYLTRANSFERASE EZH2 INHIBITOR, PREPARATION METHOD AND PHARMACEUTICAL USE THEREOF

(71) Applicant: ANCUREALL PHARMACEUTICAL (SHANGHAI) CO., LTD., Shanghai (CN)

(72) Inventors: Jutong Si, Shanghai (CN); Guan Wang, Shanghai (CN); Meifeng Jiang, Shanghai (CN); Zhihe Yang, Shanghai (CN); Chentao Zhou, Shanghai (CN)

(73) Assignee: Ancureall Pharmaceutical (Shanghai) Co., Ltd., Shanghai (CN)

( * ) Notice: Subject to any disclaimer, the term of this patent is extended or adjusted under 35 U.S.C. 154(b) by 0 days.

(21) Appl. No.: 16/478,472

(22) PCT Filed: Jan. 24, 2018

(86) PCT No.: PCT/CN2018/073946
§ 371 (c)(1),
(2) Date: Jul. 16, 2019

(87) PCT Pub. No.: WO2018/137639
PCT Pub. Date: Aug. 2, 2018

(65) Prior Publication Data
US 2019/0345139 A1 Nov. 14, 2019

(30) Foreign Application Priority Data

Jan. 25, 2017 (CN) .......................... 201710061026.0
May 16, 2017 (CN) .......................... 201710345609.6

(51) Int. Cl.
| | | |
|---|---|---|
| *C07D 401/14* | (2006.01) | |
| *A61P 35/00* | (2006.01) | |
| *C07D 213/64* | (2006.01) | |
| *C07D 401/12* | (2006.01) | |
| *C07D 413/14* | (2006.01) | |
| *C07D 491/107* | (2006.01) | |

(52) U.S. Cl.
CPC ............ *C07D 401/14* (2013.01); *A61P 35/00* (2018.01); *C07D 213/64* (2013.01); *C07D 401/12* (2013.01); *C07D 413/14* (2013.01); *C07D 491/107* (2013.01)

(58) Field of Classification Search
CPC .. C07D 401/14; C07D 401/12; C07D 213/64; C07D 413/14; C07D 491/107; A61P 35/00
See application file for complete search history.

(56) References Cited

U.S. PATENT DOCUMENTS

| | | | | |
|---|---|---|---|---|
| 8,765,792 B2* | 7/2014 | Knight | ................. | C07D 401/14 514/339 |
| 9,394,283 B2* | 7/2016 | Kuntz | ................. | C07D 405/12 |
| 2015/0313906 A1* | 11/2015 | Creasy | ................. | A61K 31/35 514/235.5 |
| 2016/0332969 A1 | 11/2016 | Kuntz et al. | | |

FOREIGN PATENT DOCUMENTS

| | | |
|---|---|---|
| CN | 104039956 A | 9/2014 |
| CN | 104768555 A | 7/2015 |
| WO | 2012/142504 A1 | 10/2012 |
| WO | 2013/155464 A1 | 10/2013 |
| WO | 2016/172199 A1 | 10/2016 |

OTHER PUBLICATIONS

Kawano, PLOS ONE, Jul. 8, 2016, 1-22. (Year: 2016).*
Zhang, TOxicology and Applied Pharmacology, vol. 304, 42-47, 2016. (Year: 2016).*
Kishner, Canadian J PHysiology and hparmacology, Feb. 1999, vol. 77, pp. 79-88. (Year: 1999).*
Bellouze, Mol Neurodeg, vol. 11(43), 2016, 1-20. (Year: 2016).*
Luo, Stroke, vol. 51, 2020, 3320-3331.' (Year: 2020).*
Malhotra, J Neuroinflamm, vol. 15(296), pp. 1336.1339, 2018. (Year: 2018).*
Morin, Ryan D. et al., "Somatic mutations altering EZH2 (Tyr641) in follicular and diffuse large B-cell lymphomas of germinal-center origin", Nature Genetics, 42:181-185 (2010).
McCabe, Michael T. et al., "Mutation of A677 in histone methyltransferase EZH2 in human B-cell lymphoma promotes hypertrimethylation of histone H3 on lysine 27 (H3K27)", Proc Natl Acad Sci USA, 109(8):2989-2994 (2012).

(Continued)

*Primary Examiner* — D Margaret M Seaman
(74) *Attorney, Agent, or Firm* — Rodney J. Fuller; Booth Udall Fuller, PLC

(57) ABSTRACT

The invention relates to a histone methyltransferase EZH2 inhibitor, a preparation method and pharmaceutical use thereof. In particular, the invention relates to a compound represented by the general formula (I), a preparation method thereof, a pharmaceutical composition containing the same, and a use thereof as a histone methyltransferase EZH2 inhibitor for treating diseases associated with the histone methyltransferase EZH2, especially cancer. The definition of each substituents in the general formula (I) is same as the definition in the specification.

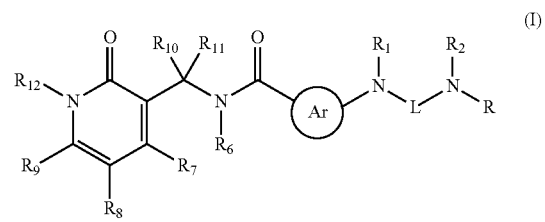

17 Claims, No Drawings

(56) References Cited

OTHER PUBLICATIONS

Ott, Heidi M. et al., "A687V F7H2 is a Driver of Histone H3 Lysine 27 (H3K27) Hypertrimethylation", Mol Cancer Ther, 13(12):3062-3073 (2014).
Majer, Christina R. et al., "A687V EZH2 is a gain-of-function mutation found in lymphoma patients", FEBS Lett., 586 (19):3448-3451 (2012).
Bitler, Benjamin G. et al., "Synthetic lethality by targeting EZH2 methyltransferase activity in ARID1A-mutated cancers", NatMed, 21:231-238 (2015).
Knutson, Sarah K. et al., "A selective inhibitor of EZH2 blocks H3K27 methylation and kills mutant lymphoma cells", Nat Chem Biol, 8(11):8-90-6 (2012).
McCabe, Michael T. et al., "EZH2 inhibition as a therapeutic strategy for lymphoma with EZH2-activating mutations", Nature, 492(7427):108-112 (2012).
Knutson, Sarah K. et al., "Selective Inhibition of EZH2 by EPZ-6438 Leads to Potent Antitumor Activity in EZH2-Mutant Non-Hodgkin Lymphoma", Mol Cancer Ther, 13(4)842-854 (2014).

\* cited by examiner

HISTONE METHYLTRANSFERASE EZH2 INHIBITOR, PREPARATION METHOD AND PHARMACEUTICAL USE THEREOF

CROSS REFERENCE TO RELATED APPLICATIONS

This application is the U.S. National Stage of International Application No. PCT/CN2018/073946, filed on Jan. 24, 2018, which claims the benefit of and priority to Chinese Patent Application Nos. 201710345609.6, filed on May 16, 2017, and 201710061026.0, filed on Jan. 25, 2017, the contents of each of which are expressly incorporated herein by reference in their entireties.

FIELD OF THE INVENTION

The invention relates to a novel histone methyltransferase EZH2 inhibitor, its preparation method and a pharmaceutical composition comprising the same, and the use of it as a histone methyltransferase EZH2 inhibitor, especially in the prevention and/or treatment of human diseases including cancer.

BACKGROUND OF THE INVENTION

Cancer including leukemia is one of the major diseases leading to clinical death. Malignant tumors such as lung cancer, gastric cancer, breast cancer, pancreatic cancer, liver cancer, colorectal cancer, ovarian cancer, cervical cancer, esophageal cancer, nasopharyngeal cancer, leukemia and malignant lymphoma have a high mortality rate. Although the clinical early detection or correct diagnosis and treatment effect for cancer patients have been improved by genetic screening, molecular diagnosis and precision medicine, there are still no effective methods or drugs up to now that can eradicate or cure most cancers, especially advanced, refractory, recurrent and drug-resistant malignant tumors. High quality anticancer drugs with good specificity, high activity, low toxicity and none acquired resistance are urgently needed for clinical treatment.

The occurrence, development, metastasis, deterioration, recurrence and drug resistance of cancer are related to many factors, among which the abnormality of normal intracellular molecular signaling pathway is one of the important factors leading to cell transformation and canceration. Genetics (changes in gene expression level caused by changes in DNA sequences, such as gene mutation, loss of heterozygosity and microsatellite instability, etc.) and epigenetics (inherited changes in gene expression level caused by mechanisms other than changes in the gene sequence, such as DNA methylation and chromatin conformation, etc.) are two important methodologies for the study of molecular signal transduction. Changes in gene sequences often directly lead to different types of human diseases, including cancers. After decades of efforts with means of the next generation DNA sequencing technology and genomic big data analytics, many genetic variants associated with human diseases have been discovered and identified. These variants can be used as biomarkers and targets for clinical diagnosis and drug development. Many drugs targeting these variant have shown good effects for many clinical diseases.

Epigenetics is a branch of genetics that does not involve genes with DNA sequence changes or protein expression changes, but can be inherited stably during development and cell proliferation. It mainly includes DNA methylation, histone covalent modification, chromatin remodeling, gene silencing and RNA editing and other regulatory mechanisms. In eukaryotic cells, DNA is packaged with histones to form chromatin, and changes in the ordered structure of chromatin can lead to changes in the transcription of related genes. This process is highly controlled because changes in gene expression patterns affect normal cellular functions such as differentiation, proliferation, and apoptosis. Covalent modification of the N-terminal of histones may mediate the changes of the chromatin structure, leading to heritable changes in gene expression without affecting the DNA sequence. Covalent modification of side chains of amino acids mediated by enzymes (e.g. methylation, acetylation, phosphorylation and ubiquitination) is one of the important functions of gene expression regulation. Histone methyltransferase (HMT) controls the selective addition of methyl groups to specific amino acid sites of histones. The expression level of a specific gene is affected by the presence or absence of one or more methyl groups at the relevant histone sites. Specific effects of methyl groups at specific histone sites persist until the methyl group is removed by histone demethylase, or until the modified histone is replaced by nucleosome turnover to control gene expression. Abnormal expression of histone methyltransferase and/or the destructive activity leads to disease status. In human cancer, for example, disorder of epigenetic enzymes promotes the occurrence and development of cancer and other cancers related characterization (such as cell migration and invasion, etc.). In addition to cancer, more and more evidences indicate that epigenetic enzymes also play a role in many other human diseases, including metabolic diseases (such as diabetes), inflammatory diseases (such as Crohn's disease), neurodegenerative diseases (such as Alzheimer's disease) and cardiovascular disease. Therefore, the clinical diagnosis and drug development targeting epigenetic variation has become a hot spot in basic research and pharmaceutical industry. Some of these drugs have been successfully applied to clinical practice such as histone deacetylase (HDAC) inhibitors.

PRC2 (Polycomb repressive complex 2) is one of the two classes of polycomb proteins (PcG). This complex has histone methyltransferase activity, primarily the trimethylation of histone H3 on lysine 27 (i.e. H3K27me3), which serves as a marker for transcriptional silencing of chromatin. PRC2 has four subunits: Suz12 (zinc finger), Eed, Ezh1 or Ezh2 (SET domain with histone methyltransferase activity) and RbAp48 (histone binding domain), in which EZH2 (Enhancer of Zeste Homolog 2) belongs to the catalytic subunit. The catalytic site of EZH2 exists in the SET domain, which is the characteristic of all known histone lysine methyltransferases except H3-K79 methyltransferase DOT1. Studies have found that mutations of Y641 (Y641F, Y64IN, Y641C, Y641S and Y641H), A677G and A687V of EZH2 were associated with follicular lymphoma (FL) and germinal center B cell-like (GCB) subtypes of diffuse large B-cell lymphoma (DLBCL) (Morin et al., Nat Genet. 2010; 42:181-5. McCabe M T et al., Proc Natl Acad Sci USA. 2012; 109(8):2989-94. Ott H M et al., Mol Cancer Ther. 2014; 13(12):3062-73. Majer C R et al., FEBS Lett. 2012; 586(19):3448-51), and inhibition of EZH2 showed synergistic lethal effect with many cancer cell mutant genes such as ARIDIA, KDM6A and SMARCA2/4, etc. (Bitler B G et al., NatMed. 2015; 21:231-8).

In general, the mutant EZH2 gene appears as a heterozygote, and all the mutants can be incorporated into the multi-protein PRC2 complex, but the complex lacks the ability to catalyze the methylation of H3-K27. Follicular lymphoma is one of the most common non-Hodgkin lymphoma and can be sensitively responded to immunochemotherapy, but many patients are extremely prone to relapse. Repeated clinical recurrence eventually leads to no response to standard treatment, and about 30% of patients are transformed into invasive lymphoma, namely diffuse large B-cell lymphoma (DLBCL). Epigenetic mutations in follicular lymphoma mainly happen in histone methyltransferase KMT2D (90%), EZH2 (25%), histone acetyltransferase CREBBP (30-60%) and EP300 (9%). Although the patients' diseases after antiCD20 monoclonal antibody (Rituxan) treatment has been significantly improved, DLBCL is still an incurable cancer, among which patients with chemical tolerance or conversion diseases still cannot get effective clinical treatment. Recent studies have shown that EZH2 inhibitors such as EPZ-6438 can effectively inhibit the growth of non-Hodgkin lymphatic cells with EZH2 mutation in vitro and in vivo, and the clinical trials have been conducted (Knutson S K et al., Nat Chem Biol. 2012; 8(11):8-90-6. McCabe M T et al., Nature. 2012; 492(7427): 108-12. Knutson S K et al., Mol Cancer Ther. 2014; 13(4): 842-54). Therefore, inhibitors of the mutated epigenetic protein-modifying enzymes will bring new hope for the clinical treatment of diffuse large B-cell lymphoma, including follicular lymphoma.

However, the existing EZH2 inhibitors are mostly combined with the SET (Su(var)3-9, Enhancer-of-Zeste, Trithorax) functional domains of EZH1/2. The following is a comparison of the amino acid sequences of SET functional domains of EZH1/2.

It can be seen from the sequence comparison that the amino acid sequences of EZH1/2 SET functional domains is highly conserved, and 95% EZH1/2 SET domains has the same amino acid sequence, that is, 116 of 122 amino acids are identical. Therefore, most EZH2 inhibitors can inhibit not only EZH2 but also EZH1.

During the long-term research and development of the inhibitors of the mutated epigenetic protein-modifying enzymes, based on the EZH2 protein sequence, crystal structure, and the binding sites of the known EZH2 inhibitors and their reversible action modes, the inventor accidentally discovered a unique cysteine 668 (NP_004447, histone-lysine N-methyltransferase EZH2 isoform a) in the SET amino acid sequence of EZH2, but the corresponding site of EZH1 is Serine 664 (NP_001982, histone-lysine N-methyltransferase EZH1 isoform 1). According to this characteristic, the compound of the present invention can form irreversible covalent binding with EZH2 and effectively inhibit the growth of cancer cells expressing EZH2 activated mutant genes (such as EZH2 A677G and Y641N), and induce apoptosis. Therefore, the present compound provides a new mechanism and direction for the development of EZH2 inhibitors.

SUMMARY OF THE INVENTION

The object of the present invention is to provide a small molecule compound with high specificity, high activity and low toxicity. It can be used as a highly selective irreversible covalent binding inhibitor of histone methyltransferase EZH2 for the prevention and/or treatment of human diseases including cancer.

In a first aspect, the invention provides a compound of general formula (I), or a pharmaceutically acceptable salt, solvate, metabolite or prodrug thereof:

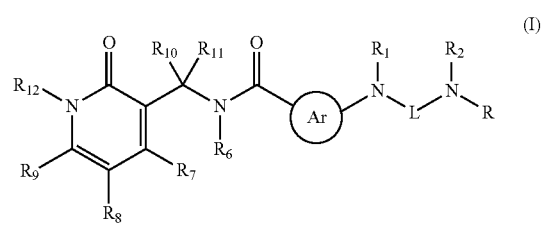

wherein:
R is selected from the group consisting of

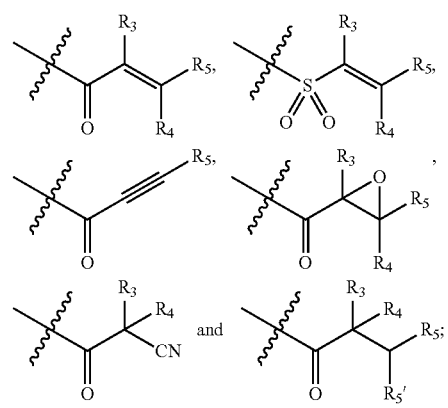

Ar is selected from a 5- or 6-membered aryl, a 5- or 6-membered heteroaryl, and a fused ring formed from a 5- or 6-membered aryl or heteroaryl, wherein Ar is optionally further substituted with one or more -Q-T groups;

L is selected from a $C_2$-$C_8$ saturated or unsaturated linear or branched hydrocarbon chain or cyclic structure, any hydrogen atom in L may be replaced by halogen, cyano, hydroxyl, or $C_1$-$C_6$ alkoxy, and any carbon atom in L may be replaced by N, O, S; L is optionally further substituted with one or more -Q-T groups;

$R_1$ and $R_2$ are each independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, 4-12 membered heterocyclic, the alkyl, alkenyl, alkynyl, cycloalkyl or heterocyclic group is optionally further substituted with one or more -Q-T groups; or $R_1$ may be attached to any position of L, and form a 4-12 membered heterocyclic group containing 0 or 1 additional hetero atom together with the N atom attached to them, the heterocyclic group is optionally further substituted with one or more -Q-T groups; or $R_2$ may be attached to any position of L, and form a 4-12 membered heterocyclic group containing 0 or 1 additional hetero atom together with the N atom attached to them, the heterocyclic group is optionally further substituted with one or more -Q-T groups; or $R_1$, $R_2$, L and the two N atoms attached to them form a 4-12 membered heterocyclic group, the heterocyclic group is optionally further substituted with one or more -Q-T groups;

$R_3$ is selected from the group consisting of hydrogen, fluorine, and $R_a$;

$R_4$ and $R_5$ are each independently selected from the group consisting of hydrogen and $R_a$;

$R_5'$ is selected from the group consisting of halogen, —OS(O)$_2$—$C_1$-$C_6$ alkyl and —OS(O)$_2$—$C_3$-$C_6$ cycloalkyl;

$R_a$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic group; the alkyl, alkenyl, alkynyl, cycloalkyl or heterocyclic group is optionally further substituted with one or more -Q-T groups;

$R_6$ and $R_{12}$ are each independently selected from the group consisting of hydrogen, $C_1$-$C_6$ alkyl and $C_3$-$C_6$ cycloalkyl;

$R_7$ and $R_9$ are each independently selected from the group consisting of hydrogen, halogen and $R_b$;

$R_b$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic; the alkyl, alkenyl, alkynyl, cycloalkyl, or heterocyclic group is optionally further substituted with one or more groups selected from the group consisting of halogen, cyano, hydroxy, $C_1$-$C_6$ alkoxy, $C_1$-$C_6$ alkyl-OC(O)—, amino, $C_1$-$C_6$ alkylamino, bis-$C_1$-$C_6$ alkylamino, and a 4-12 membered heterocyclic;

$R_8$, $R_{10}$ and $R_{11}$ are each independently selected from the group consisting of hydrogen, halogen, $C_1$-$C_3$ alkyl and cycloalkyl;

Q is selected from a bond and a $C_1$-$C_6$ alkylene group which is optionally further substituted with one or more groups selected from the group consisting of halogen, cyano, hydroxy, and $C_1$-$C_6$ alkoxy;

T is selected from the group consisting of hydrogen, halogen, cyano, hydroxy, —$NR_hR_i$, —$C(O)R_h$, $OR_h$, —C(O)O—$R_h$, $C(O)NR_hR_i$, —$NR_hC(O)R_i$, —$NR_jC(O)NR_hR_i$, —$NR_hC(O)OR_i$, and $R_k$; or -Q-T group is an oxygen;

$R_k$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- to 10-membered heteroaryl and aryl, $R_k$ is optionally further substituted with one or more -$Q_1$-$T_1$ groups;

$R_h$, $R_i$ and $R_j$ are each independently selected from hydrogen and $R_1$, and $R_1$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl, $R_1$ is optionally further substituted with one or more -$Q_1$-$T_1$ groups; or $R_h$ and $R_i$, together with the N atom attached to them, form a 4-12 membered heterocyclic group containing 0 or 1 additional hetero atom, the heterocyclic group is optionally further substituted with one or more -$Q_1$-$T_1$ groups;

$Q_1$ is a bond or a $C_1$-$C_6$ alkylene group which is optionally further substituted with one or more groups selected from the group consisting of halogen, cyano, hydroxy, and $C_1$-$C_6$ alkoxy;

$T_1$ is selected from the group consisting of hydrogen, halogen, cyano, hydroxyl, —$NR_mR_n$, —$C(O)R_m$, $OR_m$, —C(O)O—$R_m$, —$C(O)NR_mR_n$, —$NR_mC(O)R_n$, —$NR_oC(O)NR_mR_n$, —$NR_mC(O)OR_n$, —$O(CH_2)_aNR_mR_n$, —$(CH_2)_aNR_mR_n$, —$S(O)_2NR_mR_n$ and $R_p$; or -$Q_1$-$T_1$ group is an oxygen;

$R_p$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl;

$R_m$, $R_n$ and $R_o$ are each independently selected from the group consisting of hydrogen and $R_q$; $R_q$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl; Rq is optionally further substituted with one or more groups selected from the group consisting of halogen, hydroxy, 5- or 6-membered heteroaryl and aryl, wherein the heteroaryl or aryl group is optionally further substituted with one or more groups selected from the group consisting of $C_1$-$C_6$ alkyl, hydroxy and oxo; or $R_m$ and $R_n$, together with the N atom attached to them, form a 4-12 membered heterocyclic group containing 0 or 1 additional hetero atom, the heterocyclic group is optionally further substituted with one or more groups selected from the group consisting of halogen, hydroxy, oxo, $C_1$-$C_6$ alkyl, —$OR_x$, —$NR_xR_y$, —$C(O)R_x$, and —$O(CH_2)_aOR_x$;

$R_x$ and $R_y$ are each independently selected from the group consisting of hydrogen and $R_z$; $R_z$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl; $R_q$ is optionally further substituted with one or more groups selected from the group consisting of halogen, hydroxy, 5- or 6-membered heteroaryl and aryl, wherein the heteroaryl or aryl group is optionally further substituted with one or more groups selected from the group consisting of $C_1$-$C_6$ alkyl, hydroxy and oxo; or $R_x$ and $R_y$, together with the N atom attached to them, form a 4-12 membered heterocyclic group containing 0 or 1 additional hetero atom;

a is an integer from 1 to 4.

In a preferred embodiment of the present invention, the compound of general formula (I) or a pharmaceutically acceptable salt, solvate, metabolite or prodrug thereof according to the present invention, wherein:

Ar is selected from

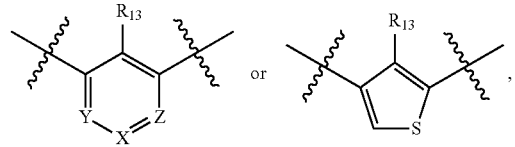

X is selected from $CR_{14}$;
Y is selected from N and $CR_{15}$;
Z is selected from N and $CR_{16}$;
$R_{13}$ is selected from the group consisting of hydrogen, halogen, $C_1$-$C_6$ alkyl and $C_3$-$C_6$ cycloalkyl;
$R_{14}$, $R_{15}$, $R_{16}$ are each independently selected from the group -Q-T;
Q is selected from a bond and a $C_1$-$C_6$ alkylene group;
T is selected from the group consisting of hydrogen, halogen, cyano, hydroxyl, —$NR_hR_i$, —$C(O)R_h$, $OR_h$, —C(O)O—$R_h$, $C(O)NR_hR_i$, —$NR_hC(O)R_i$, —$NR_jC(O)NR_hR_i$, —$NR_hC(O)OR_i$ or $R_k$;
$R_k$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5 to 10 membered heteroaryl and aryl; $R_k$ is optionally further substituted with one or more -$Q_1$-$T_1$ groups;
$R_h$, $R_i$ and $R_j$ are each independently selected from the group consisting of hydrogen and $R_1$; $R_1$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl; $R_1$ is optionally further substituted with one or more -$Q_1$-$T_1$ groups; or
$R_h$ and $R_i$, together with the N atom attached to them, form a 4-12 membered heterocyclic group containing 0 or 1 additional hetero atom; the heterocyclic group is optionally further substituted with one or more -$Q_1$-$T_1$ groups;
$Q_1$ is a bond or a $C_1$-$C_6$ alkylene group;
$T_1$ is selected from the group consisting of hydrogen, halogen, cyano, hydroxy, —$NR_mR_n$, —$C(O)R_m$, $OR_m$, —C(O)O—$R_m$, —C(O)$NR_mR_n$, —$NR_mC(O)R_n$, —$NR_oC(O)NR_mR_n$, —$NR_mC(O)OR_n$, —$O(CH_2)_aNR_mR_n$, —$(CH_2)_aNR_mR_n$, —$S(O)_2NR_mR_n$ and $R_p$;

$R_p$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl, and aryl;

$R_m$, $R_n$, $R_o$ are each independently selected from the group consisting of hydrogen and $R_q$; $R_q$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl; $R_q$ is optionally further substituted with one or more groups selected from the group consisting of halogen, hydroxy, 5- or 6-membered heteroaryl and aryl, wherein the heteroaryl or aryl group is optionally further substituted with one or more groups selected from the group consisting of $C_1$-$C_6$ alkyl, hydroxy and oxo; or $R_m$ and $R_n$, together with the N atom attached to them, form a 4-12 membered heterocyclic group containing 0 or 1 additional hetero atom; the heterocyclic group is optionally further substituted with one or more groups selected from the group consisting of halogen, hydroxy, oxo, $C_1$-$C_6$ alkyl, —$OR_x$, —$NR_xR_y$, —$C(O)R_x$, and —$O(CH_2)_aOR_x$;

$R_x$ and $R_y$ are each independently selected from the group consisting of hydrogen and $R_z$; $R_z$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl; $R_q$ is optionally further substituted with one or more groups selected from the group consisting of halogen, hydroxy, 5- or 6-membered heteroaryl and aryl, wherein the heteroaryl or aryl group is optionally further substituted with one or more groups selected from the group consisting of $C_1$-$C_6$ alkyl, hydroxy and oxo; or $R_x$ and $R_y$, together with the N atom attached to them, form a 4-12 membered heterocyclic group containing 0 or 1 additional hetero atom;

a is an integer from 1 to 4.

In another preferred embodiment of the present invention, the compound of general formula (I) or a pharmaceutically acceptable salt, solvate, metabolite or prodrug thereof according to the present invention, wherein:

Ar is

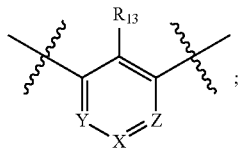

$R13$ is selected from the group consisting of hydrogen, halogen, and $C_1$-$C_6$ alkyl;

X is selected from $CR_{14}$;
Y is selected from $CR_{15}$;
Z is selected from $CR_{16}$;
$R_{14}$ is selected from the group -Q-T;
$R_{15}$ and $R_{16}$ are each independently selected from the group consisting of hydrogen and halogen;
Q is selected from a bond or a $C_1$-$C_6$ alkylene group;
T is selected from the group consisting of hydrogen, halogen, cyano, hydroxy, —$NR_hR_i$, —$C(O)R_h$, $OR_h$, —C(O)O—$R_h$, —C(O)$NR_hR_i$, —$NR_hC(O)R_i$, —$NR_jC(O)NR_hR_i$, —$NR_hC(O)OR_i$, and $R_k$;
$R_k$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl, and aryl;

the heterocyclic, heteroaryl or aryl is optionally further substituted with one or more -$Q_1$-$T_1$ group;

$R_h$, $R_i$, and $R_j$ are each independently selected from the group consisting of hydrogen and $R_1$; $R_1$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl; $R_1$ is optionally further substituted with one or more -$Q_1$-$T_1$ groups; or $R_h$ and $R_i$, together with the N atom attached to them, form a 4-12 membered heterocyclic group containing 0 or 1 additional hetero atom; the heterocyclic group is optionally further substituted with one or more-$Q_1$-$T_1$ groups;

$Q_1$ is a bond or a $C_1$-$C_6$ alkylene group;

$T_1$ is selected from the group consisting of hydrogen, halogen, cyano, hydroxy, —$NR_mR_n$, —$C(O)R_m$, $OR_m$, —C(O)O—$R_m$, —C(O)$NR_mR_n$, —$NR_mC(O)R_n$, —$NR_oC(O)NR_mR_n$, —$NR_mC(O)OR_n$, —$O(CH_2)_aNR_mR_n$, —$(CH_2)_aNR_mR_n$, —$S(O)_2NR_mR_n$ and $R_p$;

$R_p$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl, and aryl;

$R_m$, $R_n$, and $R_o$ are each independently selected from the group consisting of hydrogen and $R_q$; $R_q$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl; $R_q$ is optionally further substituted with one or more groups selected from the group consisting of halogen, hydroxy, 5- or 6-membered heteroaryl and aryl, wherein the heteroaryl or aryl group is optionally further substituted with one or more groups selected from the group consisting of $C_1$-$C_6$ alkyl, hydroxy and oxo; or $R_m$ and $R_n$, together with the N atom attached to them, form a 4-12 membered heterocyclic group containing 0 or 1 additional hetero atom; the heterocyclic group is optionally further substituted with one or more groups selected from the group consisting of halogen, hydroxy, oxo, $C_1$-$C_6$ alkyl, —$OR_x$, —$NR_xR_y$, —$C(O)R_x$, and —$O(CH_2)_aOR_x$;

$R_x$ and $R_y$ are each independently selected from the group consisting of hydrogen and $R_z$; $R_z$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl; $R_q$ is optionally further substituted with one or more groups selected from the group consisting of halogen, hydroxy, 5- or 6-membered heteroaryl and aryl, wherein the heteroaryl or aryl group is optionally further substituted with one or more groups selected from the group consisting of $C_1$-$C_6$ alkyl, hydroxy and oxo; or $R_x$ and $R_y$, together with the N atom attached to them, form a 4-12 membered heterocyclic group containing 0 or 1 additional hetero atom;

a is an integer from 1 to 4.

In another preferred embodiment of the present invention, the compound of general formula (I) or a pharmaceutically acceptable salt, solvate, metabolite or prodrug thereof according to the present invention, wherein:

Q is selected from a bond or a $C_1$-$C_6$ alkylene group;

T is selected from the group consisting of hydrogen, halogen, —$NR_hR_i$, $OR_h$, and $R_k$;

$R_k$ is selected from the group consisting of $C_1$-$C_6$ alkyl, $C_2$-$C_6$ alkenyl, $C_2$-$C_6$ alkynyl, 4-12 membered heterocyclic, 5- to 10-membered heteroaryl and $C_6$-$C_{10}$ aryl; the alkyl, alkenyl, alkynyl, heterocyclyl, heteroaryl or aryl group is optionally further substituted with one or more -$Q_1$-$T_1$ groups;

$R_h$ and $R_i$ are each independently selected from the group consisting of hydrogen and $R_1$; $R_1$ is selected from the group consisting of $C_1$-$C_6$ alkyl, 5- or 6-membered heteroaryl, and $C_6$-$C_{10}$ aryl; $R_1$ is optionally further substituted with one or more -$Q_1$-$T_1$ groups; or $R_h$ and $R_i$, together with the N atom attached to them, form a 4-12 membered heterocyclic group containing 0 or 1 additional hetero atom; the heterocyclic group is optionally further substituted with one or more -$Q_1$-$T_1$ groups;

$Q_1$ is a bond or a $C_1$-$C_6$ alkylene group;

$T_1$ is selected from the group consisting of hydrogen, halogen, hydroxyl, —$NR_mR_n$, $OR_m$, —$C(O)OR_m$, —$C(O)NR_mR_n$, —$O(CH_2)_aNR_mR_n$, —$(CH_2)_aNR_mR_n$, —$S(O)_2NR_mR_n$ and $R_p$;

$R_p$ is selected from the group consisting of a $C_1$-$C_6$ alkyl group and a 4-12 membered heterocyclic group;

$R_m$ and $R_n$ are each independently selected from the group consisting of hydrogen and $C_1$-$C_6$ alkyl, and the alkyl group is optionally further substituted with one or more groups selected from hydroxy and 5- or 6-membered heteroaryl groups, wherein the heteroaryl group is optionally further substituted with one or more groups selected from the group consisting of $C_1$-$C_6$ alkyl and oxo; or $R_m$ and $R_n$, together with the N atom attached to them, form a 4-12 membered heterocyclic group containing 0 or 1 additional hetero atom; the heterocyclic group is optionally further substituted with one or more groups selected from the group consisting of halogen, hydroxy, oxo, $C_1$-$C_6$ alkyl, —$OR_x$, —$NR_xR_y$, —$C(O)R_x$, and —$O(CH_2)_aOR_x$;

$R_x$ and $R_y$ are each independently selected from the group consisting of hydrogen and $R_z$; $R_z$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl, $R_q$ is optionally further substituted with one or more groups selected from the group consisting of halogen, hydroxy, 5- or 6-membered heteroaryl and aryl, wherein the heteroaryl or aryl group is optionally further substituted with one or more groups selected from the group consisting of $C_1$-$C_6$ alkyl, hydroxy and oxo; or $R_x$ and $R_y$, together with the N atom attached to them, form a 4-12 membered heterocyclic group containing 0 or 1 additional hetero atom;

a is an integer from 1 to 4.

In another preferred embodiment of the present invention, the compound of general formula (I) or a pharmaceutically acceptable salt, solvate, metabolite or prodrug thereof according to the present invention, wherein:

Q is selected from a bond;

T is selected from the group consisting of hydrogen, halogen, —$NR_hR_i$, $OR_h$ and $R_k$;

$R_k$ is selected from the group consisting of $C_1$-$C_6$ alkyl, $C_2$-$C_6$ alkynyl, phenyl, pyrimidinyl, pyridyl, pyrazolyl, imidazolyl, thiazolyl, oxazolyl and thiophene [3,2-b] thiophene group; the alkyl, alkynyl, phenyl, pyrimidinyl, pyridyl, pyrazolyl, imidazolyl, thiazolyl, oxazolyl or thiophene [3,2-b] thiophene group is optionally further substituted with one or more -$Q_1$-$T_1$ groups;

$R_h$ and $R_i$ are each independently selected from the group consisting of hydrogen, pyridyl, pyrimidinyl and phenyl; the pyridyl, pyrimidinyl or phenyl group is optionally further substituted with one or more -$Q_1$-$T_1$ groups; or $R_h$ and $R_i$, together with the N atom attached to them, form a 4-12 membered heterocyclic group containing 0 or 1 additional hetero atom; the heterocyclic group is optionally further substituted with one or more -$Q_1$-$T_1$ groups;

$Q_1$ is a bond or a $C_1$-$C_6$ alkylene group;

$T_1$ is selected from the group consisting of hydrogen, halogen, hydroxyl, —$NR_mR_n$, $OR_m$, —$C(O)OR_m$, —$C(O)NR_mR_n$, —$O(CH_2)_aNR_mR_n$, —$(CH_2)_aNR_mR_n$, —$S(O)_2NR_mR_n$ and $R_p$;

$R_p$ is selected from a $C_1$-$C_6$ alkyl group;

$R_m$ and $R_n$ are each independently selected from the group consisting of hydrogen and $C_1$-$C_6$ alkyl, and the alkyl group is optionally further substituted with one or more groups selected from hydroxy and 5- or 6-membered heteroaryl groups, wherein the heteroaryl group is optionally further substituted with one or more groups selected from the group consisting of $C_1$-$C_6$ alkyl and oxo; or $R_m$ and $R_n$, together with the N atom attached to them, form a 4-12 membered heterocyclic group containing 0 or 1 additional hetero atom; the heterocyclic group is optionally further substituted with one or more groups selected from the group consisting of halogen, hydroxy, oxo, $C_1$-$C_6$ alkyl, —$OR_x$, —$NR_xR_y$, —$C(O)R_x$, and —$O(CH_2)_aOR_x$;

$R_x$ and $R_y$ are each independently selected from the group consisting of hydrogen and $R_z$; $R_z$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl, $R_q$ is optionally further substituted with one or more groups selected from the group consisting of halogen, hydroxy, 5- or 6-membered heteroaryl and aryl, wherein the heteroaryl or aryl group is optionally further substituted with one or more groups selected from the group consisting of $C_1$-$C_6$ alkyl, hydroxy and oxo; or $R_x$ and $R_y$, together with the N atom attached to them, form a 4-12 membered heterocyclic group containing 0 or 1 additional hetero atom;

a is an integer from 1 to 4.

In another preferred embodiment of the present invention, the compound of general formula (I) or a pharmaceutically acceptable salt, solvate, metabolite or prodrug thereof according to the present invention, wherein:

Q is selected from a bond;

T is selected from the group consisting of hydrogen, halogen, —$NR_hR_i$, $OR_h$ and $R_k$;

$R_k$ is selected from the group consisting of $C_1$-$C_6$ alkyl, $C_2$-$C_6$ alkynyl, phenyl, pyrimidinyl, pyridyl, pyrazolyl, imidazolyl, thiazolyl, oxazolyl and thiophene [3,2-b] thiophene group, the alkyl, alkynyl, phenyl, pyrimidinyl, pyridyl, pyrazolyl, imidazolyl, thiazolyl, oxazolyl or thiophene [3,2-b] thiophene group is optionally further substituted with one or more -$Q_1$-$T_1$ groups;

$R_h$ and $R_i$ are each independently selected from the group consisting of hydrogen, pyridyl, pyrimidinyl and phenyl; the pyridyl, pyrimidinyl or phenyl group is optionally further substituted with one or more -$Q_1$-$T_1$ groups; or $R_h$ and $R_i$, together with the N atom attached to them, form a piperidinyl, piperazinyl, pyrrolidinyl or morpholinyl group, the piperidinyl, piperazinyl, pyrrolidinyl or morpholinyl group is optionally further substituted with one or more -$Q_1$-$T_1$ groups;

$Q_1$ is a bond or a $C_1$-$C_6$ alkylene group;

$T_1$ is selected from the group consisting of hydrogen, halogen, hydroxy, —$NR_mR_n$, $OR_m$, —$C(O)OR_m$, —$C(O)NR_mR_n$, —$O(CH_2)_aNR_mR_n$, —$(CH_2)_aNR_mR_n$, —$S(O)_2NR_mR_n$ and $R_p$;

$R_p$ is selected from a $C_1$-$C_6$ alkyl group;

$R_m$ and $R_n$ are each independently selected from the group consisting of hydrogen and $C_1$-$C_6$ alkyl, and the alkyl group is optionally further substituted with one or more groups selected from hydroxy and 5- or 6-membered heteroaryl groups, wherein the heteroaryl group is optionally further substituted with one or more groups selected from the group consisting of $C_1$-$C_6$ alkyl and oxo; or $R_m$ and $R_n$, together with the N atom attached to them, form a 4-12 membered heterocyclic group containing 0 or 1 additional hetero atom; the heterocyclic group is optionally further substituted with one or more groups selected from the group consisting of halogen, hydroxy, oxo, $C_1$-$C_6$ alkyl, —$OR_x$, $C_1$-$C_6$ alkoxy, —$NR_xR_y$, —$C(O)R_x$, and —$O(CH_2)_aOR_x$;

$R_x$ and $R_y$ are each independently selected from the group consisting of hydrogen and $R_z$; $R_z$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl, $R_q$ is optionally further substituted with one or more groups selected from the group consisting of halogen, hydroxy, 5- or 6-membered heteroaryl and aryl, wherein the heteroaryl or aryl group is optionally further substituted with one or more groups selected from the group consisting of $C_1$-$C_6$ alkyl, hydroxy and oxo; or $R_x$ and $R_y$, together with the N atom attached to them, form a 4-12 membered heterocyclic group containing 0 or 1 additional hetero atom;

a is an integer from 1 to 4.

In another preferred embodiment of the present invention, the compound of general formula (I) or a pharmaceutically acceptable salt, solvate, metabolite or prodrug thereof according to the present invention, wherein:

Q is selected from a bond;

T is selected from the group consisting of hydrogen, halogen, —$NR_hR_i$, $OR_h$ and $R_k$;

$R_k$ is selected from the group consisting of $C_1$-$C_6$ alkyl, $C_2$-$C_6$ alkynyl, phenyl, pyrimidinyl, pyridyl, and thiophene [3,2-b] thiophene group, the alkyl, alkynyl, phenyl, pyrimidinyl, pyridyl or thiophene [3,2-b] thiophene group is optionally further substituted with one or more -$Q_1$-$T_1$ groups;

$R_h$ and $R_i$ are each independently selected from the group consisting of hydrogen, pyridyl, pyrimidinyl and phenyl; the pyridyl, pyrimidinyl or phenyl group is optionally further substituted with one or more -$Q_1$-$T_1$ groups; or $R_h$ and $R_i$, together with the N atom attached to them, form a piperidinyl, piperazinyl and morpholinyl group, the piperidinyl, piperazinyl or morpholinyl group is optionally further substituted with one or more -$Q_1$-$T_1$ groups;

$Q_1$ is a bond or a $C_1$-$C_6$ alkylene group;

$T_1$ is selected from the group consisting of hydrogen, halogen, hydroxy, —$NR_mR_n$, $OR_m$, —$C(O)OR_m$, —$C(O)NR_mR_n$, —$O(CH_2)_aNR_mR_n$, —$(CH_2)_aNR_mR_n$, —$S(O)_2NR_mR_n$ and $R_p$;

$R_p$ is selected from a $C_1$-$C_6$ alkyl group;

$R_m$ and $R_n$ are each independently selected from the group consisting of hydrogen and $C_1$-$C_6$ alkyl, and the alkyl group is optionally further substituted with one or more groups selected from hydroxy, pyridyl and pyrimidinyl, wherein the pyridyl or pyrimidinyl group is optionally further substituted with one or more groups selected from the group consisting of $C_1$-$C_6$ alkyl and oxo; or $R_m$ and $R_n$, together with the N atom attached to them, form a piperidinyl, morpholinyl, pyrrolidinyl, piperazinyl, homopiperazinyl, azetidinyl or azaspirocyclyl group; the piperidinyl, morpholinyl, pyrrolidinyl, piperazinyl, homopiperazinyl, azetidinyl or aza-spiro group is optionally further substituted with one or more groups selected from the group consisting of halogen, oxo, $C_1$-$C_6$ alkyl, —$OR_x$, —$NR_xR_y$, —$C(O)R_x$, and —$O(CH_2)_aOR_x$;

$R_x$ and $R_y$ are each independently selected from the group consisting of hydrogen and $R_z$; $R_z$ is selected from the group consisting of $C_1$-$C_6$ alkyl and $C_3$-$C_6$ cycloalkyl, $R_q$ is optionally further substituted with one or more groups selected from the group consisting of halogen and hydroxy; or $R_x$ and $R_y$, together with the N atom attached to them, form a 4-12 membered heterocyclic group containing 0 or 1 additional hetero atom; preferably the heterocyclic group is piperidinyl, morpholinyl, pyrrolidinyl, piperazinyl, or homopiperazinyl;

a is an integer from 1 to 4.

In another preferred embodiment of the present invention, the compound of general formula (I) or a pharmaceutically acceptable salt, solvate, metabolite or prodrug thereof according to the present invention is a compound of the following formula (IIA), formula (IIB), formula (IIC), formula (IID), formula (IIE) or formula (IIF), or a pharmaceutically acceptable salt, solvate, metabolite or prodrug thereof,

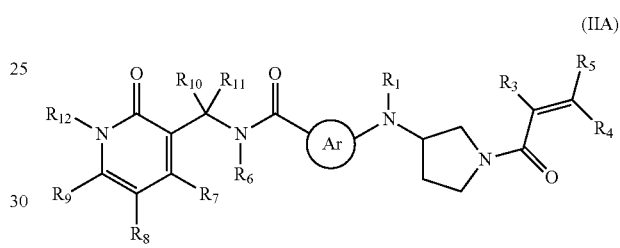

(IIA)

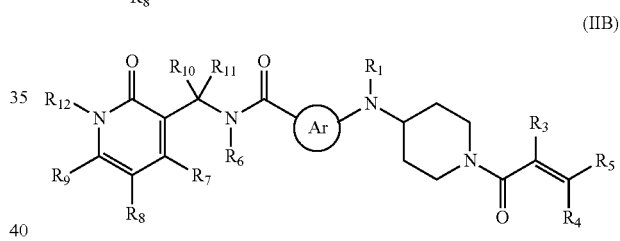

(IIB)

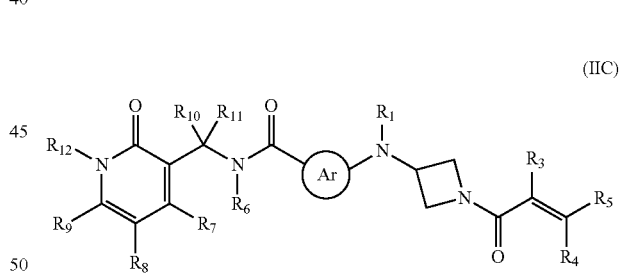

(IIC)

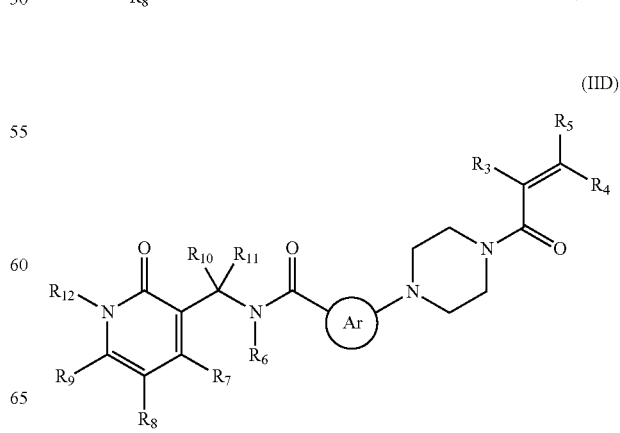

(IID)

-continued (IIE)

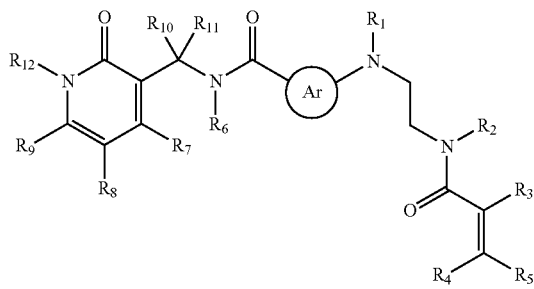

(IIF)

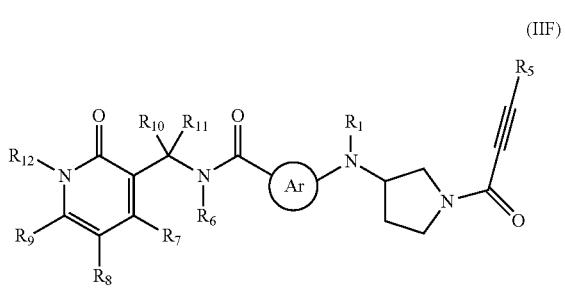

wherein, $R_1$ to $R_{12}$ and Ar are as defined in general formula (I).

In another preferred embodiment of the present invention, the compound of general formula (I) or a pharmaceutically acceptable salt, solvate, metabolite or prodrug thereof according to the present invention is a compound of the following formula (IIA), formula (IIB), formula (IIC), formula (IID), formula (IIE) or formula (IIF), or a pharmaceutically acceptable salt, solvate, metabolite or prodrug thereof, wherein:

$R_1$ and $R_2$ are each selected from the group consisting of hydrogen, $C_1$-$C_6$ alkyl, $C_3$-$C_6$ cycloalkyl, and 4-12 membered heterocyclic;

$R_3$ and $R_4$ are each selected from hydrogen;

$R_5$ is selected from the group consisting of hydrogen and $C_1$-$C_6$ alkyl, the alkyl is optionally substituted with one or more -Q-T groups;

$R_6$ and $R_{12}$ are each selected from hydrogen;

$R_7$ and $R_9$ are each selected from the group consisting of hydrogen and $C_1$-$C_6$ alkyl;

$R_8$, $R_{10}$ and $R_{11}$ are each selected from hydrogen;

-Q-T is a —$NR_hR_i$ group;

$R_h$ and $R_i$ are each independently selected from hydrogen and $C_1$-$C_6$ alkyl; or $R_h$ and $R_i$, together with the N atom attached to them, form a 4-12 membered heterocyclic group containing 0 or 1 additional hetero atom; preferably the heterocyclic group is piperidinyl, piperazinyl, morpholinyl, or pyrrolidinyl;

Ar is as defined in formula (IIA), formula (IIB), formula (IIC), formula (IID), formula (IIE) or formula (IIF).

In another preferred embodiment of the present invention, the compound of general formula (I) or a pharmaceutically acceptable salt, solvate, metabolite or prodrug thereof according to the present invention is a compound of the following formula (IIA), formula (IIB), formula (IIC), formula (IID), formula (IIE) or formula (IIF), or a pharmaceutically acceptable salt, solvate, metabolite or prodrug thereof, wherein:

Ar is a phenyl group, which is optionally further substituted with one or more -Q-T groups;

$R_1$ and $R_2$ are each selected from the group consisting of hydrogen, $C_1$-$C_6$ alkyl, $C_3$-$C_6$ cycloalkyl, and 4-12 membered heterocyclic;

$R_3$ and $R_4$ are each selected from hydrogen;

$R_5$ is selected from the group consisting of hydrogen and $C_1$-$C_6$ alkyl, the alkyl is optionally further substituted with one or more -Q-T groups;

$R_6$ and $R_{12}$ are each selected from hydrogen;

$R_7$ and $R_9$ are each selected from the group consisting of hydrogen and $C_1$-$C_6$ alkyl;

$R_8$, $R_{10}$ and $R_{11}$ are each selected from hydrogen;

-Q-T is a phenyl, which is optionally further substituted with one or more -$Q_1$-$T_1$ groups;

$Q_1$ is a bond or a $C_1$-$C_6$ alkylene group;

$T_1$ is selected from the group consisting of hydrogen, halogen, hydroxyl, —$NR_mR_n$, $OR_m$, —C(O)$OR_m$, —C(O)$NR_mR_n$, —O(CH$_2$)$_a$$NR_mR_n$, —S(O)$_2$$NR_mR_n$; or -$Q_1$-$T_1$ is oxo;

$R_m$ and $R_n$ are each independently selected from the group consisting of hydrogen and $R_q$, $R_q$ is selected from $C_1$-$C_6$ alkyl, and $R_q$ is optionally further substituted with one or more groups selected from the group consisting of halogen, hydroxy, and 5- or 6-membered heteroaryl, wherein the heteroaryl or aryl group is optionally further substituted with one or more groups selected from the group consisting of $C_1$-$C_6$ alkyl, hydroxy and oxo; or $R_m$ and $R_n$, together with the N atom attached to them, form a 4-12 membered heterocyclic group containing 0 or 1 additional hetero atom; preferably the heterocyclic group is piperidinyl, piperazinyl, homopiperazinyl, morpholinyl, pyrrolidinyl, azetidinyl and azapirocyclyl, the heterocyclic group is optionally further substituted with one or more groups selected from the group consisting of halogen, hydroxy, oxo, $C_1$-$C_6$ alkyl, —$OR_x$, —$NR_xR_y$, —C(O)$R_x$, and —O(CH$_2$)$_a$$OR_x$;

$R_x$ and $R_y$ are each independently selected from the group consisting of hydrogen and $R_z$; $R_z$ is selected from $C_1$-$C_6$ alkyl and $C_3$-$C_6$ cycloalkyl; or $R_x$ and $R_y$, together with the N atom attached to them, form a 4-12 membered heterocyclic group containing 0 or 1 additional hetero atom; preferably the heterocyclic group is piperidinyl, piperazinyl, morpholinyl, and pyrrolidinyl.

a is an integer from 1 to 4.

Exemplary compounds of the present invention include, but are not limited to the compounds in Table 1 below, or the pharmaceutically acceptable salts, solvates, metabolites or prodrugs thereof.

TABLE 1

| compound | structure | name |
|---|---|---|
| 1 | 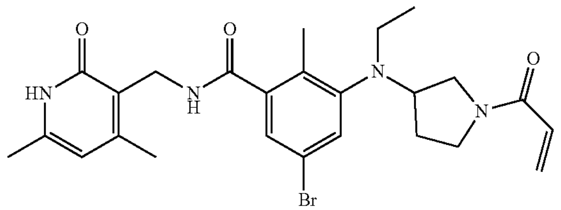 [SMILES: C=CC(=O)N1CCC(N(CC)c2cc(Br)cc(C(=O)NCc3c(C)cc(C)[nH]c3=O)c2C)C1] | 3-[(1-acryloyl-pyrrolidin-3-yl)-ethyl-amino]-5-bromo-N-(4,6-dimethyl-2-oxo-1,2-dihydro-pyridin-3-ylmethyl)-2-methyl-benzamide |
| 2 | 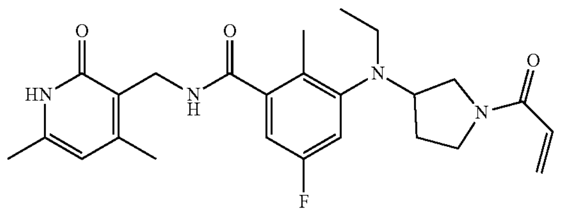 [SMILES: C=CC(=O)N1CCC(N(CC)c2cc(F)cc(C(=O)NCc3c(C)cc(C)[nH]c3=O)c2C)C1] | 3-[(1-acryloyl-pyrrolidin-3-y1)-ethyl-amino]-fluoro-N-(4,6-dimethyl-2-oxo-1,2-dihydro-pyridin-3-ylmethyl)-2-methyl-benzamide |
| 3 | 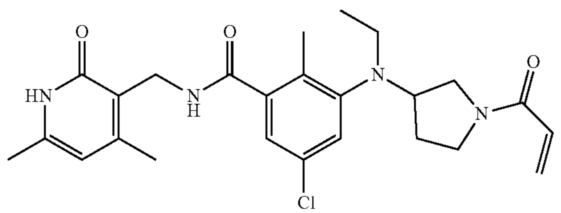 [SMILES: C=CC(=O)N1CCC(N(CC)c2cc(Cl)cc(C(=O)NCc3c(C)cc(C)[nH]c3=O)c2C)C1] | 3-[(1-acryloyl-pyrrolidin-3-y1)-ethyl-amino]-5-chloro-N-(4,6-dimethyl-2-oxo-1,2-dihydro-pyridin-3-ylmethyl)-2-methyl-benzamide |
| 4 | 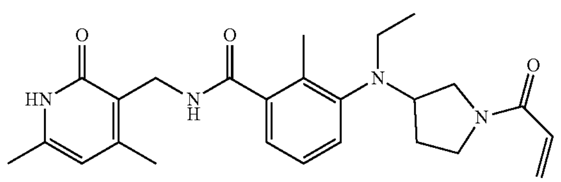 [SMILES: C=CC(=O)N1CCC(N(CC)c2cccc(C(=O)NCc3c(C)cc(C)[nH]c3=O)c2C)C1] | 3-[(1-acryloyl-pyrrolidin-3-yl)-ethyl-amino]-N-(4,6-dimethyl-2-oxo-1,2-dihydro-pyridin-3-ylmethyl)-2-methyl-benzamide |
| 5 | 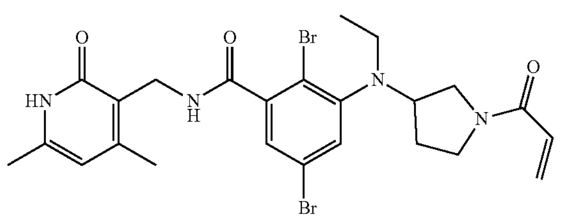 [SMILES: C=CC(=O)N1CCC(N(CC)c2cc(Br)cc(C(=O)NCc3c(C)cc(C)[nH]c3=O)c2Br)C1] | 3-[(1-acryloyl-pyrrolidin-3-yl)-ethyl-amino]-2,5-dibromo-N-(4,6-dimethyl-2-oxo-1,2-dihydro-pyridin-3-ylmethyl)-benzamide |
| 6 | 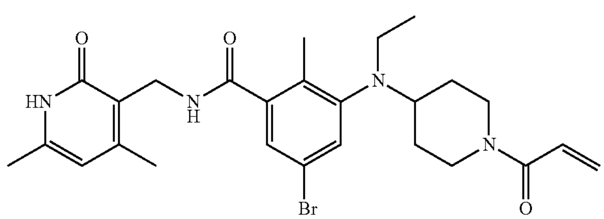 [SMILES: C=CC(=O)N1CCC(N(CC)c2cc(Br)cc(C(=O)NCc3c(C)cc(C)[nH]c3=O)c2C)CC1] | 3-[(1-acryloyl-piperidin-4-yl)-ethyl-amino]-5-bromo-N-(4,6-dimethyl-2-oxo-1,2-dihydro-pyridin-3-ylmethyl)-2-methyl-benzamide |
| 7 | 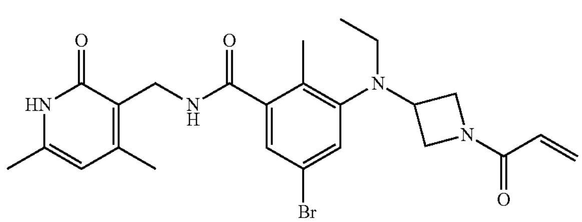 [SMILES: C=CC(=O)N1CC(N(CC)c2cc(Br)cc(C(=O)NCc3c(C)cc(C)[nH]c3=O)c2C)C1] | 3-[(1-acryloyl-azetidin-3-yl)-ethyl-amino]-5-bromo-N-(4,6-dimethyl-2-oxo-1,2-dihydro-pyridin-3-ylmethyl)-2-methyl-benzamide |

TABLE 1-continued

| compound | structure | name |
|---|---|---|
| 8 | 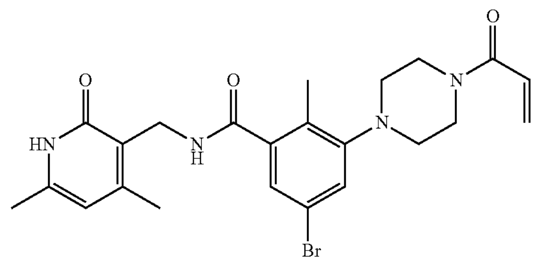 [SMILES: C=CC(=O)N1CCN(c2cc(Br)cc(C(=O)NCc3c(C)cc(C)[nH]c3=O)c2C)CC1] | 3-(4-acryloyl-piperazin-1-yl)-5-bromo-N-(4,6-dimethyl-2-oxo-1,2-dihydro-pyridin-3-ylmethyl)-2-methyl-benzamide |
| 9 | 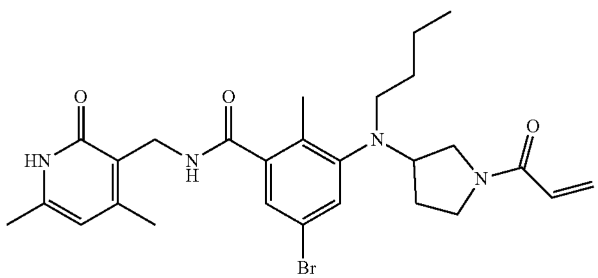 [SMILES: C=CC(=O)N1CCC(N(CCCC)c2cc(Br)cc(C(=O)NCc3c(C)cc(C)[nH]c3=O)c2C)C1] | 3-[(1-acryloyl-pyrrolidin-3-yl)-butyl-amino]-5-bromo-N-(4,6-dimethyl-2-oxo-1,2-dihydro-pyridin-3-ylmethyl)-2-methyl-benzamide |
| 10 | 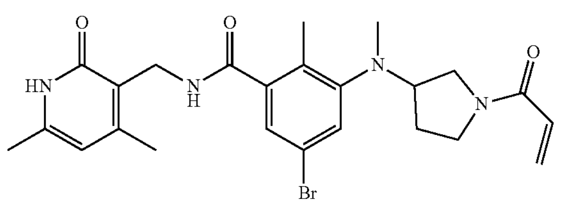 [SMILES: C=CC(=O)N1CCC(N(C)c2cc(Br)cc(C(=O)NCc3c(C)cc(C)[nH]c3=O)c2C)C1] | 3-[(1-acryloyl-pyrrolidin-3-yl)-methyl-amino]-5-bromo-N-(4,6-dimethyl-2-oxo-1,2-dihydro-pyridin-3-ylmethyl)-2-methyl-benzamide |
| 11 | 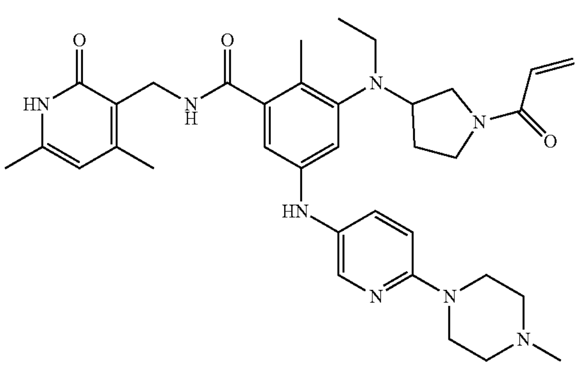 [SMILES: C=CC(=O)N1CCC(N(CC)c2cc(Nc3ccc(N4CCN(C)CC4)nc3)cc(C(=O)NCc3c(C)cc(C)[nH]c3=O)c2C)C1] | 3-[(1-acryloyl-pyrrolidin-3-yl)-ethyl-amino]-N-(4,6-dimethyl-2-oxo-1,2-dihydro-pyridin-3-ylmethyl)-2-methyl-5-[-(4-methyl-piperazin-1-yl)-pyridin-3-ylamino]-benzamide |
| 12 | 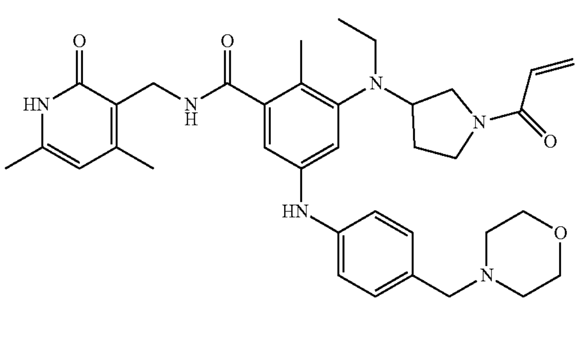 [SMILES: C=CC(=O)N1CCC(N(CC)c2cc(Nc3ccc(CN4CCOCC4)cc3)cc(C(=O)NCc3c(C)cc(C)[nH]c3=O)c2C)C1] | 3-[(1-acryloyl-pyrrolidin-3-yl)-ethyl-amino]-N-(4,6-dimethyl-2-oxo-1,2-dihydro-pyridine-3-ylmethyl)-2-methyl-5-[4-(morpholin-4-ylmethyl)-phenylamino]-benzamide |

TABLE 1-continued

| compound | structure | name |
|---|---|---|
| 13 | 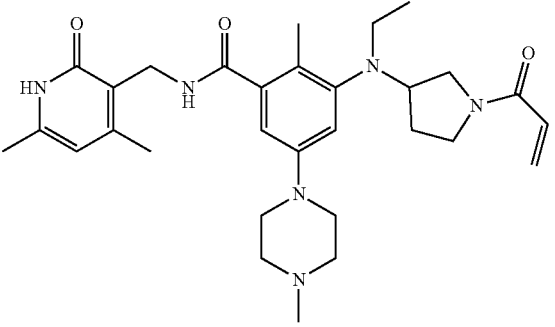 [SMILES: C=CC(=O)N1CCC(N(CC)c2cc(N3CCN(C)CC3)cc(C(=O)NCc3c(C)cc(C)[nH]c3=O)c2C)C1] | 3-[(1-acryloyl-pyrrolidin-3-yl)-ethyl-amino]-5-(4-methyl-piperazin-1-yl)-N-(4,6-dimethyl-2-oxo-1,2-dihydro-pyridin-3-ylmethyl)-2-methyl-benzamide |
| 14 | 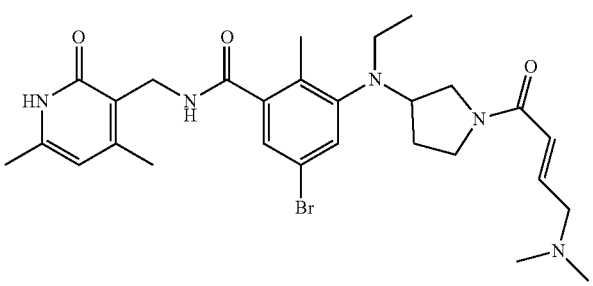 | 5-bromo-3-{[1-(4-dimethylamino-but-2-enoyl)-pyrrolidin-3-yl]-ethyl-amino}-N-(4,6-dimethyl-2-oxo-1,2-dihydro-pyridin-3-ylmethyl)-2-methyl-benzamide |
| 15 | 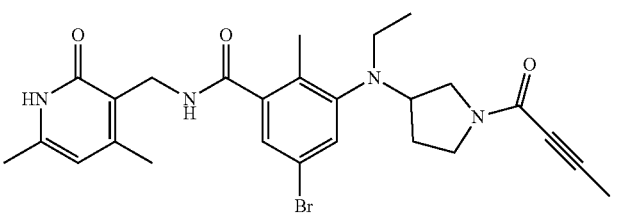 [SMILES: CC#CC(=O)N1CCC(N(CC)c2cc(Br)cc(C(=O)NCc3c(C)cc(C)[nH]c3=O)c2C)C1] | 5-bromo-3-{1-(1-oxo-but-2-ynyl)-pyrrolidin-3-yl]-ethyl-amino}-N-(4,6-dimethyl-2-oxo-1,2-dihydro-pyridin-3-ylmethyl)-2-methyl-benzamide |
| 16 | 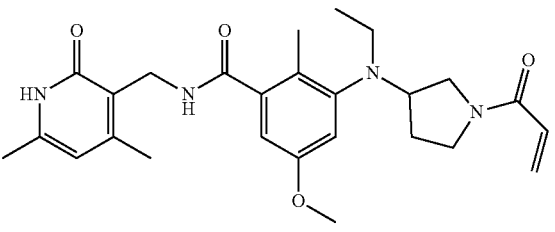 [SMILES: C=CC(=O)N1CCC(N(CC)c2cc(OC)cc(C(=O)NCc3c(C)cc(C)[nH]c3=O)c2C)C1] | 3-[(1-acryloyl-pyrrolidin-3-yl)-ethyl-amino]-5-methoxy-N-(4,6-dimethyl-2-oxo-1,2-dihydrogen-pyridin-3-ylmethyl)-2-methyl-benzamide |
| 17 | 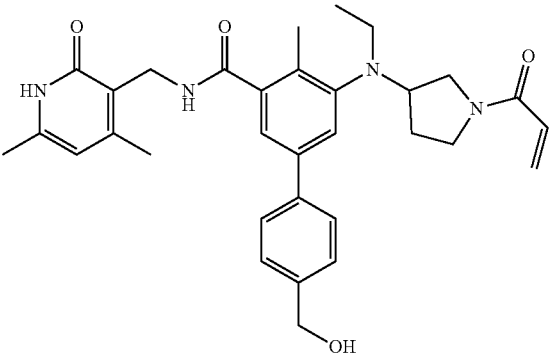 [SMILES: C=CC(=O)N1CCC(N(CC)c2cc(-c3ccc(CO)cc3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-yl-amino]-4'-hydroxymethyl-4-methyl-biphenyl-3-carboxamide |

TABLE 1-continued

| compound | structure | name |
|---|---|---|
| 18 | 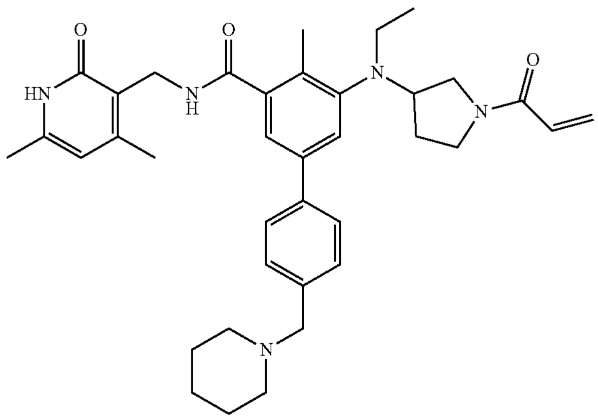 [SMILES: C=CC(=O)N1CCC(N(CC)c2cc(-c3ccc(CN4CCCCC4)cc3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-amino]-4'-(piperidin-1-ylmethyl)-4-methyl-biphenyl-3-carboxamide |
| 19 | 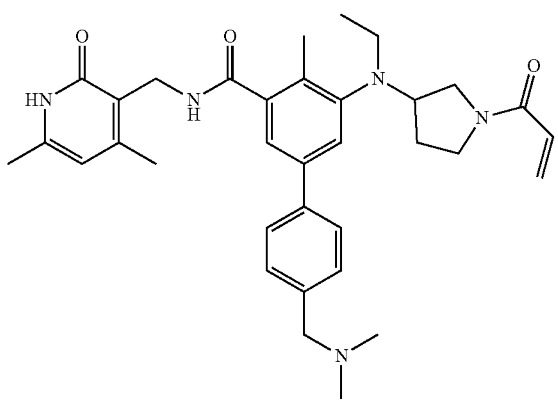 [SMILES: C=CC(=O)N1CCC(N(CC)c2cc(-c3ccc(CN(C)C)cc3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-amino]-4'-(dimethylaminomethyl)-4-methyl-biphenyl-3-carboxamide |
| 20 | 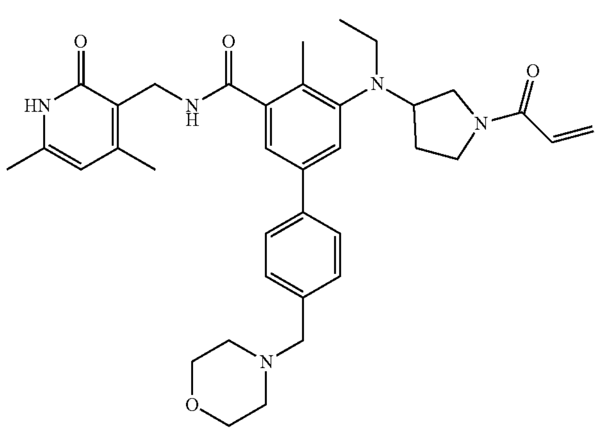 [SMILES: C=CC(=O)N1CCC(N(CC)c2cc(-c3ccc(CN4CCOCC4)cc3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-amino]-4'-(morpholin-4-ylmethyl)-4-methyl-biphenyl-3-carboxamide |

TABLE 1-continued

| compound | structure | name |
|---|---|---|
| 21 | 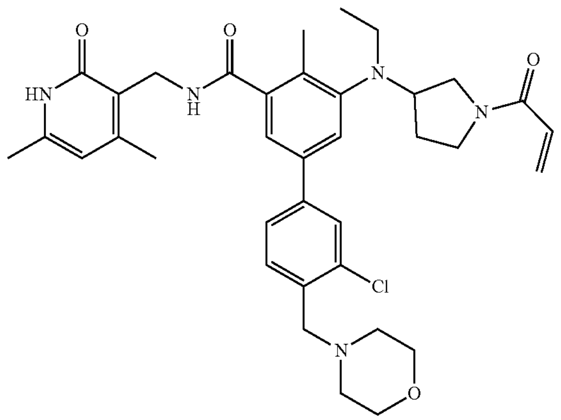 | N-(4,6-dimethyl-2-oxo-1,2-dihydro-pyridin-3-ylmethyl)-5-[(1-acryloyl-pyrrolidin-3-yl)-ethyl-amino]-3'-chloro-4'-(morpholin-4-ylmethyl)-4-methyl-biphenyl-3-carboxamide |
| 22 | 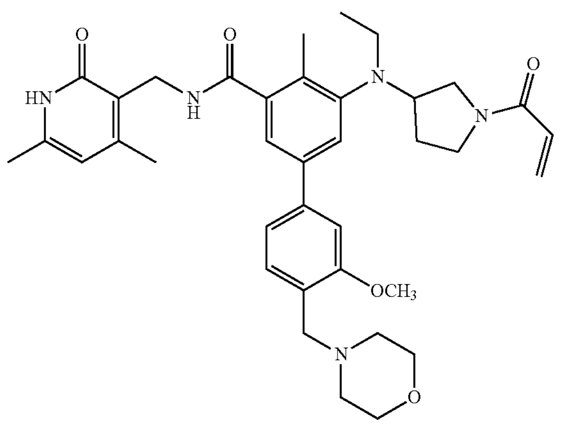 [SMILES: C=CC(=O)N1CCC(N(CC)c2cc(-c3ccc(CN4CCOCC4)c(OC)c3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-yl-amino]-3'-methoxy-4'-(morpholin-4-ylmethyl)-4-methyl-biphenyl-3-carboxamide |
| 23 | 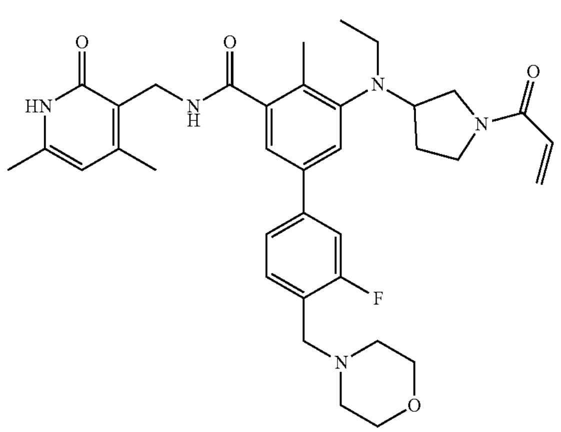 [SMILES: C=CC(=O)N1CCC(N(CC)c2cc(-c3ccc(CN4CCOCC4)c(F)c3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-amino]-3'-fluoro-4'-(morpholin-4-ylmethyl)-4-methyl-biphenyl-3-carboxamide |

TABLE 1-continued

| compound | structure | name |
|---|---|---|
| 24 | 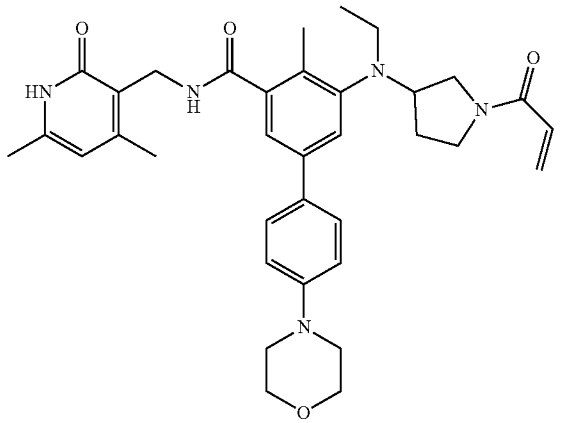 [SMILES: C=CC(=O)N1CCC(N(CC)c2cc(-c3ccc(N4CCOCC4)cc3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-amino]-4'-(morpholin-4-yl)-4-methyl-biphenyl-3-carboxamide |
| 25 | 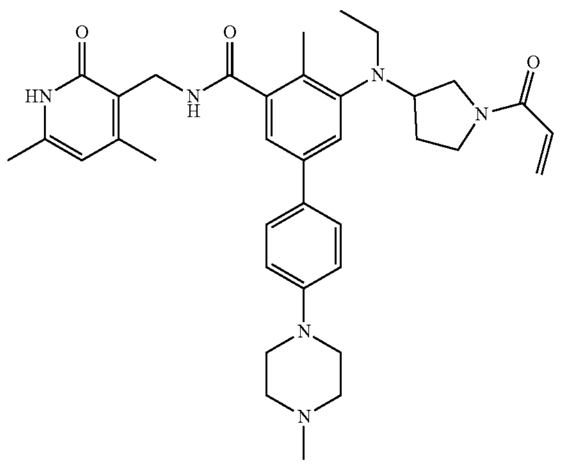 [SMILES: C=CC(=O)N1CCC(N(CC)c2cc(-c3ccc(N4CCN(C)CC4)cc3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-amino]-4'-(4-methyl-piperazin-1-yl)-4-methyl-biphenyl-3-carboxamide |
| 26 | 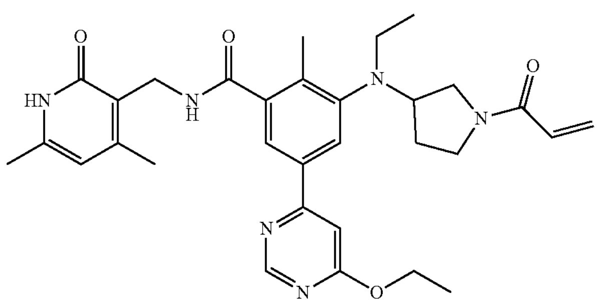 [SMILES: C=CC(=O)N1CCC(N(CC)c2cc(-c3cc(OCC)ncn3)cc(C(=O)NCc3c(C)cc(C)[nH]c3=O)c2C)C1] | N-(4,6-dimethyl-2-oxo-1,2-dihydro-pyridin-3-ylmethyl)-2-methyl-3-[(1-acryloyl-pyrrolidin-3-yl)-ethyl-amino]-5-(6-ethoxy-pyrimidin-4-yl)-benzamide |
| 27 | 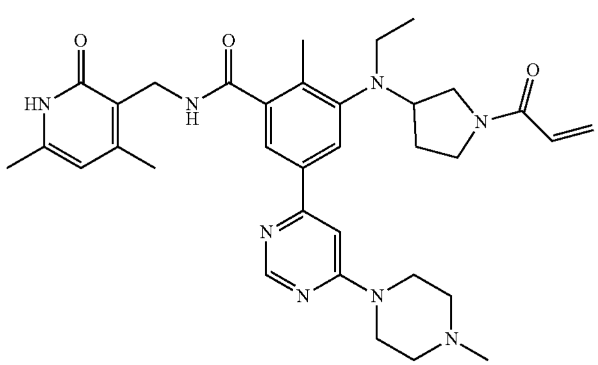 [SMILES: C=CC(=O)N1CCC(N(CC)c2cc(-c3cc(N4CCN(C)CC4)ncn3)cc(C(=O)NCc3c(C)cc(C)[nH]c3=O)c2C)C1] | N-(4,6-dimethyl-2-oxo-1,2-dihydro-pyridin-3-ylmethyl)-2-methyl-3-[(1-acryloyl-pyrrolidin-3-yl)-ethyl-amino]-5-(6-ethoxy-pyrimidin-4-yl)-benzamide |

TABLE 1-continued

| compound | structure | name |
|---|---|---|
| 28 | 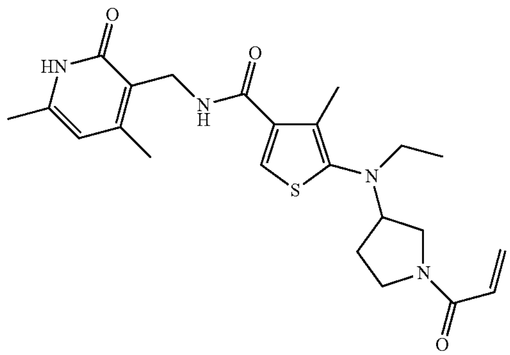 [SMILES: C=CC(=O)N1CCC(N(CC)c2scc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-amino]-4-methyl-thiophene-3-carboxamide |
| 29 | 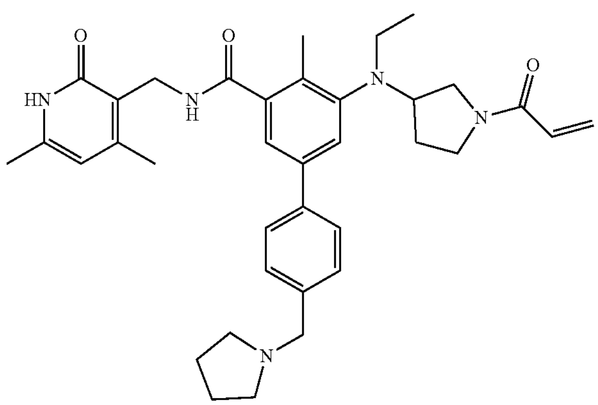 [SMILES: C=CC(=O)N1CCC(N(CC)c2cc(-c3ccc(CN4CCCC4)cc3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-amino]-4-methyl-4'-(pyrrolidin-1-ylmethyl)-[1,1'-biphenyl]-3-carboxamide |
| 30 | 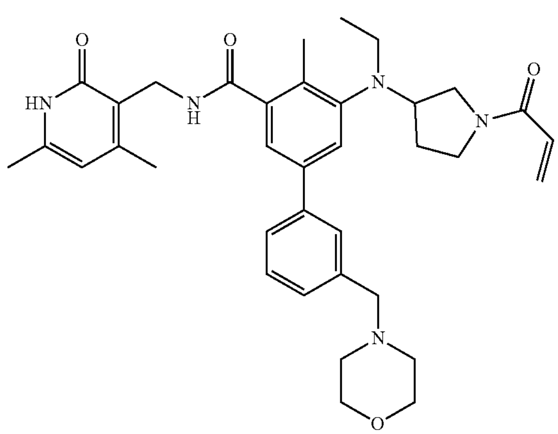 [SMILES: C=CC(=O)N1CCC(N(CC)c2cc(-c3cccc(CN4CCOCC4)c3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-amino]-4-methyl-3'-(morpholin-4-yl)-methyl-[1,1'-biphenyl]-3-carboxamide |
| 31 | 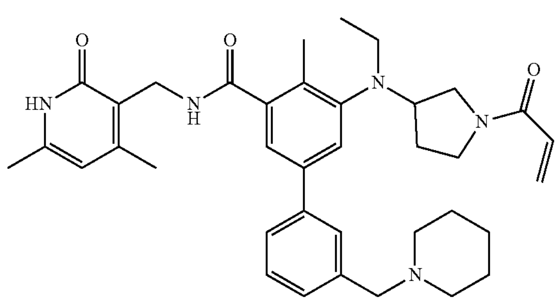 [SMILES: C=CC(=O)N1CCC(N(CC)c2cc(-c3cccc(CN4CCCCC4)c3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-amino]-4-methyl-3'-(piperidin-1-ylmethyl)-[1,1'-biphenyl]-3-carboxamide |

TABLE 1-continued

| compound | structure | name |
|---|---|---|
| 32 | 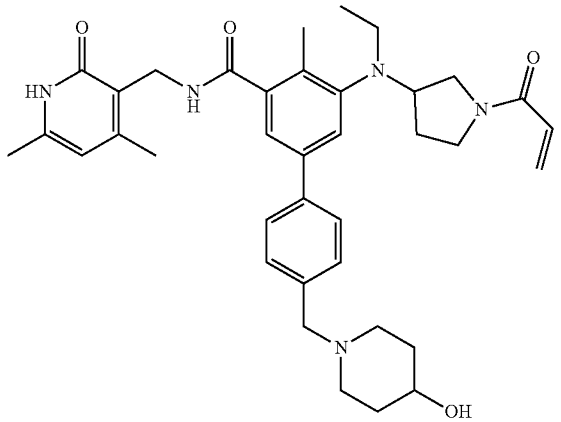 [SMILES: C=CC(=O)N1CCC(N(CC)c2cc(-c3ccc(CN4CCC(O)CC4)cc3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-amino]-4-methyl-4'-(4-hydroxypiperidin-1-ylmethyl)-[1,1'-biphenyl]-3-carboxamide |
| 33 | 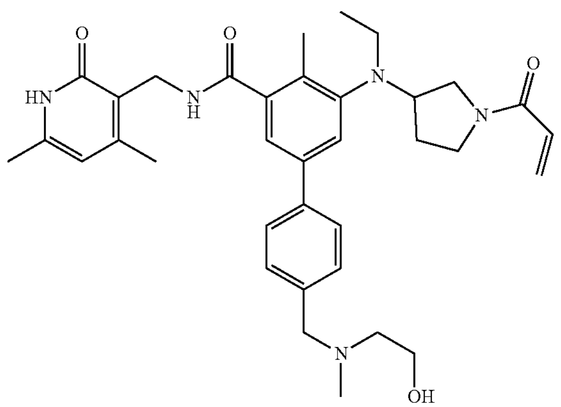 [SMILES: C=CC(=O)N1CCC(N(CC)c2cc(-c3ccc(CN(C)CCO)cc3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-amino]-4-methyl-4'-{[(2-hydroxyethyl)-methyl-amino]-methyl}-[1,1'-biphenyl]-3-carboxamide |
| 34 | 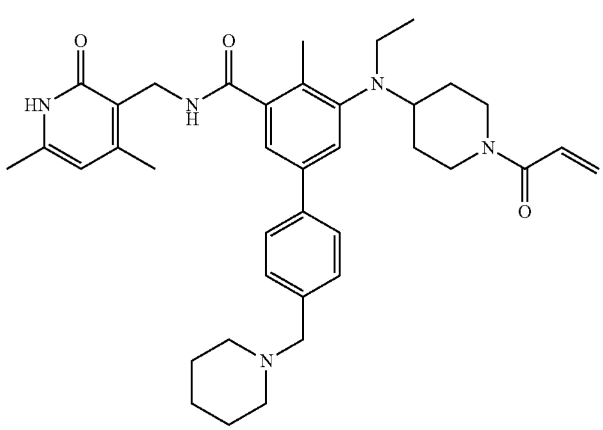 [SMILES: C=CC(=O)N1CCC(N(CC)c2cc(-c3ccc(CN4CCCCC4)cc3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-4'-(piperidin-1-ylmethyl)-[1,1'-biphenyl]-3-carboxamide |

TABLE 1-continued

| compound | structure | name |
|---|---|---|
| 35 | 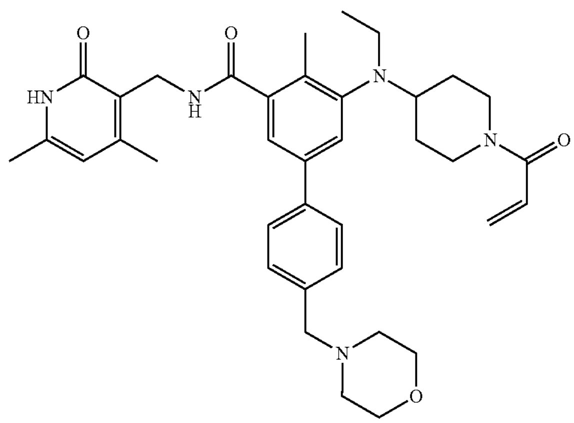 [SMILES: C=CC(=O)N1CCC(N(CC)c2cc(-c3ccc(CN4CCOCC4)cc3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-4'-(morpholin-4-ylmethyl)-[1,1'-biphenyl]-3-carboxamide |
| 36 | 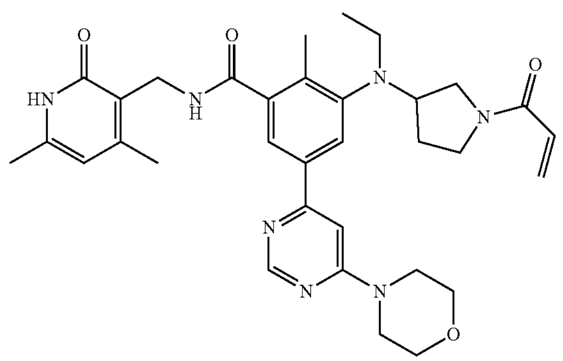 [SMILES: C=CC(=O)N1CCC(N(CC)c2cc(-c3cc(N4CCOCC4)ncn3)cc(C(=O)NCc3c(C)cc(C)[nH]c3=O)c2C)C1] | N-(4,6-dimethyl-2-oxo-1,2-dihydro-pyridin-3-ylmethyl)-2-methyl-3-[(1-acryloyl-pyrrolidin-3-yl)-ethyl-amino]-5-[6-(morpholin-4-yl)-pyrimidin-4-yl]-benzamide |
| 37 | 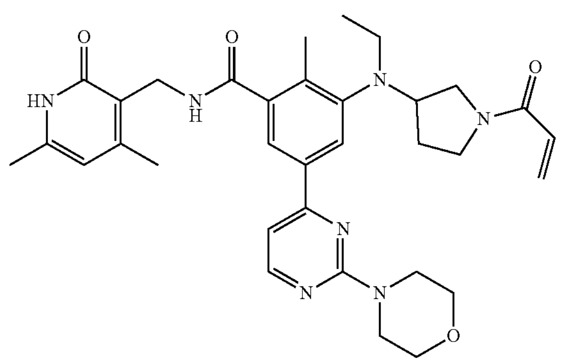 [SMILES: C=CC(=O)N1CCC(N(CC)c2cc(-c3ccnc(N4CCOCC4)n3)cc(C(=O)NCc3c(C)cc(C)[nH]c3=O)c2C)C1] | N-(4,6-dimethyl-2-oxo-1,2-dihydro-pyridin-3-ylmethyl)-3-[(1-acryloyl-pyrrolidin-3-yl)-ethyl-amino]-2-methyl-5-[2-(morpholin-4-yl)-pyrimidin-4-yl]-benzamide |
| 38 | 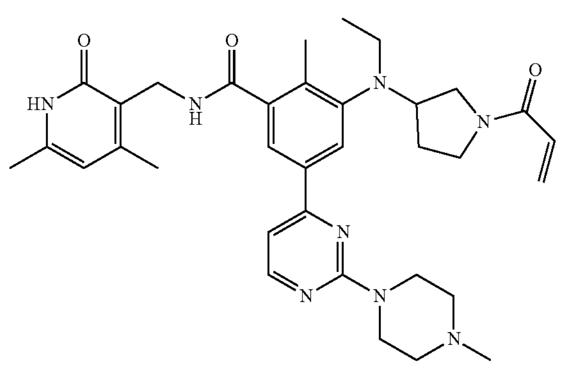 [SMILES: C=CC(=O)N1CCC(N(CC)c2cc(-c3ccnc(N4CCN(C)CC4)n3)cc(C(=O)NCc3c(C)cc(C)[nH]c3=O)c2C)C1] | N-(4,6-dimethyl-2-oxo-1,2-dihydro-pyridin-3-ylmethyl)-3-[(1-acryloyl-pyrrolidin-3-yl)-ethyl-amino]-2-methyl-5-[2-(4-methyl-piperazin-1-yl)-pyrimidin-4-yl]-benzamide |

TABLE 1-continued

| compound | structure | name |
|---|---|---|
| 39 | 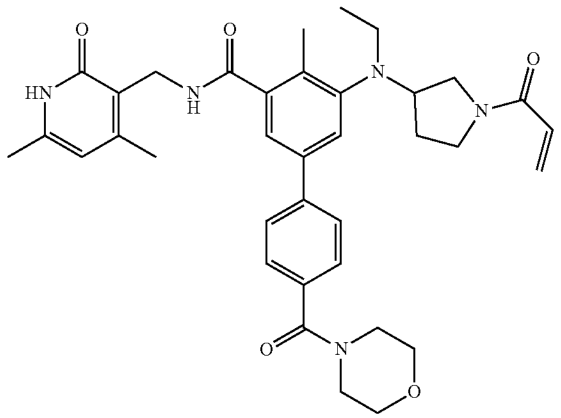 [SMILES: C=CC(=O)N1CCC(N(CC)c2cc(-c3ccc(C(=O)N4CCOCC4)cc3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-amino]-4-methyl-4'-(morpholin-4-ylformyl)-[1,1'-biphenyl]-3-carboxamide |
| 40 | 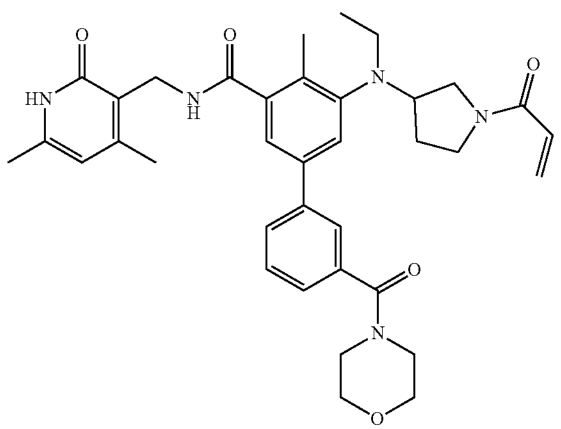 [SMILES: C=CC(=O)N1CCC(N(CC)c2cc(-c3cccc(C(=O)N4CCOCC4)c3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-amino]-4-methyl-3'-(morpholin-4-ylformyl)-[1,1'-biphenyl]-3-carboxamide |
| 41 | 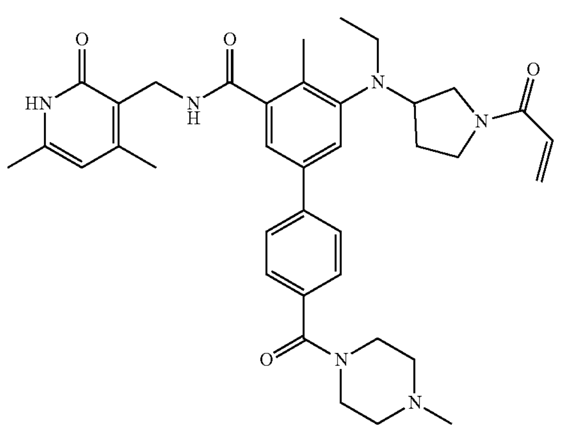 [SMILES: C=CC(=O)N1CCC(N(CC)c2cc(-c3ccc(C(=O)N4CCN(C)CC4)cc3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-amino]-4-methyl-4'-(4-methyl-piperazin-1-ylformyl)-[1,1'-biphenyl]-3-carboxamide |

TABLE 1-continued

| compound | structure | name |
|---|---|---|
| 42 | 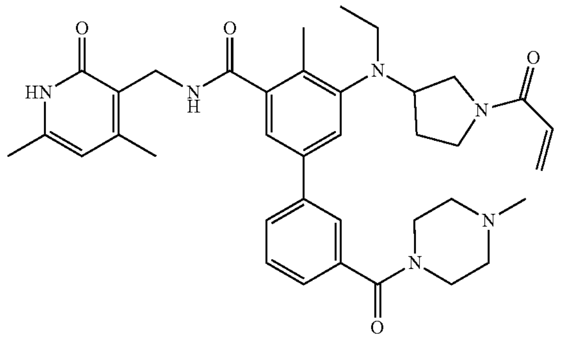 [SMILES: C=CC(=O)N1CCC(N(CC)c2cc(-c3cccc(C(=O)N4CCN(C)CC4)c3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-amino]-4-methyl-3'-(4-methyl-piperazin-1-ylformyl)-[1,1'-biphenyl]-3-carboxamide |
| 43 | 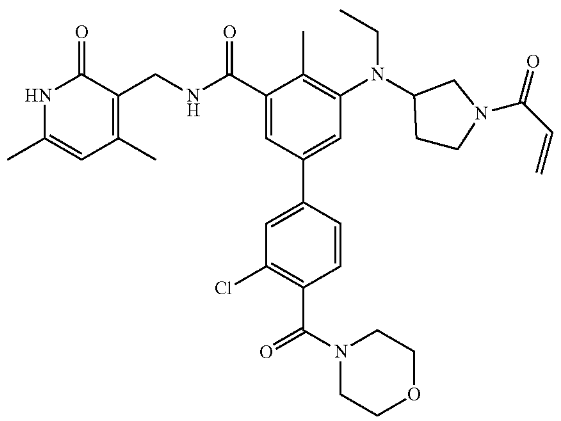 [SMILES: C=CC(=O)N1CCC(N(CC)c2cc(-c3ccc(C(=O)N4CCOCC4)c(Cl)c3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-amino]-4'-(morpholin-4-ylformyl)-3'-chloro-4-methyl-[1,1'-biphenyl]-3-carboxamide |
| 44 | 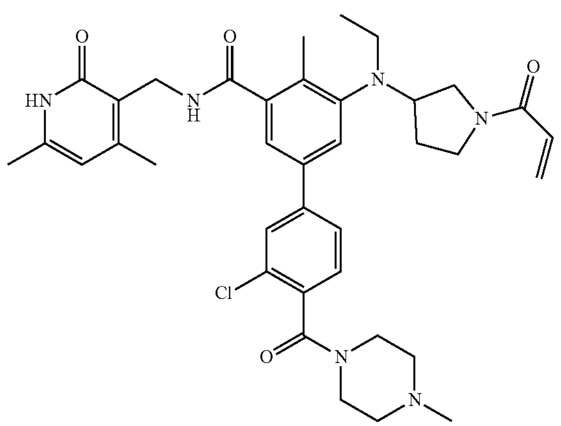 [SMILES: C=CC(=O)N1CCC(N(CC)c2cc(-c3ccc(C(=O)N4CCN(C)CC4)c(Cl)c3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-amino]-4'-(4-methyl-piperazin-1-ylformyl)-3'-chloro-4-methyl-[1,1'-biphenyl]-3-carboxamide |
| 45 | 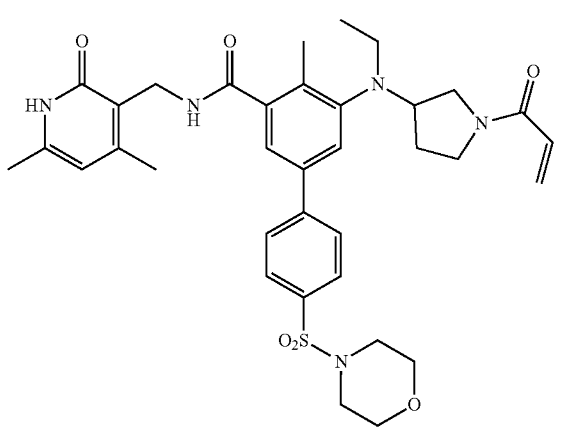 [SMILES: C=CC(=O)N1CCC(N(CC)c2cc(-c3ccc(S(=O)(=O)N4CCOCC4)cc3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-amino]-4-methyl-4'-(morpholin-4-ylsulfonyl)-[1,1'-biphenyl]-3-carboxamide |

TABLE 1-continued

| compound | structure | name |
|---|---|---|
| 46 | 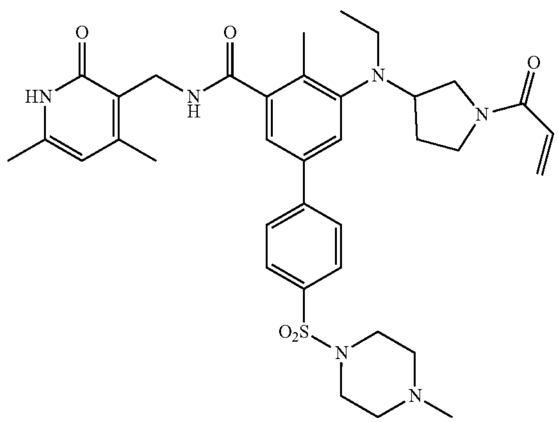 [SMILES: C=CC(=O)N1CCC(N(CC)c2cc(-c3ccc(S(=O)(=O)N4CCN(C)CC4)cc3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-amino]-4-methyl-4'-(4-methyl-piperazin-1-ylsulfonyl)-[1,1'-biphenyl]-3-carboxamide |
| 47 | 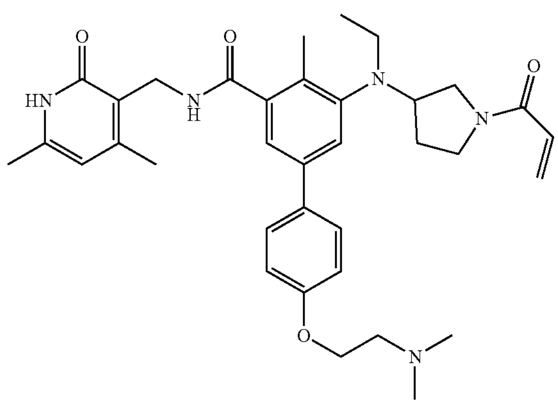 [SMILES: C=CC(=O)N1CCC(N(CC)c2cc(-c3ccc(OCCN(C)C)cc3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-amino]-4-methyl-4'-(2-dimethylaminoethoxy)-[1,1'-biphenyl]-3-carboxamide |
| 48 | 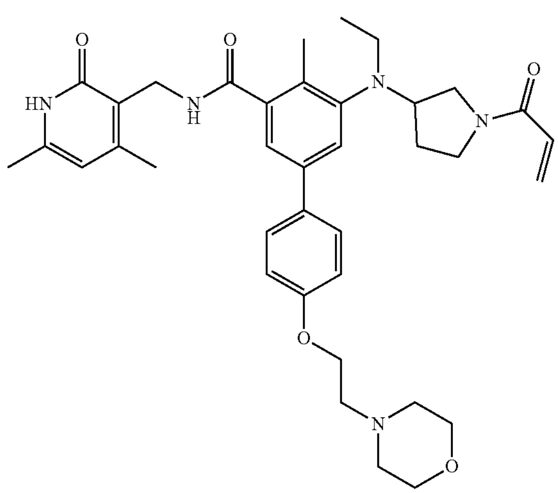 [SMILES: C=CC(=O)N1CCC(N(CC)c2cc(-c3ccc(OCCN4CCOCC4)cc3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-amino]-4-methyl-4'-[2-(morpholin-4-yl)-ethoxy]-[1,1'-biphenyl]-3-carboxamide |

TABLE 1-continued

| compound | structure | name |
|---|---|---|
| 49 | 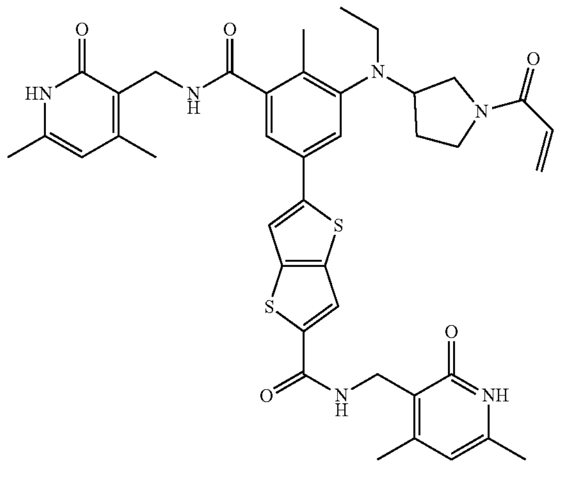 | N-(4,6-dimethyl-2-oxo-1,2-dihydro-pyridin-3-ylmethyl)-5-{3-[(1-acryloyl-pyrrolidin-3-yl)-ethyl-amino]-5-[(4,6-dimethyl-2-oxo-1,2-dihydro-pyridin-3-ylmethyl)-carbamoyl]-4-methyl-phenyl}-thiophene[3,2-b]-thiophene-2-carboxamide |
| 50 | 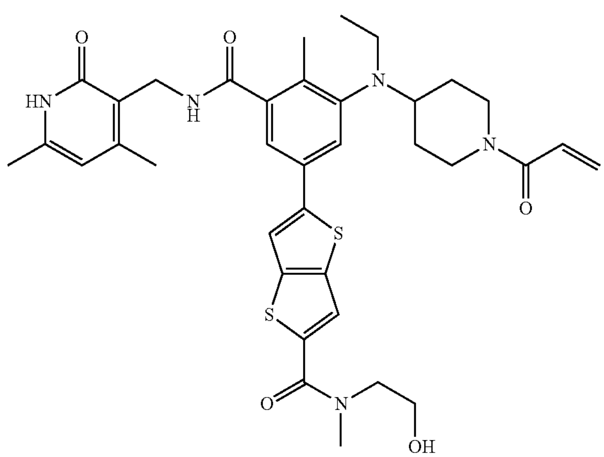 [SMILES: C=CC(=O)N1CCC(N(CC)c2cc(-c3cc4sc(C(=O)N(C)CCO)cc4s3)cc(C(=O)NCc3c(C)cc(C)[nH]c3=O)c2C)CC1] | N-(2-hydroxyethyl)-N-methyl-5-{3-[(1-acryloyl-piperidin-4-yl)-ethyl-amino]-5-(4,6-dimethyl-2-oxo-1,2-dihydro-pyridin-3-ylmethyl)-carbamoyl]-4-methyl-phenyl}-thiopheno[3,2-b]thiophene-2-carboxamide |
| 51 | 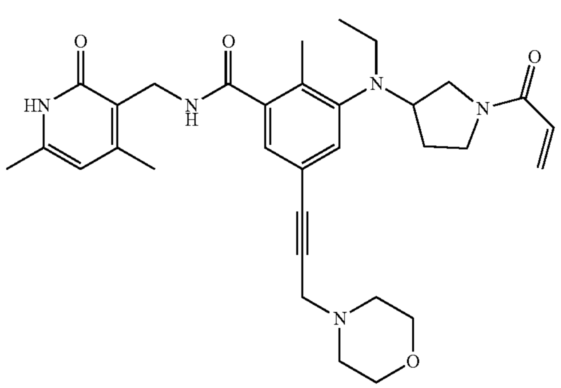 [SMILES: C=CC(=O)N1CCC(N(CC)c2cc(C#CCN3CCOCC3)cc(C(=O)NCc3c(C)cc(C)[nH]c3=O)c2C)C1] | N-(4,6-dimethyl-2-oxo-1,2-dihydro-pyridin-3-ylmethyl)-3-[(1-acryloyl-pyrrolidin-3-yl)-ethyl-amino]-2-methyl-5-[3-(morpholin-4-yl)-propyn-1-yl]-benzamide |

TABLE 1-continued

| compound | structure | name |
|---|---|---|
| 52 | 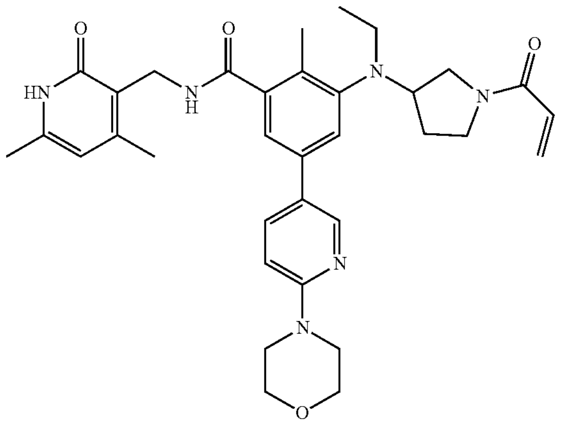 [SMILES: C=CC(=O)N1CCC(N(CC)c2cc(-c3ccc(N4CCOCC4)nc3)cc(C(=O)NCc3c(C)cc(C)[nH]c3=O)c2C)C1] | N-(4,6-dimethyl-2-oxo-1,2-dihydro-pyridin-3-ylmelhyl)-3-[(1-acryloyl-pyrrolidin-3-yl)-ethyl-amino]-2-methyl-5-[6-(morpholin-4-yl)-pyridin-3-yl]-benzamide |
| 53 | 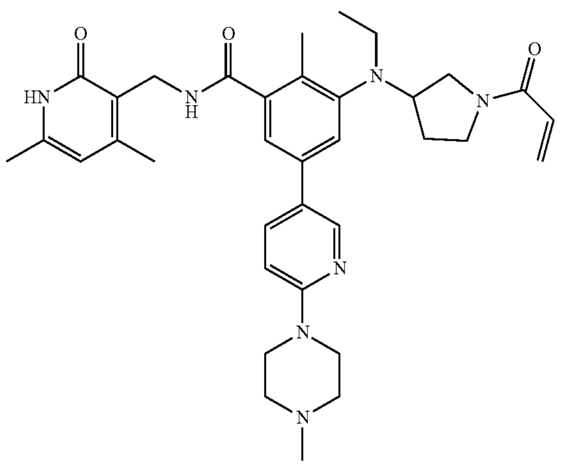 [SMILES: C=CC(=O)N1CCC(N(CC)c2cc(-c3ccc(N4CCN(C)CC4)nc3)cc(C(=O)NCc3c(C)cc(C)[nH]c3=O)c2C)C1] | N-(4,6-dimethyl-2-oxo-1,2-dihydro-pyridin-3-ylmethyl)-3-[(1-acryloyl-pyrrolidin-3-yl)-ethyl-amino]-2-methyl-5-[6-(4-methylpiperazin-1-yl)-pyridin-3-yl]-benzamide |
| 54 | 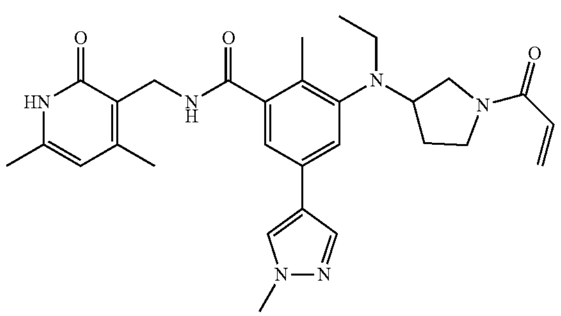 [SMILES: C=CC(=O)N1CCC(N(CC)c2cc(-c3cnn(C)c3)cc(C(=O)NCc3c(C)cc(C)[nH]c3=O)c2C)C1] | N-(4,6-dimethyl-2-oxo-1,2-dihydro-pyridin-3-ylmethyl)-3-[(1-acryloyl-pyrrolidin-3-yl)-ethyl-amino]-2-methyl-5-(1-methyl-1H-pyrazol-4-yl)-benzamide |
| 55 | 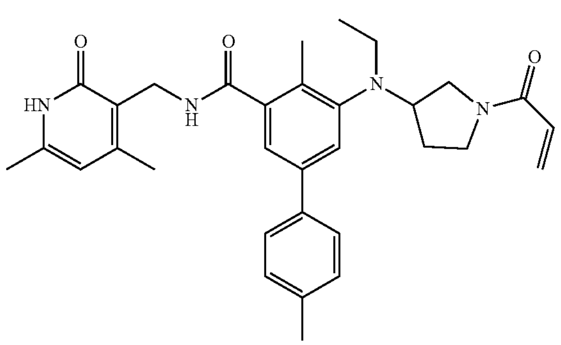 [SMILES: C=CC(=O)N1CCC(N(CC)c2cc(-c3ccc(C)cc3)cc(C(=O)NCc3c(C)cc(C)[nH]c3=O)c2C)C1] | N-(4,6-dimethyl-2-oxo-1,2-dihydro-pyridin-3-ylmethyl)-5-[(1-acryloyl-pyrrolidin-3-yl)-ethyl-amino]-4,3'-dimethyl-[1,1'-biphenyl]-3-carboxamide |

TABLE 1-continued

| compound | structure | name |
|---|---|---|
| 56 | 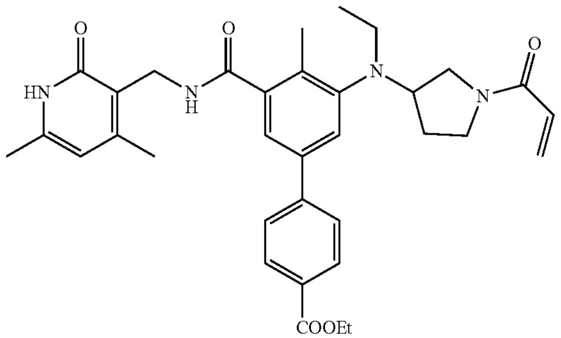 [SMILES: C=CC(=O)N1CCC(N(CC)c2cc(-c3ccc(C(=O)OCC)cc3)cc(C(=O)NCc3c(C)cc(C)[nH]c3=O)c2C)C1] | Ethyl 3'-[(4,6-dimethyl-2-oxo-1,2-dihydro-pyridin-3-ylmethyl)-formyl]-5'-[(1-acryloyl-pyrrolidin-3-yl)-ethyl-amino]-4'-methyl-[1,1'-biphenyl]-4-carboxylate |
| 57 | 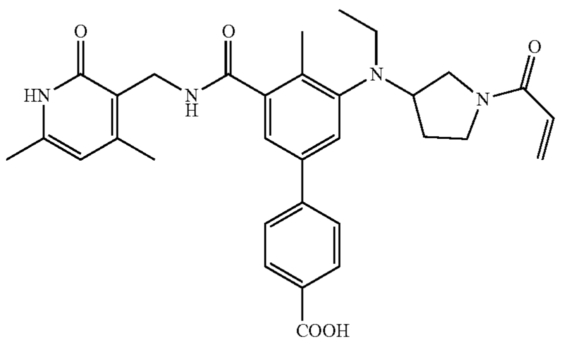 | 3'-[(4,6-dimethyl-2-oxo-1,2-dihydro-pyridin-3-ylmethyl)-formyl]-5'-[(1-acryloyl-pyrrolidin-3-yl)-ethyl-amino]-4'-methyl-[1,1-biphenyl]-4-carboxylic acid |
| 58 | 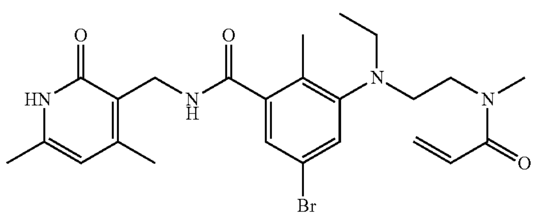 [SMILES: C=CC(=O)N(C)CCN(CC)c1cc(Br)cc(C(=O)NCc2c(C)cc(C)[nH]c2=O)c1C] | 3-{[2-(acryloyl-methyl-amino)-ethyl]-ethyl-amino}-5-bromo-N-(4,6-dimethyl-2-oxo-1,2-dihydro-pyridin-3-ylmethyl)-2-methyl-benzamide |
| 59 | 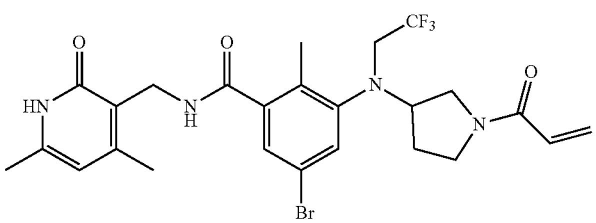 [SMILES: C=CC(=O)N1CCC(N(CC(F)(F)F)c2cc(Br)cc(C(=O)NCc3c(C)cc(C)[nH]c3=O)c2C)C1] | N-(4,6-dimethyl-2-oxo-1,2-dihydro-pyridin-3-ylmethyl)-3-[(1-acryloyl-pyrrolidin-3-yl)-(2,2,2-trifluoroethyl)-amino]-2-methyl-5-bromobenzamide |
| 60 | 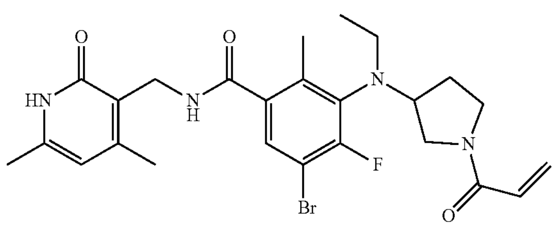 [SMILES: C=CC(=O)N1CCC(N(CC)c2c(C)c(C(=O)NCc3c(C)cc(C)[nH]c3=O)cc(Br)c2F)C1] | N-(4,6-dimethyl-2-oxo-1,2-dihydro-pyridin-3-ylmethyl)-3-[(1-acryloyl-pyrrolidin-3-yl)-ethyl-amino]-5-bromo-4-fluoro-2-methyl-benzamide |
| 61 | 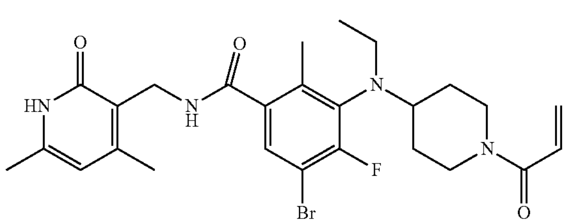 [SMILES: C=CC(=O)N1CCC(N(CC)c2c(C)c(C(=O)NCc3c(C)cc(C)[nH]c3=O)cc(Br)c2F)CC1] | N-(4,6-dimethyl-2-oxo-1,2-dihydro-pyridin-3-ylmethyl)-3-[(1-acryloyl-piperidin-4-yl)-ethyl-amino]-5-bromo-4-fluoro-2-methyl-benzamide |

TABLE 1-continued

| compound | structure | name |
|---|---|---|
| 62 | 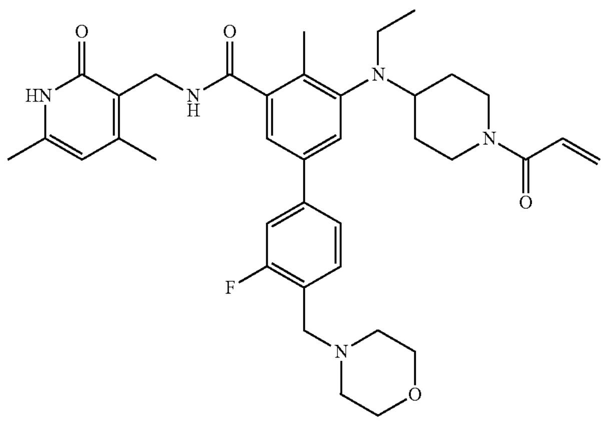 [SMILES: C=CC(=O)N1CCC(N(CC)c2cc(-c3ccc(CN4CCOCC4)c(F)c3)cc(C(=O)NCc3c(C)cc(C)[nH]c3=O)c2C)CC1] | N-(4,6-dimethyl-2-oxo-1,2-dihydro-pyridin-3-ylmethyl)-5-[(l-acryloyl-piperidin-4-yl)-ethyl-amino]-3'-fluoro-4-methyl-4'-(morpholin-4-ylmethyl)-[1,1'-biphenyl]-3-carboxamide |
| 63 | 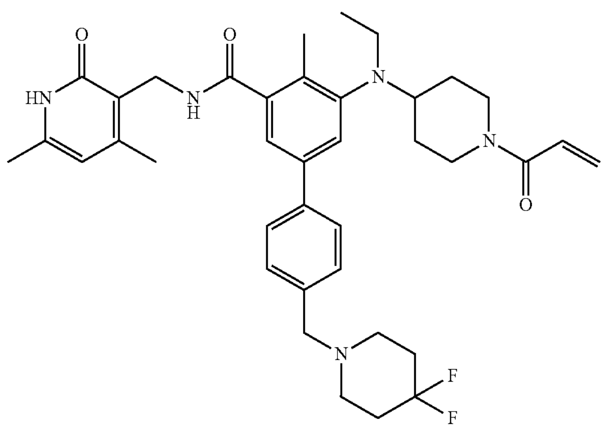 [SMILES: C=CC(=O)N1CCC(N(CC)c2cc(-c3ccc(CN4CCC(F)(F)CC4)cc3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-4'-(4,4-difluoro-piperidin-1-ylmethyl)-[1,1'-biphenyl]-3-carboxamide |
| 64 | 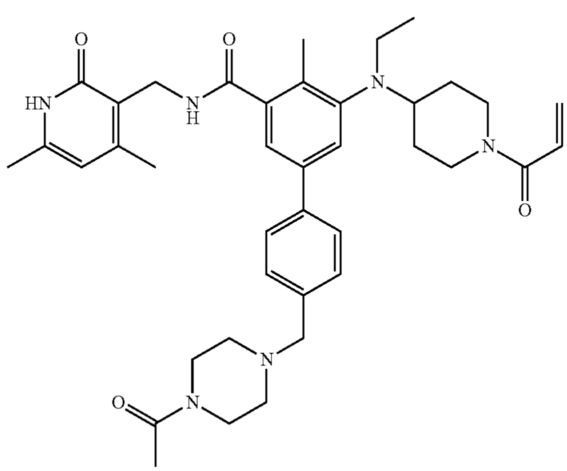 [SMILES: C=CC(=O)N1CCC(N(CC)c2cc(-c3ccc(CN4CCN(C(C)=O)CC4)cc3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-4'-(4-acetyl-piperazin-1-yl methyl)-[1,1'-biphenyl]-3-carboxamide |

TABLE 1-continued

| compound | structure | name |
|---|---|---|
| 65 | 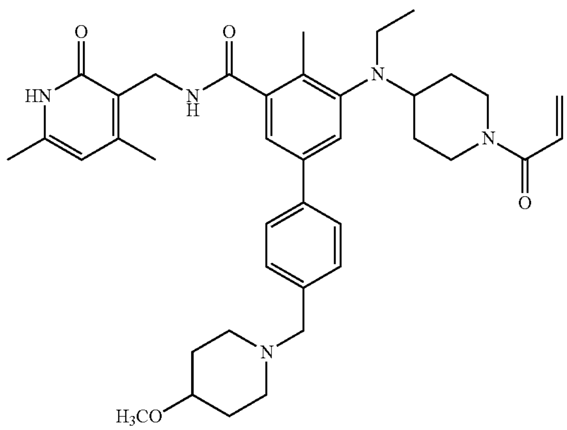 [SMILES: C=CC(=O)N1CCC(N(CC)c2cc(-c3ccc(CN4CCC(OC)CC4)cc3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-4'-(4-methoxypiperidin-1-ylmethyl)-[1,1'-biphenyl]-3-carboxamide |
| 66 | 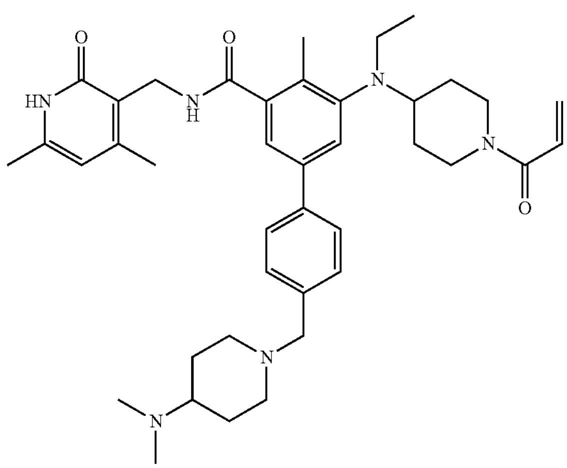 [SMILES: C=CC(=O)N1CCC(N(CC)c2cc(-c3ccc(CN4CCC(N(C)C)CC4)cc3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-4'-(4-dimethylamino-piperidin-1-ylmethyl)-[1,1'-biphenyl]-3-carboxamide |
| 67 | 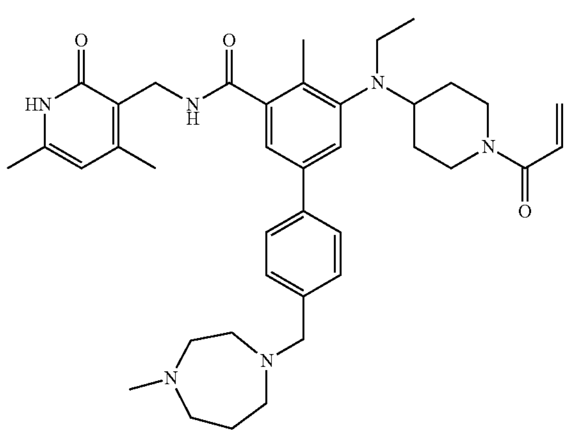 [SMILES: C=CC(=O)N1CCC(N(CC)c2cc(-c3ccc(CN4CCCN(C)CC4)cc3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-4'-(4-methylhomopiperazin-1-ylmethyl)-[1,1'-biphenyl]-3-carboxamide |

TABLE 1-continued

| compound | structure | name |
|---|---|---|
| 68 | 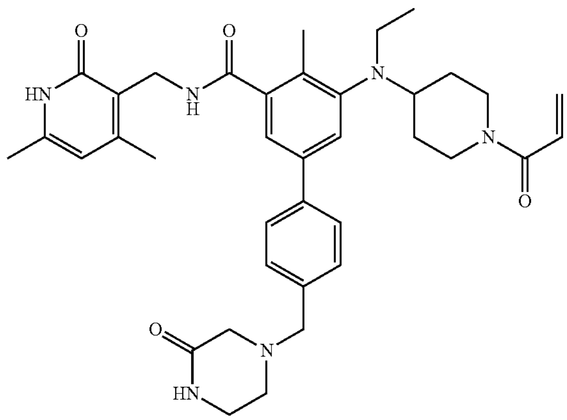 [SMILES: C=CC(=O)N1CCC(N(CC)c2cc(-c3ccc(CN4CCNC(=O)C4)cc3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-4'-(3-oxopiperin-1-ylmethyl)-[1,1'-biphenyl]-3-carboxamide |
| 69 | 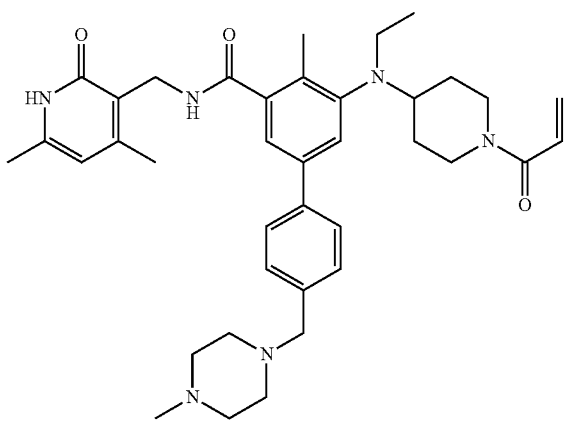 [SMILES: C=CC(=O)N1CCC(N(CC)c2cc(-c3ccc(CN4CCN(C)CC4)cc3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-4'-(4-methylpiperazin-1-yl methyl)-[1,1'-biphenyl]-3-carboxamide |
| 70 | 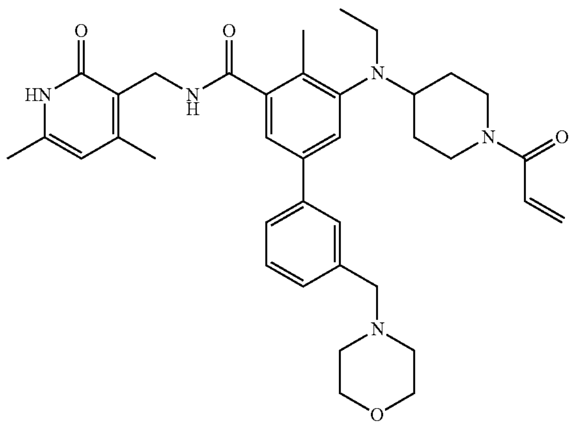 [SMILES: C=CC(=O)N1CCC(N(CC)c2cc(-c3cccc(CN4CCOCC4)c3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-3'-(morpholin-4-ylmethyl)-[1,1'-biphenyl]-3-carboxamide |

TABLE 1-continued

| compound | structure | name |
|---|---|---|
| 71 | 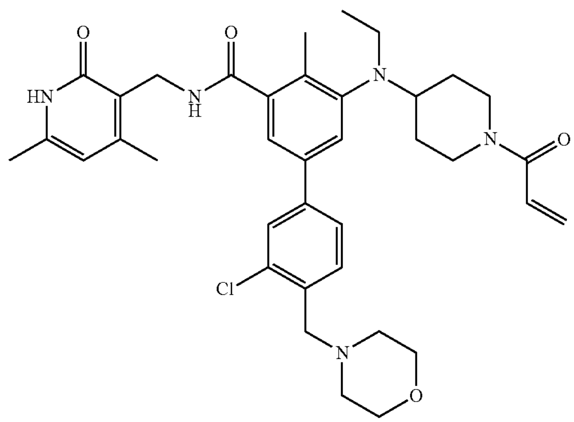 [SMILES: C=CC(=O)N1CCC(N(CC)c2cc(-c3ccc(CN4CCOCC4)c(Cl)c3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-3'-chloro-4-methyl-4'-(morpholin-4-ylmethyl)-[1,1'-biphenyl]-3-carboxamide |
| 72 | 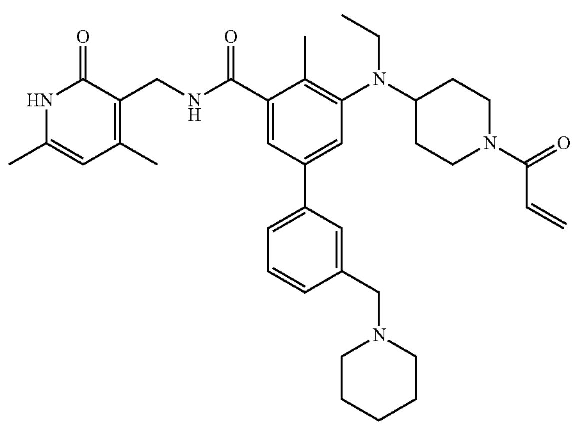 [SMILES: C=CC(=O)N1CCC(N(CC)c2cc(-c3cccc(CN4CCCCC4)c3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-3'-(piperidin-1-ylmethyl)-[1,1'-biphenyl]-3-carboxamide |
| 73 | 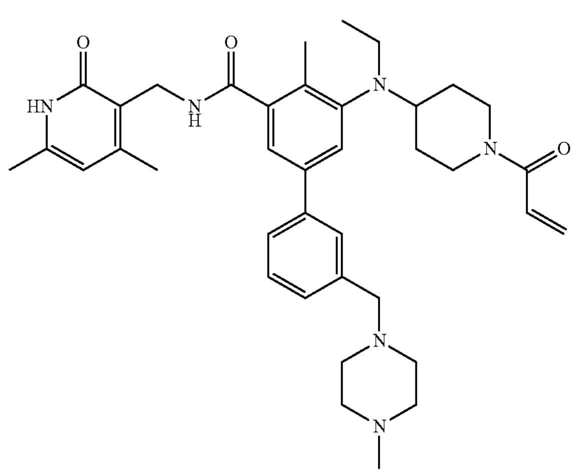 [SMILES: C=CC(=O)N1CCC(N(CC)c2cc(-c3cccc(CN4CCN(C)CC4)c3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-3'-(4-methylpiperazin-1-ylmethyl)-[1,1'-biphenyl]-3-carboxamide |

TABLE 1-continued

| compound | structure | name |
|---|---|---|
| 74 | 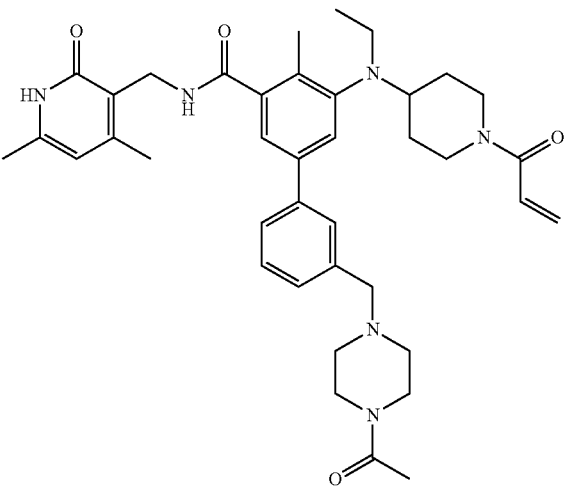 [SMILES: C=CC(=O)N1CCC(N(CC)c2cc(-c3cccc(CN4CCN(C(C)=O)CC4)c3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-3'-(4-acetylpiperazin-1-yl methyl)-[1,1'-biphenyl]-3-carboxamide |
| 75 | 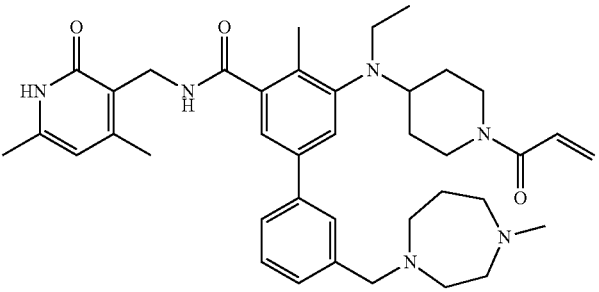 [SMILES: C=CC(=O)N1CCC(N(CC)c2cc(-c3cccc(CN4CCCN(C)CC4)c3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-3'-(4-methylhomopiperazin-1-ylmethyl)-[1,1'-biphenyl]-3-carboxamide |
| 76 | 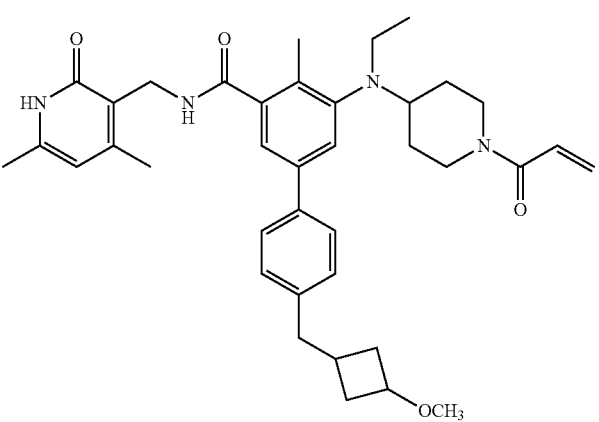 [SMILES: C=CC(=O)N1CCC(N(CC)c2cc(-c3ccc(CC4CC(OC)C4)cc3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-4'-(3-methoxy-1-azetidinyl methyl)-[1,1'-biphenyl]-3-carboxamide |

TABLE 1-continued

| compound | structure | name |
|---|---|---|
| 77 | 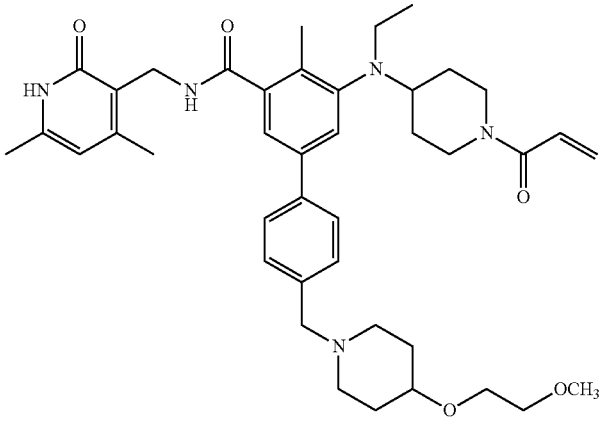 [SMILES: C=CC(=O)N1CCC(N(CC)c2cc(-c3ccc(CN4CCC(OCCOC)CC4)cc3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-4'-[4-(2-methoxyethyloxy)-piperidin-1-ylmethyl]-[1,1'-biphenyl]-3-carboxamide |
| 78 | 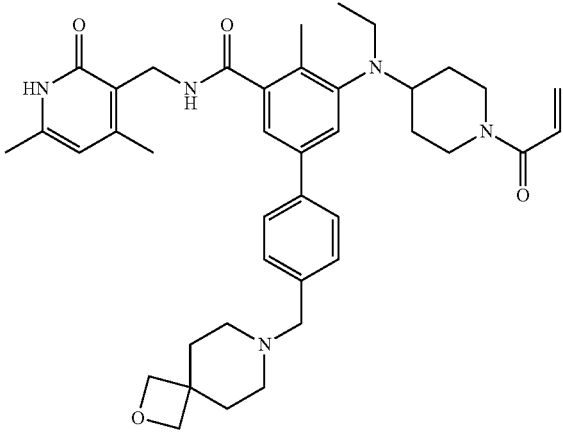 [SMILES: C=CC(=O)N1CCC(N(CC)c2cc(-c3ccc(CN4CCC5(CC4)COC5)cc3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-4'-(2-oxa-7-aza-spiro[3.5]dec-7-ylmethyl)-[1,1'-biphenyl]-3-carboxamide |
| 79 | 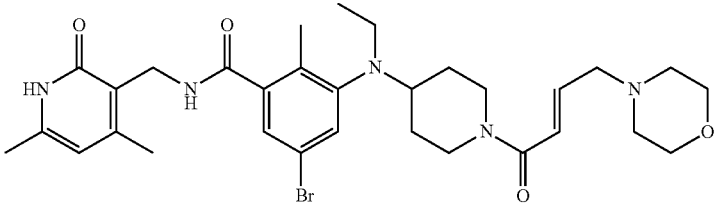 [SMILES: CCN(c1cc(Br)cc(C(=O)NCc2c(C)cc(C)[nH]c2=O)c1C)C1CCN(C(=O)/C=C/CN2CCOCC2)CC1] | N-(4,6-dimethyl-2-oxo-1,2-dihydro-pyridin-3-ylmethyl)-5-bromo-3-{ethyl-[1-(4-morpholin-4-yl-but-2-enoyl)-piperidin-4-yl]-amino}-2-methyl-benzamide |

TABLE 1-continued

| compound | structure | name |
|---|---|---|
| 80 | 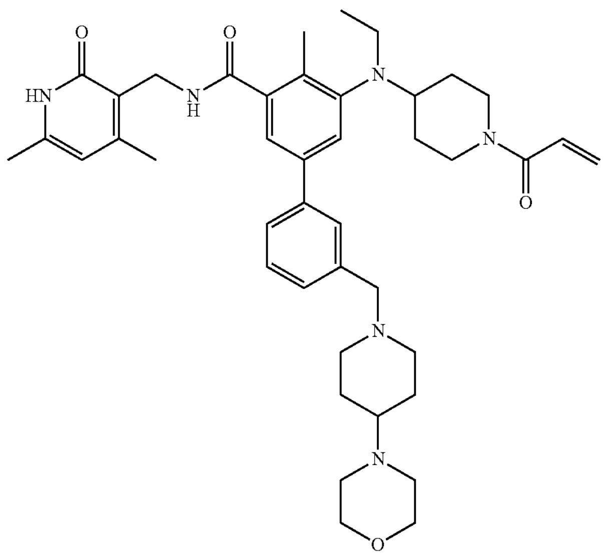 [SMILES: C=CC(=O)N1CCC(N(CC)c2cc(-c3cccc(CN4CCC(N5CCOCC5)CC4)c3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-3'-[4-(morpholin-4-yl)-piperazin-1-ylmethyl]-biphenyl-3-carboxamide |
| 81 | 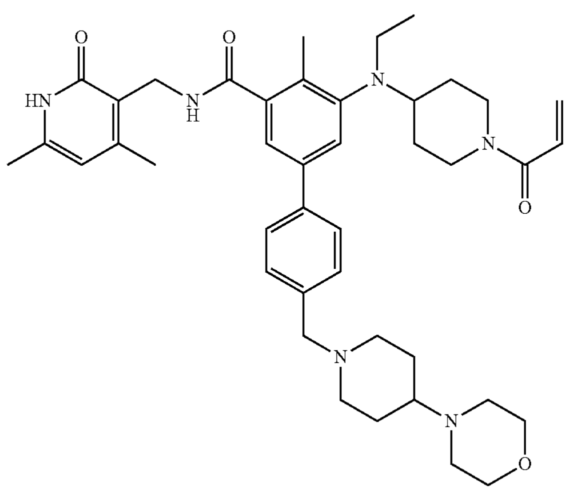 [SMILES: C=CC(=O)N1CCC(N(CC)c2cc(-c3ccc(CN4CCC(N5CCOCC5)CC4)cc3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-4'-[4-(morpholin-4-yl)-piperazin-1-ylmethyl]-[1,1'-biphenyl]-3-carboxamide |
| 82 | 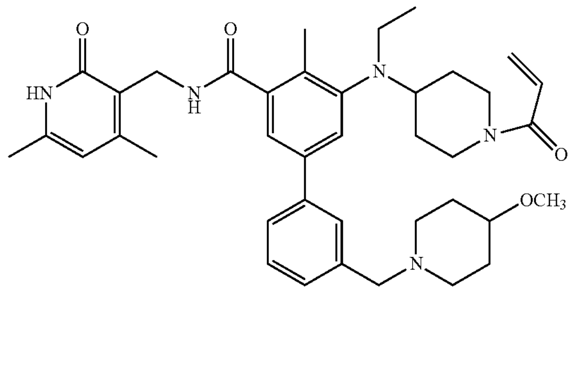 [SMILES: C=CC(=O)N1CCC(N(CC)c2cc(-c3cccc(CN4CCC(OC)CC4)c3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-3'-(4-methoxypiperidin-1-ylmethyl)-[1,1'-biphenyl]-3-carboxamide |

TABLE 1-continued

| compound | structure | name |
|---|---|---|
| 83 | 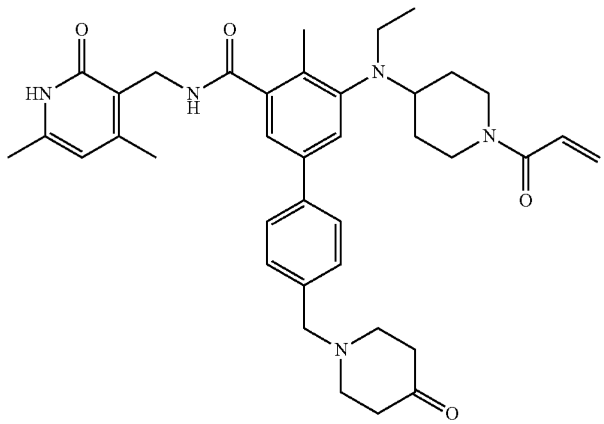 [SMILES: C=CC(=O)N1CCC(N(CC)c2cc(-c3ccc(CN4CCC(=O)CC4)cc3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-4'-(4-oxo-piperidin-1-ylmethyl)-[1,1'-biphenyl]-3-carboxamide |
| 84 | 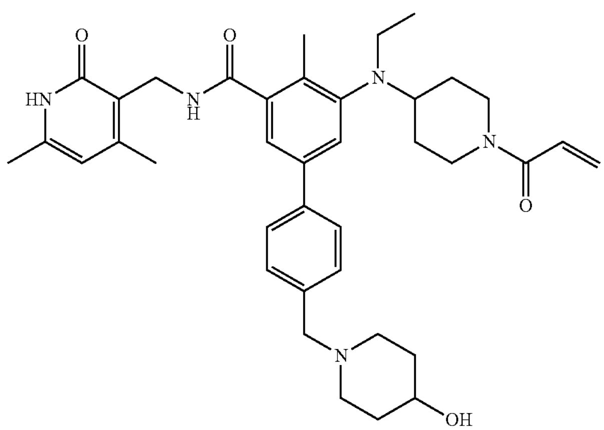 [SMILES: C=CC(=O)N1CCC(N(CC)c2cc(-c3ccc(CN4CCC(O)CC4)cc3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-4'-(4-hydroxypiperidin-1-ylmethyl)-[1,1'-biphenyl]-3-carboxamide |
| 85 | 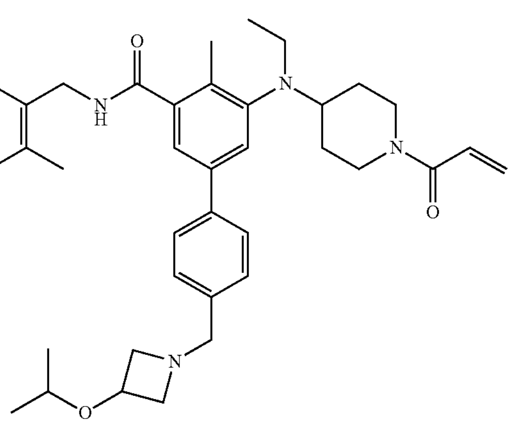 | N-(4,6-dimethyl-2-oxo-1,2-dihydro-pyridin-3-ylmethyl)-5-[(1-acryloyl-piperidin-4-yl)-ethyl-amino]-4-methyl-4'-(3-isopropoxy-1-azetidinylmethyl)-[1,1'-biphenyl]-3-carboxamide |

TABLE 1-continued

| compound | structure | name |
|---|---|---|
| 86 | 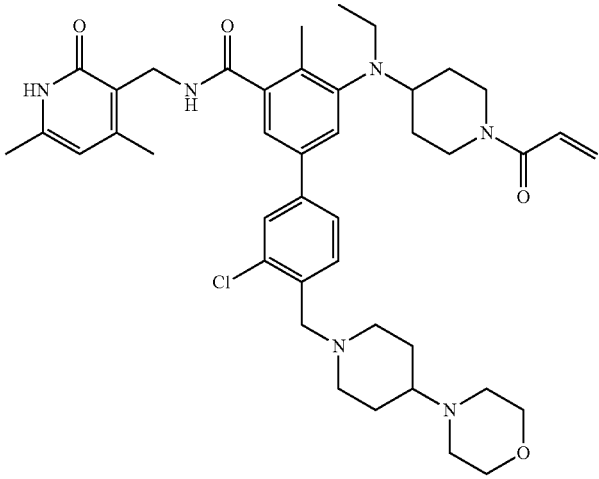 [SMILES: C=CC(=O)N1CCC(N(CC)c2cc(-c3ccc(CN4CCC(N5CCOCC5)CC4)c(Cl)c3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-3'-chloro-4-methyl-4'-[4-(morpholin-4-yl)-piperidin-1-ylmethyl]-[1,1'-biphenyl]-3-carboxamide |
| 87 | 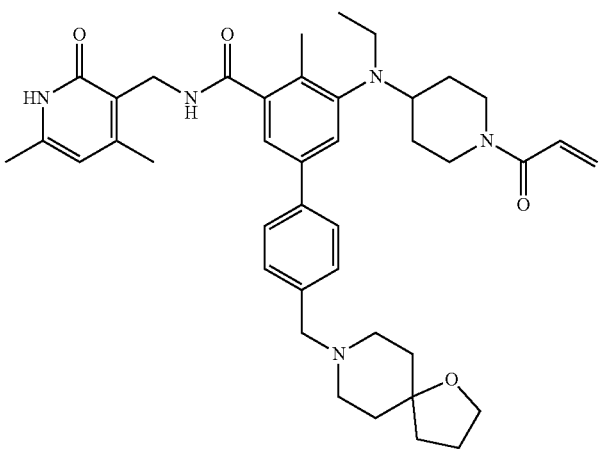 [SMILES: C=CC(=O)N1CCC(N(CC)c2cc(-c3ccc(CN4CCC5(CCCO5)CC4)cc3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-4'-(1-oxa-8-aza-spiro[4.5]decane-8-ylmethyl)-[1,1'-biphenyl]-3-carboxamide |
| 88 | 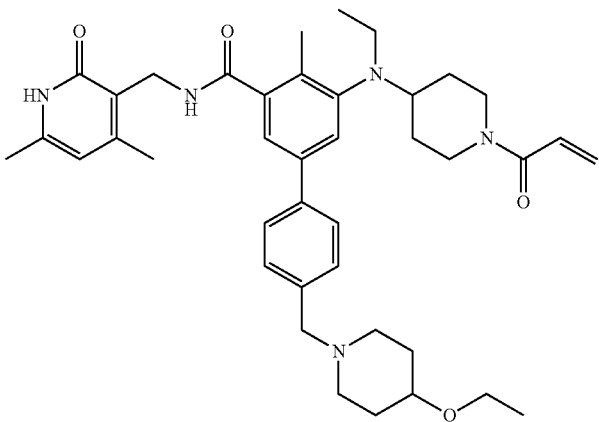 [SMILES: C=CC(=O)N1CCC(N(CC)c2cc(-c3ccc(CN4CCC(OCC)CC4)cc3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-4'-(4-ethoxypiperidin-1-yl methyl)-[1,1'-biphenyl]-3-carboxamide |

TABLE 1-continued

| compound | structure | name |
|---|---|---|
| 89 | 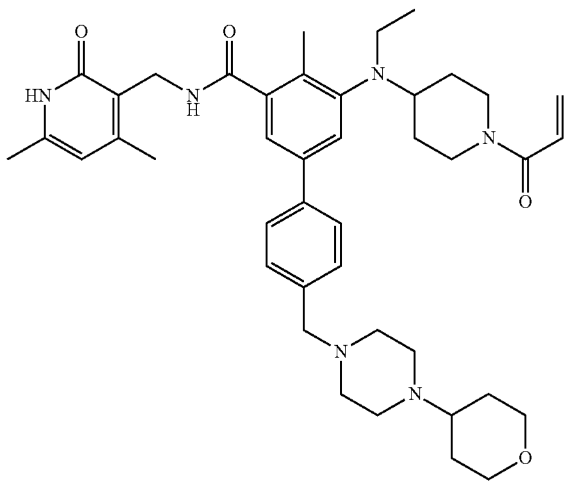 | N-(4,6-dimethyl-2-oxo-1,2-dihydro-pyridin-3-ylmethyl)-5-[(1-acryloyl-piperidin-4-yl)-ethyl-amino]-4-methyl-4'-[4-(tetrahydropyran-4-yl)-piperazin-1-ylmethyl]-[1,1'-biphenyl]-3-carboxamide |
| 90 | 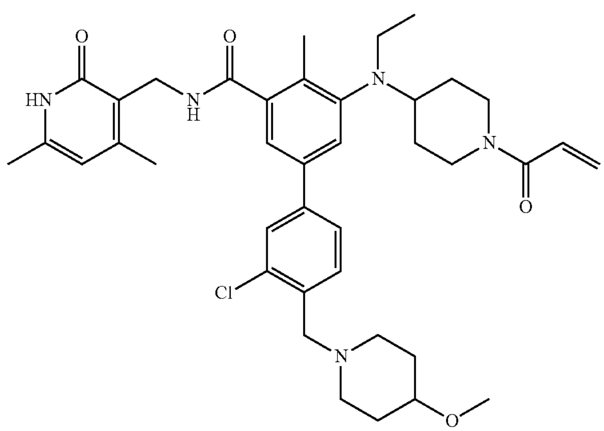 [SMILES: C=CC(=O)N1CCC(N(CC)c2cc(-c3ccc(CN4CCC(OC)CC4)c(Cl)c3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-3'-chloro-4-methyl-4'-(4-methoxypiperidin-4-ylmethyl)-[1,1'-biphenyl]-3-carboxamide |
| 91 | 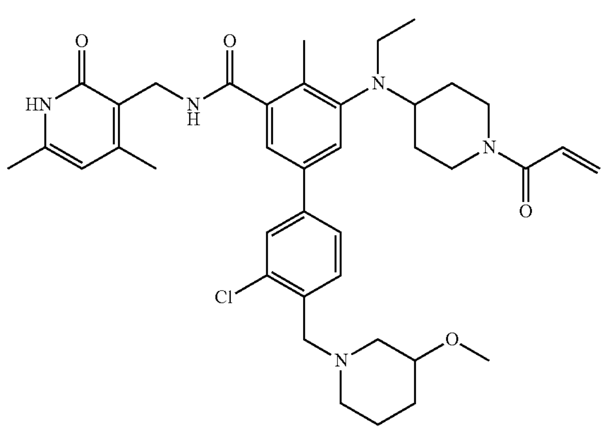 [SMILES: C=CC(=O)N1CCC(N(CC)c2cc(-c3ccc(CN4CCCC(OC)C4)c(Cl)c3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-3'-chloro-4-methyl-4'-(3-methoxypiperidin-4-ylmethyl)-[1,1'-biphenyl]-3-carboxamide |

TABLE 1-continued

| compound | structure | name |
|---|---|---|
| 92 | 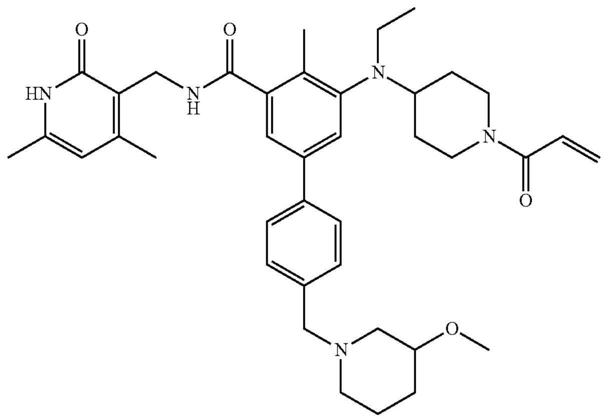 [SMILES: C=CC(=O)N1CCC(N(CC)c2cc(-c3ccc(CN4CCCC(OC)C4)cc3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-4-methyl-4'-(3-methoxypiperidin-4-ylmethyl)-[1,1'-biphenyl]-3-carboxamide |
| 93 | 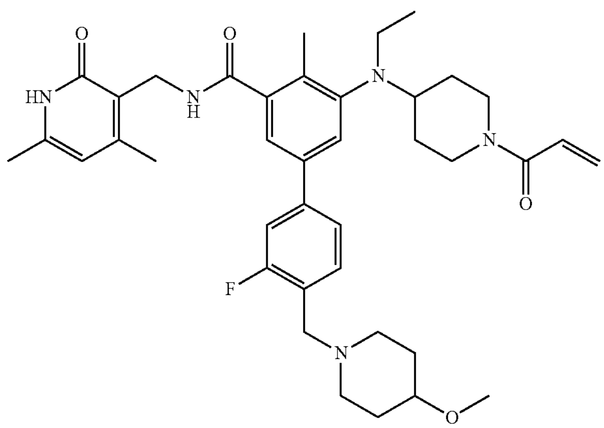 | N-(4,6-dimethyl-2-oxo-1,2-dihydro-pyridin-3-ylmethyl)-5-[(1-acryloyl-piperidin-4-yl)-ethyl-amino]-3'-fluoro-4-methyl-4'-(3-methoxypiperidin-4-ylmethyl)-[1,1'-biphenyl]-3-carboxamide |
| 94 | 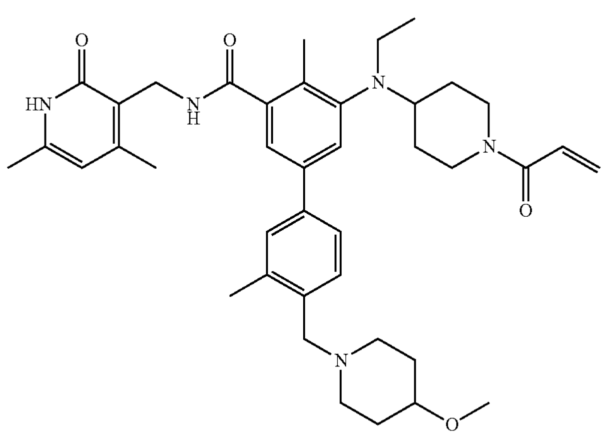 [SMILES: C=CC(=O)N1CCC(N(CC)c2cc(-c3ccc(CN4CCC(OC)CC4)c(C)c3)cc(C(=O)NCc3c(C)cc(C)[nH]c3=O)c2C)CC1] | N-(4,6-dimethyl-2-oxo-1,2-dihydro-pyridin-3-ylmethyl)-5-[(1-acryloyl-piperidin-4-yl)-ethyl-amino]-3',4-dimethyl-4'-(3-methoxypiperidin-4-ylmethyl)-[1,1'-biphenyl]-3-carboxamideboxamide |

TABLE 1-continued

| compound | structure | name |
|---|---|---|
| 95 | 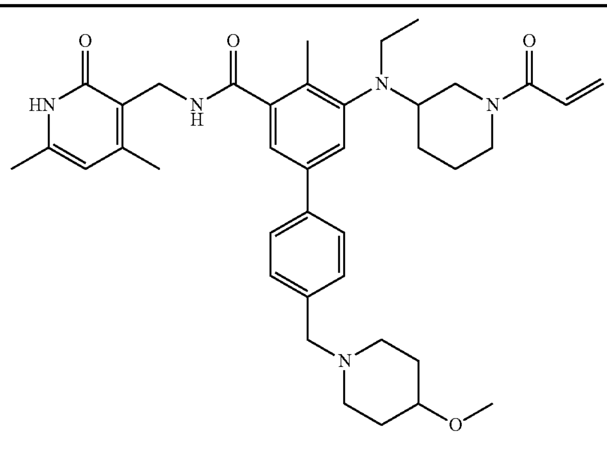 | N-(4,6-dimethyl-2-oxo-1,2-dihydro-pyridin-3-ylmethyl)-5-[(1-acryloyl-piperidin-3-yl)-ethyl-amino]-4-methyl-4'-(4-methoxypiperidin-1-ylmethyl)-[1,1'-biphenyl]-3-carboxamide |
| 96 | 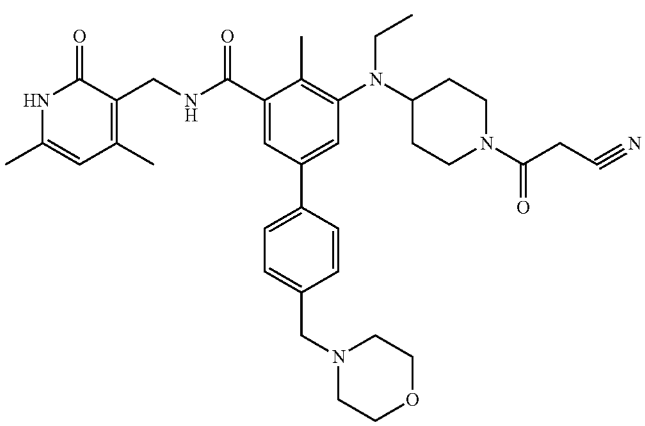 [SMILES: CCN(c1cc(-c2ccc(CN3CCOCC3)cc2)cc(C(=O)NCc2c(C)cc(C)[nH]c2=O)c1C)C1CCN(C(=O)CC#N)CC1] | 5-((1-(2-cyanoacetyl)piperidin-4-yl)(ethyl)amino)-N-((4,6-dimethyl-2-oxo-1,2-dihydropyridin-3-yl)methyl)-4-methyl-4'-(morpholin-4-ylmethyl)biphenyl-3-carboxamide |

Another aspect of the present invention relates to a deuterated compound of the general formula (I) according to the present invention, which is used for increasing the in vivo metabolic stability, wherein one or more of the hydrogen atoms of the compound of general formula (I) are independently replaced by a deuterium atom, the deuterated compounds include, but are not limited to:

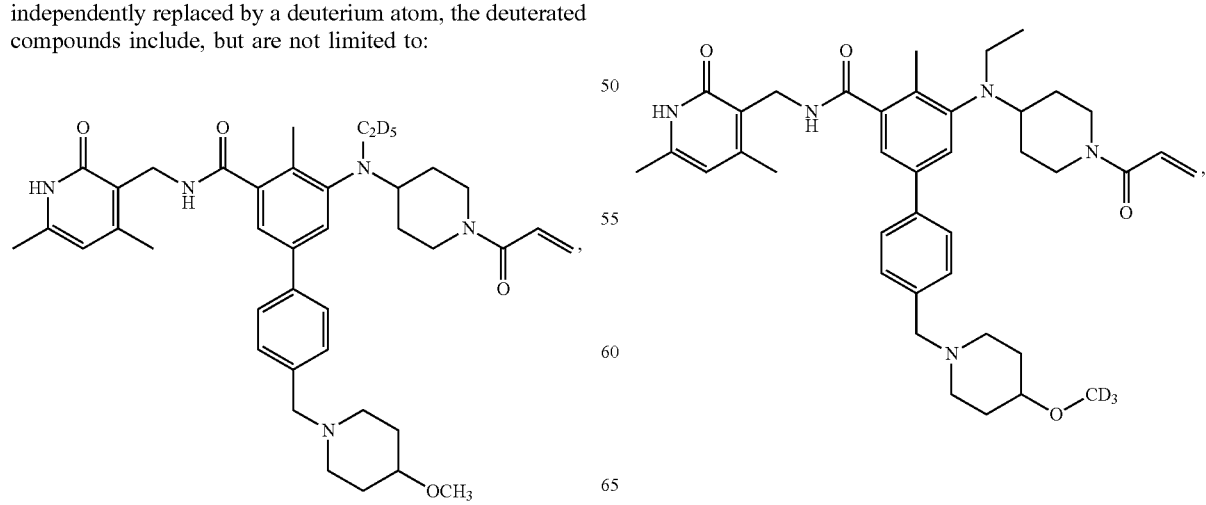

-continued

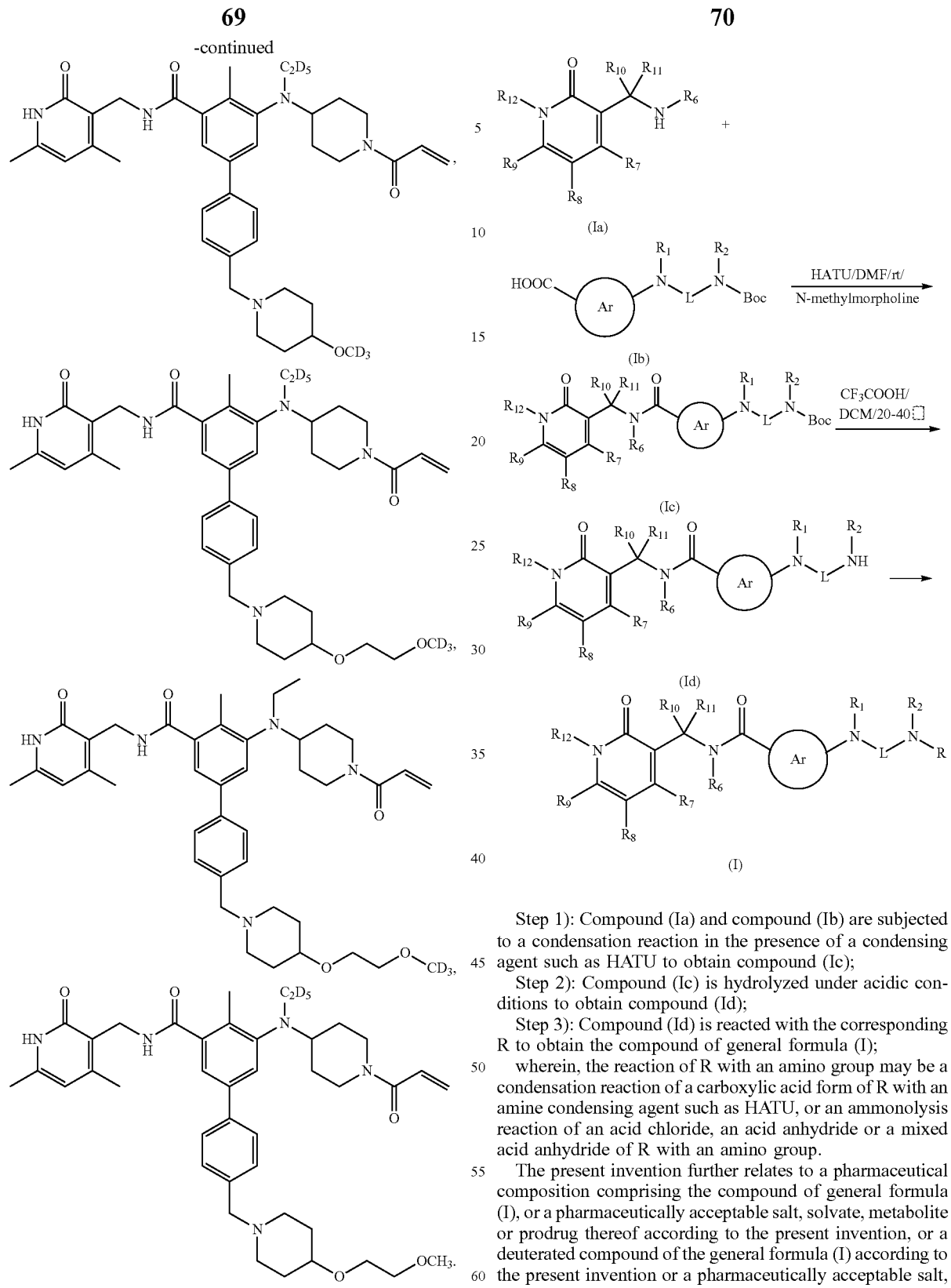

Another aspect of the invention relates to a process for the preparation of the compound of general formula (I) or a pharmaceutically acceptable salt, solvate or prodrug thereof according to the present invention, which comprises the steps of:

Step 1): Compound (Ia) and compound (Ib) are subjected to a condensation reaction in the presence of a condensing agent such as HATU to obtain compound (Ic);

Step 2): Compound (Ic) is hydrolyzed under acidic conditions to obtain compound (Id);

Step 3): Compound (Id) is reacted with the corresponding R to obtain the compound of general formula (I);

wherein, the reaction of R with an amino group may be a condensation reaction of a carboxylic acid form of R with an amine condensing agent such as HATU, or an ammonolysis reaction of an acid chloride, an acid anhydride or a mixed acid anhydride of R with an amino group.

The present invention further relates to a pharmaceutical composition comprising the compound of general formula (I), or a pharmaceutically acceptable salt, solvate, metabolite or prodrug thereof according to the present invention, or a deuterated compound of the general formula (I) according to the present invention or a pharmaceutically acceptable salt, solvate, metabolite or prodrug thereof, and one or more pharmaceutically acceptable carriers.

The present invention further relates to the use of the compound of general formula (I) or a pharmaceutically acceptable salt, solvate, metabolite or prodrug thereof according to the present invention, or a deuterated compound of the general formula (I) according to the present invention or a pharmaceutically acceptable salt, solvate, metabolite or prodrug thereof, or a pharmaceutical composition containing the same, in the preparation of EZH2 histone methyltransferase inhibitors.

The present invention further relates to the use of the compound of general formula (I) or a pharmaceutically acceptable salt, solvate, metabolite or prodrug thereof according to the present invention, or a deuterated compound of the general formula (I) according to the present invention or a pharmaceutically acceptable salt, solvate, metabolite or prodrug thereof, or a pharmaceutical composition containing the same, in the preparation of medicaments for the treatment of diseases associated with EZH2 histone methyltransferase. The diseases associated with EZH2 histone methyltransferase are selected from cancer, diabetes, inflammation, immune system diseases, cardiovascular diseases, neurological diseases and respiratory diseases. The cancers are selected from lung cancer, stomach cancer, liver cancer, breast cancer, nasopharyngeal carcinoma, pancreatic cancer, ovarian cancer, cervical cancer, colorectal cancer, glioma, melanoma, prostate cancer, kidney cancer, esophageal cancer, mesothelioma, head and neck cancer, bladder cancer, salivary gland carcinoma, anaplastic large cell lymphoma, leukemia, lymphoma, non-hodgkin's lymphoma and multiple myeloma.

The present invention further relates to a compound of general formula (I) or a pharmaceutically acceptable salt, solvate, metabolite or prodrug thereof according to the present invention, or a deuterated compound of the general formula (I) according to the present invention or a pharmaceutically acceptable salt, solvate, metabolite or prodrug thereof, or a pharmaceutical composition containing the same, for use as EZH2 histone methyltransferase inhibitors.

The present invention further relates to a compound of general formula (I) or a pharmaceutically acceptable salt, solvate, metabolite or prodrug thereof according to the present invention, or a deuterated compound of the general formula (I) according to the present invention or a pharmaceutically acceptable salt, solvate, metabolite or prodrug thereof, or a pharmaceutical composition containing the same, for use as a drug for the treatment of diseases associated with EZH2 histone methyltransferase. The diseases involving EZH2 histone methyltransferase are selected from cancer, diabetes, inflammation, immune system diseases, cardiovascular diseases, neurological diseases and respiratory diseases. The cancers are selected from lung cancer, stomach cancer, liver cancer, breast cancer, nasopharyngeal carcinoma, pancreatic cancer, ovarian cancer, cervical cancer, colorectal cancer, glioma, melanoma, prostate cancer, kidney cancer, esophageal cancer, mesothelioma, head and neck cancer, bladder cancer, salivary gland carcinoma, anaplastic large cell lymphoma, leukemia, lymphoma, non-hodgkin's lymphoma and multiple myeloma.

The present invention also relates to a method for inhibiting EZH2 histone methyltransferase including administering to the patients in need of it an effective amount of the compound of general formula (I) or the pharmaceutically acceptable salt, solvate, metabolite or prodrug thereof according to the present invention, or the deuterated compound of general formula (I) according to the present invention or the pharmaceutically acceptable salt, solvate, metabolite or prodrug thereof, or a pharmaceutical composition comprising the same.

Another aspect of the invention relates to a method of treating a disease associated with EZH2 histone methyltransferase including administering an effective amount of the compound of general formula (I) or the pharmaceutically acceptable salt, solvate, metabolite or prodrug thereof according to the present invention, or the deuterated compound of general formula (I) according to the present invention or the pharmaceutically acceptable salt, solvate, metabolite or prodrug thereof, or a pharmaceutical composition comprising the same. The diseases associated with the EZH2 histone methyltransferase may be cancer, diabetes inflammation, immune system diseases, cardiovascular diseases, neurological diseases, and respiratory diseases. The cancer may be lung cancer, gastric cancer, liver cancer, breast cancer, nasopharyngeal cancer, pancreatic cancer, ovarian cancer, cervical cancer, colorectal cancer, glioma, melanoma, prostate cancer, kidney cancer, esophageal cancer, mesothelium. Tumor, head and neck cancer, bladder cancer, salivary gland cancer, anaplastic large cell lymphoma, leukemia, lymphoma, non-Hodgkin's lymphoma, and multiple myeloma.

DETAILED DESCRIPTION OF THE INVENTION

Unless otherwise specified, all technical and scientific terms used herein have the same meaning as commonly understood by the person skilled in the art. If there are multiple definitions for the terms used herein, unless otherwise indicated, the terms in this section shall prevail.

The term "alkyl" refers to a saturated straight or branched aliphatic hydrocarbon group including 1-20 carbon atoms. Preferably, an alkyl group is an alkyl having 1 to 12 carbon atoms, more preferably 1 to 6 carbon atoms. Representative examples include, but are not limited to, methyl, ethyl, n-propyl, isopropyl, n-butyl, isobutyl, tert-butyl, sec-butyl, n-pentyl, 1,1-dimethylpropyl, 1,2-dimethyl propyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methyl hexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethyl hexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-decyl, 2-methyl-2-ethylhexyl, 2-methyl-3-ethylhexyl, 2,2-diethylpentyl, n-decyl, 3,3-diethylhexyl, 2,2-diethylhexyl, and its various branched isomers, and the like. More preferably, an alkyl group is a lower alkyl group having 1 to 6 carbon atoms, and representative examples include, but are not limited to, methyl, ethyl, n-propyl, isopropyl, n-butyl, isobutyl, tert-butyl, sec-butyl, n-pentyl, 1,1-dimethylpropyl, 1,2-dimethyl propyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. Alkyl may be substituted or unsubstituted. When substituted, the substituents may be substituted at any available point. The substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycle alkoxy, cycloalkylthio, heterocycloalkylthio, oxo, carboxy, or carboxylate groups.

The term "alkylene" refers to that one hydrogen atom of the alkyl group is further substituted, for example, "methylene" refers to —CH$_2$—, "ethylene" refers to —(CH$_2$)$_2$—, "propylene" refers to —(CH$_2$)$_3$—, "butylene" refers to —(CH$_2$)$_4$—, and the like.

The term "alkenyl" refers to an alkyl group as defined above consisting of at least two carbon atoms and at least one carbon-carbon double bond, for example, vinyl, 1-propenyl, 2-propenyl, 1-, 2- or 3-butenyl, and the like. The alkenyl group may be substituted or unsubstituted, and when substituted, the substituent is preferably one or more groups independently selected from alkyl, alkenyl, alkynyl, alkoxy, alkylthio, alkylamino, halogen, thiol, hydroxy, nitro, cyano, cycloalkyl, heterocycloalkyl, aryl, heteroaryl, cycloalkoxy, heterocycloalkoxy, cycloalkylthio, and heterocycloalkylthio.

The term "alkynyl" refers to an alkyl group as defined above consisting of at least two carbon atoms and at least one carbon-carbon triple bond, such as ethynyl, propynyl, butynyl and the like. The alkynyl group may be substituted or unsubstituted, and when substituted, the substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocycloalkyl, aryl, heteroaryl, cycloalkoxy, heterocycloalkoxy, cycloalkylthio, and heterocycloalkylthio. The term "cycloalkyl" refers to a saturated or partially unsaturated monocyclic or polycyclic cyclic hydrocarbon groups. The cycloalkyl ring has 3 to 20 carbon atoms, preferably 3 to 12 carbon atoms, more preferably 3 to 6 carbon atoms. Representative examples of monocyclic cycloalkyl groups include, but are not limited to cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Polycyclic cycloalkyl groups include spiro, fused, and bridged cycloalkyl groups.

The term "spirocycloalkyl" refers to a polycyclic group in which 5 to 20 membered monocycle shares one carbon atom (referred to as spiro atom). A spirocycloalkyl may contain one or more double bonds, but none of the rings have a fully conjugated π electronic system. A spirocycloalkyl is preferably 6 to 14 membered, more preferably 7 to 10 membered. Depending on the numbers of the common spiro atoms between the rings, the spirocycloalkyl group is classified into a monospirocycloalkyl group, a bispirocycloalkyl group or a polyspirocycloalkyl group, preferably a monospirocycloalkyl group and a bispirocycloalkyl group, more preferably 4-membered/4-membered, 4-membered/5-membered, 4-membered/6-membered, 5-membered/5-membered or 5-membered/6-membered monospirocycloalkyl group. Representative examples of spirocycloalkyl groups include, but are not limited to:

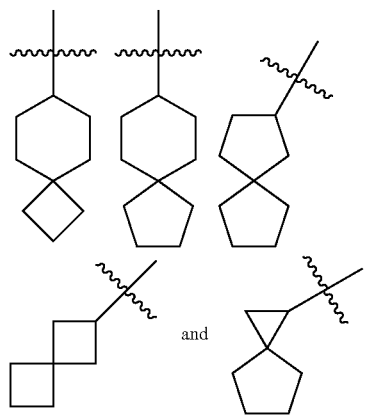

The term "fused cycloalkyl" refers to 5 to 20 membered all-carbon polycyclic group, in which each ring in the system shares an adjacent pair of carbon atoms with other rings in the system, and one or more of the rings may contain one or more double bonds, but none of the rings have a fully conjugated π-electron system. A fused cycloalkyl is preferably 6 to 14 membered, more preferably 7 to 10 membered. Depending on the numbers of rings, it may be classified into a bicyclic, tricyclic, tetracyclic or polycyclic fused cycloalkyl group, preferably a bicyclic or tricyclic alkyl, more preferably a 5-membered/5-membered or 5-membered/6-membered bicycloalkyl group. Representative examples of fused cycloalkyl groups include, but are not limited to:

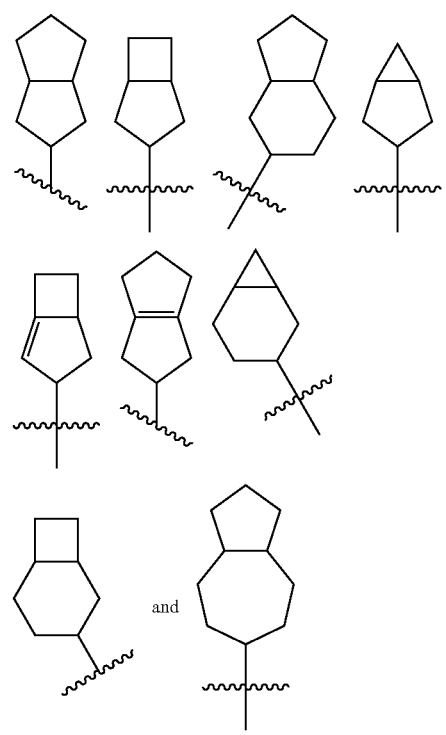

The term "bridged cycloalkyl" refers to 5 to 20 membered all-carbon polycyclic group, in which any two rings share two carbon atoms which are not linked directly. A bridged cycloalkyl may contain one or more double bonds, but none of the rings have complete conjugate π-electron system. A bridged cycloalkyl is preferably 6 to 14 membered, more preferably 7 to 10 membered. Depending on the numbers of rings, it may be classified into a bicyclic, tricyclic, tetracyclic or polycyclic bridged cycloalkyl group, preferably a bicyclic, tricyclic or tetracyclic alkyl, and more preferably a bicyclic ring or a tricyclic alkyl. Representative examples of bridged cycloalkyl groups include, but are not limited to:

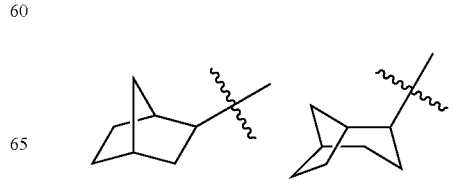

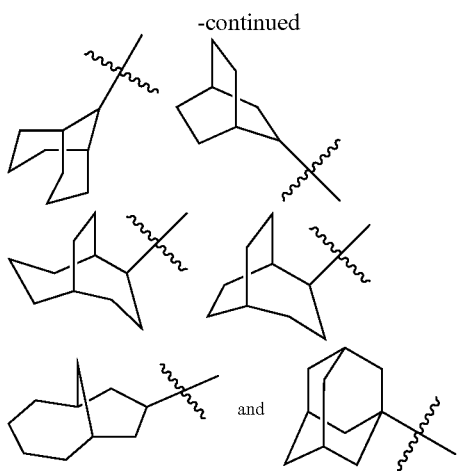

The cycloalkyl ring may be fused to an aryl, heteroaryl or heterocycloalkyl ring, wherein the ring to which the parent structure is attached is a cycloalkyl group. Representative examples include, but are not limited to indanyl, tetrahydronaphthyl, benzocycloheptyl, and the like. The cycloalkyl group may be optionally substituted or unsubstituted, and when substituted, the substituent is preferably one or more groups independently selected from alkyl, alkenyl, alkynyl, alkoxy, alkylthio, alkylamino, halogen, thiol, hydroxy, nitro, cyano, cycloalkyl, heterocycloalkyl, aryl, heteroaryl, cycloalkoxy, heterocycloalkoxy, cycloalkylthio, heterocycloalkylthio, oxo, carboxyl or carboxylate.

The term "heterocyclyl" refers to a saturated or partially unsaturated monocyclic or polycyclic hydrocarbon group containing 3 to 20 ring atoms, wherein one or more of the ring atoms is a hetero atom selected from the group consisting of nitrogen, oxygen and S(O)$_m$ (where m is an integer from 0 to 2), but not include a ring moiety of —O—O—, —O—S— or —S—S—, and the remaining ring atoms are carbon. A heterocyclyl comprises preferably 3 to 12 ring atoms, wherein 1 to 4 ring atoms are heteroatoms; more preferably 3 to 8 ring atoms, wherein 1 to 3 ring atoms are heteroatoms; most preferably 5 to 6 ring atoms, wherein 1 to 2 or 1 to 3 ring atoms are hetero atoms. Representative examples of monocyclic heterocyclic groups include, but are not limited to pyrrolidinyl, imidazolidinyl, tetrahydrofuranyl, tetrahydrothiophenyl, dihydroimidazolyl, dihydrofuranyl, dihydropyrazolyl, dihydropyrrolyl, piperidinyl, piperazinyl, morpholinyl, thiomorpholinyl, homopiperazinyl, pyranyl, and the like; preferably 1,2,5-oxadiazolyl, pyranyl or morpholinyl. Polycyclic heterocyclic groups include spiro, fused, and bridged heterocyclic groups.

The term "spiroheterocyclyl" refers to a polycyclic heterocyclic group in which 5 to 20 membered single ring shares one atom (called a spiro atom). One or more of the ring atoms is a hetero atom selected from the group consisting of nitrogen, oxygen and S(O)$_m$ (where m is an integer from 0 to 2), and the remaining ring atoms are carbon. It may contain one or more double bonds, but none of the rings have a fully conjugated pi-electron system. It is preferably 6 to 14 membered, more preferably 7 to 10 membered. The spiroheterocyclyl group is classified into a monospiroheterocyclic group, a dispiroheterocyclic group or a polyspirocyclic group according to the numbers of the shared spiro atoms between the rings, and is preferably a monospiroheterocyclic group and a dispiroheterocyclic group. More preferably, it is 4-membered/4-membered, 4-membered/5-membered, 4-membered/6-membered, 5-membered/5-membered or 5-membered/6-membered monospiroheterocyclic group. Representative examples of spiroheterocyclyl groups include, but are not limited to:

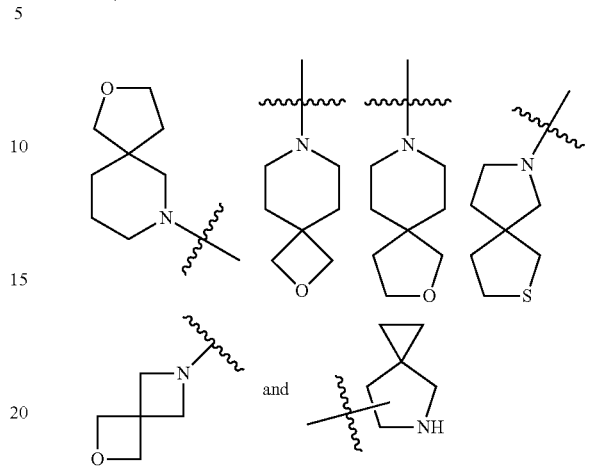

The term "fused heterocyclyl" refers to 5 to 20 membered polycyclic heterocyclic groups, in which each ring in the system shares an adjacent pair of atoms with other rings in the system, and one or more rings may contain one or more double bonds, but none of the rings have a fully conjugated π-electron system. One or more ring atoms are selected from the group consisting of nitrogen, oxygen and S(O)$_m$ (where m is an integer between 0 to 2), and the remaining ring atoms are carbon atoms. It is preferably 6 to 14 membered, more preferably 7 to 10 membered. Depending on the numbers of the rings, it may be classified into a bicyclic, tricyclic, tetracyclic or polycyclic fused heterocyclic group, preferably a bicyclic or tricyclic ring, more preferably a 5-membered/5-membered or 5-membered/6-membered bicyclic fused heterocyclic group. Representative examples of fused heterocyclyl groups include, but are not limited to:

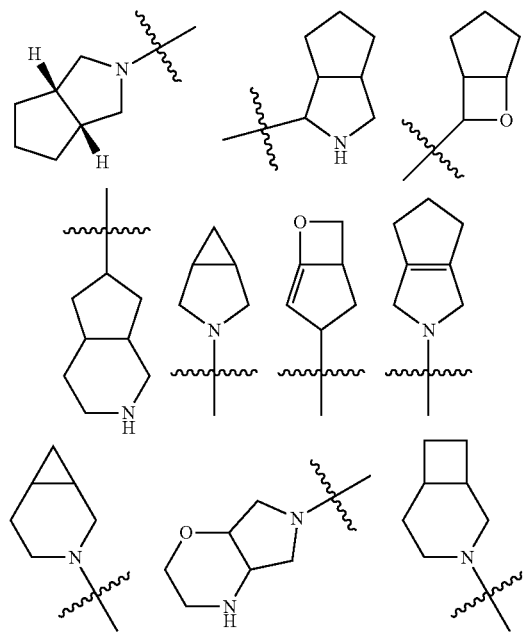

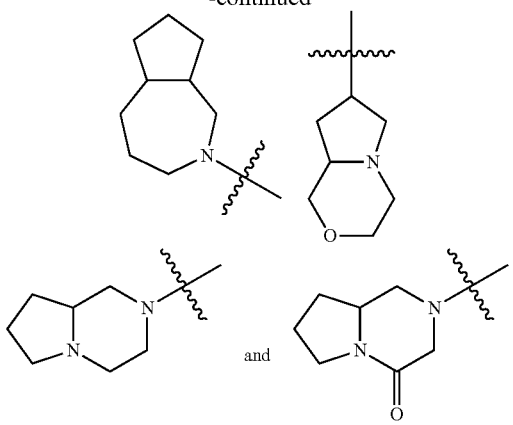

The term "bridge heterocyclyl" refers to a 5 to 14 membered polycyclic heterocyclic group, in which any two rings share two atoms which are not linked directly. A bridge heterocyclyl may contain one or more double bonds, but none of the rings have a fully conjugated π-electron system. One or more ring atoms are selected from the group consisting of nitrogen, oxygen and $S(O)_m$ (where m is an integer between 0 to 2), and the remaining ring atoms are carbon atoms. It is preferably 6 to 14 membered, more preferably 7 to 10 membered. Depending on the numbers of the rings, it may be classified into a bicyclic, tricyclic, tetracyclic or polycyclic bridged heterocyclic groups. It is preferably a bicyclic ring, a tricyclic ring or a tetracyclic ring, and more preferably a double ring or a triple ring. Representative examples of bridge heterocyclyl groups include, but are not limited to:

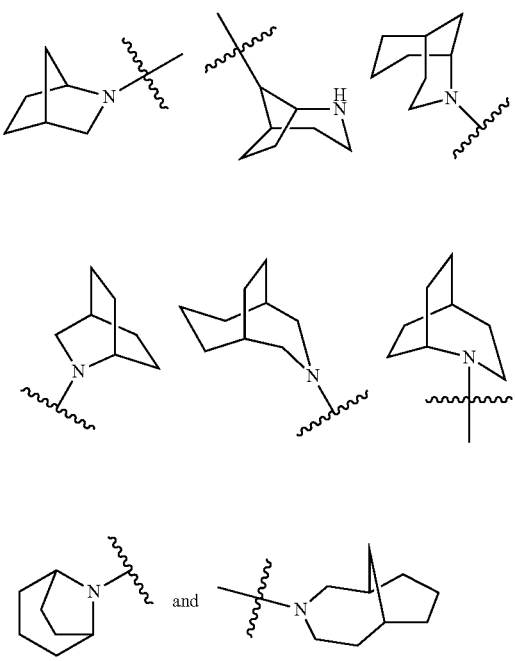

The heterocyclyl ring may be fused to an aryl, heteroaryl or cycloalkyl ring, wherein the ring to which the parent structure is attached is a heterocyclic group. Representative examples include, but are not limited to:

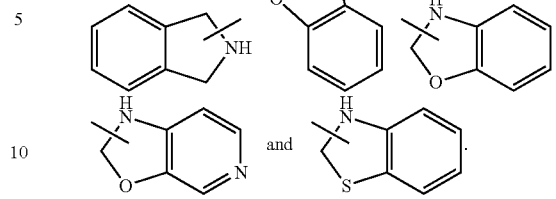

The heterocyclic group may be optionally substituted or unsubstituted, and when substituted, the substituent is preferably one or more of groups independently selected from the group consisting of alkyl, alkenyl, alkynyl, alkoxy, alkylthio, alkylamino, halogen, thiol, hydroxy, nitro, cyano, cycloalkyl, heterocycloalkyl, aryl, heteroaryl, cycloalkoxy, heterocycloalkoxy, cycloalkylthio, heterocycloalkylthio, oxo, carboxy and carboxylate.

The term "aryl" refers to a 6 to 14 membered all-carbon monocyclic or fused polycyclic ring (i.e. the ring that shares a pair of adjacent carbon atoms) having a conjugated π-electron system, preferably 6 to 10 membered, such as phenyl and naphthyl; more preferably phenyl. The aryl ring may be fused to a heteroaryl, heterocyclyl or cycloalkyl ring, wherein the ring to which the parent structure is attached is an aryl ring. Representative examples include, but are not limited to:

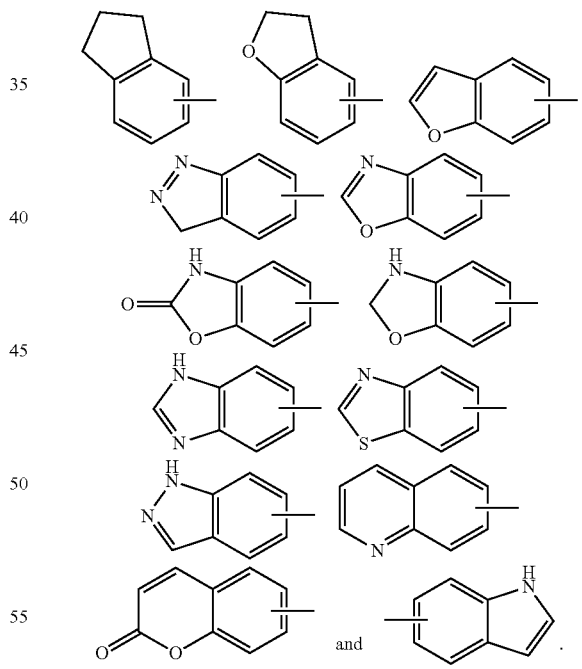

The aryl group may be substituted or unsubstituted. When substituted, the substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, carboxyl, and carboxylate groups.

The term "heteroaryl" refers to a heteroaromatic system containing 1 to 4 heteroatoms and 5 to 14 ring atoms, wherein the heteroatom is selected from the group consisting of oxygen, sulfur and nitrogen. Heteroaryl is preferably 5 to 10-membered, containing 1 to 3 hetero atoms; more preferably 5 or 6 membered, containing 1 to 2 heteroatoms; such as imidazolyl, furyl, thienyl, thiazolyl, pyrazolyl, oxazolyl, pyrrolyl, tetrazolyl, pyridyl, pyrimidinyl, thiadiazole, pyrazinyl and the like, preferably imidazolyl, thiazolyl, pyrazolyl, pyrimidinyl, thiazolyl; more preferably pyrazolyl or thiazolyl. The heteroaryl ring may be fused to an aryl, heterocyclyl, or cycloalkyl ring, wherein the ring attached to the parent structure is a heteroaryl ring, and its non-limited examples include:

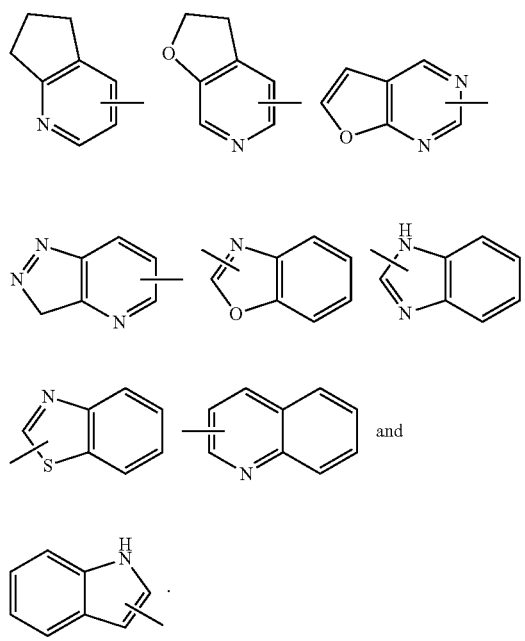

Heteroaryl may be optionally substituted or unsubstituted. When substituted, the substituent is preferably one or more groups independently selected from the group consisting of alkyl, alkenyl, alkynyl, alkoxy, alkylthio, alkylamino, halogen, thiol, hydroxyl, nitro, cyano, cycloalkyl, heterocyclyl, aryl, heteroaryl, cycloalkoxyl, heterocycloalkoxyl, cycloalkylthio, heterocycloalkylthio, carboxyl, and carboxylate groups.

The term "alkoxyl" refers to —O-(alkyl) and —O-(unsubstituted cycloalkyl), wherein alkyl is as defined above. Non-limited examples include methoxyl, ethoxyl, propoxyl, butoxyl, cyclopropyloxyl, cyclobutyloxyl, cyclopentyloxyl, cyclohexyloxyl and the like. Alkoxyl may be optionally substituted or unsubstituted. When substituted, the substituent is preferably one or more groups independently selected from the group consisting of alkyl, alkenyl, alkynyl, alkoxyl, alkylthiol, alkylamino, halogen, thiol, hydroxyl, nitro, cyano, cycloalkyl, heterocyclyl, aryl, heteroaryl, cycloalkoxyl, heterocycloalkoxyl, cycloalkylthio heterocycloalkylthio, carboxyl, and carboxylate groups.

The term "deuterated" refers to the modification that a hydrogen atom in the original compound is replaced by a deuterium atom.

The term "hydroxy" refers to an —OH group.

The term "halogen" refers to fluorine, chlorine, bromine, or iodine.

The term "amino" refers to —NH$_2$.

The term "cyano" refers to —CN.

The term "nitro" refers to —NO$_2$.

The term "oxo" refers to =O.

The term "carboxyl" refers to —C(O)OH.

In the present invention,

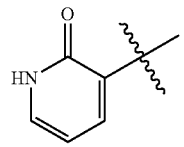 [SMILES: *c1ccc[nH]c1=O]

can be read as

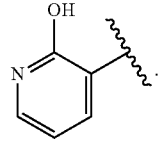

"Optional" or "optionally" means that the subsequently described event or environment may, but need not, occur, including where the event or environment occurs or does not occur. For example, "heterocyclic group optionally substituted by an alkyl group" means that an alkyl group may be, but is not necessarily, present, and the description includes the case where the heterocyclic group is substituted with an alkyl group and the case where the heterocyclic group is not substituted with an alkyl group.

"Substituted" refers to one or more hydrogen atoms in the group, preferably up to 5, more preferably 1 to 3, hydrogen atoms are each independently replaced by a corresponding number of substituents. It goes without saying that the substituents are only in their possible chemical positions, and those skilled in the art will be able to determine (by experiment or theory) substitutions that may or may not be possible without undue effort. For example, an amino group or a hydroxyl group having a free hydrogen may be unstable when combined with a carbon atom having an unsaturated (e.g., olefinic) bond.

The term "pharmaceutical composition" refers to a mixture comprising one or more of the compounds described herein, or a physiologically/pharmaceutically acceptable salt or prodrug thereof, and other chemical components, as well as other components such as physiologically/pharmaceutically acceptable carrier and excipients. The purpose of the pharmaceutical composition is to promote the administration to the organism, which facilitates the absorption of the active ingredient and thereby exerts biological activity.

The term "pharmaceutically acceptable salt" refers to a salt of a compound of the invention which is safe and effective for use in a mammal and which possesses the desired biological activity.

The Method for Preparing the Compound of the Present Invention

In order to achieve the purpose of the present invention, the following schemes are applied.

Scheme 1
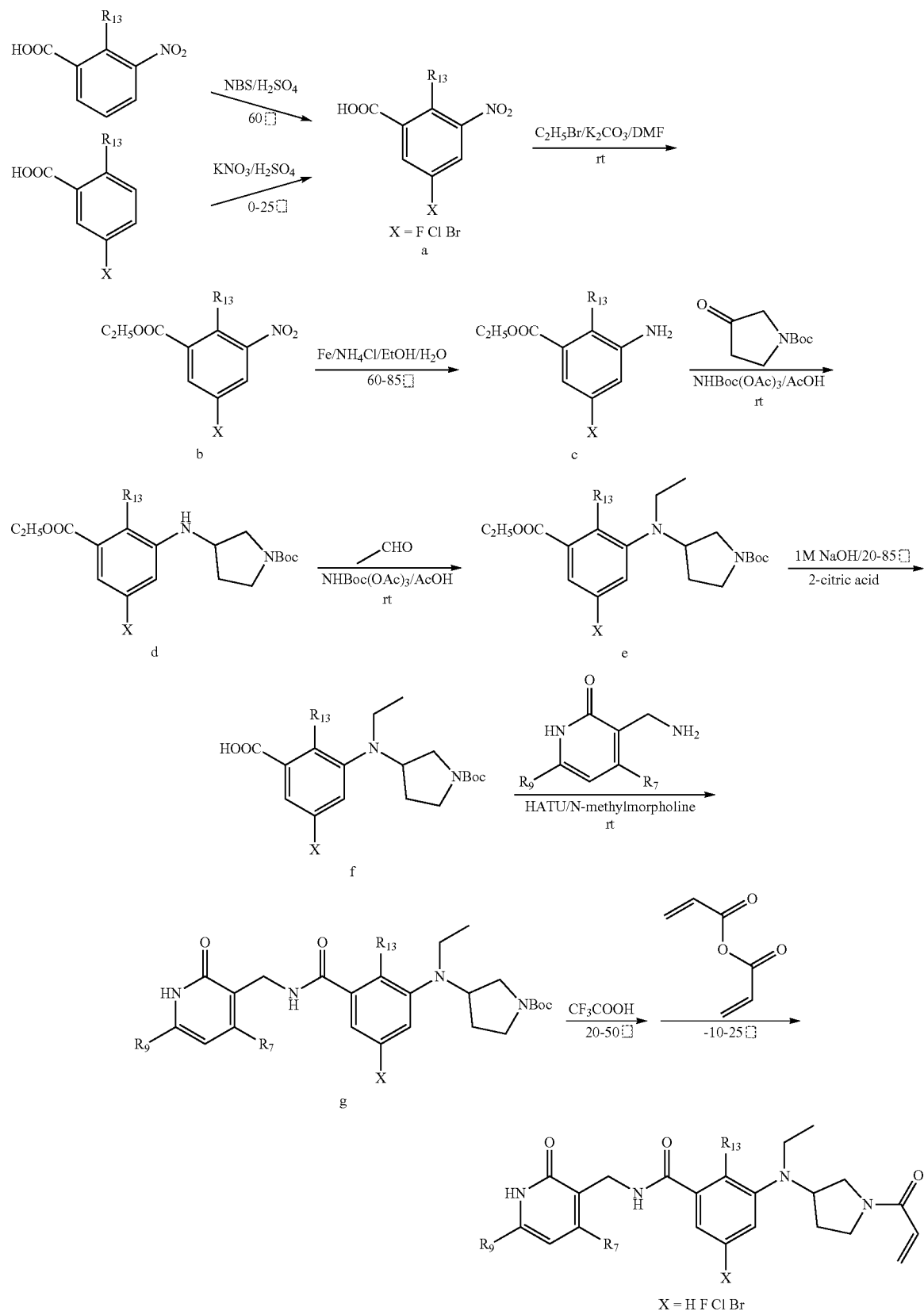

Step 1) a nitrobenzoic acid compound or a halogenated benzoic acid compound is used as a starting material to be subjected to a halogenation or a nitration reaction respectively to obtain an intermediate a; said halogenation or nitration reaction is commonly known in the art, for example is carried out in the presence of sulfuric acid with NBS or KNO3;

Step 2) intermediate a is reacted with bromoethane under alkaline conditions to obtain intermediate b; said alkaline condition may be potassium carbonate;

Step 3) the nitro compound of intermediate b is subjected to a reduction reaction to obtain amino intermediate c, and the reduction condition is commonly known in the art, such as iron powder ammonium chloride method;

Step 4) the intermediate c and 1-Boc-3-pyrrolidone are subjected to a reductive amination reaction in the presence of catalyst under acidic conditions to obtained intermediate d; said catalyst may be sodium triacetoxyborohydride;

Step 5) the intermediate d and acetaldehyde are subjected to another reductive amination reaction in the presence of catalyst under acidic conditions to obtain intermediate e;

Step 6) the intermediate e is subjected to ester hydrolysis to obtain intermediate f;

Step 7) intermediate f and corresponding aminomethylpyridone compound are subjected to an amidation reaction in the presence of catalyst to obtain intermediate g; said catalyst may be HATU or N-methyl morpholine;

Step 8) the intermediate g is hydrolyzed with Boc firstly, and then reacted with acrylic anhydride in the presence of a catalyst to obtain the compound of the present invention; said catalyst may be n-methyl morpholine.

For the compounds wherein Ar is substituted with aryl groups, such as phenyl groups, they can be prepared by the following scheme 2.

Scheme 2

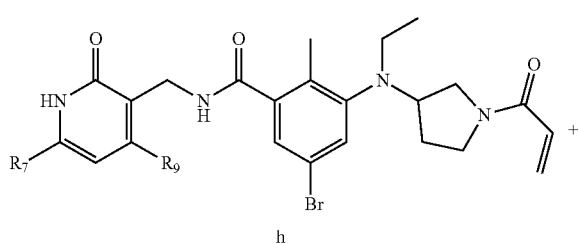

h

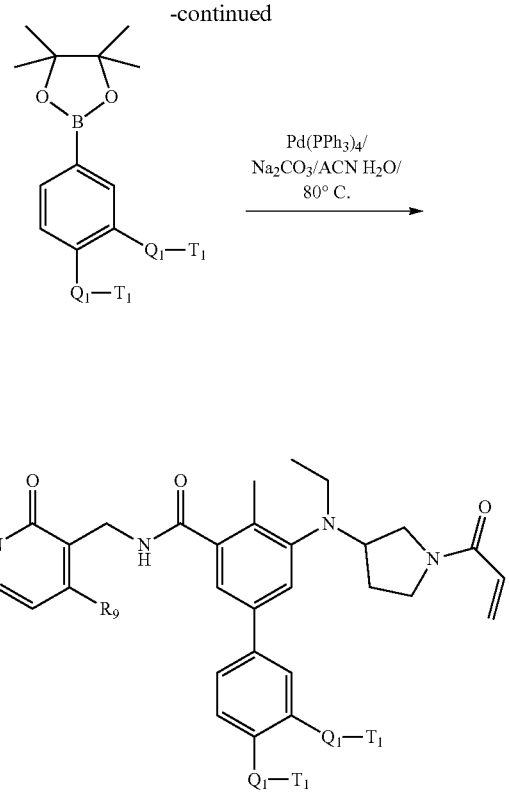

First, the compound h is obtained through the above scheme 1, and then is reacted with corresponding phenylboronic acid pinacol ester in the presence of a catalyst to obtain the compound of the present invention.

For the compounds wherein Ar is substituted with a heteroaryl group, such as pyrimidinyl, and the heteroaryl group is further substituted with a heterocyclic ring, they can be prepared by the following scheme 3.

Scheme 3

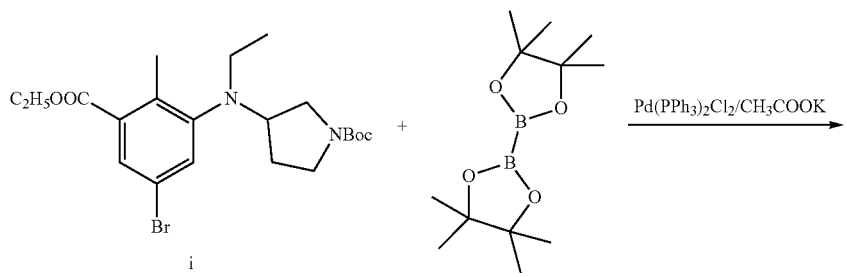

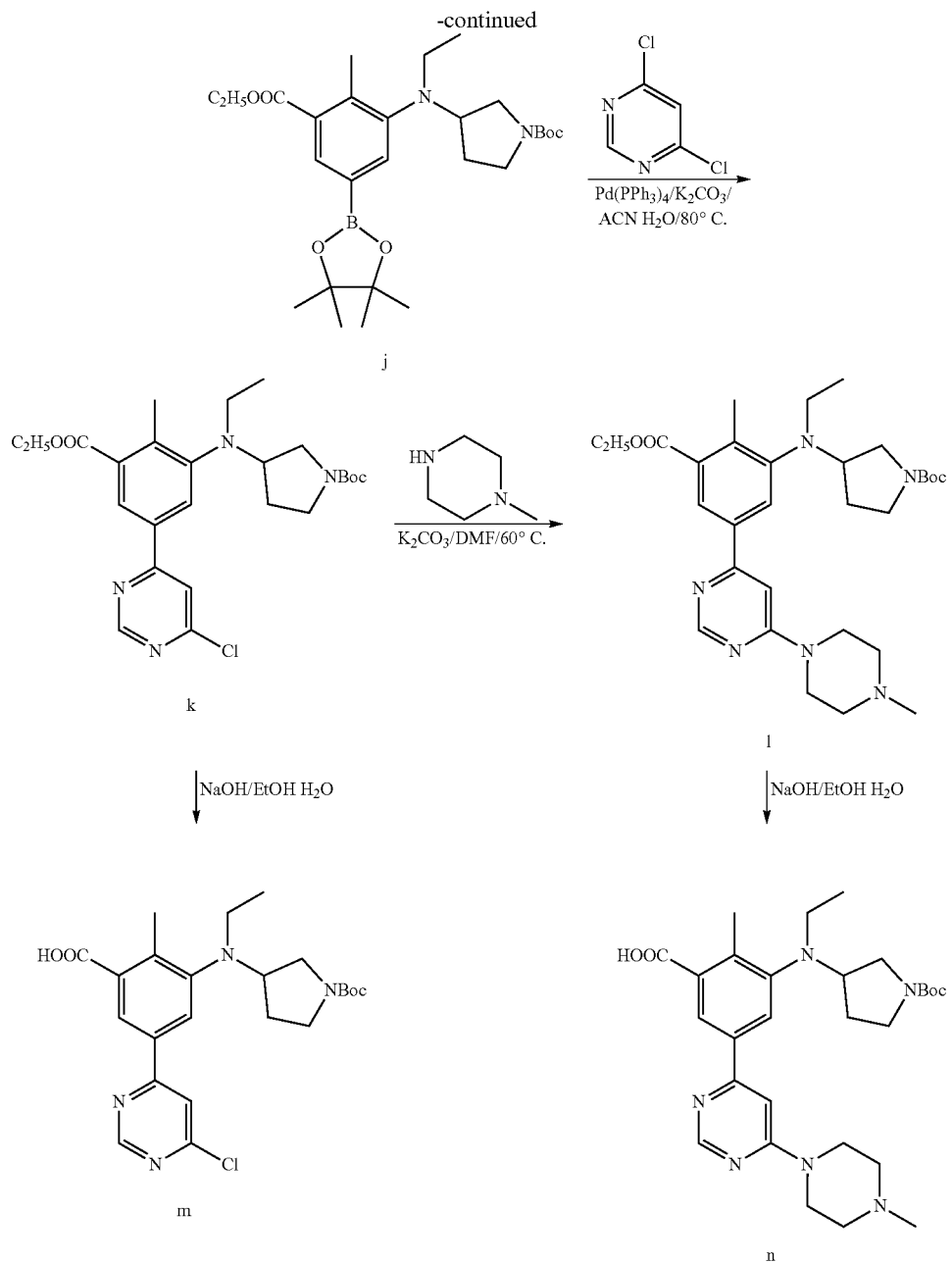

Firstly, intermediate i is prepared through the above scheme 1, and then is reacted with bis(pinacolato)diboron in the presence of a catalyst to obtain intermediate j; intermediate j is reacted with dichloropyrimidine to obtain intermediate k; intermediate k is reacted with the corresponding heterocyclic ring, such as piperidine, under alkaline conditions to obtained intermediate l; intermediate k is subjected to ester hydrolysis to obtain intermediate m, and intermediate l is subjected to ester hydrolysis to obtain intermediate n; then the preparation method of scheme 1 is applied except for replacing intermediate f with intermediate m or n to obtain the compound of the present invention.

For the compounds wherein Ar is substituted with aryl group, such as phenyl, and the phenyl group is further substituted with an aminoalkyl group, they can be prepared by the following scheme 4.

Scheme 4

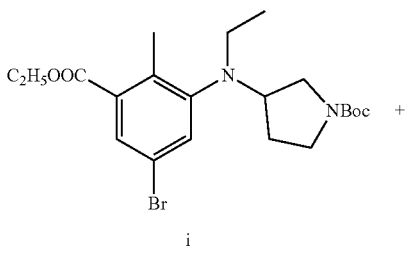

-continued

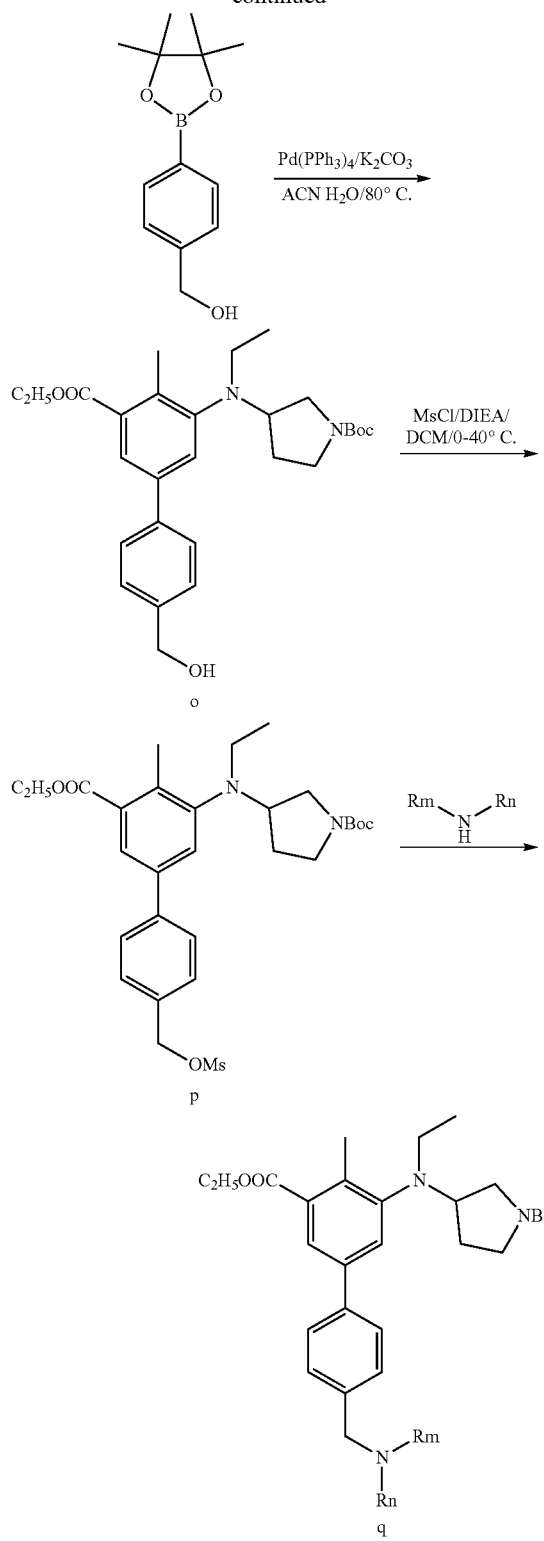

Firstly, intermediate i is reacted with hydroxymethylphenylboronic acid pinacol ester in the presence of a catalyst to obtain intermediate o; the intermediate o is then reacted with methanesulfonyl chloride to obtain intermediate p; then the intermediate p is reacted with the corresponding various amines to obtain intermediate q; then, then the preparation method of scheme 1 is applied except for replacing intermediate e with intermediate q to obtain the compound of the present invention.

For the compounds wherein Ar is directly substituted with an amino group, they can be prepared by the following scheme 5.

Scheme 5

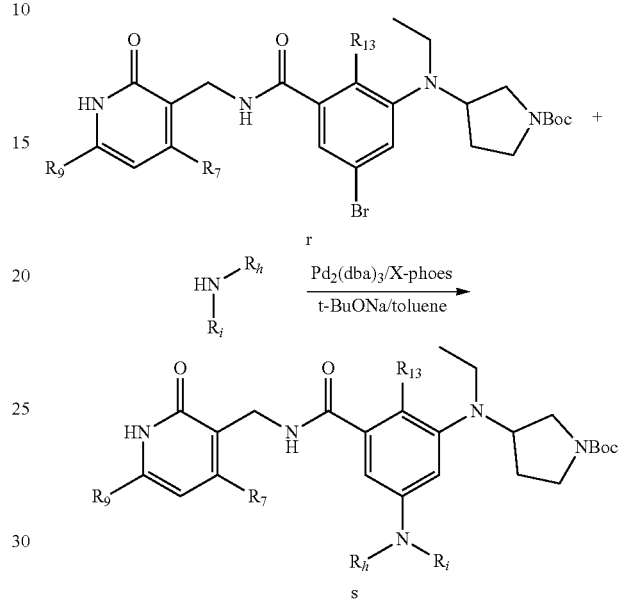

The intermediate r is firstly prepared through the above scheme 1, and then is reacted with the corresponding amine in the presence of the catalyst to obtain intermediate s; then, the preparation method of scheme 1 is applied except for replacing intermediate g with intermediate s to obtain the compound of the present invention.

Scheme 6

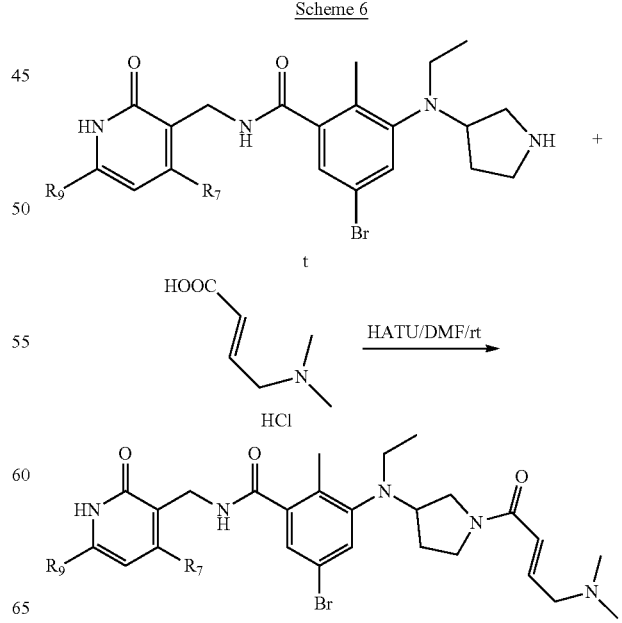

Scheme 6 is a preparation method for certain special compounds of the present invention. Firstly, intermediate t is prepared through scheme 1. Then the intermediate t is reacted with 4-dimethylaminocrotonic acid hydrochloride to obtain the present compounds.

Wherein $R_7$, $R_9$, $R_{13}$, $R_m$, $R_n$, $R_h$, $R_i$, -$Q_1$-$T_1$ are as defined in formula (I).

The pharmaceutically acceptable salt of the compound of general formula (I) of the present invention may be an acid addition salt or a base addition salt. The acid may be an inorganic acid, including but not limited to hydrochloric acid, sulfuric acid, phosphoric acid, or hydrobromic acid; or an organic acid, including but not limited to, citric acid, maleic acid, oxalic acid, formic acid, acetic acid, propionic acid, glycolic acid, benzoic acid, fumaric acid, trifluoroacetic acid, succinic acid, tartaric acid, lactic acid, glutamic acid, aspartic acid, salicylic acid, pyruvic acid, methanesulfonic acid, benzenesulfonic acid, p-toluenesulfonic acid and the like. The base may be an inorganic base, including but not limited to sodium hydroxide, potassium hydroxide, magnesium hydroxide, or calcium hydroxide; or an organic base, including but not limited to ammonium hydroxide, triethylamine, arginine, or lysine.

The compound of general formula (I) of the present invention or a pharmaceutically acceptable salt thereof may be present in a solvated form or in an unsolvated form, for example, a hydrated form and the like.

The prodrug of the compound of general formula (I) of the present invention should follow the prodrug design principle, and can release the original active compound of formula (I) by enzymatic hydrolysis, hydrolysis, acid hydrolysis or metabolic degradation under normal physiological conditions in body. A prodrug includes, but is not limited to, esterification of hydroxyl groups on the compound (such as the formation of phosphates and carbonates), the protection of amino groups and carboxyl groups. Prodrug design references (1) Karaman R, Prodrugs design based on inter- and intramolecular chemical processes. Chem Biol Drug Des. 82 (6): 643-68, 2013; (2) Rautio J et al. Prodrugs:design and clinical applications. Nat Rev Drug Discov. 7(3):255-70 2008; (3) Jampilek J. Prodrugs: pharmaceutical design and current perspectives. Curr Pharm Des. 17(32):3480-1, 2011; (4) Bundgaard H. Design of Progrugs. Elsevier, 1985.

In another aspect of the present invention, a compound of general formula (I) or a pharmaceutically acceptable salt or prodrug thereof is prepared into a clinically acceptable pharmaceutical composition. According to clinical indications, administration route and way, such pharmaceutical preparations include, but are not limited to, oral preparations such as tablets, gels, soft/hard capsules, emulsions, dispersible powders, granules, and water/oil emulsions; injections including intravenous injections, intramuscular injections, intraperitoneal injections, rectal administration suppositories, and intracranial injections, which may be aqueous solutions or oil solutions; topical preparations including creams, ointments, gels, water/oil solutions, and inclusion preparations; inhalation dosage forms including fine powders, liquid aerosols, and various dosage forms suitable for implantation in vivo.

The pharmaceutical composition of the present invention may be added with conventional pharmaceutical excipients as needed. These excipients should be in accordance with the pharmaceutical preparation process rules and compatible with the active ingredients. The solid oral preparation excipients include, but are not limited to, mannitol, lactose, starch, magnesium stearate, cellulose, glucose, sucrose, cyclodextrin, and the intestinal absorption molecular carrier vitamin E-PEG1000. Oral formulations may be incorporated with suitable colorants, sweeteners, flavoring agents, and preservatives.

The compound of general formula (I) of the present invention is administered to a warm-blooded animal at a unit dose of 0.1 to 100 mg/kg.

A pharmaceutical composition comprising the compound of formula (I) of the present invention or a pharmaceutically acceptable salt thereof may be used as an active ingredient, mainly for the treatment of a clinical disease associated with EZH2, which includes, but is not limited to, cancer, diabetes inflammation, immune system diseases, cardiovascular diseases, neurological diseases, and respiratory diseases.

Among the above clinical diseases, the cancer includes, but is not limited to, lung cancer, gastric cancer, liver cancer, breast cancer, nasopharyngeal cancer, pancreatic cancer, ovarian cancer, cervical cancer, colorectal cancer, glioma, melanoma, prostate cancer, kidney cancer, esophagus cancer, mesothelioma, head and neck cancer, bladder cancer, salivary gland cancer, anaplastic large cell lymphoma, leukemia, lymphoma, non-Hodgkin's lymphoma, and multiple myeloma.

The pharmaceutical compositions of the present invention in above cancer treatment can be used alone or in combination with one or more of the following therapies: surgery, radiation therapy, chemotherapy, immunotherapy, oncolytic virus therapy, RNAi, cancer adjuvant therapy, including but not limited to the following anti-tumor drugs and treatment methods:

1) Alkylating agents, such as cisplatin, cisplatin, oxaliplatin, chlorambucil, cyclophosphamide, nitrogen mustard, melphalan, temozolomide, busulfan, and nitrosoureas.

2) Anti-tumor antibiotics, such as doxorubicin, bleomycin, doxorubicin, daunorubicin, epirubicin, idarubicin, mitomycin C, actinomycin, or mithramycin; anti-mitotic drugs such as vincristine, vinblastine, vindesine, vinorelbine, paclitaxel, taxotere, and Polo kinase inhibitors.

3) Antimetabolites and antifolates, such as fluoropyrimidine, methotrexate, cytarabine, raltitrexed, hydroxyurea.

4) Topoisomerase inhibitors such as epipodophyllotoxin and camptothecin.

5) Cell growth inhibitors, such as anti-estrogen/anti-androgen drugs, such as tamoxifen, fulvestrant, toremifene, raloxifene, droloxifene, idoxifene, bicalutamide, flutamide, nilutamide, and cyproterone acetate;

LHRH antagonists or LHRH agonists, such as goserelin, leuprolide, and buserelin; progestogens such as megestrol acetate;

Aromatase inhibitors, such as anastrozole, letrozole, vorozole, exemestane, and 5a-reductase inhibitors such as finasteride.

6) Anti-invasive agents, such as c-Src kinase family inhibitors, metalloproteinase inhibitors, inhibitors of urokinase plasminogen activator receptor function, and heparinase-like antibodies.

7) Growth function inhibitors, e.g. growth factor antibodies and growth factor receptor antibodies such as anti-HER2 antibody Trastuzumab, anti-EGFR antibody Panitumumab, anti-EGFR antibody Cetuximab; such inhibitors also include other tyrosine kinase inhibitors and serine/threonine kinase inhibitors, such as Ras/Raf signal conduction inhibitor, cell signaling inhibitors of MEK and/or AKT kinase, c-kit inhibitor, abl kinase inhibitor, PI3 kinase inhibitor, FLT3 kinase inhibitor, CSF-1R kinase inhibitor, IGF receptor kinase inhibitor, aurora kinase inhibitor, NTRKA/B/C kinase inhibitor, cyclin-dependent kinase inhibitors, e.g. CDK2 and or CDK4, CDK6 inhibitor and transcription kinase CDK7/9/12/13 inhibitor.

8) Antiangiogenic agents, e.g. Bevacizumab, a drug that inhibits vascular endothelial growth factor, and VEGF receptor tyrosine kinase inhibitor.

9) Tumor immunotherapy, including any in vitro and in vivo methods to increase the immunogenicity of a patient for tumor cells. For example, transfections of cytokines IL-2, IL-4, or GM-CSF; methods of reducing the ineffectiveness of T cells such as anti-PD-1/PD-L mAbs; methods of using transfected immune cells such as dendritic cells transfected with cytokines; methods of using the tumor cell lines transfected with cytokines; methods of reducing the functions of immunosuppressive cells such as regulatory T cells, myeloid-derived suppressor cells, or dendritic cells expressing indoleamine 2,3-deoxygenase; agonist that increases immune cell activity; as well as methods of cancer vaccines consisting of tumor-associated antigen proteins or peptides.

10) Chimeric antigen receptor T-cell immunotherapy (CART).

11) Oncogene therapy such as CRISPR-Cas 9, RNAi and gene transduction.

It should be noted that if the numbers of any given substituent is not specified (for example, a haloalkyl group), one or more substituents may be present. For example, "haloalkyl" can contain one or more of the same or different halogens.

In the description herein, if the chemical structure and chemical name contradict each other, the chemical structure will prevail.

As used herein, unless otherwise indicated, abbreviations for any protecting group and other compounds are indicated by their commonly accepted abbreviations, or by the IUPAC-IUB Commission on Biochemical Nomenclature (Biochem. 1972, 77:942-944).

The present invention will be illustrated in detail with reference to the following examples. However, it should be understood that the present invention is not limited to these examples.

The structure of the compound is determined by nuclear magnetic resonance (NMR) or/and mass spectrometry (MS). The NMR shift (δ) is given by the unit of $10^{-6}$ (ppm). The NMR is determined by a Bruker AVANCE-400 NMR spectrometer. The solvents used are deuterated dimethyl sulfoxide (DMSO-$d_6$), deuterated chloroform (CDCl$_3$), and the internal standard is tetramethylsilane (TMS).

MS is determined using a 1100 Series LC/MSD Trap (ESI) mass spectrometer (manufacturer: Agilent).

Qingdao Ocean Chemical GF254 silica gel plate is used for thin layer chromatography (TLC), and the specification is 0.15 mm to 0.2 mm, the specification for separation and purification of product is 0.4 mm to 0.5 mm.

Qingdao Ocean Chemical silica gel of 200-300 mesh is used as carrier for column chromatography.

The known raw materials of the present invention may be synthesized using or in accordance with the methods known in the art, or may be obtained commercially. Unless otherwise stated, they are obtained commercially.

Unless otherwise specified in the examples, the reactions can all be carried out under an argon or nitrogen atmosphere.

The argon or nitrogen atmosphere means that the reaction flask is connected to an argon or nitrogen gas balloon of about 1 L in volume.

Unless otherwise specified in the examples, the solution refers to an aqueous solution.

Unless otherwise specified in the examples, the reaction temperature is room temperature, approximately 20° C. to 30° C.

The eluent system used for the column chromatography and the developing system used for the thin layer chromatography include: A: dichloromethane/methanol system, B: petroleum ether/ethyl acetate system. The volume ratio of the solvent is adjusted depending on the polarity of the compound, and may be adjusted by adding a small amount of an alkaline or acidic reagent such as ammonia or acetic acid.

EXAMPLES

Example 1

Preparation of 3-[(1-acryloyl-pyrrolidin-3-yl)-ethyl-amino]-5-bromo-N-(4,6-dimethyl-2-oxo-1,2-dihydro-pyridin-3-ylmethyl)-2-methyl-benzamide

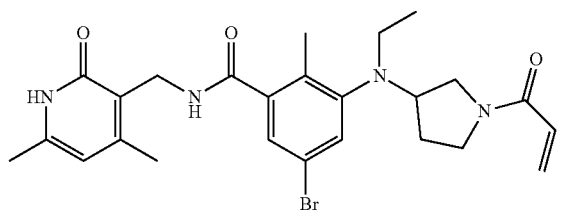

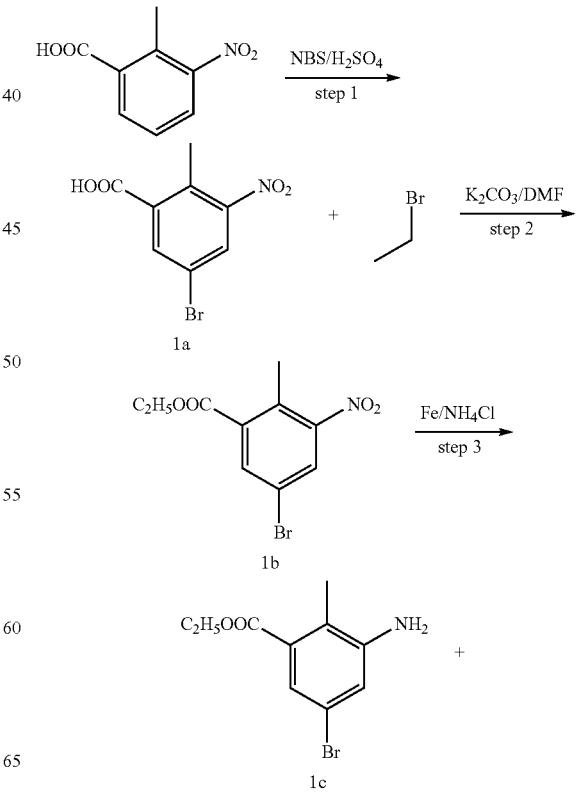

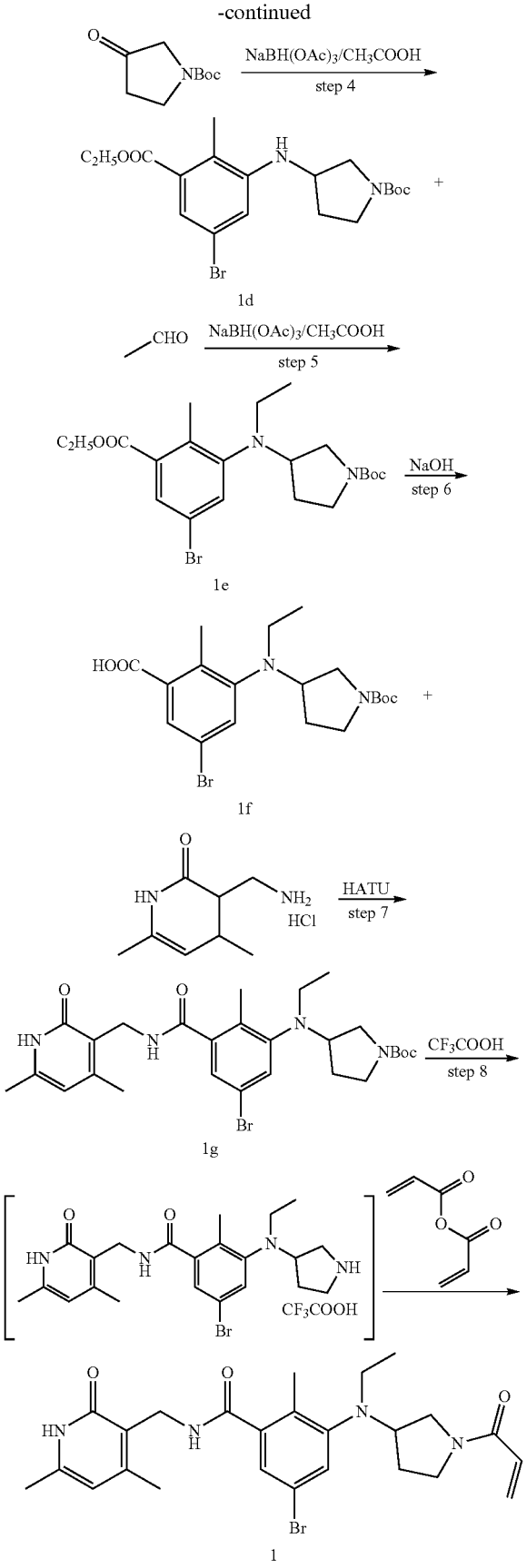

Step 1: Preparation of 5-bromo-3-nitro-2-methylbenzoic acid (1a)

3-Nitro-2-methylbenzoic acid (27.1 g, 150 mmol) was dissolved in 100 mL of sulfuric acid and heated to 60° C. NBS (29.36 g, 165 mmol) was added in portions. After addition, the reaction solution was stirred for 5 hours, and then cooled to room temperature. The reaction solution was added with 500 mL of ice water and stirred for 30 minutes. The mixture was filtered, and the filter cake was rinsed with water and dried to give 36 g of title product.

Step 2: Preparation of ethyl 5-bromo-3-nitro-2-methyl benzoate (1b)

5-Bromo-3-nitro-2-methylbenzoic acid (36 g, 138 mmol), ethyl bromide (22.64 g, 208 mmol) and potassium carbonate (38 g, 276 mmol) were added to 120 mL of DMF, and stirred at room temperature for 15 hours. The reaction solution was added with water and ethyl acetate. The organic phase was dried over anhydrous sodium sulfate, filtered and the filtrate was concentrated under reduced pressure to give 39 g of title product, which was used directly in the next step without any further purification.

Step 3: Preparation of ethyl 5-bromo-3-amino-2-methyl benzoate (1c)

Ethyl 5-bromo-3-nitro-2-methyl benzoate (26 g, 90 mmol), iron powder (20.2 g, 360 mmol) and ammonium chloride (19.3 g, 360 mmol) were added with a mixed solvent of 260 mL of ethanol and 100 mL of water. The mixture was stirred under reflux for 2 hours. The iron sludge was filtered off and the filtrate was concentrated under reduced pressure. The residues were purified via column chromatography (eluent: petroleum ether:ethyl acetate 40:1~5:1) to give 1.5 g of title product.

Step 4: Preparation of tert-butyl 3-(5-bromo-3-ethoxycarbonyl-2-methyl-phenylamino)-pyrrolidin-1-ylcarboxylate (1d)

Ethyl 5-bromo-3-amino-2-methylbenzoate (5.7 g, 22.1 mmol) and 1-Boc-3-pyrrolidone (4.92 g, 26.6 mmol) were dissolved in 30 mL of acetic acid. Sodium triacetoxyborohydride (9.4 g, 44.3 mmol) was added in portions. After addition, the reaction solution was stirred for 2 hours, and then added with water and ethyl acetate. The ethyl acetate layer was washed with an aqueous solution of sodium hydroxide, dried over anhydrous sodium sulfate, and filtered. The filtrate was concentrated under reduced pressure. The residues were purified via column chromatography (eluent: petroleum ether:ethyl acetate 50:1~5:1) to give 6.4 g of title product.

Step 5: Preparation of tert-butyl 3-[(5-bromo-3-ethoxycarbonyl-2-methyl-phenyl)-ethyl-amino]-pyrrolidin-1-ylcarboxylate (1e)

Tert-butyl 3-(5-bromo-3-ethoxycarbonyl-2-methyl-phenylamino)-pyrrolidine-1-ylcarboxylate (3.2 g, 7.5 mmol) and acetaldehyde (0.66 g, 15 mmol) were dissolved in 20 mL of acetic acid, and then added with sodium triacetoxyborohydride (3.2 g, 15 mmol) in portions. After addition, the reaction solution was stirred for 2 hours, and then added with water and ethyl acetate. The ethyl acetate layer was washed with an aqueous solution of sodium hydroxide, dried over anhydrous sodium sulfate, and filtered. The filtrate was concentrated under reduced pressure. The residues were purified via column chromatography (eluent: petroleum ether:ethyl acetate 50:1~5:1) to give 3.3 g of title product.

Step 6: Preparation of tert-butyl 3-[(5-bromo-3-formyl-2-methyl-phenyl)-ethyl-amino]-pyrrolidin-1-ylcarboxylate (1f)

Tert-butyl 3-[(5-bromo-3-ethoxycarbonyl-2-methyl-phenyl)-ethyl-amino]-pyrrolidin-1-ylcarboxylate (3.3 g, 7.25 mmol) and sodium hydroxide (1 g, 25 mmol) were added to a mixed solvent of 30 mL of ethanol and 10 mL of water, and the mixture was stirred under reflux for 1 hour and then cooled to room temperature. The reaction solution was adjusted to pH 3-4 with 1 M aqueous solution of citric acid, and then extracted with ethyl acetate. The ethyl acetate layer was washed with water, dried over anhydrous sodium sulfate, and filtered. The filtrate was concentrated under reduced pressure to give 3.15 g of title product.

Step 7: Preparation of tert-butyl 3-({5-bromo-3-[(4,6-dimethyl-2-oxo-1,2-dihydro-pyridin-3-ylmethyl)-carbamoyl]-2-methyl)-phenyl}-ethyl-amino)-pyrrolidin-1-ylcarboxylate (1 g)

Tert-butyl 3-[(5-bromo-3-formyl-2-methyl-phenyl)-ethyl-amino]-pyrrolidin-1-ylcarboxylate (3.15 g, 7.4 mmol), 3-aminomethyl-4,6-dimethyl-1H-pyridin-2one hydrochloride (1.95 g, 10.4 mmol) and N-methyl morpholine (6 g, 59.2 mmol) were added to 18 mL of DMF and stirred to dissolve. HATU (4.22 g, 11.1 mmol) was added and stirred for two hours. The reaction solution was added with 18 mL of water dropwise. The resulting solid was filtered and dried to give 4.3 g of title product.

Step 8: Preparation of 3-[(1-acryloyl-pyrrolidin-3-yl)-ethyl-amino]-5-bromo-N-(4,6-dimethyl-2-oxo-1,2-dihydro-pyridin-3-ylmethyl)-2-methyl-benzamide Tert-butyl 3-({5-bromo-3-[(4,6-dimethyl-2-oxo-1,2-dihydro-pyridin-3-ylmethyl)-carbamoyl]-2-methyl)-phenyl}-ethyl-amino)-pyrrolidin-1-ylcarboxylate (280 mg, 0.5 mmol) was dissolved in 10 ml of dichloromethane, and added with 1 mL of trifluoroacetic acid. The mixture was refluxed for 10 hours. The reaction solution was concentrated under reduced pressure, and then added with 10 mL of dichloromethane and N-methyl morpholine (400 mg, 4 mmol). Acrylic anhydride (75 mg, 0.6 mmol) was added under an ice water bath and stirred for 2 hours, then water and dichloromethane were added for extraction. The organic layer was dried over anhydrous sodium sulfate and filtered. The filtrate was concentrated under reduced pressure. The residues were purified via column chromatography (eluent: dichloromethane:methanol 20:1) to give 30 mg of title product.

$^1$H-NMR (CDCl$_3$) δ: 0.87 (3H, t), 1.65-2.08 (2H, m), 2.27 (3H, s), 2.28 (3H, s), 2.41 (3H, s), 2.97-3.02 (2H, m), 3.22-3.35 (1H, m), 3.42-3.55 (1H, m), 3.65-3.85 (3H, m), 4.54 (2H, d), 5.65-5.71 (1H, m), 6.01 (1H, s), 6.34-6.42 (2H, m), 7.16-7.21 (1H, t), 7.26-7.30 (2H, m), 12.00 (1H, br).

m/z ESI M+H$^+$ 517.0.

Example 2

Preparation of 3-[(1-acryloyl-pyrrolidin-3-yl)-ethyl-amino]-5-fluoro-N-(4,6-dimethyl-2-oxo-1,2-dihydro-pyridin-3-ylmethyl)-2-methyl-benzamide

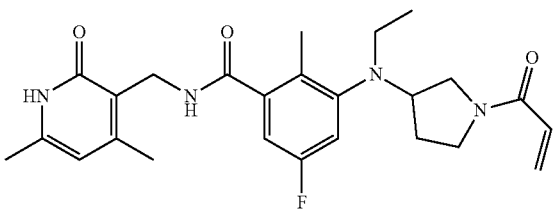

2

Step 1: Preparation of 5-fluoro-3-nitro-2-methylbenzoic acid (2a)

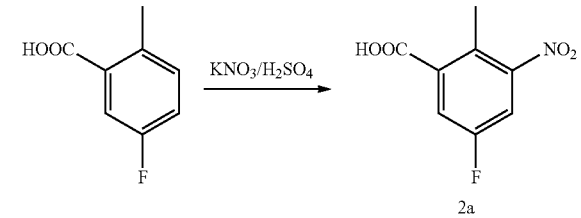

5-Fluoro-2-methylbenzoic acid (7.7 g, 50 mmol) was dissolved in 60 mL of sulfuric acid, and added with potassium nitrate (6.1 g, 60 mmol) in portions. After addition, the reaction solution was stirred at room temperature for 2 hours, and then poured into 350 ml of ice water and stirred for 30 mins. The mixture was filtered, and the filter cake was rinsed with water and dried to give 3.7 g of title product.

The remaining steps were the same as those of Steps 2 to 8 of Example 1, to obtain Compound 2.

$^1$H-NMR (CDCl$_3$) δ: 0.88 (3H, t), 1.80-1.91 (1H, m), 2.01-2.09 (1H, m), 2.26 (3H, s), 2.28 (3H, s), 2.41 (3H, s), 2.98-3.05 (2H, q), 3.22-3.35 (1H, m), 3.40-3.55 (1H, m), 3.62-3.85 (3H, m), 4.54 (2H, d), 5.65-5.71 (1H, m), 5.97 (1H, s), 6.33-6.42 (2H, m), 6.87-6.94 (2H, m), 7.20 (1H, t), 11.05 (1H, br).

m/z ESI M+H$^+$ 454.9.

Example 3

Preparation of 3-[(1-acryloyl-pyrrolidin-3-yl)-ethyl-amino]-5-chloro-N-(4,6-dimethyl-2-oxo-1,2-dihydro-pyridin-3-ylmethyl)-2-methyl-benzamide

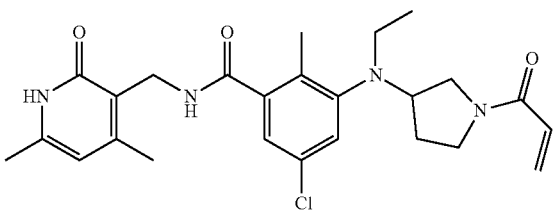

3

The preparation method was the same as Example 2, except that 5-chloro-2-methylbenzoic acid was used instead of 5-fluoro-2-methylbenzoic acid to give compound 3.

¹H-NMR (CDCl₃) δ: 0.88 (3H, t), 1.75-1.86 (1H, m), 1.99-2.08 (1H, m), 2.26 (3H, s), 2.29 (3H, s), 2.40 (3H, s), 2.96-3.04 (2H, q), 3.22-3.32 (1H, m), 3.40-3.55 (1H, m), 3.60-3.85 (3H, m), 4.54 (2H, d), 5.62-5.71 (1H, m), 5.99 (1H, s), 6.33-6.42 (2H, m), 7.11-7.15 (2H, m), 7.23 (1H, t), 12.01 (1H, br).

m/z ESI M+H⁺ 470.8.

Example 4

Preparation of 3-[(1-acryloyl-pyrrolidin-3-yl)-ethyl-amino]-N-(4,6-dimethyl-2-oxo-1,2-dihydro-pyridin-3-ylmethyl)-2-methyl-benzamide

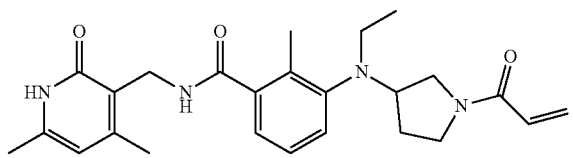

4

The preparation method was the same as Example 1, except that 3-nitro-2-methylbenzoic acid was used instead of 5-bromo-3-nitro-2-methylbenzoic acid to give compound 4.

¹H-NMR (DMSO-d6) δ: 0.81 (3H, t), 1.66-1.95 (1H, m), 1.98-2.07 (1H, m), 2.11 (3H, s), 2.20 (3H, s), 2.21 (3H, s), 2.95-3.03 (2H, m), 3.20-3.27 (1H, m), 3.46-3.55 (2H, m), 3.65-3.72 (1H, m), 3.75-3.85 (1H, m), 4.27 (2H, d), 5.58-5.66 (1H, m), 5.86 (1H, s), 6.05-6.14 (1H, m), 6.48-6.58 (1H, m), 7.01 (1H, d), 7.18 (1H, t), 7.28 (1H, d), 8.05-8.09 (1H, t), 11.46 (1H, s).

m/z ESI M+H⁺ 437.2.

Example 5

Preparation of 3-[(1-acryloyl-pyrrolidin-3-yl)-ethyl-amino]-2,5-dibromo-N-(4,6-dimethyl-2-oxo-1,2-dihydro-pyridin-3-ylmethyl)-benzamide

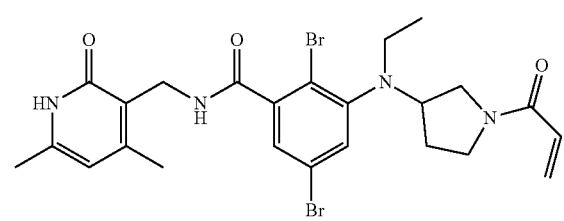

5

The preparation method was the same as Example 2, except that 2,5-dibromobenzoic acid was used instead of 5-fluoro-2-methylbenzoic acid to give compound 5.

¹H-NMR (DMSO-d6) δ: 0.84 (3H, t), 1.80-1.92 (1H, m), 1.95-2.04 (1H, m), 2.11 (3H, s), 2.20 (3H, s), 3.05-3.13 (2H, m), 3.26-3.32 (1H, m), 3.46-3.58 (2H, m), 3.68-3.80 (1H, m), 3.88-3.96 (1H, m), 4.26 (2H, d), 5.60-5.67 (1H, m), 5.87 (1H, s), 6.08-6.12 (1H, m), 6.51-6.59 (1H, m), 7.21 (1H, d), 7.58 (1H, d), 8.36-8.42 (1H, t), 11.50 (1H, br).

m/z ESI M+H⁺ 581.0.

Example 6

Preparation of 3-[(1-acryloyl-piperidin-4-yl)-ethyl-amino]-5-bromo-N-(4,6-dimethyl-2-oxo-1,2-dihydro-pyridin-3-ylmethyl)-2-methyl-benzamide

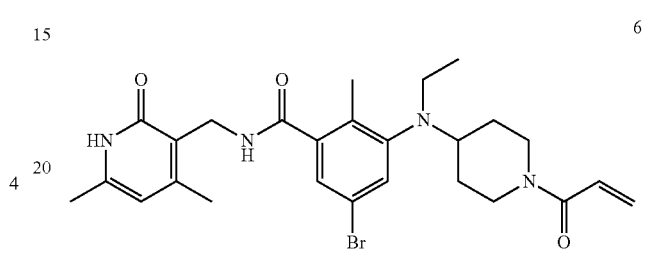

6

The preparation method was the same as Example 1, except that N-Boc-piperidin-4-one was used instead of N-Boc-pyrrolidin-3-one to give compound 6.

¹H-NMR (DMSO-d₆) δ: 0.79 (3H, t), 1.32-1.50 (2H, m), 1.72 (2H, br), 2.12 (2H, s), 2.16 (3H, s), 2.20 (3H, s), 2.58-2.63 (1H, m), 2.95-3.10 (4H, m), 3.99 (1H, br), 4.26 (2H, br), 4.36 (1H, br), 5.65 (1H, dd), 5.87 (1H, s), 6.07 (1H, dd), 6.78 (1H, dd), 7.10 (1H, d), 7.32 (1H, d), 8.24 (1H, br), 11.48 (1H, s).

m/z ESI M+H⁺ 529.0.

Example 7

Preparation of 3-[(1-acryloyl-azetidin-3-yl)-ethyl-amino]-5-bromo-N-(4,6-dimethyl-2-oxo-1,2-dihydro-pyridin-3-ylmethyl)-2-methyl-benzamide

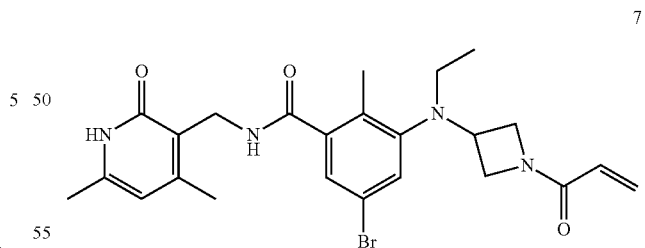

7

The preparation method was the same as Example 1, except that N-Boc-azetidin-3-one was used instead of N-Boc-pyrrolidin-3-one to give compound 7.

¹H-NMR (DMSO-d₆) δ: 0.82 (3H, t), 2.11 (3H, s), 2.17 (3H, s), 2.19 (3H, s), 2.95 (2H, q), 3.57 (1H, m), 3.80 (1H, m), 4.00 (1H, m), 4.20-4.35 (4H, m), 5.64 (1H, dd), 5.87 (1H, s), 6.08 (1H, dd), 6.29 (1H, dd), 7.12 (1H, d), 7.19 (1H, d), 8.27 (1H, t), 11.49 (1H, s).

m/z ESI M+H⁺ 501.0.

Example 8

Preparation of 3-(4-acryloyl-piperazin-1-yl)-5-bromo-N-(4,6-dimethyl-2-oxo-1,2-dihydro-pyridin-3-ylmethyl)-2-methyl-benzamide

8

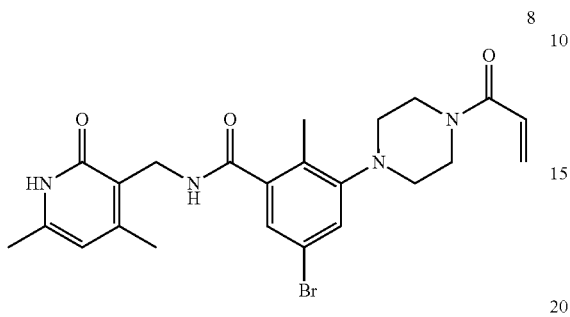

Step 1: Preparation of tert-butyl 4-(5-bromo-3-ethoxycarbonyl-2-methyl-phenyl)-piperidin-1-carboxylate (8a)

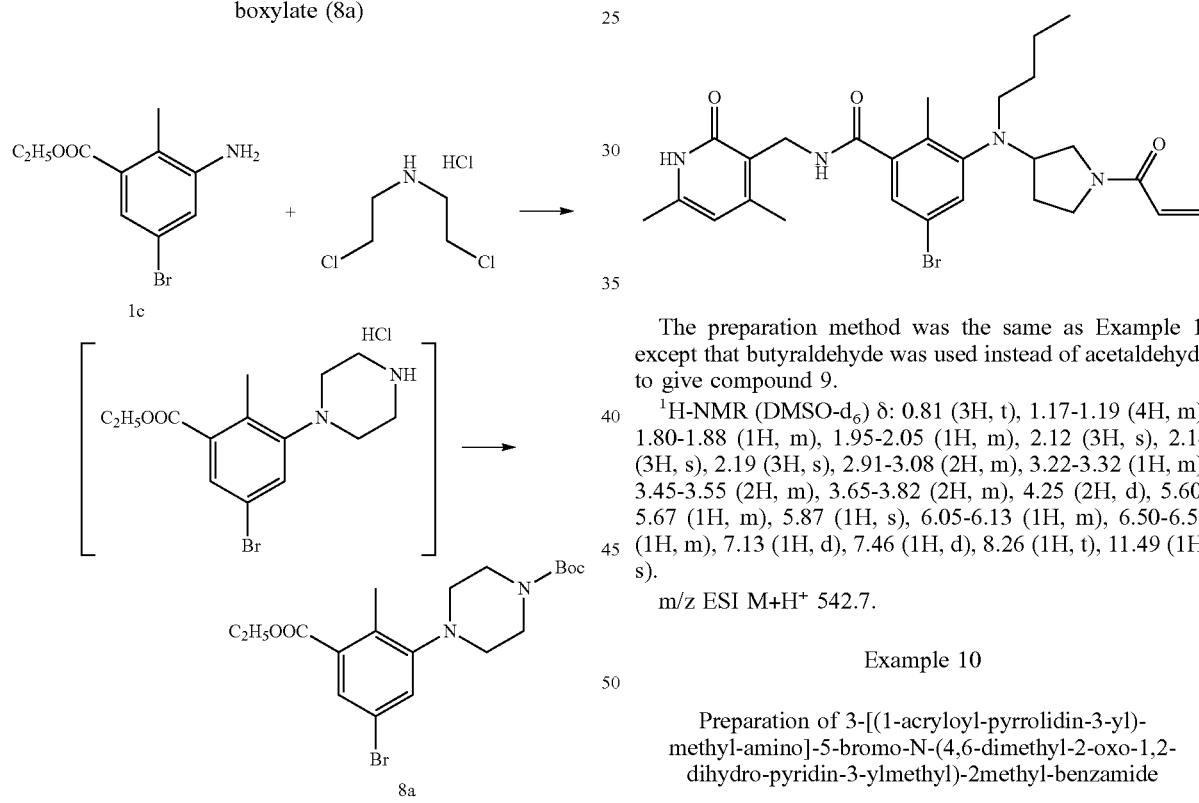

Ethyl 5-bromo-3-amino-2-methyl-benzoate (1c) (1.4 g, 5.5 mmol) was mixed with bis(2-chloroethyl)-amine hydrochloride (1.06 g, 6 mmol). The mixture was heated to 170° C. under a nitrogen atmosphere, and subjected to melting reaction for 1 hour. The reaction mixture was added with Bis(2-chloroethyl)-amine hydrochloride (1.06 g, 6 mmol) and subjected to reaction for another 1 hour. The reaction solution was cooled to room temperature and 50 mL of dichloromethane and 25 mL of 1M aqueous solution of sodium hydroxide were then added. (Boc)$_2$O (3.3 g, 15 mmol) was added under stirring and stirred for 1 hour. The organic layer was dried over anhydrous sodium sulfate and filtered. The filtrate was concentrated under reduced pressure. The residues were purified via column chromatography (eluent: petroleum ether:ethyl acetate 40:1~10:1) to give 0.7 g of title product.

The remaining steps were the same as in Example 1, except that Compound 8a was used instead of Compound 1e of Example 1 to give Compound 8.

$^1$H-NMR (DMSO-d$_6$) δ: 2.13 (3H, s), 2.20 (6H, s), 2.84 (4H, br), 3.69 (4H, br), 4.28 (2H, d), 5.69 (1H, dd), 5.85 (1H, s), 6.12 (1H, dd), 6.79 (1H, dd), 7.10 (1H, d), 7.18 (1H, d), 8.05 (1H, br), 11.29 (1H, s).

m/z ESI M+H$^+$ 489.1.

Example 9

Preparation of 3-[(1-acryloyl-pyrrolidin-3-yl)-butyl-amino]-5-bromo-N-(4,6-dimethyl-2-oxo-1,2-dihydro-pyridin-3-ylmethyl)-2methyl-benzamide

9

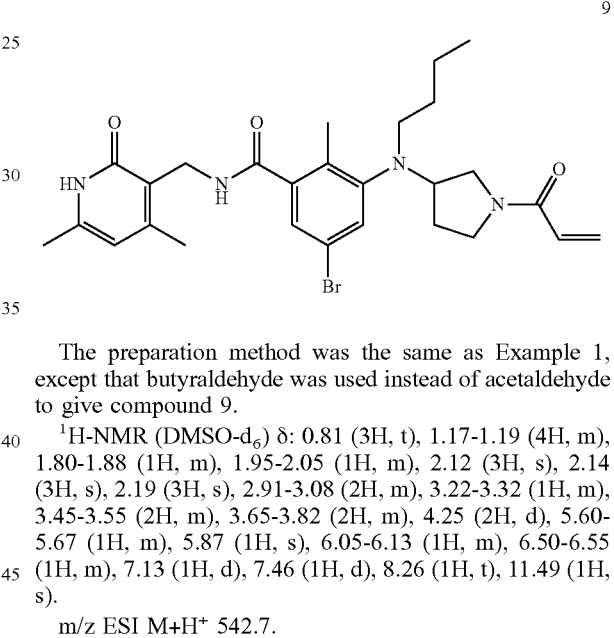

The preparation method was the same as Example 1, except that butyraldehyde was used instead of acetaldehyde to give compound 9.

$^1$H-NMR (DMSO-d$_6$) δ: 0.81 (3H, t), 1.17-1.19 (4H, m), 1.80-1.88 (1H, m), 1.95-2.05 (1H, m), 2.12 (3H, s), 2.14 (3H, s), 2.19 (3H, s), 2.91-3.08 (2H, m), 3.22-3.32 (1H, m), 3.45-3.55 (2H, m), 3.65-3.82 (2H, m), 4.25 (2H, d), 5.60-5.67 (1H, m), 5.87 (1H, s), 6.05-6.13 (1H, m), 6.50-6.55 (1H, m), 7.13 (1H, d), 7.46 (1H, d), 8.26 (1H, t), 11.49 (1H, s).

m/z ESI M+H$^+$ 542.7.

Example 10

Preparation of 3-[(1-acryloyl-pyrrolidin-3-yl)-methyl-amino]-5-bromo-N-(4,6-dimethyl-2-oxo-1,2-dihydro-pyridin-3-ylmethyl)-2methyl-benzamide

10

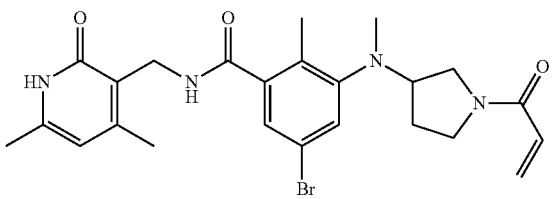

101

Step 1: Preparation of tert-butyl 3-[(5-bromo-3-ethoxycarbonyl-2-methyl-phenyl)-methyl-amino]-pyrrolidin-1-ylcarboxylate (10a)

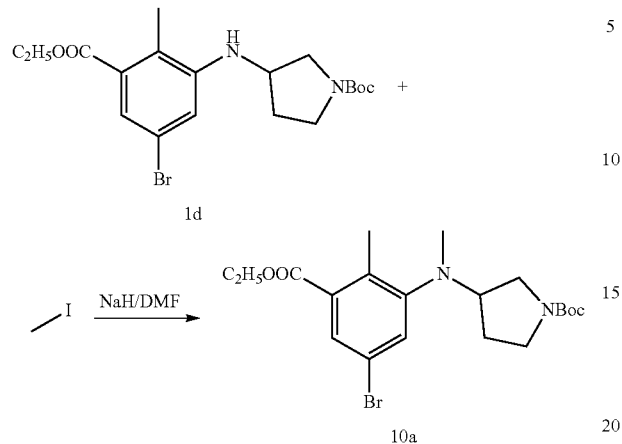

Tert-butyl 3-(5-bromo-3-ethoxycarbonyl-2-methyl-phenylamino)-pyrrolidin-1-yl-carboxylate (1d) (1.5 g, 3.5 mmol), methyl iodide (0.98 g, 7 mmol) and sodium hydride (0.43 g, 10.6 mmol) were dissolved in 4 mL of DMF and stirred for 3 hours. The reaction solution was added with water and ethyl acetate. The organic layer was dried over anhydrous sodium sulfate and filtered. The filtrate was concentrated under reduced pressure. The residues were purified by column chromatography (eluent: petroleum ether:ethyl acetate 50:1 to 10:1) to give 0.6 g of title product.

The remaining steps were the same as in Example 1, except that Compound 10a was used instead of Compound 1e of Example 1, to obtain Compound 10.

$^1$H-NMR (CDCl$_3$) δ: 1.85-1.96 (1H, m), 2.01-2.06 (1H, m), 2.25 (3H, s), 2.28 (3H, s), 2.41 (3H, s), 2.59 (3H, s), 3.37-3.41 (1H, m), 3.47-3.56 (1H, m), 3.62-3.81 (3H, m), 4.53 (2H, d), 5.65-5.70 (1H, m), 6.01 (1H, s), 6.35-6.41 (2H, m), 7.16 (1H, t), 7.23-7.28 (2H, m), 12.11 (1H, br).

m/z ESI M+H$^+$ 501.1.

Example 11

Preparation of 3-[(1-acryloyl-pyrrolidin-3-yl)-ethyl-amino]-N-(4,6-dimethyl-2-oxo-1,2-dihydro-pyridin-3-ylmethyl)-2-methyl-5-[6-(4-methyl-piperazin-1-yl)-pyridin-3-ylamino]-benzamide

102

Step 1: Preparation of 2-(4-methyl-piperazin-1-yl)-5-aminopyridine (11a)

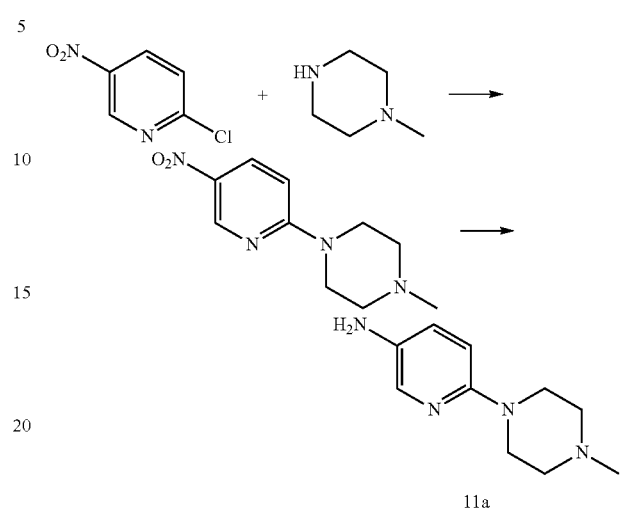

2-Chloro-5-nitropyridine (3.17 g, 20 mmol), N-methyl-piperazine (3 g, 30 mmol) and potassium carbonate (5.52 g, 40 mmol) were added to 5 mL of DMF and heated to 60° C. for 1 hour. The reaction solution was cooled to room temperature and then poured into 50 mL of water. A solid was precipitated. The solid was filtered out and the product was added to a mixed solvent of 5 mL of water and 20 mL of ethanol, and then added with iron powder (4.48 g, 80 mmol) and hydrochloric acid (2 mL) and refluxed for 2 hours. The reaction solution was adjusted to pH 8 with sodium hydroxide and then filtered. The filtrate was concentrated under reduced pressure. The residues were purified by column chromatography (eluent: dichloromethane:methanol 100:1~30:1) to give 0.67 g of title product.

Step 2: Preparation of tert-butyl 3-({5-[2-(4-methyl-piperazin-1-yl)-pyridin-5-amino]-3-[(4,6-dimethyl-2-oxo-1,2-dihydro-pyridin-3-ylmethyl)-carbamoyl]-2-methyl-phenyl}-ethyl-amino)-pyrrolidin-1-ylcarboxylate (11b)

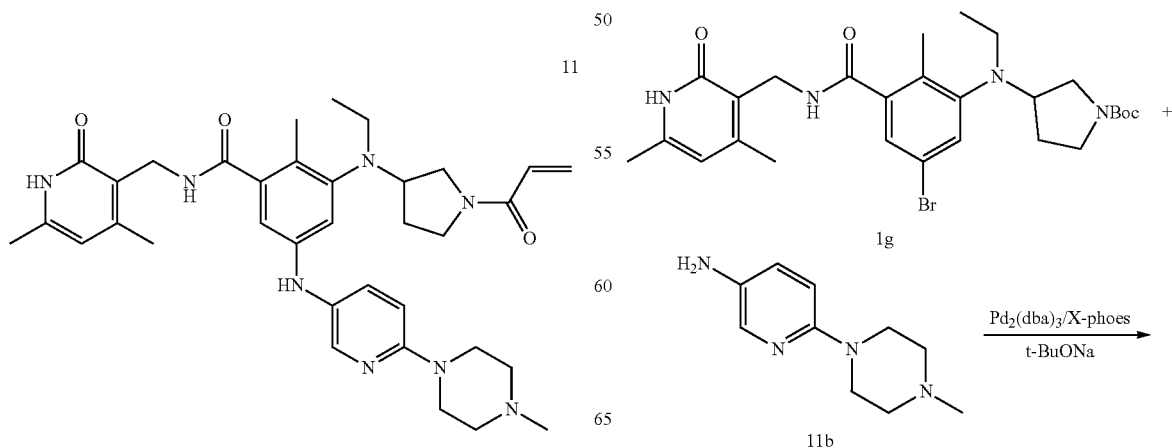

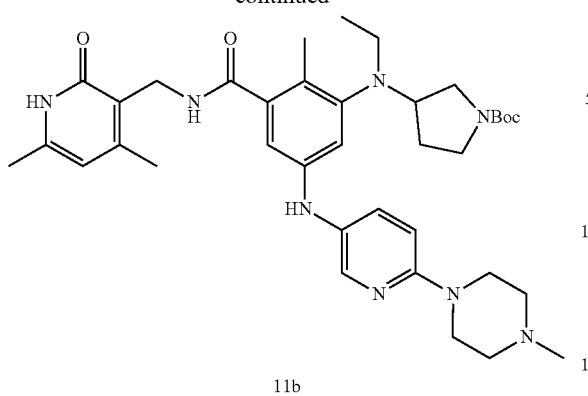

11b

Tert-butyl 3-({5-bromo-3-[(4,6-dimethyl-2-oxo-1,2-dihydro-pyridin-3-ylmethyl)-carbamoyl]-2-methyl-phenyl}-ethyl-amino)-pyrrolidin-1-ylcarboxylate (1 g) (170 mg, 0.3 mmol), 2-(4-methyl-piperazin-1-yl)-5-aminopyridine (11a) (64 mg, 0.33 mmol), Pd₂(dba)₃ (28 mg, 0.03 mmol), X-phoes (29 mg, 0.06 mmol), and sodium tert-butoxide (115 mg, 1.2 mmol) were added to 20 mL of toluene, and the mixture was heated to 90° C. for 2 hours under a nitrogen atmosphere. The reaction solution was filtered and then concentrated under reduced pressure. The residues were purified by column chromatography (eluent: dichloromethane:methanol 80:1~25:1) to give 110 mg of title product.

The remaining steps were the same as in Example 1, except that Compound 11b was used instead of Compound 1g to give Compound 11.

¹H-NMR (DMSO-d₆) δ: 0.84 (3H, t), 1.60-1.95 (2H, m), 2.08 (3H, s), 2.11 (3H, s), 2.17 (3H, s), 2.31 (3H, s), 2.55 (4H, br), 2.92-3.05 (2H, m), 3.23-3.31 (H, m), 3.52 (2H, br), 3.70 (2H, br), 4.24 (2H, d), 5.64 (1H, m), 5.86 (1H, s), 6.11 (1H, m), 6.50-6.56 (2H, m), 6.75 (1H, s), 6.82 (1H, d), 7.36 (1H, d), 7.75 (1H, d), 7.97-8.03 (2H, m), 11.46 (1H, s).

m/z ESI M+H⁺ 628.2.

Example 12

Preparation of 3-[(1-acryloyl-pyrrolidin-3-yl)-ethyl-amino]-N-(4,6-dimethyl-2-oxo-1,2-dihydro-pyridin-3-ylmethyl)-2-methyl-5-[4-(morpholin-4-ylmethyl)phenylamino]-benzamide Step 1: Preparation of 4-(morpholin-4-ylmethyl) aniline (12a)

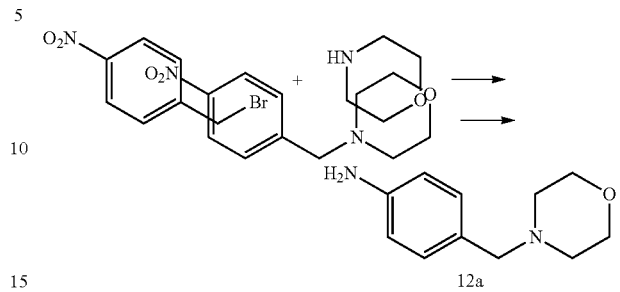

12a

4-Nitrobenzyl bromide (10.8 g, 50 mmol), morpholine (4.6 g, 52.5 mmol) and potassium carbonate (10.35 g, 75 mmol) were added to 25 mL of acetonitrile and heated to 60° C. for 4 hours. The reaction solution was cooled to room temperature and poured into 100 mL of water and extracted with ethyl acetate. The organic layer was dried over anhydrous sodium sulfate and filtered. The filtrate was concentrated under reduced pressure. The residues were added to a mixed solvent of 40 ml of water and 100 ml of ethanol, and then added with iron powder (10.1 g, 180 mmol) and hydrochloric acid (4 mL) and refluxed for 2 hours. The reaction solution was adjusted to pH 8 with sodium hydroxide, and then filtered. The filtrate was concentrated under reduced pressure. The residues were purified by column chromatography (eluent: dichloromethane:methanol 100:1~25:1) to give 7.2 g of title product.

The remaining steps were the same as in Example 11, except that Compound 12a was used instead of Compound 11a to give Compound 12.

¹H-NMR (CDCl₃) δ: 0.89 (3H, t), 1.85-1.93 (1H, m), 2.01-2.05 (1H, m), 2.23 (3H, s), 2.26 (3H, s), 2.39 (3H, s), 2.95-3.03 (2H, m), 3.23-3.35 (1H, m), 3.38-3.85 (12H, m), 4.51 (2H, d), 5.63-5.71 (1H, m), 5.87 (1H, br), 5.92 (1H, s), 6.32-6.42 (2H, m), 6.86-6.99 (4H, m), 7.13-7.18 (1H, br), 7.21-7.28 (2H, d), 11.63 (1H, br).

m/z ESI M+H⁺ 627.3.

Example 13

Preparation of 3-[(1-acryloyl-pyrrolidin-3-yl)-ethyl-amino]-5-(4-methyl-piperazin-1-yl)-N-(4,6-dimethyl-2-oxo-1,2-dihydro-pyridin-3-ylmethyl)-2-methyl-benzamide

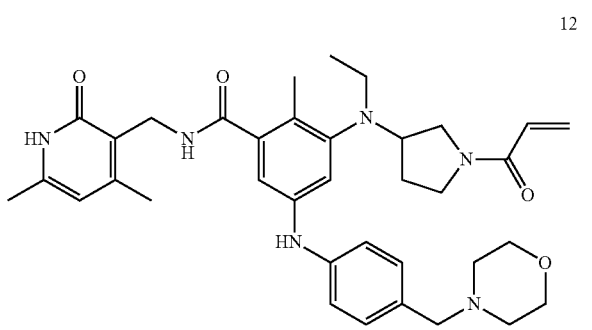 [SMILES: C=CC(=O)N1CCC(N(CC)c2cc(Nc3ccc(CN4CCOCC4)cc3)cc(C(=O)NCc3c(C)cc(C)[nH]c3=O)c2C)C1]

12

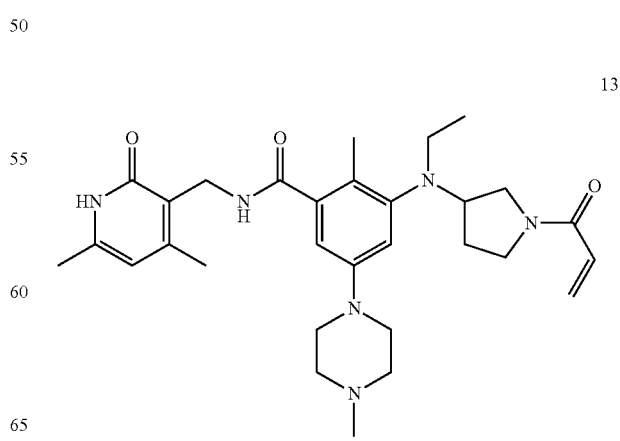

13

105

Step 1: Preparation of tert-butyl 3-({5-(4-methyl-piperazin-1-yl)-3-[(4,6-dimethyl-2-oxo-1,2-dihydro-pyridin-3-ylmethyl)-carbamoyl]-2-methyl-phenyl}-ethyl-amino)-pyrrolidin-1-carboxylate

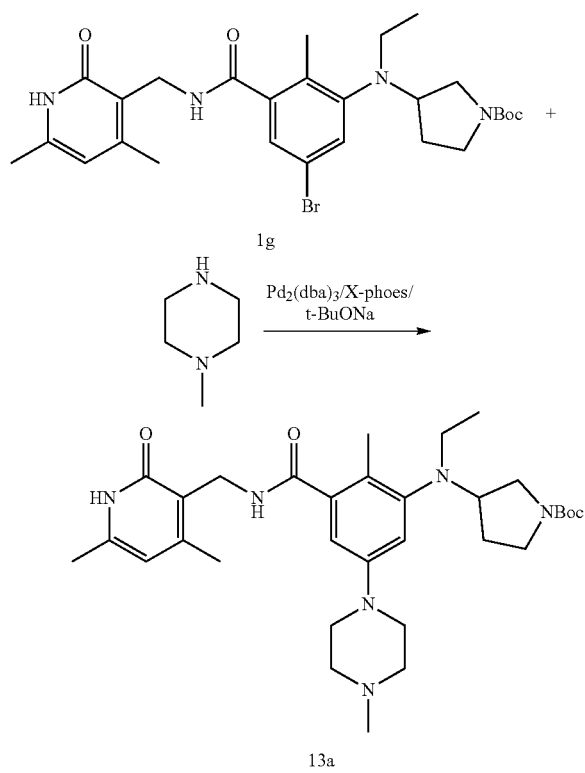

Tert-butyl 3-({5-bromo-3-[(4,6-dimethyl-2-oxo-1,2-dihydro-pyridin-3-ylmethyl)-carbamoyl]-2-methyl)-phenyl}-ethyl-amino)-pyrrolidin-1-ylcarboxylate (1 g) (0.84 g, 1.5 mmol), N-methyl-piperazine (0.23 g, 2.3 mmol), Pd$_2$(dba)$_3$ (0.18 g, 0.2 mmol) and X-phoes (0.19 g, 0.4 mmol) were added to 35 mL of toluene, and then added with sodium tert-butoxide (0.77 g, 8 mmol). The reaction solution was stirred at 100° C. for 15 hours under a nitrogen atmosphere, and then added with water and ethyl acetate. The organic layer was dried over anhydrous sodium sulfate and filtered. The filtrate was concentrated under reduced pressure. The residues were purified by column chromatography (eluent: dichloromethane:methanol 100:1~30:1) to give 0.3 g of title product.

The remaining steps were the same as in Example 1, except that Compound 13a was used instead of Compound 1g to give Compound 13.

$^1$H-NMR (CDCl3) δ: 0.86 (3H, t), 1.85-1.93 (1H, m), 2.01-2.08 (1H, m), 2.22 (3H, s), 2.25 (3H, s), 2.41 (3H, s), 2.49 (3H, s), 2.77 (4H, br), 2.98 (2H, q), 3.24-3.33 (5H, m), 3.41-3.82 (4H, m), 4.53 (2H, d), 5.61-5.68 (1H, m), 5.98 (1H, s), 6.32-6.42 (2H, m), 6.74-6.77 (2H, d), 7.02-7.12 (1H, br), 11.63 (1H, br).

m/z ESI M+H$^+$ 535.0.

106

Example 14

Preparation of 5-bromo-3-{[1-(4-dimethylamino-but-2-enoyl)-pyrrolidin-3-yl]-ethyl-amino}-N-(4,6-dimethyl-2-oxo-1,2-dihydro-pyridin-3-ylmethyl)-2-methyl-benzamide

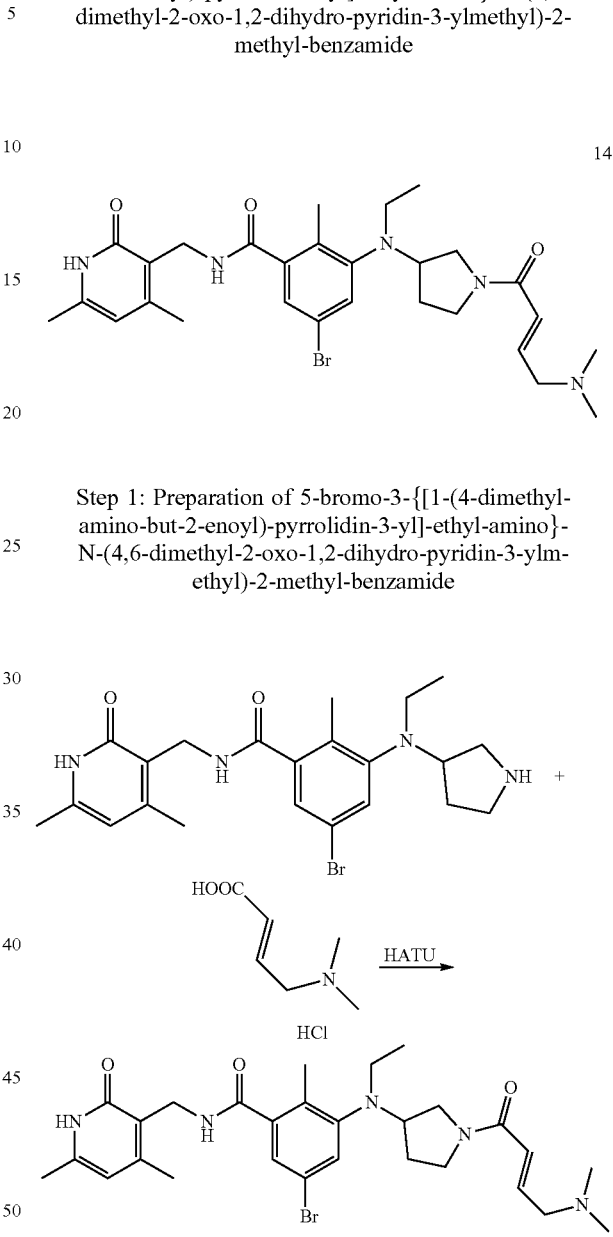

Step 1: Preparation of 5-bromo-3-{[1-(4-dimethyl-amino-but-2-enoyl)-pyrrolidin-3-yl]-ethyl-amino}-N-(4,6-dimethyl-2-oxo-1,2-dihydro-pyridin-3-ylm-ethyl)-2-methyl-benzamide 5-Bromo-N-(4,6-dimethyl-2-oxo-1,2-dihydro-pyridin-3-ylmethyl)-3-(ethyl-pyrrolidin-3-yl-amino)-2-methyl-benz-amide (1 g) (0.23 g, 0.5 mmol), 4-dimethylamino crotonic acid hydrochloride (0.16 g, 1 mmol) and N-methyl-morpholine (0.3 g, 3 mmol) were dissolved in 4 mL of DMF, and then HATU (0.57 g, 1.5 mmol) was added with stirring and stirred for 20 hours. The reaction solution was added with water and ethyl acetate. The organic layer was dried over anhydrous sodium sulfate and filtered. The filtrate was concentrated under reduced pressure. The residues were purified by column chromatography (eluent: dichlorometh-ane:methanol 15:1) to give 15 mg of title product.

$^1$H-NMR (CDCl$_3$) δ: 0.88 (3H, t), 1.85-1.95 (1H, m), 1.98-2.08 (1H, m), 2.23 (3H, s), 2.29 (3H, s), 2.38 (3H, s), 2.52 (6H, s), 2.99 (2H, q), 3.16-3.78 (7H, m), 4.51 (2H, d), 5.96 (1H, s), 6.29-6.46 (1H, m), 6.80-6.91 (1H, m), 7.20-7.30 (3H, m), 12.05 (1H, br).
m/z ESI M+H⁺ 571.8.

Example 15

Preparation of 5-bromo-3-[1-(1-oxo-butyl-2-alkynyl)-pyrrolidin-3-yl]-ethyl-amino}-N-(4,6-dimethyl-2-oxo-1,2-dihydro-pyridin-3-ylmethyl)-2-methyl-benzamide

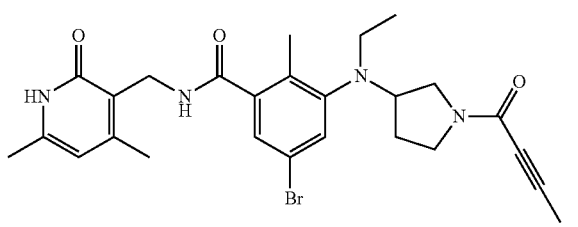

The preparation method was the same as in Example 14, except that 2-butynoic acid was used instead of 4-dimethylamino crotonic acid hydrochloride to give Compound 15.

$^1$H-NMR (DMSO-d$_6$) δ: 0.80 (3H, t), 1.72-1.83 (1H, m), 1.90-2.05 (4H, m), 2.12 (3H, s), 2.14 (3H, s), 2.19 (3H, s), 2.93-3.00 (2H, m), 3.20-3.30 (1H, m), 3.43-3.53 (2H, m), 3.65-3.72 (1H, m), 3.80-3.86 (1H, m), 4.25 (2H, d), 5.87 (1H, s), 7.15 (1H, d), 7.44 (1H, d), 8.26 (1H, t), 11.49 (1H, s).
m/z ESI M+H⁺ 528.7.

Example 16

Preparation of 3-[(1-acryloyl-pyrrolidin-3-yl)-ethyl-amino]-5-methoxy-N-(4,6-dimethyl-2-oxo-1,2-dihydrogen-pyridin-3-ylmethyl)-2methyl-benzamide

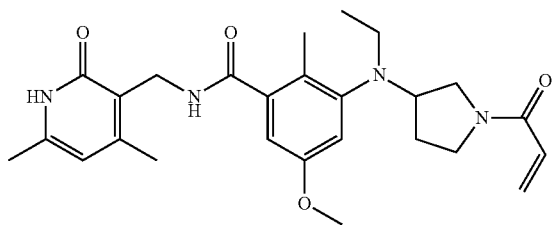

Step 1: Preparation of ethyl 5-hydroxy-3-nitro-2-methyl-benzoate

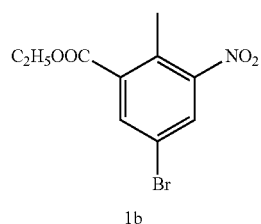

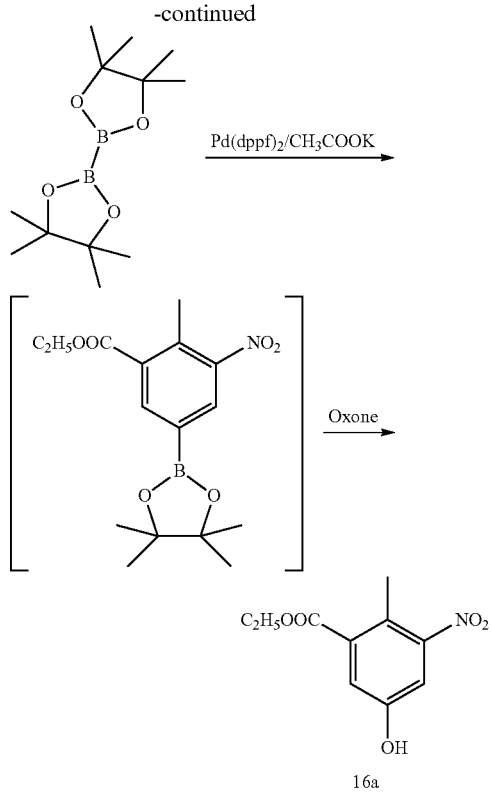

Ethyl 5-bromo-3-nitro-2-methyl-benzoate (1b) (13.8 g, 47.9 mmol), bis(pinacolato)diboron (12.8 g, 50.3 mmol), potassium acetate (9.4 g, 95.8 mmol) and Pd(dppf)$_2$Cl$_2$ (0.5 g) were added to 140 mL of dioxane, and the reaction mixture was refluxed for 20 hours under a nitrogen atmosphere. The reaction solution was concentrated under reduced pressure, and the residues were added with water and ethyl acetate. The organic layer was concentrated under reduced pressure to give a black solid. The solid was added to 200 mL of acetone, and then added with 75 mL of a saturated aqueous solution of Oxone, and stirred at room temperature for 1.5 hours. The excess of Oxone was quenched by addition of aqueous solution of sodium sulfite. The reaction mixture was concentrated under reduced pressure, and the residues were added with water and ethyl acetate. The organic layer was dried over anhydrous sodium sulfate and filtered. The filtrate was concentrated under reduced pressure to give 16.6 g of crude product which was used directly in the next step without any further purification.

Step 2: Preparation of tert-butyl 3-[(5-hydroxy-3-ethoxycarbonyl-2-methyl-phenyl)-ethyl-amino]-pyrrolidin-1-ylcarboxylate (16b)

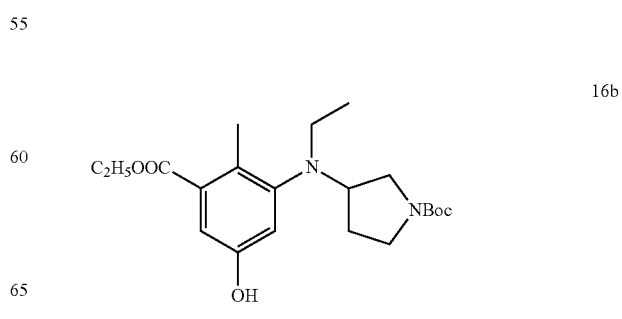

The preparation method was the same as that of steps 3, 4, and 5 in Example 1, except that the compound 16a was used instead of the compound 1b to obtain the compound 16b.

Step 3: Preparation of tert-butyl 3-[(5-methoxy-3-ethoxycarbonyl-2-methyl-phenyl)-ethyl-amino]-pyrrolidin-1-ylcarboxylate

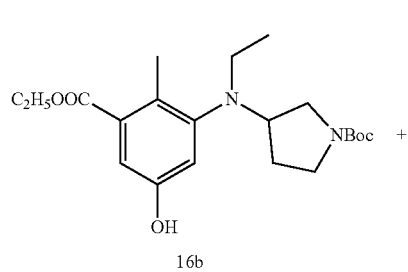

16b

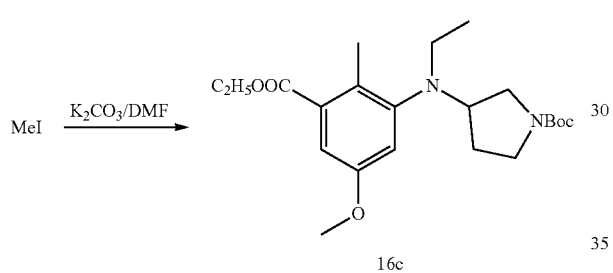

16c

Tert-butyl 3-[(5-hydroxy-3-ethoxycarbonyl-2-methyl-phenyl)-ethyl-amino]-pyrrolidin-1-ylcarboxylate (0.4 g, 1 mmol), iodomethane (0.52 g, 3 mmol), potassium carbonate (0.42 g, 3 mmol) were added to 2 mL of DMF and stirred at room temperature for 16 hours. The reaction solution was added with water and ethyl acetate. The organic layer was dried over anhydrous sodium sulfate and filtered. The filtrate was concentrated under reduced pressure. The residues were purified by column chromatography (eluent: petroleum ether:ethyl acetate 100:1~10:1) to give 0.32 g of title product.

The remaining steps were the same as in Example 1 except that compound 16c was used instead of compound 1e to give compound 16.

$^1$H-NMR (CDCl$_3$) δ: 0.87 (3H, t), 1.82-1.90 (1H, m), 2.01-2.08 (1H, m), 2.23 (3H, s), 2.27 (3H, s), 2.43 (3H, s), 2.95-3.03 (2H, m), 3.20-3.35 (1H, m), 3.42-3.53 (1H, m), 3.62-3.84 (6H, m), 4.54 (2H, d), 5.62-5.69 (1H, m), 6.01 (1H, s), 6.33-6.42 (2H, m), 6.71-6.78 (2H, m), 7.03-7.10 (1H, br), 12.05 (1H, br).

m/z ESI M+H$^+$ 466.9.

Example 17

Preparation of N-(4,6-dimethyl-2-oxo-1,2-dihydro-pyridin-3-ylmethyl)-5-[(1-acryloyl-pyrrolidin-3-yl)-ethyl-amino]-4'-hydroxymethyl-4-methyl-biphenyl-3-carboxamide

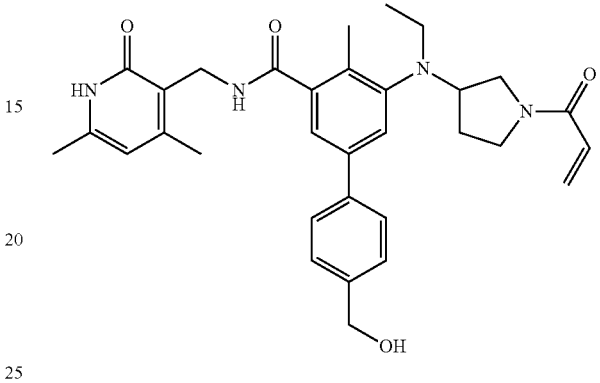

17

Step 1: Preparation of 4-hydroxymethylphenylboronic acid pinacol ester

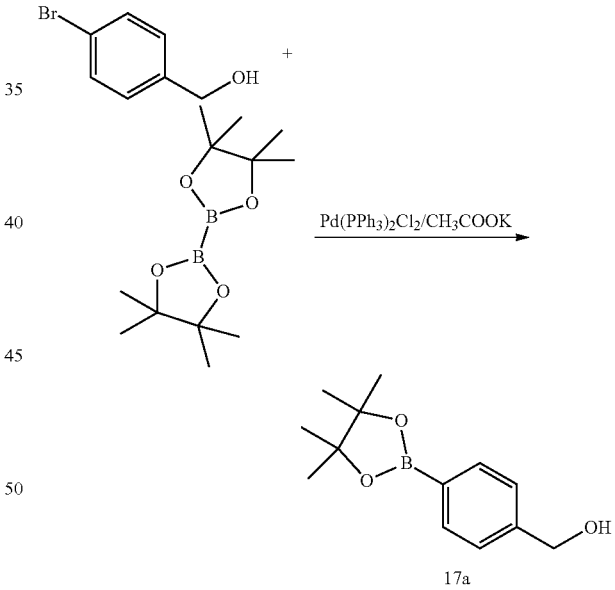

17a

4-Bromobenzyl alcohol (15 g, 80.2 mmol), bis(pinacolato)diboron (30.6 g, 120.3 mmol), potassium acetate (23.6 g, 240 mmol) and Pd (PPh$_3$)$_2$Cl$_2$ (5.6 g, 8 mmol) were added to 150 mL of dioxane, and the mixture was stirred at 85° C. for 3 hours under a nitrogen atmosphere. The reaction solution was filtered and concentrated under reduced pressure, and then extracted with water and ethyl acetate. The organic layer was dried over anhydrous sodium sulfate and filtered. The filtrate was concentrated under reduced pressure. The residues were purified by column chromatography (eluent: petroleum ether:ethyl acetate 60:1~10:1) to give 16 g of title product.

Step 2: Preparation of N-(4,6-dimethyl-2-oxo-1,2-dihydro-pyridin-3-ylmethyl)-5-[(1-tert-butoxycarbonyl-pyrrolidin-3-yl)-ethyl-amino]-4'-hydroxymethyl-4-methyl-biphenyl-3-carboxamide

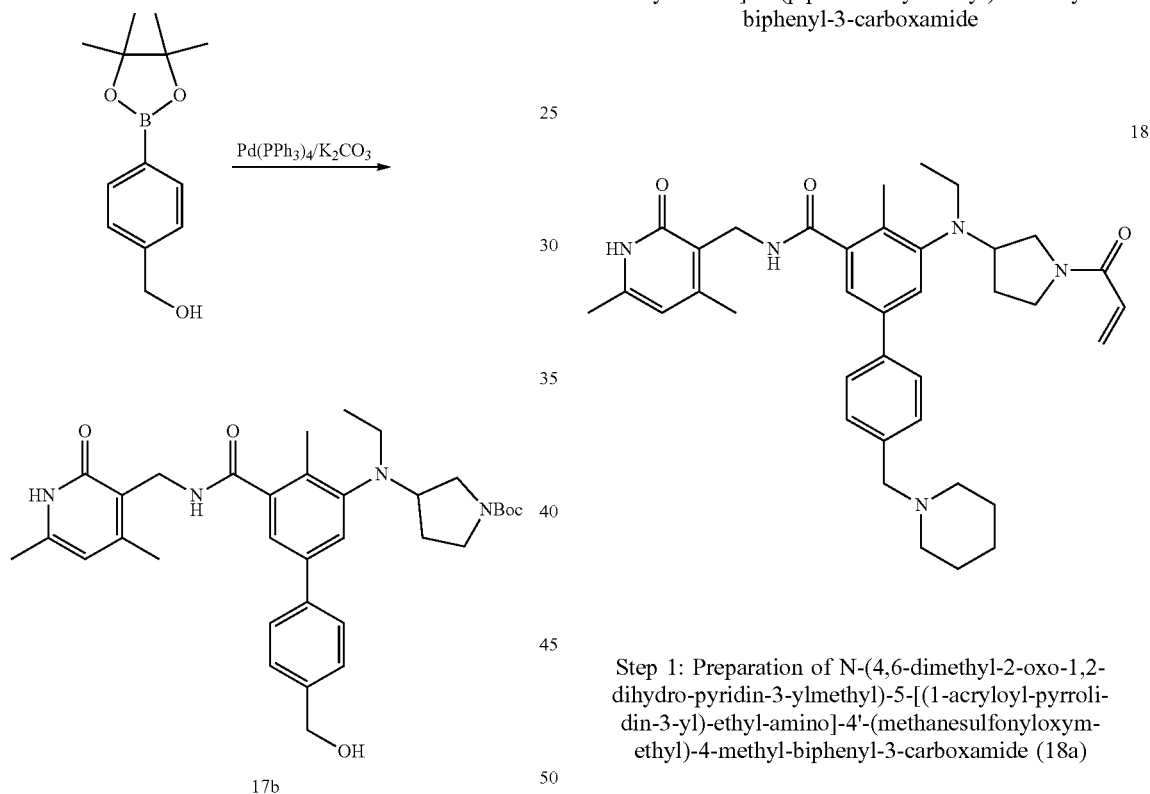

Tert-butyl 3-({5-bromo-3-[(4,6-dimethyl-2-oxo-1,2-dihydro-pyridin-3-ylmethyl)-carbamoyl]-2-methyl-phenyl}-ethyl-amino)-pyrrolidin-1-ylcarboxylate (1 g) (2.3 g, 4.1 mmol), 4-hydroxymethylphenylboronic acid pinacol ester (0.96 g, 4.1 mmol), tetrakis(triphenylphosphine)palladium (0.47 g, 0.41 mmol) and potassium carbonate (1.13 g, 8.2 mmol) were added to a mixed solvent of 30 mL of acetonitrile and 15 mL of water, and refluxed for 4 hours under a nitrogen atmosphere. The reaction solution was filtered and concentrated under reduced pressure, and then extracted with water and ethyl acetate. The organic layer was dried over anhydrous sodium sulfate and filtered. The filtrate was concentrated under reduced pressure. The residues were purified by column chromatography (eluent: petroleum ether:ethyl acetate 50:1~1:1) to give 0.62 g of title product.

The remaining steps were the same as in Example 1, except that compound 17b was used instead of compound 1g to give compound 17.

$^1$H-NMR (DMSO-d6) δ: 0.86 (3H, t), 1.80-1.89 (1H, m), 1.95-2.05 (1H, m), 2.11 (3H, s), 2.21 (3H, s), 2.25 (3H, s), 3.01-3.08 (2H, m), 3.27-3.32 (1H, m), 3.48-3.55 (2H, m), 3.67-3.74 (1H, m), 3.91-3.98 (1H, m), 4.30 (2H, d), 4.54 (2H, d), 5.23 (1H, t), 5.57-5.65 (1H, m), 5.87 (1H, s), 6.05-6.13 (1H, m), 6.48-6.58 (1H, m), 7.28 (1H, d), 7.40 (2H, d), 7.52 (1H, d), 7.63 (2H, d), 8.20-8.26 (1H, t), 11.48 (1H, s).

m/z ESI M+H$^+$ 542.8.

Example 18

Preparation of N-(4,6-dimethyl-2-oxo-1,2-dihydro-pyridin-3-ylmethyl)-5-[(1-acryloyl-pyrrolidin-3-yl)-ethyl-amino]-4'-(piperidin-1-ylmethyl)-4-methyl-biphenyl-3-carboxamide

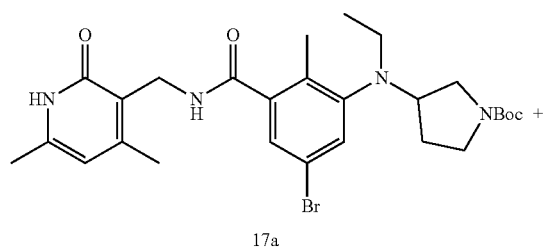

Step 1: Preparation of N-(4,6-dimethyl-2-oxo-1,2-dihydro-pyridin-3-ylmethyl)-5-[(1-acryloyl-pyrrolidin-3-yl)-ethyl-amino]-4'-(methanesulfonyloxymethyl)-4-methyl-biphenyl-3-carboxamide (18a)

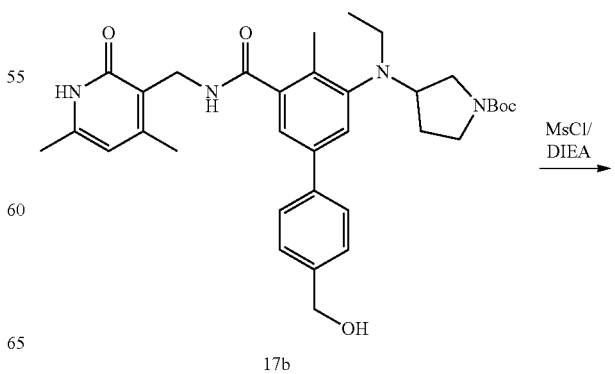

-continued

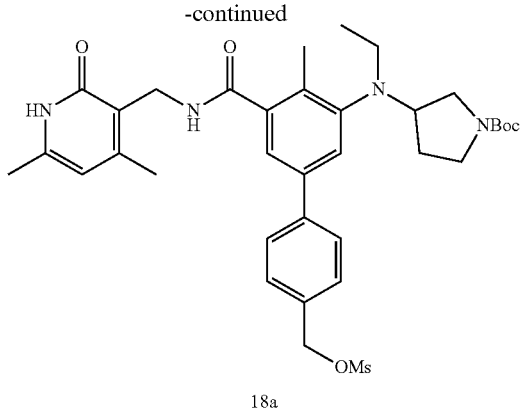

18a

N-(4,6-dimethyl-2-oxo-1,2-dihydro-pyridin-3-ylmethyl)-5-[(1-acryloyl-pyrrolidin-3-yl)-ethyl-amino]-4'-hydroxymethyl-4-methyl-biphenyl-3-carboxamide (0.58 g, 1 mmol) and DIEA (0.26 g, 2 mmol) were dissolved in 10 mL of dichloromethane. A solution of methanesulfonyl chloride (0.14 g, 1.2 mmol) in 2 mL of dichloromethane was added dropwise under ice water bath, and then stirred for 2 hours. The reaction solution was added with water and dichloromethane. The organic layer was dried over anhydrous sodium sulfate and filtered. The filtrate was concentrated under reduced pressure. The residues were purified by column chromatography (eluent: petroleum ether:ethyl acetate 50:1~2:1) to give 0.14 g of title product.

Step 2: Preparation of N-(4,6-dimethyl-2-oxo-1,2-dihydro-pyridin-3-ylmethyl)-5-[(1-acryloyl-pyrrolidin-3-yl)-ethyl-amino]-4'-(piperidin-1-ylmethyl)-4-methyl-biphenyl-3-carboxamide (18b)

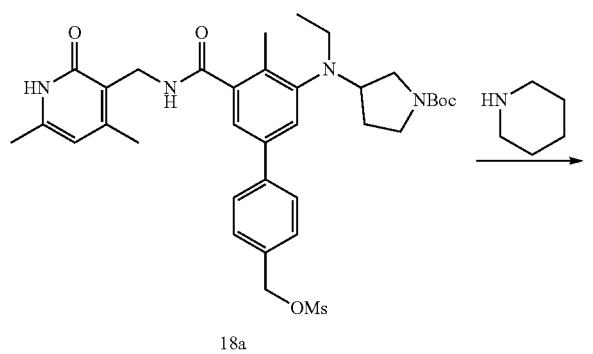

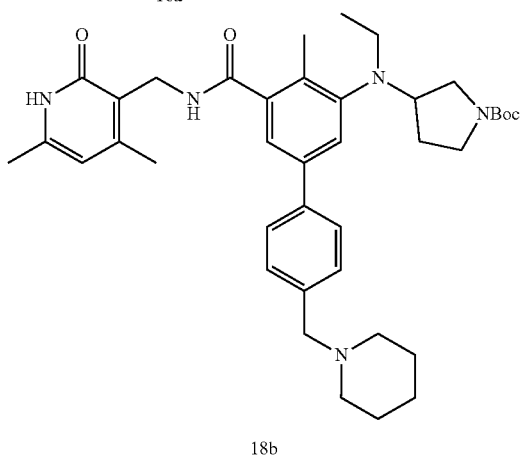

18b

N-(4,6-dimethyl-2-oxo-1,2-dihydro-pyridin-3-ylmethyl)-5-[(1-acryloyl-pyrrolidin-3-yl)-ethyl-amino]-4'-methanesulfonyloxymethyl-4-methyl-biphenyl-3-carboxamide (0.14 g, 0.2 mmol) was added to 2 mL of piperidine and stirred for 2 hours. The reaction solution was added with water and dichloromethane. The organic layer was dried over anhydrous sodium sulfate and filtered. The filtrate was concentrated under reduced pressure. The residues were purified by column chromatography (eluent: dichloromethane:methanol 20:1) to give 90 mg of title product.

The remaining steps were the same as in Example 1, except that compound 18b was used instead of compound 1g to give compound 18.

$^1$H-NMR (DMSO-$d_6$) δ: 0.85 (3H, t), 1.52-2.05 (8H, m), 2.11 (3H, s), 2.21 (3H, s), 2.25 (3H, s), 2.33-2.92 (4H, m), 2.95-3.12 (2H, m), 3.25-3.32 (1H, m), 3.52 (2H, s), 3.70-3.76 (2H, m), 3.90-3.97 (2H, m), 4.30 (2H, d), 5.60-5.67 (1H, m), 5.87 (1H, s), 6.07-6.12 (1H, m), 6.52-6.55 (1H, m), 7.13 (1H, d), 7.50-7.65 (3H, m), 7.71 (2H, d), 8.24 (1H, t), 11.48 (1H, s).

m/z ESI M+H$^+$ 609.9.

Example 19

Preparation of N-(4,6-dimethyl-2-oxo-1,2-dihydro-pyridin-3-ylmethyl)-5-[(1-acryloyl-pyrrolidin-3-yl)-ethyl-amino]-4'-(dimethylaminomethyl)-4-methyl-biphenyl-3-carboxamide

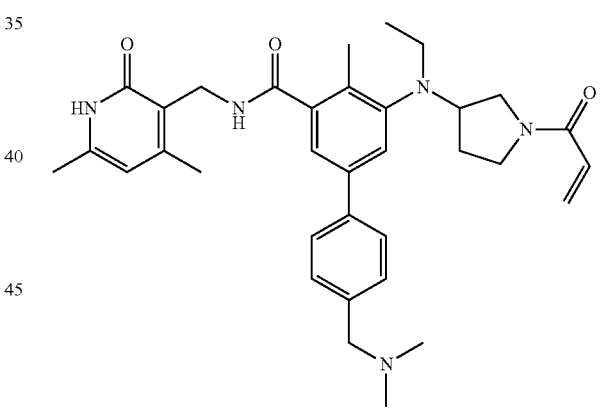

19

The preparation method was the same as Example 18, except that a solution of dimethylamine in tetrahydrofuran was used instead of piperidine to give Compound 19.

$^1$H-NMR (DMSO-d6) δ: 0.85 (3H, t), 1.70-1.89 (1H, m), 1.95-2.05 (1H, m), 2.11 (3H, s), 2.21 (3H, s), 2.26 (3H, s), 2.69 (6H, s), 2.97-3.08 (2H, m), 3.24-3.31 (1H, m), 3.50-3.58 (2H, m), 3.67-3.77 (1H, m), 3.91-3.98 (1H, m), 4.22 (2H, s), 4.30 (2H, d), 5.59-5.67 (1H, m), 5.87 (1H, s), 6.07-6.12 (1H, m), 6.50-6.57 (1H, m), 7.33 (1H, d), 7.55-7.62 (3H, m), 7.75-7.81 (2H, d), 8.20-8.28 (1H, t), 11.48 (1H, s).

m/z ESI M/2+H$^+$ 285.8.

Example 20

Preparation of N-(4,6-dimethyl-2-oxo-1,2-dihydro-pyridin-3-ylmethyl)-5-[(1-acryloyl-pyrrolidin-3-yl)-ethyl-amino]-4'-(morpholin-4-ylmethyl)-4-methyl-biphenyl-3-carboxamide

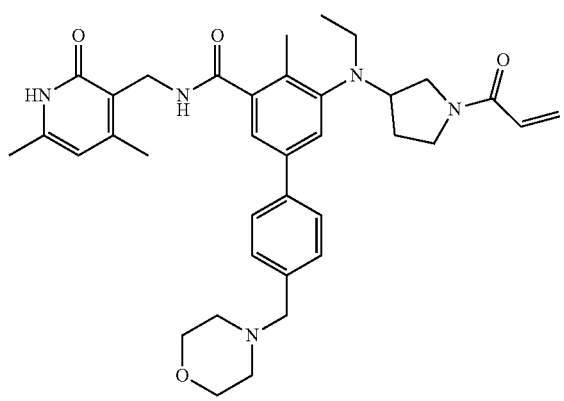

The preparation method was the same as Example 18, except that morpholine was used instead of piperidine to give Compound 20.

$^1$H-NMR (DMSO-$d_6$) δ: 0.85 (3H, t), 1.73-1.91 (1H, m), 1.96-2.05 (1H, m), 2.11 (3H, s), 2.21 (3H, s), 2.24 (3H, s), 2.38 (4H, br), 3.01-3.08 (2H, m), 3.25-3.32 (1H, m), 3.48-3.55 (4H, m), 3.58 (4H, br), 3.67-3.77 (1H, m), 3.91-3.98 (1H, m), 4.29 (2H, d), 5.57-5.65 (1H, m), 5.87 (1H, s), 6.05-6.13 (1H, m), 6.48-6.58 (1H, m), 7.28 (1H, d), 7.39 (2H, d), 7.52 (1H, d), 7.62 (2H, d), 8.20-8.26 (1H, t), 11.48 (1H, s).

m/z ESI M+H$^+$ 612.3.

Example 21

Preparation of N-(4,6-dimethyl-2-oxo-1,2-dihydro-pyridin-3-ylmethyl)-5-[(1-acryloyl-pyrrolidin-3-yl)-ethyl-amino]-3'-chloro-4'-(morpholin-4-ylmethyl)-4-methyl-biphenyl-3-carboxamide

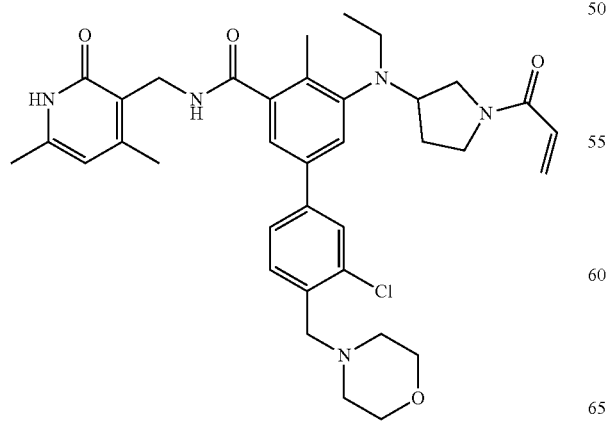

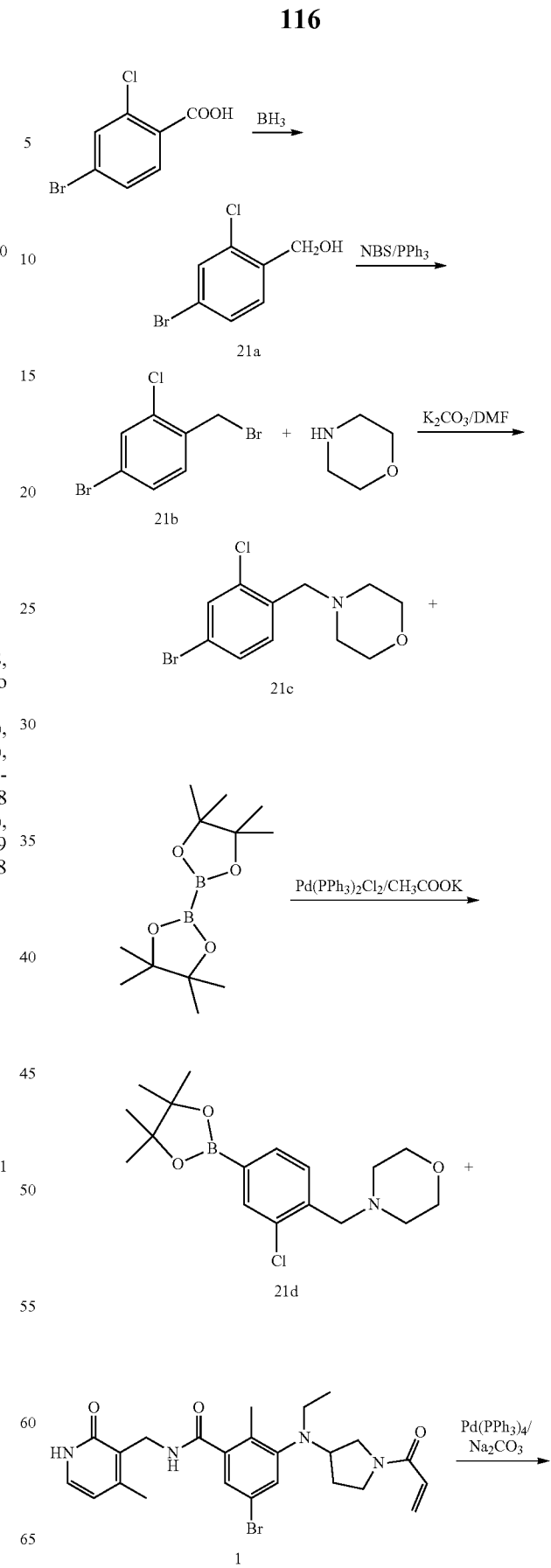

-continued

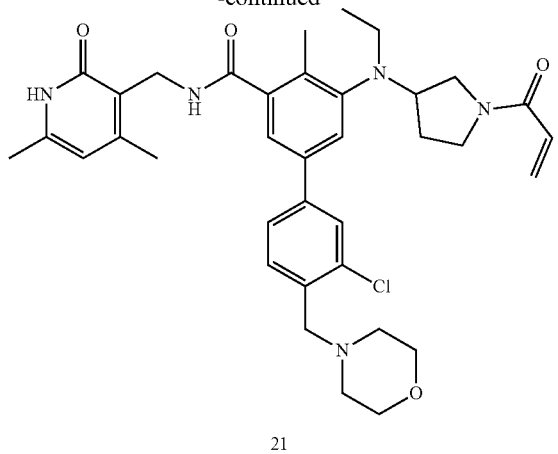

21

Step 1: Preparation of 4-bromo-2-chlorobenzyl alcohol (21a)

4-Bromo-2-chlorobenzoic acid (1.5 g, 6.41 mmol) was dissolved in 20 mL of THF. 15 mL of a solution of borane in tetrahydrofuran (1 M) was added dropwise in an ice water bath under a nitrogen atmosphere and stirred for 3 h. The reaction mixture was slowly poured into water, and extracted with ethyl acetate. The organic phase was washed twice with saturated sodium chloride solution, dried over anhydrous sodium sulfate, and filtered. The filtrate was concentrated under reduced pressure to give 1.6 g of crude title product which was used directly in the next step without purification.

Step 2: Preparation of 4-bromo-2-chlorobenzyl bromide (21b)

4-Bromo-2-chlorobenzyl alcohol (1.6 g, 7.34 mmol) and triphenylphosphine (3.85 g, 14.68 mol) were dissolved in 50 mL of dichloromethane. NBS (2.74 g, 15.41 mmol) was slowly added in an ice water bath under a nitrogen atmosphere and stirred at this temperature for 30 minutes. The reaction mixture was concentrated under reduced pressure and the residues were purified by column chromatography (eluent: petroleum ether:ethyl acetate 100:0~60:1) to give 0.95 g of title product.

Step 3: Preparation of 4-(morpholin-4-ylmethyl)-4-bromo-2-chlorobenzene (21c)

4-Bromo-2-chlorobenzyl bromide (0.95 g, 3.38 mmol), morpholine (0.59 g, 6.67 mmol) and potassium carbonate (1.2 g, 8.45 mmol) were added to 20 mL of DMF, and the reaction mixture was stirred at 70° C. for 1 h. The reaction solution was cooled to room temperature, and then poured slowly into water and extracted with ethyl acetate. The organic phase was washed twice with saturated sodium chloride solution, dried over anhydrous sodium sulfate, and filtered. The filtrate was concentrated under reduced pressure. The residues were purified by column chromatography (eluent: dichloromethane:methanol 100:1 to 25:1) to give 0.95 g of the title product.

Step 4: Preparation of 4-(morpholin-4-ylmethyl)-2-chloro-phenyl-4-boronic acid pinacol ester (21d)

4-(Morpholin-4-ylmethyl)-4-bromo-2-chlorobenzene (0.95 g, 3.28 mmol), bis(pinacolato)diboron (1.25 g, 4.93 mmol), potassium acetate (0.97 g, 9.86) mmol) and Pd (PPh$_3$)$_2$Cl$_2$ (0.23 g, 0.33 mmol) were added to 20 mL of dioxane, and stirred for 3 hours at 80° C. under a nitrogen atmosphere. The reaction solution was cooled to room temperature, and then poured into water and extracted with ethyl acetate. The organic phase was washed twice with saturated sodium chloride solution, dried over anhydrous sodium sulfate, and filtered. The filtrate was concentrated under reduced pressure. The residues were purified by column chromatography (eluent: dichloromethane:methanol 100:1 to 30:1) to give 0.42 g of the title product.

Step 5: Preparation of N-(4,6-dimethyl-2-oxo-1,2-dihydro-pyridin-3-ylmethyl)-5-[(1-acryloyl-pyrrolidin-3-yl)-ethyl-amino]-3'-chloro-4'-(morpholin-4-ylmethyl)-4-methyl-biphenyl-3-carboxamide 3-[(1-Acryloyl-pyrrolidin-3-yl)-ethyl-amino]-5-bromo-N-(4,6-dimethyl-2-oxo-1,2-dihydro-pyridin-3-ylmethyl)-2-methyl-benzamide (Compound 1) (100 mg, 0.19 mmol), 4-(morpholin-4-ylmethyl)-2-chloro-phenyl-4-boronic acid pinacol ester (131 mg, 0.39 mmol), sodium carbonate (51 mg, 0.49 mmol) and Pd(PPh$_3$)$_4$ (22 mg, 0.02 mmol) were added to a mixed solvent of 10 mL of 1,4-dioxane and 2 mL of water, and stirred at 80° C. for 2 hours under a nitrogen atmosphere. The reaction solution was cooled to room temperature, and then poured into water and extracted with ethyl acetate. The organic phase was washed twice with saturated sodium chloride solution, dried over anhydrous sodium sulfate, and filtered. The filtrate was concentrated under reduced pressure. The residues were purified by column chromatography (eluent: dichloromethane:methanol 100:1 to 25:1) to give 66 mg of the title product.

$^1$H-NMR (CDCl$_3$) δ: 0.89 (3H, t), 1.70-1.95 (1H, m), 2.03-2.09 (1H, m), 2.18 (3H, s), 2.36 (3H, s), 2.42 (3H, s), 2.54 (4H, br), 3.02-3.08 (2H, m), 3.27-3.31 (1H, m), 3.53-3.95 (10H, m), 4.53 (2H, d), 5.63-5.71 (1H, m), 5.93 (1H, s), 6.32-6.42 (2H, m), 7.18-7.22 (1H, br), 7.33-7.41 (3H, m), 7.48-7.55 (2H, m), 11.30 (1H, br).

m/z ESI M+H$^+$ 646.3.

Example 22

Preparation of N-(4,6-dimethyl-2-oxo-1,2-dihydro-pyridin-3-ylmethyl)-5-[(1-acryloyl-pyrrolidin-3-yl)-ethyl-amino]-3'-methoxy-4'-(morpholin-4-ylmethyl)-4-methyl-biphenyl-3-carboxamide

22

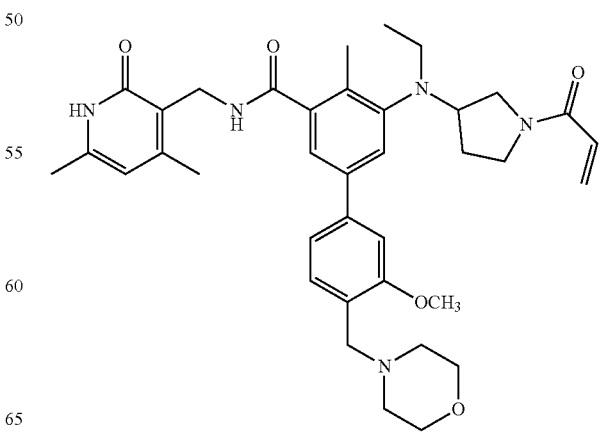

The preparation method was the same as Example 21, except that 4-bromo-2-methoxybenzoic acid was used instead of 4-bromo-2-chlorobenzoic acid to give Compound 22.

¹H-NMR (DMSO-d₆) δ: 0.84 (3H, t), 1.67-2.05 (2H, m), 2.11 (3H, s), 2.21 (3H, s), 2.24 (3H, s), 2.40 (4H, br), 3.01-3.08 (2H, m), 3.25-3.31 (1H, m), 3.45-3.80 (9H, m), 3.83-3.98 (4H, m), 4.30 (2H, d), 5.57-5.67 (1H, m), 5.86 (1H, s), 6.05-6.13 (1H, m), 6.48-6.58 (1H, m), 7.15-7.23 (2H, m), 7.30 (1H, s), 7.38 (1H, d), 7.52 (1H, d), 8.18-8.25 (1H, br), 11.47 (1H, s).

m/z ESI M+H⁺ 642.3.

Example 23

Preparation of N-(4,6-dimethyl-2-oxo-1,2-dihydro-pyridin-3-ylmethyl)-5-[(1-acryloyl-pyrrolidin-3-yl)-ethyl-amino]-3'-fluoro-4'-(morpholin-4-ylmethyl)-4-methyl-biphenyl-3-carboxamide

23

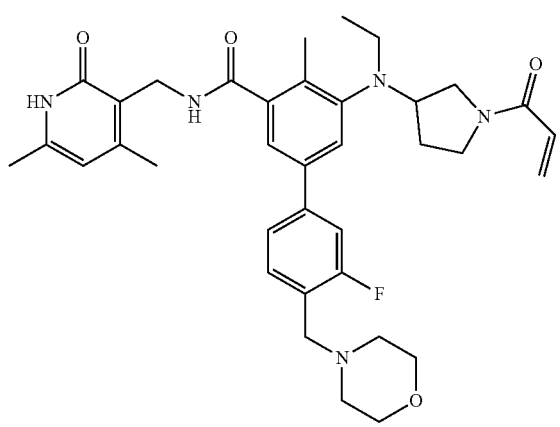

The preparation method was the same as Example 21, except that 4-bromo-2-fluorobenzoic acid was used instead of 4-bromo-2-chlorobenzoic acid to give Compound 23.

¹H-NMR (DMSO-d₆) δ: 0.84 (3H, t), 1.65-2.05 (2H, m), 2.11 (3H, s), 2.21 (3H, s), 2.25 (3H, s), 2.40 (4H, br), 3.01-3.08 (2H, m), 3.25-3.31 (1H, m), 3.49-3.60 (8H, m), 3.67-3.78 (1H, m), 3.92-3.98 (4H, m), 4.30 (2H, d), 5.58-5.66 (1H, m), 5.87 (1H, s), 6.05-6.13 (1H, m), 6.48-6.58 (1H, m), 7.33 (1H, s), 7.45-7.60 (4H, m), 8.20-8.28 (1H, br), 11.48 (1H, s).

m/z ESI M+H⁺ 630.3.

Example 24

Preparation of N-(4,6-dimethyl-2-oxo-1,2-dihydro-pyridin-3-ylmethyl)-5-[(1-acryloyl-pyrrolidin-3-yl)-ethyl-amino]-4'-(morpholin-4-yl)-4-methyl-biphenyl-3-carboxamide

24

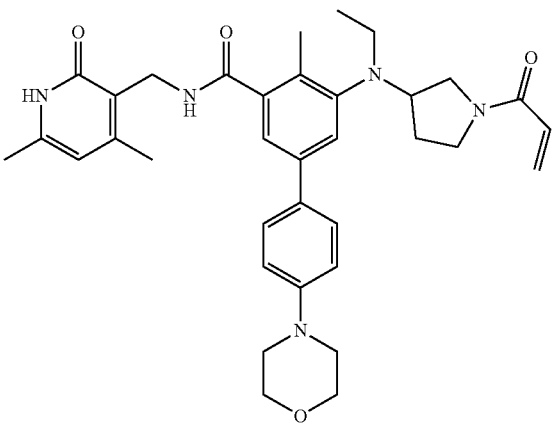

The preparation method was the same as steps 4 and 5 of Example 21, except that 4-(morpholin-4-yl)-bromobenzene was used instead of 4-(morpholin-4-ylmethyl)-4-bromo-2-chlorobenzene to give Compound 24.

¹H-NMR (CDCl₃) δ: 0.89 (3H, t), 1.65-1.93 (1H, m), 1.98-2.03 (1H, m), 2.16 (3H, s), 2.35 (3H, s), 2.42 (3H, s), 3.03-3.08 (2H, m), 3.15-3.55 (6H, m), 3.65-3.95 (7H, m), 4.57 (2H, d), 5.61-5.69 (1H, m), 5.92 (1H, s), 6.32-6.42 (2H, m), 6.91-6.97 (1H, t), 7.10-7.25 (2H, m), 7.32-7.48 (4H, m), 11.95 (1H, br).

m/z ESI M+H⁺ 598.3.

Example 25

Preparation of N-(4,6-dimethyl-2-oxo-1,2-dihydro-pyridin-3-ylmethyl)-5-[(1-acryloyl-pyrrolidin-3-yl)-ethyl-amino]-4'-(4-methyl-piperazin-1-yl)-4-methyl-biphenyl-3-carboxamide

25

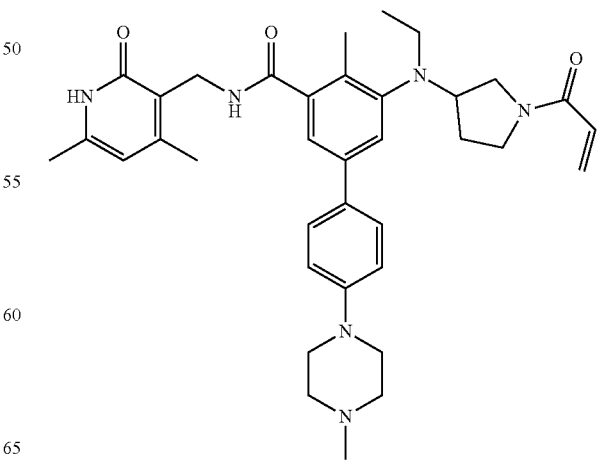

The preparation method was the same as Example 24, except that 4-(4-methyl-piperazin-1-yl)-bromobenzene was used instead of 4-(morpholin-4-yl)-bromobenzene to give Compound 25.

¹H-NMR (CDCl₃) δ: 0.88 (3H, t), 1.69-2.05 (2H, m), 2.16 (3H, s), 2.37 (3H, s), 2.43 (3H, s), 2.62 (3H, s), 2.94 (4H, br), 3.03-3.08 (2H, m), 3.28-3.55 (6H, m), 3.65-3.95 (3H, m), 4.56 (2H, d), 5.61-5.69 (1H, m), 5.95 (1H, s), 6.32-6.42 (2H, m), 6.77 (1H, d), 6.88 (1H, d), 7.30-7.45 (5H, m), 12.20 (1H, br).

m/z ESI M+H⁺ 611.5.

Example 26

Preparation of N-(4,6-dimethyl-2-oxo-1,2-dihydro-pyridin-3-ylmethyl)-2-methyl-3-[(1-acryloyl-pyrrolidin-3-yl)-ethyl-amino]-5-(6-ethoxy-pyrimidin-4-yl)-benzamide

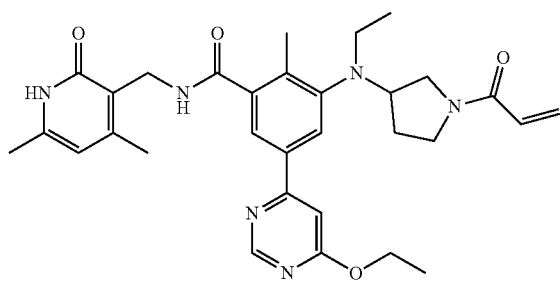

26

Step 1: Preparation of tert-butyl 3-{[3-ethoxycarbonyl-2-methyl-5-(4,4,5,5-tetramethyl-[1,3,2]-dioxaborolan-2-yl)-phenyl]-ethyl-amino}-pyrrolidin-1-ylcarboxylate (26a)

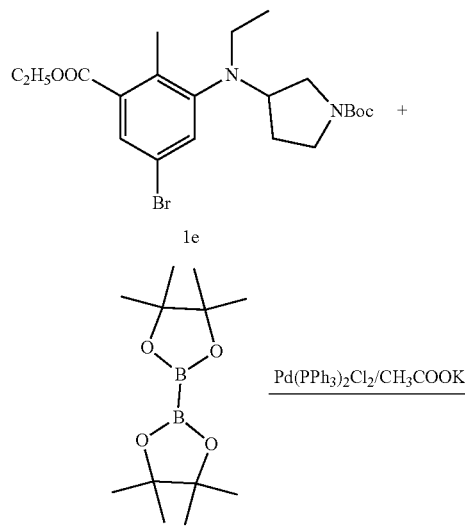

Tert-butyl 3-[(5-bromo-3-ethoxycarbonyl-2-methyl-phenyl)-ethyl-amino]-pyrrolidin-1-ylcarboxylate (1e) (1.6 g, 3.5 mmol), bis(pinacolato)diboron (1.34 g, 5.3 mmol), potassium acetate (1 g, 10.5 mmol) and bis(triphenylphosphine)palladium dichloride (0.25 g, 0.35 mmol) were added to 20 mL of dioxane. The mixture was stirred at 85° C. for 4 hours under a nitrogen atmosphere. The reaction solution was concentrated under reduced pressure, and then extracted with water and ethyl acetate. The organic phase was dried over anhydrous sodium sulfate and filtered. The filtrate was concentrated under reduced pressure. The residues were purified by column chromatography (eluent: petroleum ether:ethyl acetate 40:1~3:1) to give 1.7 g of the title product.

Step 2: Preparation of Ethyl 2-methyl-3-[(1-boc-pyrrolidin-3-yl)-ethyl-amino]-5-(6-chloro-pyrimidin-4-yl)-benzoate (26b)

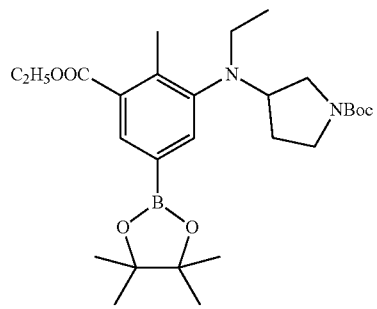

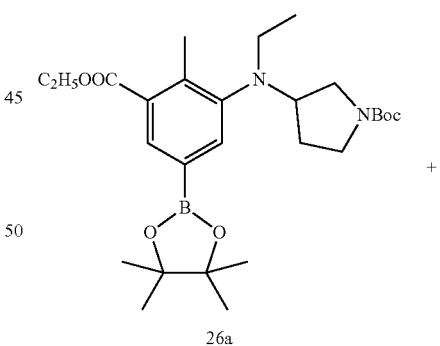

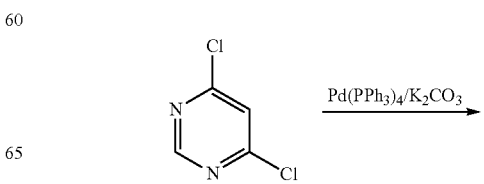

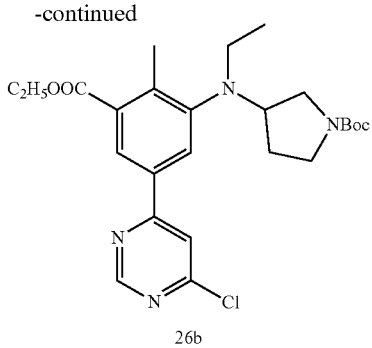

26b

Tert-butyl 3-{[3-ethoxycarbonyl-2-methyl-5-(4,4,5,5-tetramethyl-[1,3,2]dioxaborolan-2-yl)-phenyl]-ethyl-amino}-pyrrolidin-1-ylcarboxylate (1.7 g, 3.4 mmol), 4,6-dichloropyrimidine (2 g, 13.5 mmol), tetrakistriphenylphosphine palladium (0.4 g, 0.34 mmol) and potassium carbonate (0.94 g, 6.8 mmol) were added to a mixed solvent of 30 mL of acetonitrile and 15 mL of water, and stirred at 85° C. for 1.5 hours under a nitrogen atmosphere. The reaction solution was concentrated under reduced pressure and extracted with water and ethyl acetate. The organic phase was dried over anhydrous sodium sulfate and filtered. The filtrate was concentrated under reduced pressure. The residues were purified by column chromatography (eluent: petroleum ether:ethyl acetate 40:1~3:1) to give 0.98 g of the title product.

Step 3: Preparation of 2-methyl-3-[(1-acryloyl-pyrrolidin-3-yl)-ethyl-amino]-5-(6-ethoxy-pyrimidin-4-yl)-benzoic acid (26c)

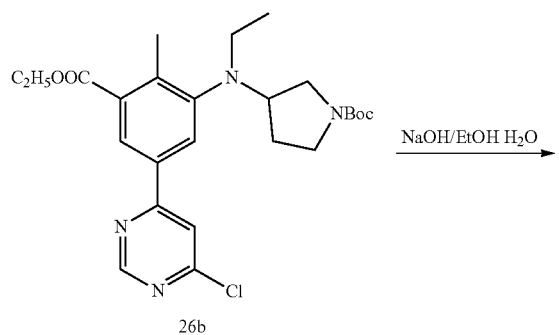

26b

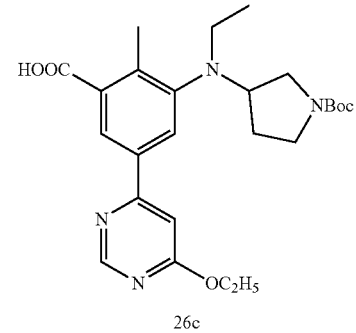

26c

Ethyl 2-methyl-3-[(1-Boc-pyrrolidin-3-yl)-ethyl-amino]-5-(6-chloro-pyrimidin-4-yl)-benzoate (1.3 g, 2.66 mmol) and sodium hydroxide (0.32 g, 8 mmol) were added to a mixed solvent of 15 mL of ethanol and 5 mL of water, and stirred at room temperature for 20 hours and then refluxed for 3 hours. The reaction mixture was concentrated under reduced pressure, and then adjusted to an acidic PH with 1M aqueous solution of citric acid, and extracted with ethyl acetate. The organic phase was dried over anhydrous sodium sulfate and filtered. The filtrate was concentrated under reduced pressure to give 1.17 g of title product.

The remaining steps were the same as in Example 1, except that Compound 26c was used instead of Compound 1f to give Compound 26.

$^1$H-NMR (DMSO-$d_6$) δ: 0.84 (3H, t), 1.37 (3H, t), 1.69-1.98 (2H, m), 2.12 (3H, s), 2.22 (3H, s), 2.27 (3H, s), 2.98-3.08 (2H, m), 3.25-3.31 (1H, m), 3.49-3.58 (2H, m), 3.68-3.76 (1H, m), 3.92-3.98 (1H, m), 4.31 (2H, d), 4.44 (2H, m), 5.57-5.67 (1H, m), 5.87 (1H, s), 6.07-6.13 (1H, m), 6.46-6.59 (1H, m), 7.55 (1H, d), 7.84 (1H, d), 8.04 (1H, s), 8.25 (1H, t), 8.83 (1H, s), 11.49 (1H, s).

m/z ESI M+H$^+$ 559.2.

Example 27

Preparation of N-(4,6-dimethyl-2-oxo-1,2-dihydro-pyridin-3-ylmethyl)-2-methyl-3-[1(1-acryloyl-pyrrolidin-3)-yl)-ethyl-amino]-5-[6-(4-methyl-piperazin-1-yl)-pyrimidin-4-yl]-benzamide

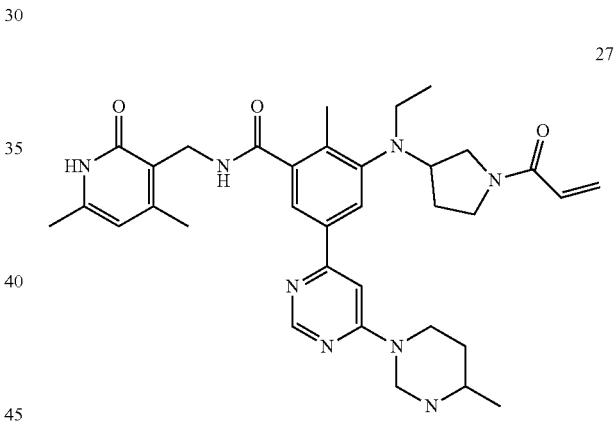

27

Step 1: Preparation of ethyl 2-methyl-3-[(1-Boc-pyrrolidin-3-yl)-ethyl-amino]-5-[6-(4-methyl-piperazin-1-yl)-pyrimidin-4-yl]-benzoate (27a)

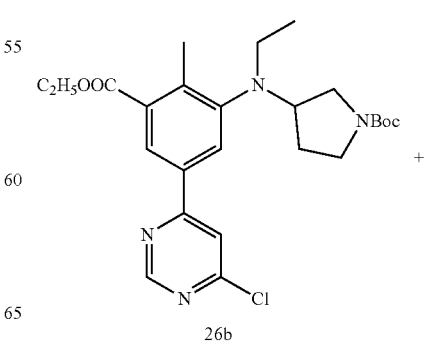

26b

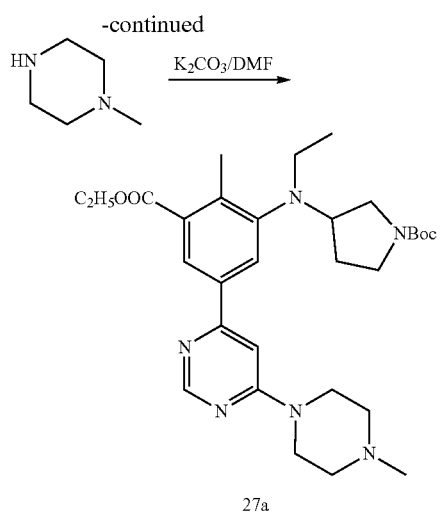

Ethyl 2-methyl-3-[(1-Boc-pyrrolidin-3-yl)-ethyl-amino]-5-(6-chloro-pyrimidin-4-yl)-benzoate (26b) (0.72 g, 1.5 mmol), N-methyl-piperazine (0.22 g, 2.2 mmol) and potassium carbonate (0.42 g, 3 mmol) were dissolved in 10 mL of DMF and stirred at 60° C. for 2 hours. The reaction solution was extracted with water and ethyl acetate. The organic phase was dried over anhydrous sodium sulfate and filtered. The filtrate was concentrated under reduced pressure. The residues were purified by column chromatography (eluent: dichloromethane:methanol 100:1~25:1) to give 0.4 g of the title product.

The remaining steps were the same as in Example 1, except that Compound 27a was used instead of Compound 1e to give Compound 27.

$^1$H-NMR (DMSO-$d_6$) δ: 0.84 (3H, t), 1.71-2.03 (2H, m), 2.11 (3H, s), 2.22-2.26 (9H, t), 2.40 (4H, br), 2.98-3.08 (2H, m), 3.25-3.30 (1H, m), 3.49-3.58 (2H, m), 3.68-3.78 (5H, m), 3.88-3.92 (1H, m), 4.30 (2H, d), 5.57-5.67 (1H, m), 5.87 (1H, s), 6.05-6.12 (1H, m), 6.48-6.58 (1H, m), 7.30 (1H, s), 7.84 (1H, d), 8.04 (1H, d), 8.25 (1H, br), 8.56 (1H, s), 11.49 (1H, s).

m/z ESI M+H$^+$ 613.3.

Example 28

Preparation of N-(4,6-dimethyl-2-oxo-1,2-dihydro-pyridin-3-ylmethyl)-5-[(1-acryloyl-pyrrolidin-3-yl)-ethyl-amino]-4-methyl-thiophene-3-carboxamide

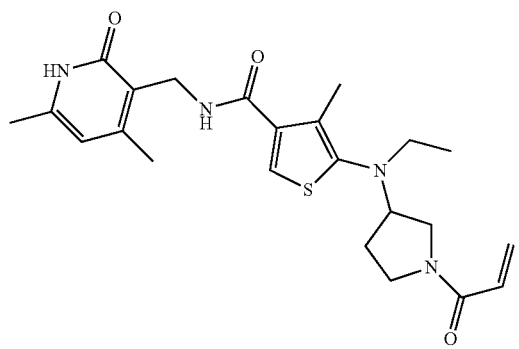

Step 1: Preparation of ethyl 2-amino-4-methylthiophene-3-carboxylate (28a)

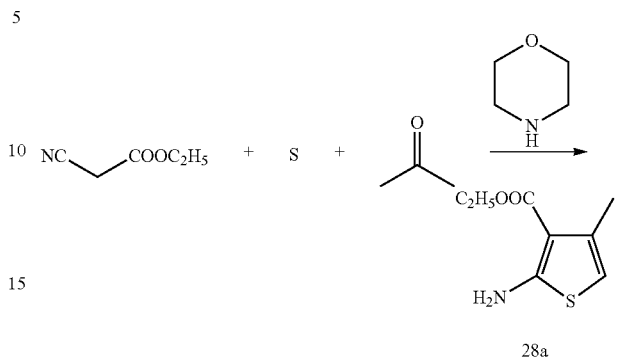

Ethyl cyanoacetate (30 g, 265 mmol), sulfur (8.5 g, 265 mmol), morpholine (34.63 g, 400 mmol) and acetone (15.37 g, 265 mmol) were added to 200 mL of ethanol and stirred at 50° C. for 24 hours. The reaction mixture was concentrated under reduced pressure, and the residues were purified by column chromatography (eluent: petroleum ether:ethyl acetate 50:1~5:1) to give 7.3 g of title product.

Step 2: Preparation of ethyl 2-iodo-4-methylthiophene-3-carboxylate (28b)

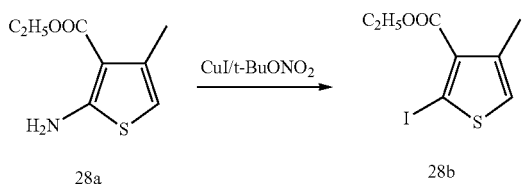

Ethyl 2-amino-4-methylthiophene-3-carboxylate (13 g, 70 mmol) was added to 300 ml suspension of cuprous iodide (26.7 g, 140 mmol) and tert-butyl nitrite (10.8 g, 105 mmol) in acetonitrile, and stirred for 4 hours. The insoluble material was filtered off, and the filtrate was concentrated under reduced pressure and then added with water and ethyl acetate. The organic phase was dried over anhydrous sodium sulfate and filtered. The filtrate was concentrated under reduced pressure. The residues were purified by column chromatography (eluent: petroleum ether:ethyl acetate 100:1~5:1) to give 1.5 g of the title product.

Step 3: Preparation of ethyl 2-iodo-5-nitro-4-methylthiophene-3-carboxylate (28c)

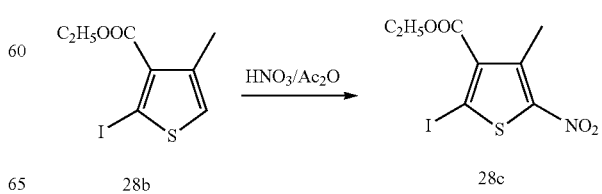

Ethyl 2-iodo-4-methylthiophene-3-carboxylate (1.37 g, 5.8 mmol) was dissolved in 20 mL of acetic anhydride, and added dropwise with 4 mL of nitric acid under an ice water bath, and then stirred for 2 hours. The reaction solution was poured into water and extracted with ethyl acetate. The organic layer was washed with sodium hydroxide until alkaline, and then dried over anhydrous sodium sulfate and filtered. The filtrate was concentrated under reduced pressure to give crude product which was used directly in the next step without purification.

Step 4: Preparation of ethyl 2-amino-3-methylthiophene-4-carboxylate (28d)

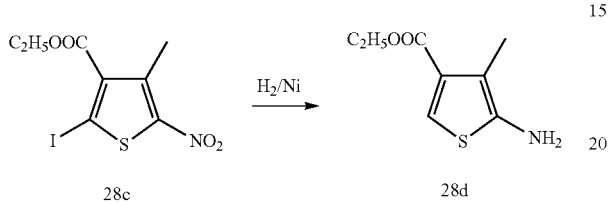

The crude ethyl 2-iodo-5-nitro-4-methylthiophene-3-carboxylate and raney nickel (1.6 g) were added to 35 mL of ethanol and stirred under a hydrogen atmosphere for 20 hours. The reaction solution was filtered, and the filtrate was concentrated under reduced pressure. The residues were purified by column chromatography (eluent: petroleum ether:ethyl acetate 50:1 to 5:1) to give 0.6 g of title product.

The remaining steps were the same as in Example 1, except that Compound 28d was used instead of Compound 1c to give Compound 28.

$^1$H-NMR (DMSO-d$_6$) δ: 0.86 (3H, t), 1.72-1.92 (1H, m), 1.96-2.05 (1H, m), 2.12 (3H, s), 2.13 (3H, s), 2.18 (3H, s), 2.82-2.95 (2H, m), 3.10-3.18 (1H, m), 3.45-3.75 (4H, m), 4.23 (2H, d), 5.60-5.68 (1H, m), 5.87 (1H, s), 6.08-6.14 (1H, m), 6.48-6.56 (1H, dd), 7.71 (1H, s), 8.01 (1H, br), 11.50 (1H, s).

m/z ESI M+H$^+$ 443.2.

Example 29

Preparation of N-(4,6-dimethyl-2-oxo-1,2-dihydropyridin-3-ylmethyl)-5-[(1-acryloyl-pyrrolidin-3-yl)-ethyl-amino]-4-methyl-4'-(pyrrolidin-1-ylmethyl)-[1, 1'-biphenyl]-3-carboxamide

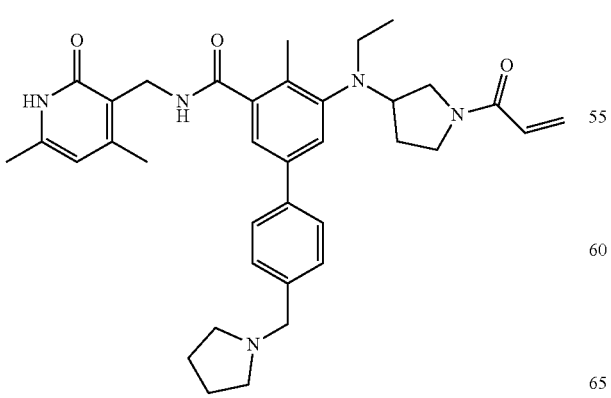

The preparation method was the same as Example 18, except that tetrahydropyrrole was used instead of piperidine to give Compound 29.

$^1$H-NMR (DMSO-d$_6$) δ: 0.84 (3H, t), 1.69-2.02 (6H, m), 2.11 (3H, s), 2.21 (3H, s), 2.25 (3H, s), 2.90-3.08 (6H, m), 3.25-3.31 (1H, m), 3.49-3.58 (2H, m), 3.68-3.78 (1H, m), 3.90-3.98 (1H, m), 4.15 (2H, s), 4.29 (2H, d), 5.57-5.65 (1H, m), 5.87 (1H, s), 6.07-6.13 (1H, m), 6.48-6.59 (1H, m), 7.31 (1H, d), 7.55 (1H, d), 7.58 (2H, d), 7.72 (2H, d), 8.25 (1H, t), 11.49 (1H, s).

m/z ESI M+H$^+$ 596.4.

Example 30

Preparation of N-(4,6-dimethyl-2-oxo-1,2-dihydropyridin-3-ylmethyl)-5-[(1-acryloyl-pyrrolidin-3-yl)-ethyl-amino]-4-methyl-3'-(morpholin-4-yl)-methyl-[1,1'-biphenyl]-3-carboxamide

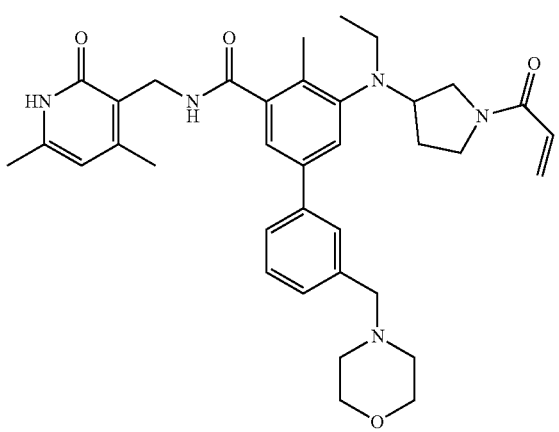

The preparation method was the same as Example 20, except that 3-hydroxymethylphenylboronic acid pinacol ester was used instead of 4-hydroxymethylphenylboronic acid pinacol ester to give Compound 30.

$^1$H-NMR (DMSO-d$_6$) δ: 0.85 (3H, t), 1.65-2.02 (2H, m), 2.11 (3H, s), 2.21 (3H, s), 2.25 (3H, s), 2.38 (4H, br), 3.01-3.08 (2H, m), 3.24-3.31 (1H, m), 3.50-3.81 (9H, m), 3.89-3.96 (1H, m), 4.30 (2H, d), 5.58-5.67 (1H, m), 5.87 (1H, s), 6.07-6.13 (1H, m), 6.48-6.58 (1H, m), 7.27-7.33 (2H, m), 7.42 (1H, t), 7.51-7.58 (3H, m), 8.25 (1H, t), 11.48 (1H, s).

m/z ESI M+H$^+$ 613.2.

Example 31

Preparation of N-(4,6-dimethyl-2-oxo-1,2-dihydro-pyridin-3-ylmethyl)-5-[(1-acryloyl-pyrrolidin-3-yl)-ethyl-amino]-4-methyl-3'-(piperidin-1-ylmethyl)-[1,1'-biphenyl]-3-carboxamide

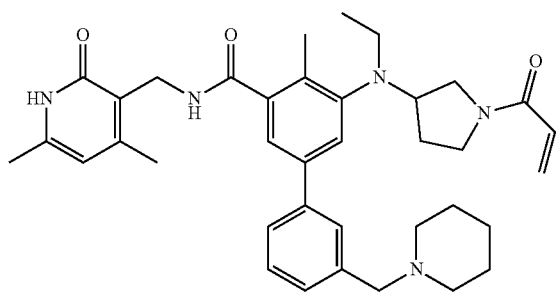

The preparation method was the same as Example 18, except that 3-hydroxymethylphenylboronic acid pinacol ester was used instead of 4-hydroxymethylphenylboronic acid pinacol ester to give Compound 31.

$^1$H-NMR (DMSO-d$_6$) δ: 0.85 (3H, t), 1.55-2.02 (8H, m), 2.11 (3H, s), 2.21 (3H, s), 2.25 (3H, s), 2.36-2.80 (4H, m), 3.01-3.08 (2H, m), 3.26-3.32 (1H, m), 3.50-4.02 (6H, m), 4.29 (2H, d), 5.58-5.67 (1H, m), 5.87 (1H, s), 6.07-6.13 (1H, m), 6.48-6.58 (1H, m), 7.32 (1H, d), 7.40-7.53 (2H, m), 7.56-7.75 (3H, m), 8.25 (1H, t), 11.49 (1H, s). Six hydrogens coincide with the solvent peak.

m/z ESI M+H$^+$ 610.3.

Example 32

Preparation of N-(4,6-dimethyl-2-oxo-1,2-dihydro-pyridin-3-ylmethyl)-5-[(1-acryloyl-pyrrolidin-3-yl)-ethyl-amino]-4-methyl-4'-(4-hydroxypiperidin-1-ylmethyl)-[1,1'-biphenyl]-3-carboxamide

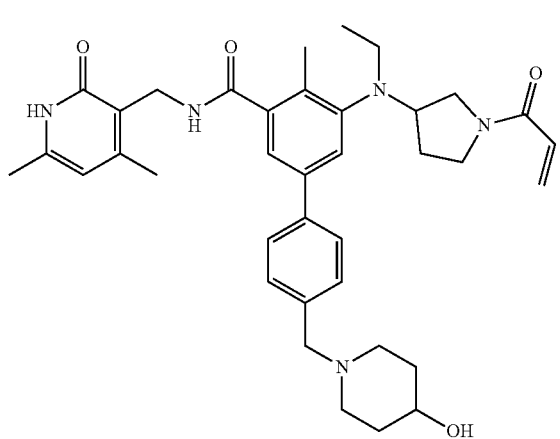

The preparation method was the same as Example 18, except that 4-hydroxypiperidine was used instead of piperidine to give Compound 32.

$^1$H-NMR (DMSO-d6) δ: 0.84 (3H, t), 1.60-2.05 (6H, m), 2.11 (3H, s), 2.21 (3H, s), 2.25 (3H, d), 2.84-3.15 (6H, m), 3.22-3.28 (1H, m), 3.48-3.81 (4H, m), 3.90-3.98 (1H, m), 4.20-4.32 (4H, m), 5.02 (1H, br), 5.58-5.67 (1H, m), 5.87 (1H, s), 6.06-6.13 (1H, m), 6.48-6.58 (1H, m), 7.32 (1H, s), 7.56 (1H, s), 7.73 (4H, br), 8.26 (1H, t), 10.97 (1H, br), 11.50 (1H, s).

m/z ESI M+H$^+$ 626.4.

Example 33

Preparation of N-(4,6-dimethyl-2-oxo-1,2-dihydro-pyridin-3-ylmethyl)-5-[(1-acryloyl-pyrrolidin-3-yl)-ethyl-amino]-4-methyl-4'-{[(2-hydroxyethyl)-methyl-amino]-methyl}-[1,1'-biphenyl]-3-carboxamide

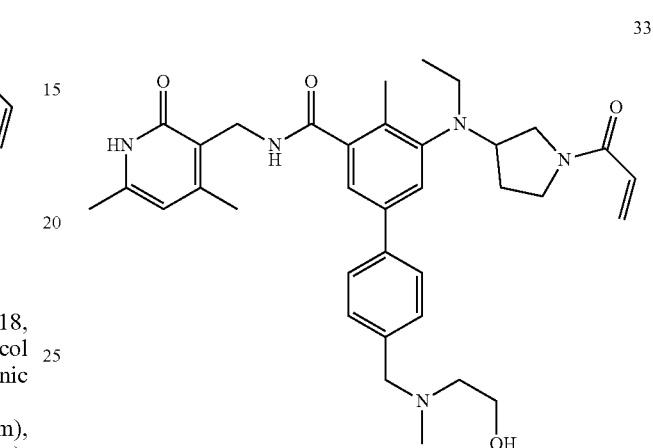

The preparation method was the same as Example 18, except that N-methyl-ethanolamine was used instead of piperidine to give Compound 33.

$^1$H-NMR (DMSO-d6) δ: 0.85 (3H, t), 1.60-2.05 (2H, m), 2.11 (3H, s), 2.21 (3H, s), 2.25 (3H, d), 2.37 (3H, s), 2.67 (2H, t), 2.97-3.07 (2H, m), 3.22-3.28 (1H, m), 3.48-3.81 (7H, m), 3.90-3.98 (1H, m), 4.29 (2H, d), 4.68 (1H, br), 5.58-5.67 (1H, m), 5.87 (1H, s), 6.06-6.13 (1H, m), 6.48-6.58 (1H, m), 7.30 (1H, s), 7.49-7.54 (3H, m), 7.67 (2H, d), 8.26 (1H, t), 11.49 (1H, s).

m/z ESI M+H$^+$ 600.3.

Example 34

Preparation of N-(4,6-dimethyl-2-oxo-1,2-dihydro-pyridin-3-ylmethyl)-5-[(1-acryloyl-piperidin-4-yl)-ethyl-amino]-4-methyl-4'-(piperidin-1-ylmethyl)-[1,1'-biphenyl]-3-carboxamide

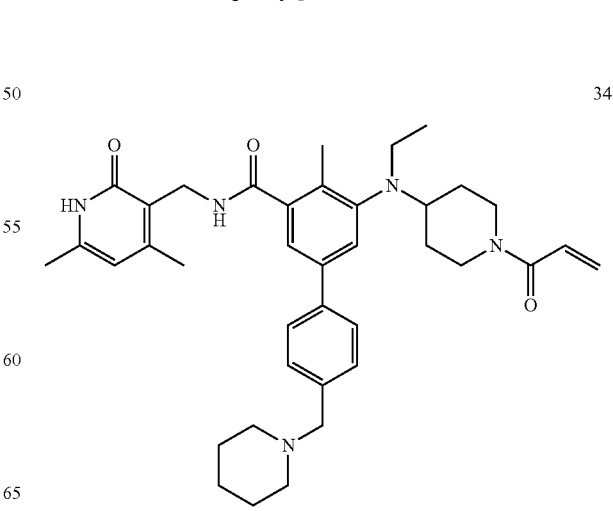

The preparation method was the same as Example 18, except that 1-Boc-4-piperidone was used instead of 1-Boc-3-pyrrolidone to give Compound 34.

¹H-NMR (DMSO-d6) δ: 0.84 (3H, t), 1.35-1.82 (10H, m), 2.11 (3H, s), 2.22 (3H, s), 2.26 (3H, s), 2.32 (1H, m), 2.41-2.80 (4H, m), 2.99-3.14 (4H, m), 3.63 (2H, s), 3.96-4.06 (1H, m), 4.27-4.41 (3H, m), 5.62-5.67 (1H, m), 5.87 (1H, s), 6.05-6.10 (1H, m), 6.75-6.82 (1H, m), 7.26 (1H, d), 7.43 (1H, d), 7.53 (2H, d), 7.67 (2H, d), 8.22 (1H, t), 11.48 (1H, s).

m/z ESI M+H⁺ 624.3.

Example 35

Preparation of N-(4,6-dimethyl-2-oxo-1,2-dihydro-pyridin-3-ylmethyl)-5-[(1-acryloyl-piperidin-4-yl)-ethyl-amino]-4-methyl-4'-(morpholin-4-ylmethyl)-[1,1'-biphenyl]-3-carboxamide

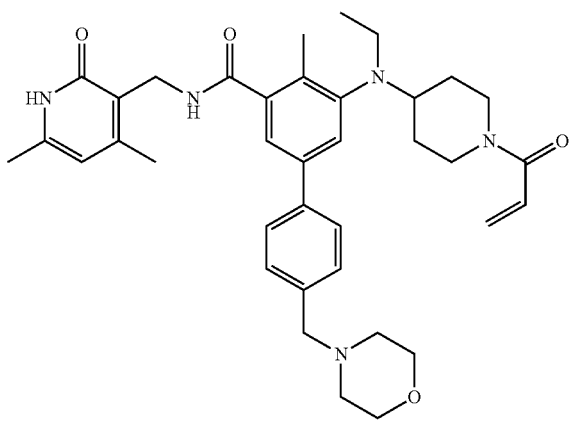

The preparation method was the same as Example 34, except that morpholine was used instead of piperidine to give Compound 35.

¹H-NMR (DMSO-d6) δ: 0.84 (3H, t), 1.35-1.48 (2H, m), 1.75-1.82 (2H, m), 2.11 (3H, s), 2.21 (3H, s), 2.25 (3H, s), 2.37 (4H, br), 2.61-2.71 (1H, m), 2.97-3.12 (4H, m), 3.49 (2H, s), 3.59 (4H, br), 3.97-4.05 (1H, m), 4.27-4.39 (3H, m), 5.62-5.66 (1H, m), 5.87 (1H, s), 6.05-6.10 (1H, m), 6.74-6.82 (1H, m), 7.23 (1H, d), 7.36-7.42 (3H, m), 7.59 (2H, d), 8.20 (1H, t), 11.47 (1H, s).

m/z ESI M+H⁺ 626.3.

Example 36

Preparation of N-(4,6-dimethyl-2-oxo-1,2-dihydro-pyridin-3-ylmethyl)-3-[(1-acryloyl-pyrrolidin-3-yl)-ethyl-amino]-2-methyl-5-[6-(morpholin-4-yl)-pyrimidin-4-yl]-benzamide

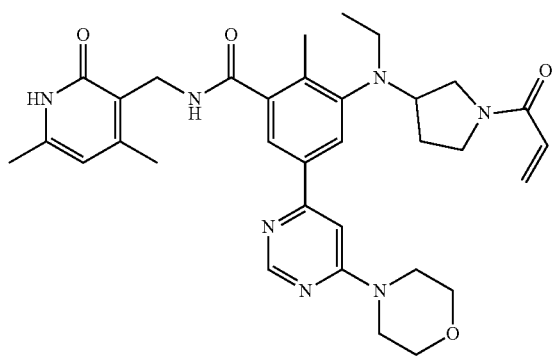

The preparation method was the same as Example 27, except that morpholine was used instead of N-methyl-piperazine to give Compound 36.

¹H-NMR (DMSO-d6) δ: 0.84 (3H, t), 1.65-2.02 (2H, m), 2.11 (3H, s), 2.22 (3H, s), 2.25 (3H, s), 3.01-3.08 (2H, m), 3.25-3.31 (1H, m), 3.49-3.57 (2H, m), 3.58-3.65 (1H, m), 3.71 (8H, s), 3.86-3.95 (1H, m), 4.30 (2H, d), 5.57-5.66 (1H, m), 5.87 (1H, s), 6.05-6.13 (1H, m), 6.50-6.58 (1H, m), 7.31 (1H, d), 7.84 (1H, d), 8.03 (1H, s), 8.22 (1H, t), 8.59 (1H, s), 11.48 (1H, s).

m/z ESI M+H⁺ 600.3.

Example 37

Preparation of N-(4,6-dimethyl-2-oxo-1,2-dihydro-pyridin-3-ylmethyl)-3-[(1-acryloyl-pyrrolidin-3-yl)-ethyl-amino]-2-methyl-5-[2-(morpholin-4-yl)-pyrimidin-4-yl]-benzamide

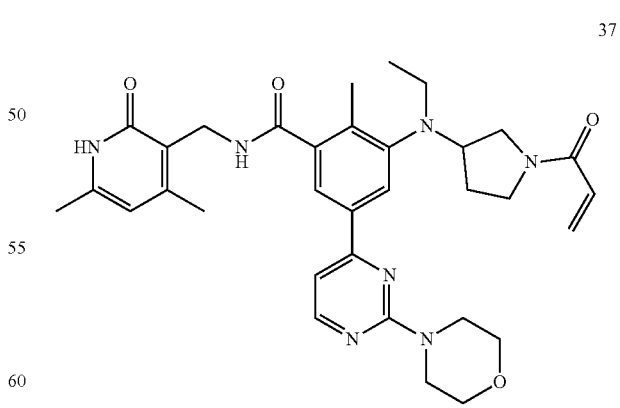

The preparation method was the same as Example 36, except that 2,4-dichloropyrimidine was used instead of 4,6-dichloropyrimidine to give Compound 37.

¹H-NMR (DMSO-d6) δ: 0.84 (3H, t), 1.65-2.02 (2H, m), 2.11 (3H, s), 2.21 (3H, s), 2.25 (3H, s), 3.01-3.08 (2H, m), 3.24-3.31 (1H, m), 3.49-3.58 (2H, m), 3.67-3.78 (9H, m), 3.88-3.95 (1H, m), 4.29 (2H, d), 5.57-5.67 (1H, m), 5.87 (1H, s), 6.05-6.11 (1H, m), 6.48-6.58 (1H, m), 7.28 (1H, t), 7.77 (1H, d), 7.95 (1H, d), 8.25 (1H, t), 8.44 (1H, d), 11.48 (1H, s).

m/z ESI M+H$^+$ 600.3.

Example 38

Preparation of N-(4,6-dimethyl-2-oxo-1,2-dihydro-pyridin-3-ylmethyl)-3-[(1-acryloyl-pyrrolidin-3-yl)-ethyl-amino]-2-methyl-5-[2-(4-methyl-piperazin-1-yl)-pyrimidin-4-yl]-benzamide

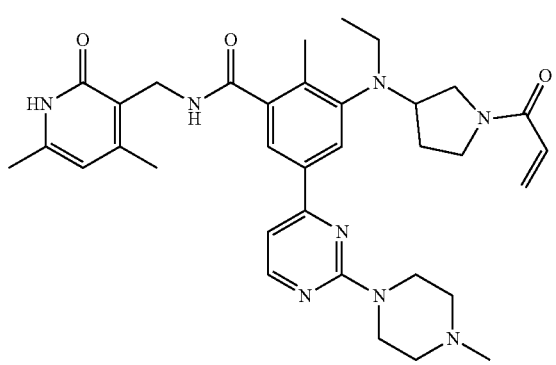

38

The preparation method was the same as Example 27, except that 2,4-dichloropyrimidine was used instead of 4,6-dichloropyrimidine to give Compound 38.

$^1$H-NMR (DMSO-d6) δ: 0.83 (3H, t), 1.65-2.02 (2H, m), 2.12 (3H, s), 2.22 (3H, s), 2.26 (3H, s), 2.32 (3H, s), 2.55 (4H, br), 2.99-3.08 (2H, m), 3.24-3.31 (1H, m), 3.50-3.57 (2H, m), 3.65-3.98 (7H, m), 4.30 (2H, d), 5.58-5.67 (1H, m), 5.88 (1H, s), 6.07-6.13 (1H, m), 6.48-6.58 (1H, m), 7.27 (1H, t), 7.77 (1H, d), 7.94 (1H, d), 8.27 (1H, t), 8.43 (1H, d), 11.50 (1H, s).

m/z ESI M+H$^+$ 613.2.

Example 39

Preparation of N-(4,6-dimethyl-2-oxo-1,2-dihydro-pyridin-3-ylmethyl)-5-[(1-acryloyl-pyrrolidin-3-yl)-ethyl-amino]-4-methyl-4'-(morpholin-4-ylformyl)-[1,1'-biphenyl]-3-carboxamide

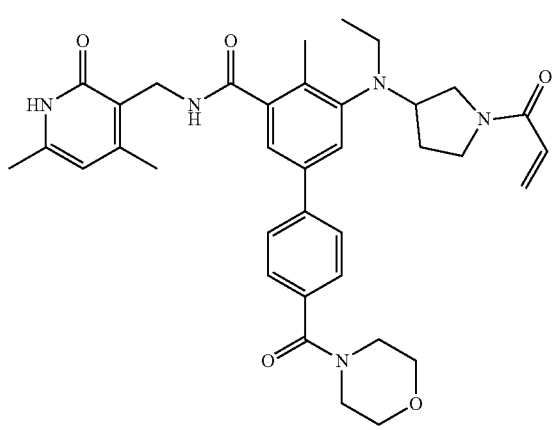

39

Step 1: Preparation of 4-bromobenzoylmorpholine

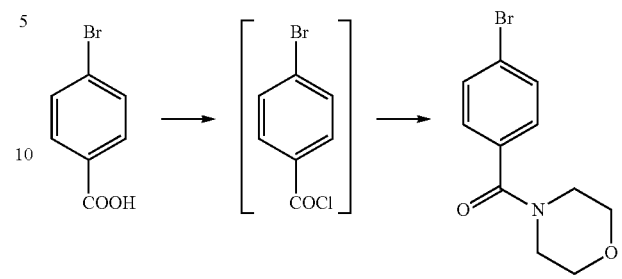

4-Bromobenzoic acid (2 g, 10 mmol) was suspended in 20 mL of dichloromethane, and added with oxalyl chloride (2.55 g, 20 mmol) and 1 drop of DMF. The mixture was refluxed for 1 hour. The dichloromethane and oxalyl chloride were removed under reduced pressure, and the residues were dissolved in 20 ml of dichloromethane. Morpholine (2.61 g, 30 mmol) was added under an ice water bath and stirred for 30 minutes. The reaction solution was added with water and dichloromethane. The dichloromethane phase was purified by column chromatography (eluent: petroleum ether:ethyl acetate 20:1 to 2:1) to give 1.9 g of 4-bromobenzoylmorpholine.

Step 2: Preparation of ethyl 5-[(1-Boc-pyrrolidin-3-yl)-ethyl-amino]-4-methyl-4'-(morpholin-4-ylformyl)-[1,1'-biphenyl]-3-carboxylate

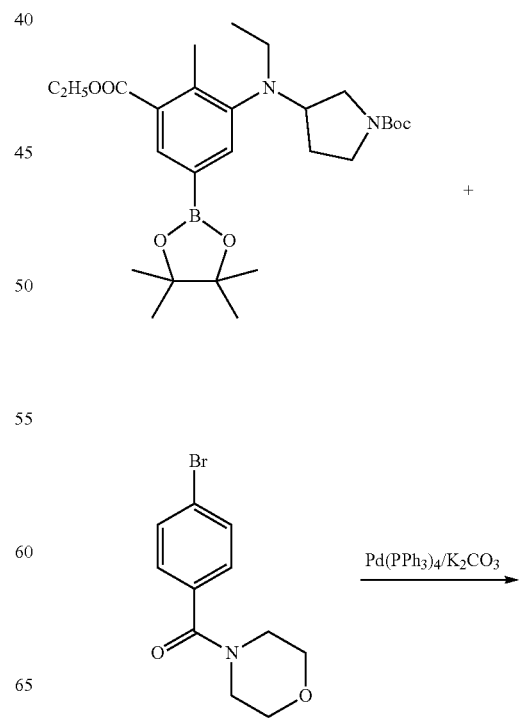

-continued

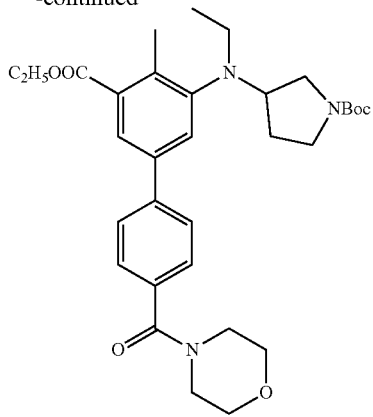

39a

Tert-butyl 3-{[3-ethoxycarbonyl-2-methyl-5-(4,4,5,5-tetramethyl-[1,3,2]dioxaborolan-2-yl)-phenyl]-ethyl-amino}-pyrrolidin-1-ylcarboxylate 26a (0.35 g, 0.7 mmol), 4-bromobenzoylmorpholine (0.17 g, 0.63 mmol), Pd(PPh$_3$)$_4$ (0.08 g, 0.07 mmol) and potassium carbonate (0.19 g, 1.4 mmol) were added to 15 mL of acetonitrile and 5 mL of water. The reaction mixture was refluxed for 18 hours under nitrogen atmosphere. The reaction solution was concentrated under reduced pressure, and the residues were purified by column chromatography (eluent: petroleum ether:ethyl acetate 20:1~1:1) to give 0.32 g of title product.

The remaining steps were the same as in Example 27, except that Compound 39a was used instead of Compound 27a to give Compound 39.

$^1$H-NMR (DMSO-d6) δ: 0.84 (3H, t), 1.65-2.02 (2H, m), 2.11 (3H, s), 2.22 (3H, s), 2.26 (3H, s), 2.99-3.12 (2H, m), 3.25-3.31 (1H, m), 3.41-3.81 (10H, m), 3.92-3.98 (1H, m), 4.30 (2H, d), 5.58-5.65 (1H, m), 5.87 (1H, s), 6.05-6.12 (1H, m), 6.48-6.58 (1H, m), 7.33 (1H, d), 7.50 (2H, d), 7.57 (1H, d), 7.75 (2H, d), 8.25 (1H, t), 11.49 (1H, s).

m/z ESI M+H$^+$ 626.2.

Example 40

Preparation of N-(4,6-dimethyl-2-oxo-1,2-dihydropyridin-3-ylmethyl)-5-[(1-acryloyl-pyrrolidin-3-yl)-ethyl-amino]-4-methyl-3'-(morpholin-4-ylformyl)-[1,1'-biphenyl]-3-carboxamide

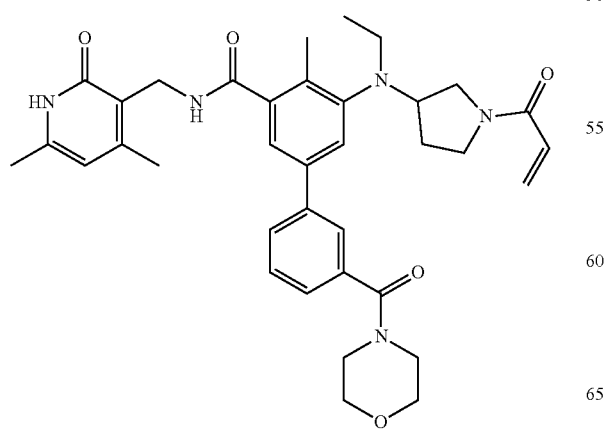

40

The preparation method was the same as Example 39, except that 3-bromobenzoic acid was used instead of 4-bromobenzoic acid to give Compound 40.

$^1$H-NMR (DMSO-d6) δ: 0.84 (3H, t), 1.65-2.02 (2H, m), 2.11 (3H, s), 2.22 (3H, s), 2.26 (3H, s), 3.01-3.08 (2H, m), 3.25-3.31 (1H, m), 3.42-3.80 (11H, m), 3.92-3.98 (1H, m), 4.30 (2H, d), 5.57-5.66 (1H, m), 5.87 (1H, s), 6.07-6.13 (1H, m), 6.50-6.58 (1H, m), 7.31 (1H, t), 7.39 (1H, d), 7.51-7.58 (2H, m), 7.67-7.70 (1H, m), 7.73-7.78 (1H, m), 8.25 (1H, t), 11.48 (1H, s).

m/z ESI M+H$^+$ 626.2.

Example 41

Preparation of N-(4,6-dimethyl-2-oxo-1,2-dihydropyridin-3-ylmethyl)-5-[(1-acryloyl-pyrrolidin-3-yl)-ethyl-amino]-4-methyl-4'-(4-methyl-piperazin-1-ylformyl)-[1,1'-biphenyl]-3-carboxamide

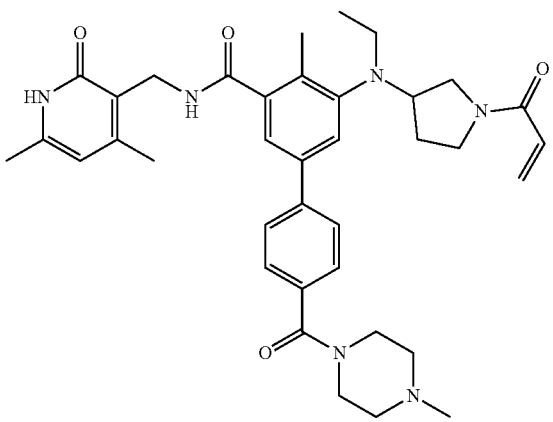

41

The preparation method was the same as Example 39, except that N-methyl-piperazine was used instead of morpholine to give Compound 41.

$^1$H-NMR (DMSO-d6) δ: 0.84 (3H, t), 1.65-2.02 (2H, m), 2.11 (3H, s), 2.21 (6H, s), 2.25-2.43 (7H, m), 3.01-3.08 (2H, m), 3.24-3.31 (1H, m), 3.45-3.80 (7H, m), 3.95-3.99 (1H, m), 4.30 (2H, d), 5.57-5.67 (1H, m), 5.87 (1H, s), 6.07-6.12 (1H, m), 6.50-6.58 (1H, m), 7.32 (1H, d), 7.45-7.58 (2H, d), 7.57 (1H, d), 7.74 (2H, d), 8.25 (1H, t), 11.48 (1H, s).

m/z ESI M+H$^+$ 639.2.

Example 42

Preparation of N-(4,6-dimethyl-2-oxo-1,2-dihydro-pyridin-3-ylmethyl)-5-[(1-acryloyl-pyrrolidin-3-yl)-ethyl-amino]-4-methyl-3'-(4-methyl-piperazin-1-ylformyl)-[1,1'-biphenyl]-3-carboxamide

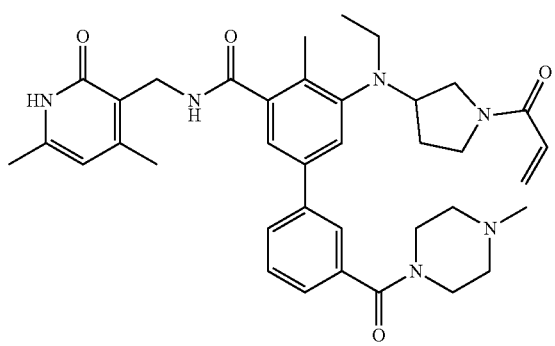

42

The preparation method was the same as Example 41, except that 3-bromobenzoic acid was used instead of 4-bromobenzoic acid to give Compound 42.

¹H-NMR (DMSO-d6) δ: 0.85 (3H, t), 1.65-2.02 (2H, m), 2.11 (3H, s), 2.21 (6H, d), 2.26 (3H, s), 2.38 (4H, br), 3.01-3.08 (2H, m), 3.26-3.32 (1H, m), 3.50-3.81 (7H, m), 3.91-3.98 (1H, m), 4.30 (2H, d), 5.58-5.67 (1H, m), 5.87 (1H, s), 6.07-6.13 (1H, m), 6.48-6.58 (1H, m), 7.31-7.38 (2H, m), 7.50-7.57 (2H, m), 7.64 (1H, d), 7.76 (1H, m), 8.25 (1H, t), 11.49 (1H, s).

m/z ESI M+H⁺ 639.2.

Example 43

Preparation of N-(4,6-dimethyl-2-oxo-1,2-dihydro-pyridin-3-ylmethyl)-5-[(1-acryloyl-pyrrolidin-3-yl)-ethyl-amino]-4'-(morpholin-4-ylformyl)-3'-chloro-4-methyl-[1,1'-biphenyl]-3-carboxamide

43

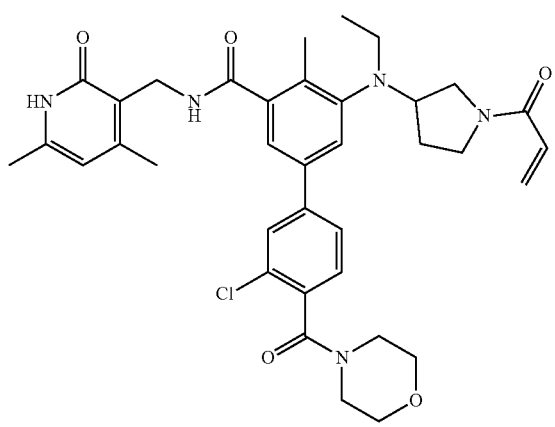

The preparation method was the same as Example 39, except that 2-chloro-4-bromobenzoic acid was used instead of 4-bromobenzoic acid to give Compound 43.

¹H-NMR (DMSO-d6) δ: 0.84 (3H, t), 1.65-2.02 (2H, m), 2.11 (3H, s), 2.22 (3H, s), 2.26 (3H, s), 2.34 (3H, s), 3.01-3.08 (2H, m), 3.19 (2H, br), 3.26-3.32 (1H, m), 3.48-3.58 (4H, m), 3.62-3.80 (5H, m), 3.93-4.01 (1H, m), 4.29 (2H, d), 5.58-5.67 (1H, m), 5.87 (1H, s), 6.06-6.13 (1H, m), 6.48-6.58 (1H, m), 7.35 (1H, s), 7.47 (1H, d), 7.62 (1H, s), 7.72-7.78 (1H, m), 7.86 (1H, m), 8.24 (1H, t), 11.49 (1H, s).

m/z ESI M+H⁺ 660.2.

Example 44

Preparation of N-(4,6-dimethyl-2-oxo-1,2-dihydro-pyridin-3-ylmethyl)-5-[(1-acryloyl-pyrrolidin-3-yl)-ethyl-amino]-4'-(4-methyl-piperazin-1-ylformyl)-3'-chloro-4-methyl-[1,1'-biphenyl]-3-carboxamide

44

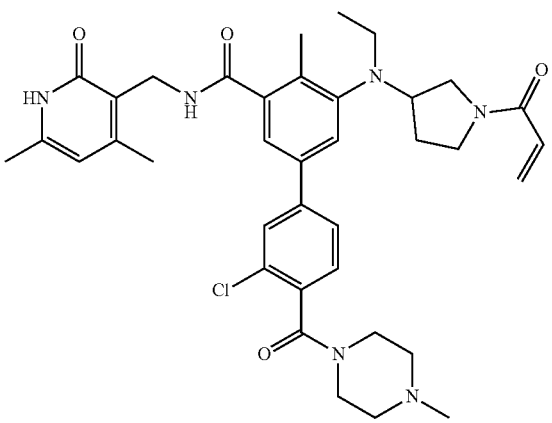

The preparation method was the same as Example 41, except that 2-chloro-4-bromobenzoic acid was used instead of 4-bromobenzoic acid to give Compound 44.

¹H-NMR (DMSO-d6) δ: 0.84 (3H, t), 1.65-2.02 (2H, m), 2.11 (3H, s), 2.22 (6H, d), 2.26-2.40 (7H, m), 3.01-3.08 (2H, m), 3.17 (2H, br), 3.26-3.32 (1H, m), 3.48-3.75 (5H, m), 3.93-4.02 (1H, m), 4.30 (2H, d), 5.58-5.67 (1H, m), 5.87 (1H, s), 6.06-6.13 (1H, m), 6.48-6.58 (1H, m), 7.35 (1H, s), 7.43 (1H, d), 7.62 (1H, s), 7.70-7.75 (1H, m), 7.85 (1H, m), 8.28 (1H, t), 11.49 (1H, s).

m/z ESI M/2+H⁺ 337.2.

Example 45

Preparation of N-(4,6-dimethyl-2-oxo-1,2-dihydropyridin-3-ylmethyl)-5-[(1-acryloyl-pyrrolidin-3-yl)-ethyl-amino]-4-methyl-4'-(morpholin-4-ylsulfonyl)-[1,1'-biphenyl]-3-carboxamide

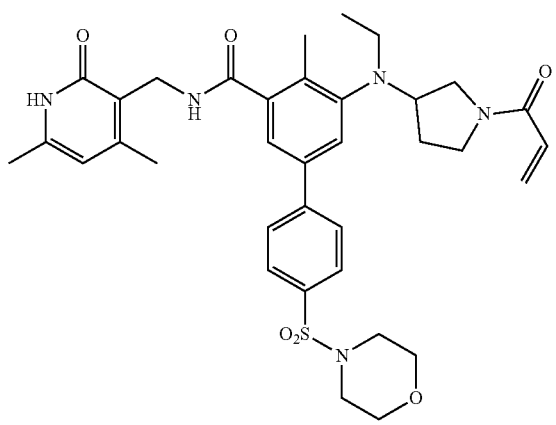

45

The preparation method was the same as Example 39, except that 4-bromobenzenesulfonyl chloride was used instead of 4-bromobenzoic acid to give Compound 45.

¹H-NMR (DMSO-d6) δ: 0.85 (3H, t), 1.65-2.05 (2H, m), 2.12 (3H, s), 2.22 (3H, s), 2.27 (3H, s), 2.90 (4H, br), 3.02-3.07 (2H, m), 3.25-3.33 (1H, m), 3.50-3.81 (7H, m), 3.90-3.98 (1H, m), 4.31 (2H, d), 5.58-5.67 (1H, m), 5.87 (1H, s), 6.06-6.13 (1H, m), 6.48-6.58 (1H, m), 7.40 (1H, d), 7.66 (1H, d), 7.79 (2H, d), 7.97 (2H, d), 8.30 (1H, t), 11.54 (1H, s).
m/z ESI M+H⁺ 662.3.

Example 46

Preparation of N-(4,6-dimethyl-2-oxo-1,2-dihydropyridin-3-ylmethyl)-5-[(1-acryloyl-pyrrolidin-3-yl)-ethyl-amino]-4-methyl-4'-(4-methyl-piperazin-1-ylsulfonyl)-[1,1'-biphenyl]-3-carboxamide

46

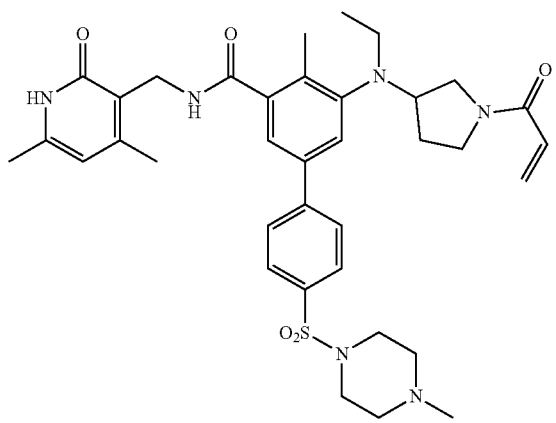

The preparation method was the same as Example 45, except that N-methyl-piperazine was used instead of morpholine to give Compound 46.

¹H-NMR (DMSO-d6) δ: 0.85 (3H, t), 1.65-2.05 (2H, m), 2.11 (3H, s), 2.14 (3H, s), 2.21 (3H, s), 2.26 (3H, s), 2.37 (4H, br), 2.91 (4H, br), 3.02-3.07 (2H, m), 3.25-3.33 (1H, m), 3.50-3.55 (2H, m), 3.68-3.81 (1H, m), 3.91-3.98 (1H, m), 4.29 (2H, d), 5.58-5.67 (1H, m), 5.87 (1H, s), 6.06-6.13 (1H, m), 6.48-6.58 (1H, m), 7.38 (1H, d), 7.64 (1H, d), 7.78 (2H, d), 7.96 (2H, m), 8.29 (1H, t), 11.53 (1H, s).
m/z ESI M+H⁺ 675.3.

Example 47

Preparation of N-(4,6-dimethyl-2-oxo-1,2-dihydropyridin-3-ylmethyl)-5-[(1-acryloyl-pyrrolidin-3-yl)-ethyl-amino]-4-methyl-4'-(2-dimethylaminoethoxy)-[1,1'-biphenyl]-3-carboxamide

47

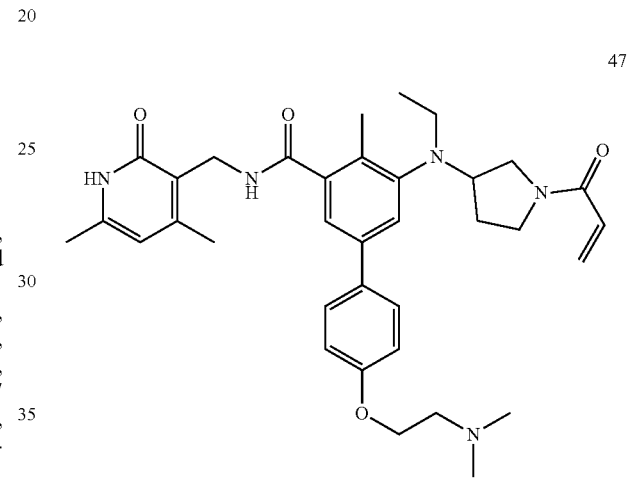

Step 1: Preparation of [2-(4-bromophenoxy)-ethyl]-dimethylamine

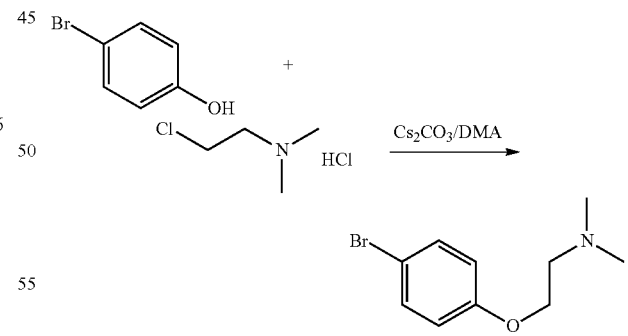

4-Bromophenol (1 g, 5.8 mmol), (2-chloroethyl) dimethylamine hydrochloride (1.25 g, 8.7 mmol) and cesium carbonate (5.67 g, 17.4 mmol) were added to 5 mL of DMA, and then heated to 90° C. for 2 hours. After cooling to room temperature, ethyl acetate and water were added to the reaction mixture for extraction. The organic layer was dried over anhydrous sodium sulfate and filtered. The filtrate was concentrated under reduced pressure to give 1.3 g of title product.

The remaining steps were the same as in Example 39, except that [2-(4-bromophenoxy)-ethyl]-dimethylamine was used instead of 4-bromobenzoylmorpholine to give Compound 47.

¹H-NMR (DMSO-d6) δ: 0.84 (3H, t), 1.65-2.05 (2H, m), 2.11 (3H, s), 2.21 (3H, d), 2.23 (3H, s), 2.34 (6H, s), 2.80 (2H, t), 2.96-3.04 (2H, m), 3.22-3.31 (1H, m), 3.48-3.55 (2H, m), 3.68-3.76 (1H, m), 3.88-3.97 (1H, m), 4.14 (2H, t), 4.29 (2H, d), 5.58-5.66 (1H, m), 5.87 (1H, s), 6.06-6.13 (1H, m), 6.48-6.58 (1H, m), 7.03 (2H, d), 7.24 (1H, s), 7.47 (1H, s), 7.56-7.62 (2H, m), 8.24 (1H, t), 11.49 (1H, s).

m/z ESI M+H⁺ 600.4.

Example 48

Preparation of N-(4,6-dimethyl-2-oxo-1,2-dihydro-pyridin-3-ylmethyl)-5-[(1-acryloyl-pyrrolidin-3-yl)-ethyl-amino]-4-methyl-4'-[2-(morpholin-4-yl)-ethoxy]-[1,1'-biphenyl]-3-carboxamide

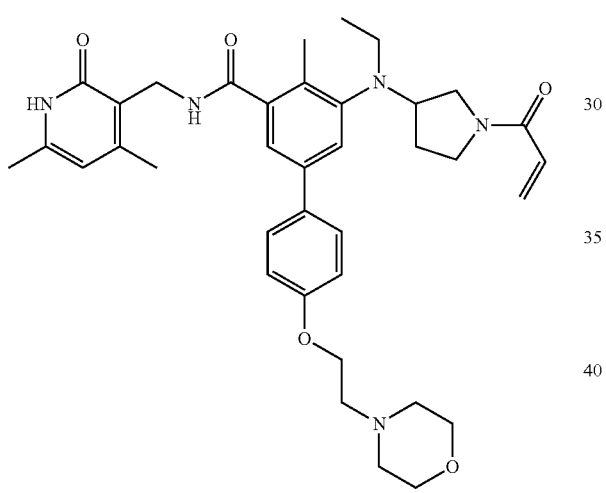

48

The preparation method was the same as Example 47, except that N-(2-chloroethyl)-morpholine hydrochloride was used instead of (2-chloroethyl) dimethylamine hydrochloride to give Compound 48.

¹H-NMR (DMSO-d6) δ: 0.84 (3H, t), 1.65-2.05 (2H, m), 2.11 (3H, s), 2.21 (3H, s), 2.23 (3H, s), 2.47 (4H, br), 2.70 (2H, t), 2.99-3.05 (2H, m), 3.22-3.31 (1H, m), 3.48-3.61 (6H, m), 3.67-3.77 (1H, m), 3.88-3.97 (1H, m), 4.12 (2H, t), 4.29 (2H, d), 5.58-5.66 (1H, m), 5.87 (1H, s), 6.06-6.13 (1H, m), 6.47-6.59 (1H, m), 7.02 (2H, d), 7.23 (1H, s), 7.47 (1H, s), 7.55-7.62 (2H, m), 8.20-8.28 (1H, m), 11.52 (1H, s).

m/z ESI M+H⁺ 642.3.

Example 49

Preparation of N-(4,6-dimethyl-2-oxo-1,2-dihydro-pyridin-3-ylmethyl)-5-{3-[(1-acryloyl-pyrrolidin-3-yl))-ethyl-amino]-5-[(4,6-dimethyl-2-oxo-1,2-di-hydro-pyridin-3-ylmethyl)-carbamoyl]-4-methyl-phenyl}-thiopheno[3,2-b]thiophene-2-carboxamide

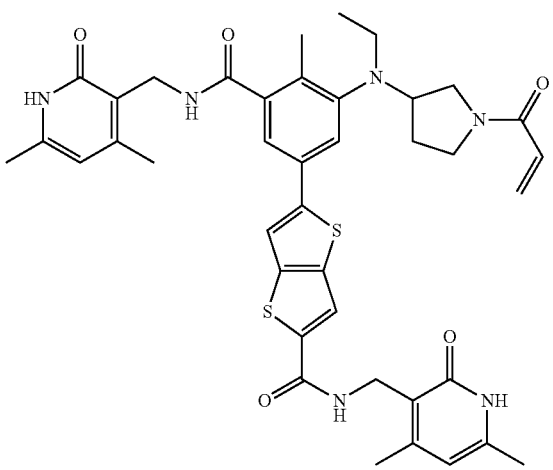

49

Step 1: Preparation of N-(2-hydroxyethyl)-N-methyl-5-bromo-thiopheno[3,2-b]thiophene-2-carboxamide

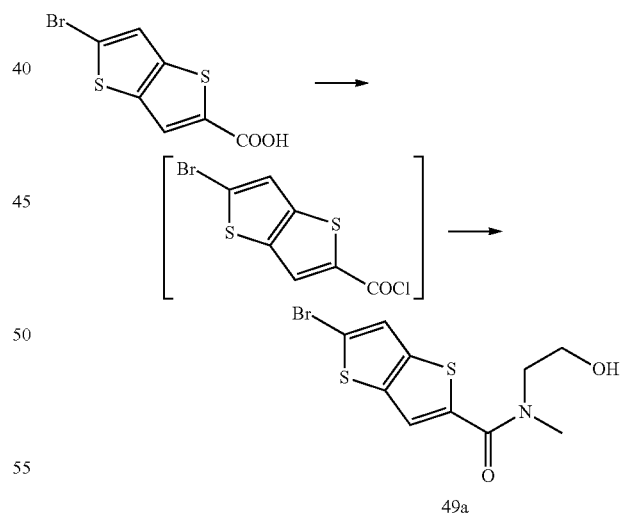

49a

5-Bromo-thiopheno[3,2-b]thiophene-2-carboxylic acid (0.5 g, 1.9 mmol) was suspended in 25 mL of dichloromethane, and added with oxalyl chloride (0.48 g, 3.8 mmol) and 1 drop of DMF. The mixture was refluxed for 1 hour. Dichloromethane and oxalyl chloride were removed under reduced pressure. The residues were dissolved in 20 ml of dichloromethane and cooled in an ice-water bath. N-methyl-ethanolamine (0.29 g, 3.8 mmol) was added and stirred for 15 min. The reaction solution was purified by column chromatography (eluent: petroleum ether:ethyl acetate 10:1~ 2:1) to give 0.37 g of title product.

The remaining steps were the same as in Example 39, except that N-(2-hydroxyethyl)-N-methyl-5-bromo-thiopheno[3,2-b] thiophene-2-carboxamide was used instead of 4-bromobenzoylmorpholine to give Compound 49.

¹H-NMR (DMSO-d6) δ: 0.84 (3H, t), 1.65-2.05 (2H, m), 2.12 (6H, d), 2.19 (3H, s), 2.21 (6H, s), 3.01-3.06 (2H, m), 3.22-3.31 (1H, m), 3.48-3.58 (2H, m), 3.68-3.78 (1H, m), 3.88-3.97 (1H, m), 4.29 (4H, d), 5.58-5.66 (1H, m), 5.87 (2H, d), 6.06-6.13 (1H, m), 6.48-6.58 (1H, m), 7.27 (2H, s), 7.60 (1H, s), 7.98 (1H, d), 8.16 (1H, s), 8.25-8.33 (1H, m), 8.56 (1H, t), 11.53 (2H, s).

m/z ESI M+H⁺ 753.2.

Example 50

Preparation of N-(2-hydroxyethyl)-N-methyl-5-{3-[(1-acryloyl-piperidin-4-yl)-ethyl-amino]-5-[(4,6-dimethyl-2-oxo-1,2-dihydro-pyridin-3-ylmethyl)-carbamoyl]-4-methyl-phenyl}-thiopheno[3,2-b] thiophene-2-carboxamide

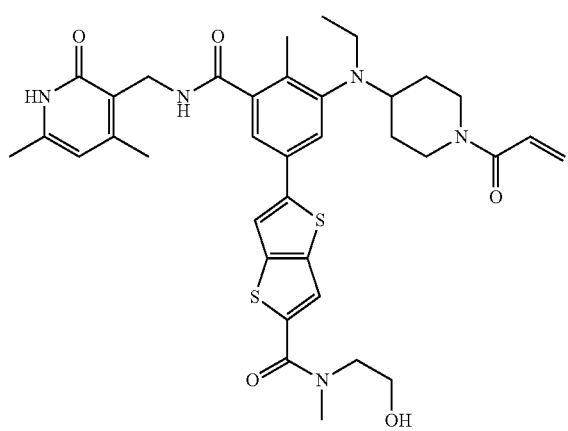

Step 1: Preparation of tert-butyl 4-{[3-benzyloxy-carbonyl-2-methyl-5-(4,4,5,5-tetramethyl-[1,3,2] dioxaborolan-2-yl)-phenyl]-ethyl-amino}-piperidin-1-ylcarboxylate (50a)

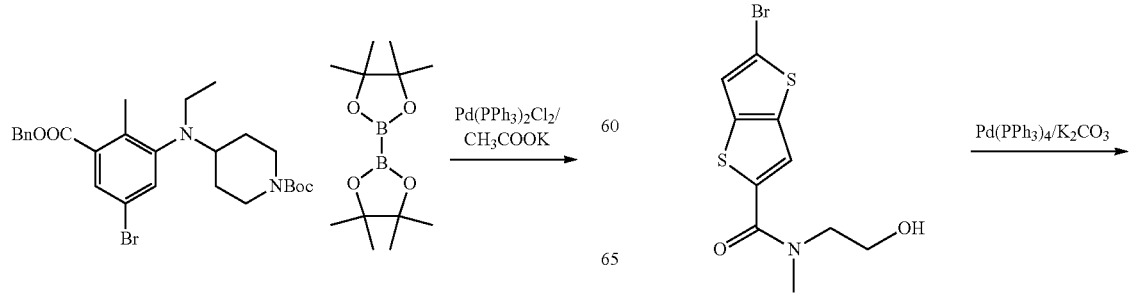

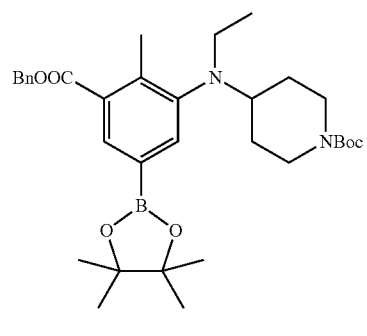

50a

The preparation method was the same as that of the intermediate 26a, except that tert-butyl 4-[(3-benzyloxycarbonyl-2-methyl-5-bromo-phenyl)-ethyl-amino]-piperidin-1-ylcarboxylate (preparation method was the same as that of the intermediate 1e, except that benzyl bromide was used instead of bromoethane, and 1-Boc-4-piperidone was used instead of 1-Boc-3-pyrrolidone) was used instead of 1e to give title product.

Step 2: Preparation of N-(2-hydroxyethyl)-N-methyl-5-{3-[(1-Boc-piperidin-4-yl)-ethyl-amino]-5-(benzyloxycarbonyl)-4-methyl-phenyl}-thiopheno[3,2-b]-thiophene-2-carboxamide 145
-continued

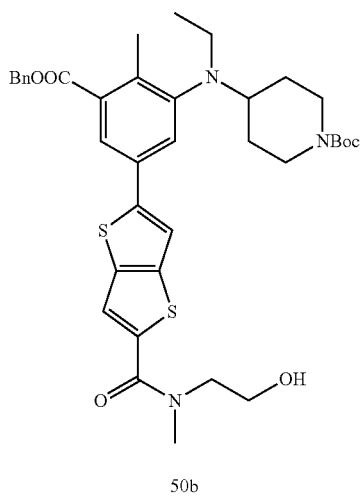

50b

146
-continued

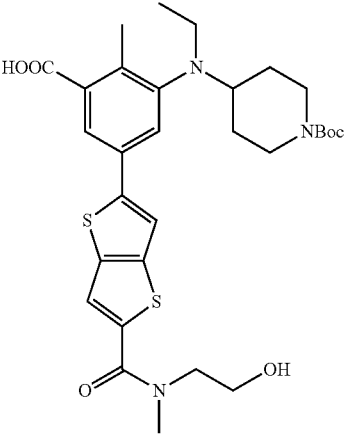

50c

Compound 50b (0.35 g, 0.5 mmol) was dissolved in 15 mL of methanol and added with 10% Pd—C (30 mg). The mixture was stirred at room temperature for 3 hours under hydrogen atmosphere. The Pd—C was filtered off, and the filtrate was concentrated under reduced pressure to yield 0.29 g of title product.

The remaining steps were the same as in Example 26, except that compound 50c was used instead of compound 26c to give Compound 49.

¹H-NMR (DMSO-d6) δ: 0.83 (3H, t), 1.38-1.49 (2H, m), 1.75-1.82 (2H, m), 2.12 (3H, s), 2.23 (6H, d), 2.66 (1H, t), 2.99-3.25 (7H, m), 3.57-3.67 (4H, m), 4.02 (1H, d), 4.29 (2H, d), 4.36 (1H, d), 4.81 (1H, br), 5.63-5.68 (1H, m), 5.88 (1H, s), 6.04-6.11 (1H, m), 6.75-6.82 (1H, m), 7.24 (1H, d), 7.50 (1H, d), 7.94 (2H, d), 8.28 (1H, t), 11.50 (1H, s).

m/z ESI M+H⁺ 690.3.

The preparation method was the same as that of the intermediate 39a, except that tert-butyl 4-{[3-benzyloxycarbonyl-2-methyl-5-(4,4,5,5-tetramethyl-[1,3,2]dioxaborolan-2-yl)-phenyl]-ethyl-amino}-piperidin-1-ylcarboxylate was used instead of tert-butyl 3-{[3-ethoxycarbonyl-2-methyl-5-(4,4,5,5-tetramethyl-[1,3,2]dioxaborolan-2-yl)-phenyl]-ethyl-amino}-pyrrolidin-1-ylcarboxylate 26a, and N-(2-hydroxyethyl)-N-methyl-5-bromo-thiopheno[3,2-b]thiophene-2-carboxamide (49a) was used instead of 4-bromobenzoylmorpholine to give compound 50b.

Step 3: Preparation of N-(2-hydroxyethyl)-N-methyl-5-{3-[(1-Boc-piperidin-4-yl)-ethyl-amino]-5-carboxy-4-methyl-phenyl}-thiopheno[3,2-b]-thiophene-2-carboxamide Example 51

Preparation of N-(4,6-dimethyl-2-oxo-1,2-dihydropyridin-3-ylmethyl)-3-[(1-acryloyl-pyrrolidin-3-yl)-ethyl-amino]-2-methyl-5-[3-(morpholin-4-yl)-propyn-1-yl]-benzamide

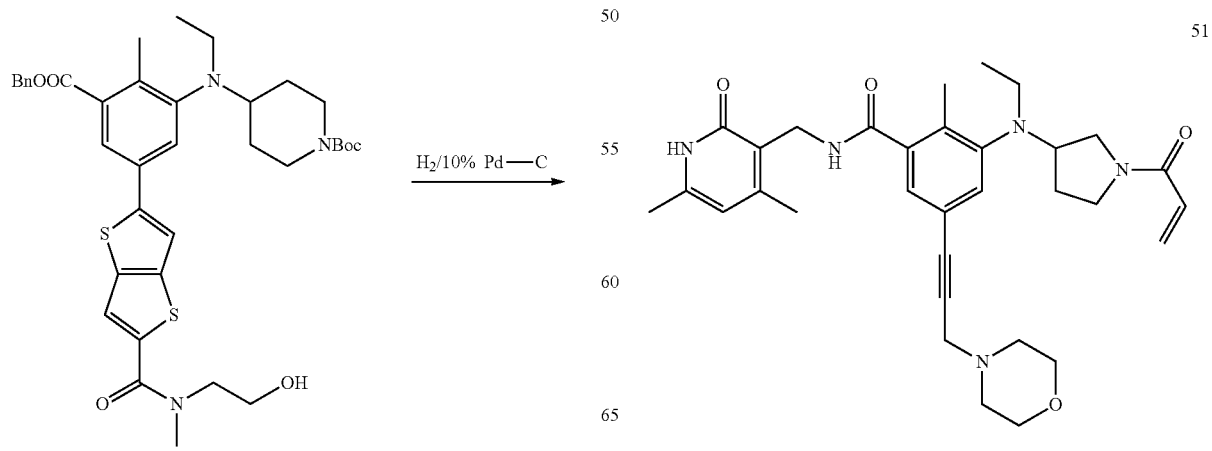

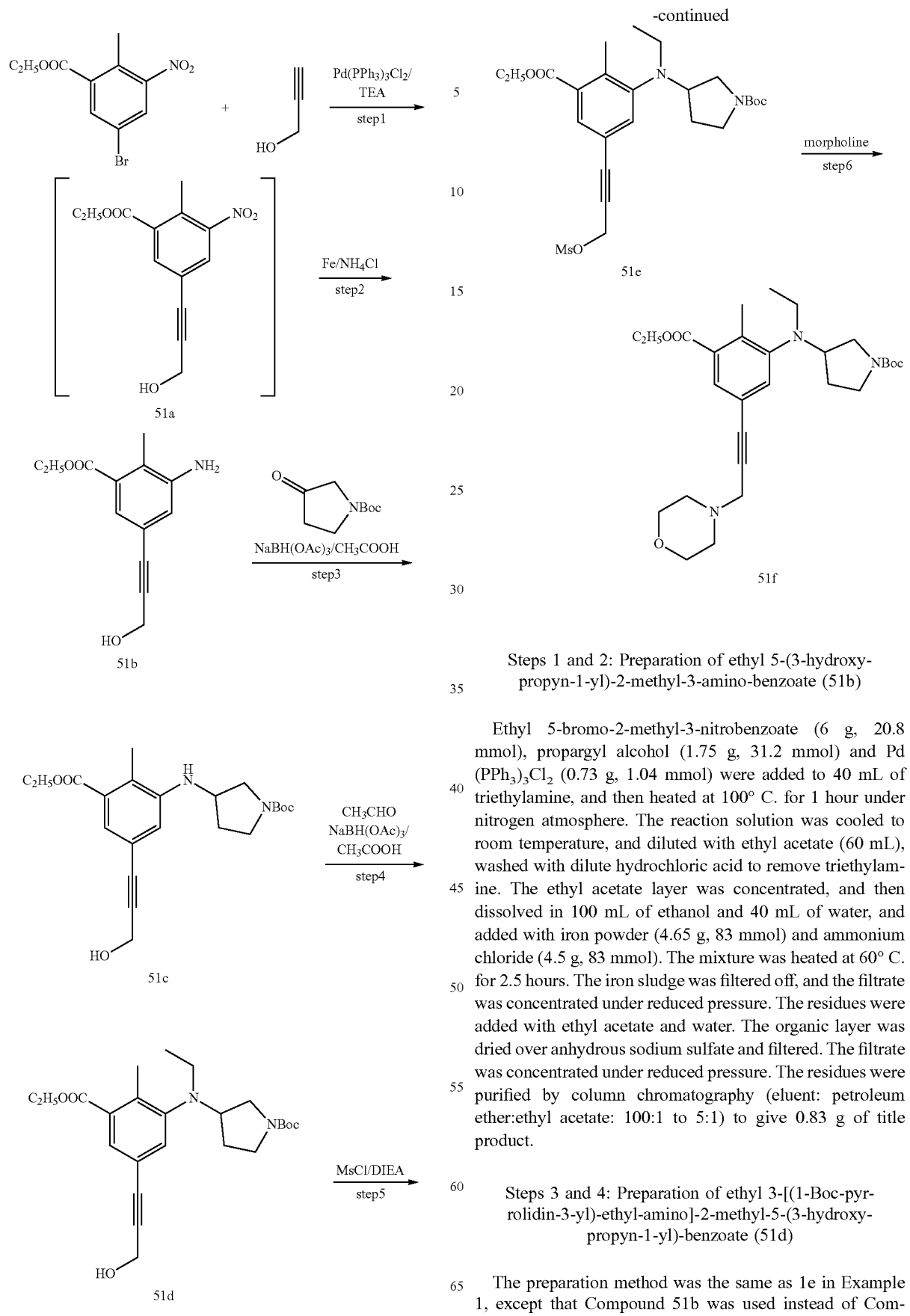

Steps 1 and 2: Preparation of ethyl 5-(3-hydroxy-propyn-1-yl)-2-methyl-3-amino-benzoate (51b)

Ethyl 5-bromo-2-methyl-3-nitrobenzoate (6 g, 20.8 mmol), propargyl alcohol (1.75 g, 31.2 mmol) and Pd(PPh$_3$)$_3$Cl$_2$ (0.73 g, 1.04 mmol) were added to 40 mL of triethylamine, and then heated at 100° C. for 1 hour under nitrogen atmosphere. The reaction solution was cooled to room temperature, and diluted with ethyl acetate (60 mL), washed with dilute hydrochloric acid to remove triethylamine. The ethyl acetate layer was concentrated, and then dissolved in 100 mL of ethanol and 40 mL of water, and added with iron powder (4.65 g, 83 mmol) and ammonium chloride (4.5 g, 83 mmol). The mixture was heated at 60° C. for 2.5 hours. The iron sludge was filtered off, and the filtrate was concentrated under reduced pressure. The residues were added with ethyl acetate and water. The organic layer was dried over anhydrous sodium sulfate and filtered. The filtrate was concentrated under reduced pressure. The residues were purified by column chromatography (eluent: petroleum ether:ethyl acetate: 100:1 to 5:1) to give 0.83 g of title product.

Steps 3 and 4: Preparation of ethyl 3-[(1-Boc-pyrrolidin-3-yl)-ethyl-amino]-2-methyl-5-(3-hydroxy-propyn-1-yl)-benzoate (51d)

The preparation method was the same as 1e in Example 1, except that Compound 51b was used instead of Compound 1c to give Compound 51d.

Steps 5 and 6: Preparation of ethyl 3-[(1-Boc-pyrrolidin-3-yl)-ethyl-amino]-2-methyl-5-[3-(morpholin-4-yl)propyn-1-yl]-benzoate (51f)

The preparation method was the same as 18b in Example 18, except that Compound 51d was used instead of Compound 17a and morpholine was used instead of piperidine, to give Compound 51f.

The remaining steps were the same as in Example 39, except that compound 51f was used instead of compound 39a to give Compound 51.

$^1$H-NMR (DMSO-d6) δ: 0.80 (3H, t), 1.65-1.95 (2H, m), 2.11 (3H, s), 2.19 (3H, s), 2.20 (3H, d), 2.94-3.00 (2H, m), 3.22-3.28 (1H, m), 3.48-3.55 (4H, m), 3.58-3.72 (5H, m), 3.77-3.85 (1H, m), 4.26 (2H, d), 5.58-5.67 (1H, m), 5.86 (1H, s), 6.06-6.14 (1H, m), 6.48-6.58 (1H, m), 7.04 (1H, s), 7.32 (1H, d), 8.22 (1H, t), 11.47 (1H, s).

m/z ESI M+H$^+$ 560.2.

Example 52

Preparation of N-(4,6-dimethyl-2-oxo-1,2-dihydropyridin-3-ylmethyl)-3-[(1-acryloyl-pyrrolidin-3-yl)-ethyl-amino]-2-methyl-5-[6-(morpholin-4-yl)-pyridin-3-yl]-benzamide nitrogen atmosphere. The reaction solution was cooled to room temperature and then extracted with water and ethyl acetate. The ethyl acetate layer was concentrated under reduced pressure, and the residues were purified by column chromatography (eluent: dichloromethane:methanol 100:1 to 40:1) to give 0.8 g of title product.

The remaining steps were the same as in Example 47, except that 2-(morpholin-4-yl)-5-bromopyridine was used instead of [2-(4-bromophenoxy)-ethyl]-dimethylamine to give Compound 52.

$^1$H-NMR (DMSO-d6) δ: 0.84 (3H, t), 1.65-2.05 (2H, m), 2.11 (3H, s), 2.21 (3H, s), 2.23 (3H, s), 3.01-3.06 (2H, m), 3.22-3.31 (1H, m), 3.48-3.58 (6H, m), 3.68-3.73 (5H, m), 3.88-3.97 (1H, m), 4.29 (2H, d), 5.58-5.66 (1H, m), 5.87 (1H, s), 6.06-6.13 (1H, m), 6.47-6.59 (1H, m), 6.93 (1H, d), 7.25 (1H, s), 7.50 (1H, s), 7.88-7.94 (1H, m), 8.25-8.33 (1H, m), 8.45-8.49 (1H, m), 11.49 (1H, s).

m/z ESI M+H$^+$ 599.3.

Example 53

Preparation of N-(4,6-dimethyl-2-oxo-1,2-dihydropyridin-3-ylmethyl)-3-[(1-acryloyl-pyrrolidin-3-yl)-ethyl-amino]-2-methyl-5-[6-(4-methylpiperazin-1-yl)-pyridin-3-yl]-benzamide

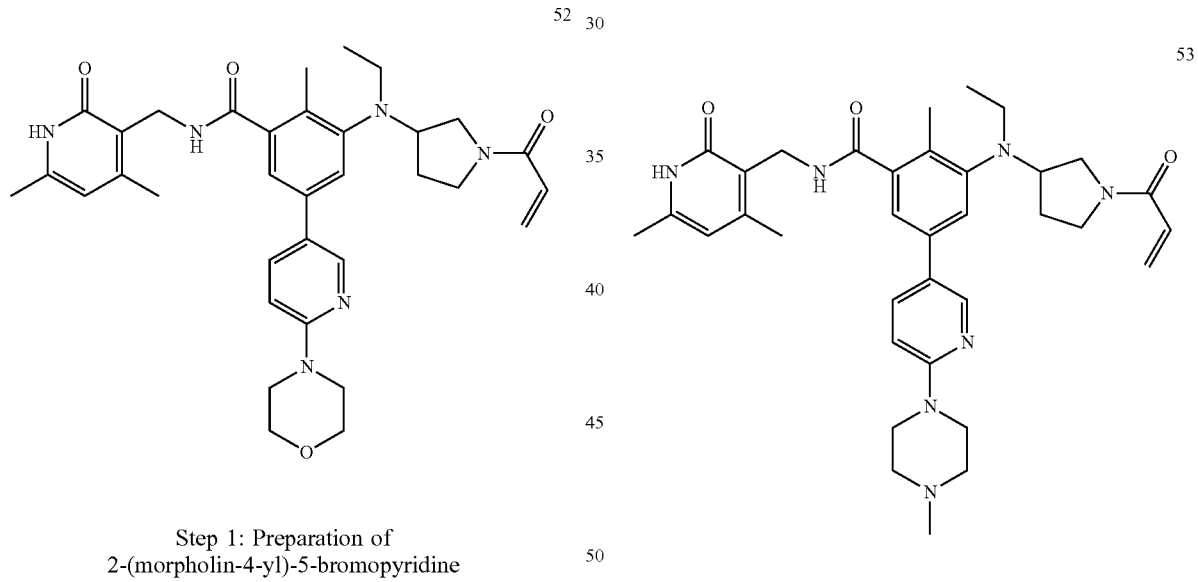

Step 1: Preparation of 2-(morpholin-4-yl)-5-bromopyridine

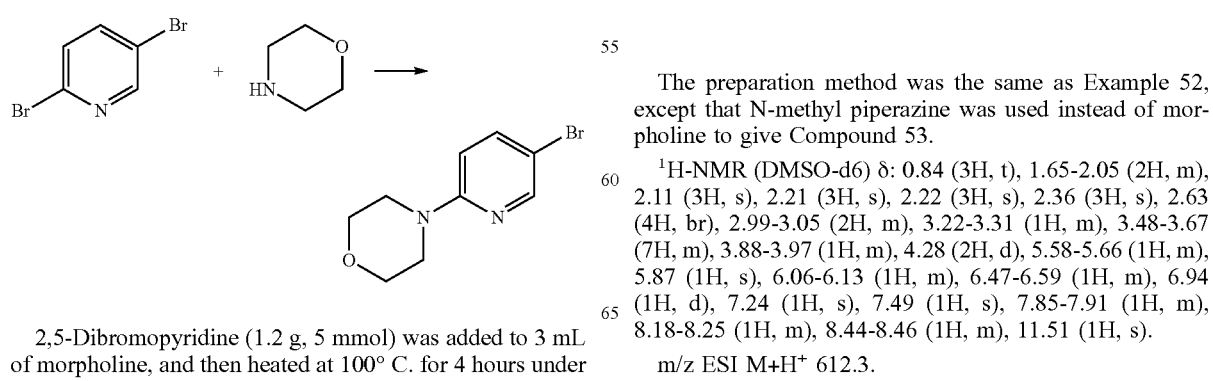

2,5-Dibromopyridine (1.2 g, 5 mmol) was added to 3 mL of morpholine, and then heated at 100° C. for 4 hours under The preparation method was the same as Example 52, except that N-methyl piperazine was used instead of morpholine to give Compound 53.

$^1$H-NMR (DMSO-d6) δ: 0.84 (3H, t), 1.65-2.05 (2H, m), 2.11 (3H, s), 2.21 (3H, s), 2.22 (3H, s), 2.36 (3H, s), 2.63 (4H, br), 2.99-3.05 (2H, m), 3.22-3.31 (1H, m), 3.48-3.67 (7H, m), 3.88-3.97 (1H, m), 4.28 (2H, d), 5.58-5.66 (1H, m), 5.87 (1H, s), 6.06-6.13 (1H, m), 6.47-6.59 (1H, m), 6.94 (1H, d), 7.24 (1H, s), 7.49 (1H, s), 7.85-7.91 (1H, m), 8.18-8.25 (1H, m), 8.44-8.46 (1H, m), 11.51 (1H, s).

m/z ESI M+H$^+$ 612.3.

Example 54

Preparation of N-(4,6-dimethyl-2-oxo-1,2-dihydro-pyridin-3-ylmethyl)-3-[(1-acryloyl-pyrrolidin-3-yl)-ethyl-amino]-2-methyl-5-(1-methyl-1H-pyrazol-4-yl)-benzamide

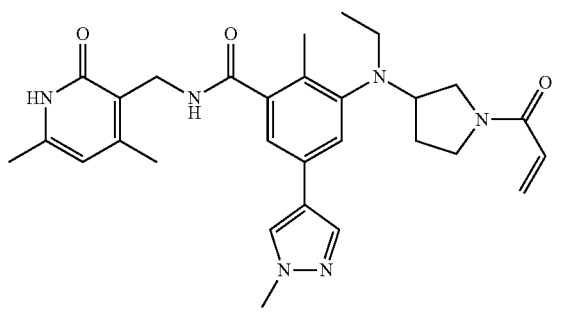

54

The preparation method was the same as Example 39, except that 1-methyl-4-bromopyrazole was used instead of 4-bromobenzoylmorpholine to give Compound 54.

$^1$H-NMR (DMSO-d6) δ: 0.83 (3H, t), 1.65-2.05 (2H, m), 2.11 (3H, s), 2.17 (3H, d), 2.21 (3H, s), 2.96-3.04 (2H, m), 3.22-3.31 (1H, m), 3.50-3.55 (2H, m), 3.68-3.74 (1H, m), 3.85-3.95 (4H, m), 4.28 (2H, d), 5.58-5.66 (1H, m), 5.87 (1H, s), 6.06-6.13 (1H, m), 6.48-6.58 (1H, m), 7.20 (1H, s), 7.45 (1H, s), 7.86 (1H, d), 8.08-8.18 (2H, m), 11.48 (1H, s).

m/z ESI M+H$^+$ 517.3.

Example 55

Preparation of N-(4,6-dimethyl-2-oxo-1,2-dihydro-pyridin-3-ylmethyl)-5-[(1-acryloyl-pyrrolidin-3-yl)-ethyl-amino]-4,3'-dimethyl-[1,1'-biphenyl]-3-carbox-amide

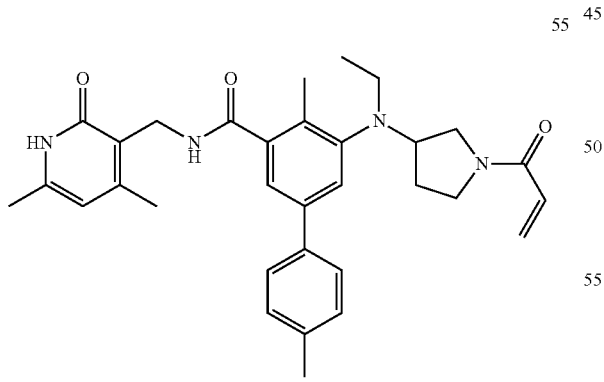

55

The preparation method was the same as Example 39, except that 4-bromotoluene was used instead of 4-bromobenzoylmorpholine to give Compound 55.

$^1$H-NMR (DMSO-d6) δ: 0.84 (3H, t), 1.65-2.02 (2H, m), 2.11 (3H, s), 2.21 (3H, d), 2.24 (3H, d), 2.34 (3H, s), 3.01-3.08 (2H, m), 3.26-3.32 (1H, m), 3.48-3.57 (2H, m), 3.68-3.77 (1H, m), 3.91-3.98 (1H, m), 4.29 (2H, d), 5.57-5.67 (1H, m), 5.86 (1H, s), 6.06-6.13 (1H, m), 6.48-6.58 (1H, m), 7.26-7.29 (3H, m), 7.48-7.58 (3H, m), 8.24 (1H, t), 11.48 (1H, s).

m/z ESI M+H$^+$ 527.2.

Example 56

Preparation of ethyl 3'-[(4,6-dimethyl-2-oxo-1,2-dihydro-pyridin-3-ylmethyl)-formyl]-5'-[(1-acryloyl-pyrrolidine-3-yl)-ethyl-amino]-4'-methyl-[1,1'-biphenyl]-4-carboxylate

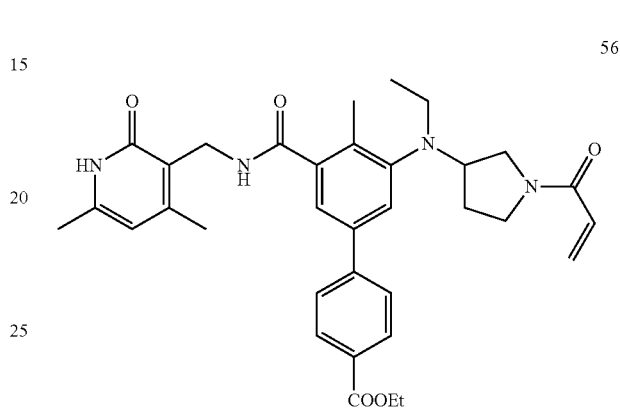

56

The preparation method was the same as Example 50, except that ethyl 4-bromo-benzoate was used instead of N-(2-hydroxyethyl)-N-methyl-5-bromo-thiopheno[3,2-b]thiophene-2-carboxamide, and 1-Boc-3-pyrrolidone was used instead of 1-Boc-4-piperidone, to give Compound 56.

$^1$H-NMR (DMSO-d6) δ: 0.85 (3H, t), 1.34 (3H, t), 1.65-2.02 (2H, m), 2.11 (3H, s), 2.21 (3H, s), 2.26 (3H, s), 3.01-3.08 (2H, m), 3.24-3.31 (1H, m), 3.48-3.81 (2H, m), 3.68-3.78 (1H, m), 3.91-3.98 (1H, m), 4.28-4.37 (4H, m), 5.58-5.67 (1H, m), 5.87 (1H, s), 6.07-6.13 (1H, m), 6.48-6.58 (1H, m), 7.37 (1H, d), 7.62 (1H, d), 7.85 (2H, d), 8.03 (2H, d), 8.30 (1H, t), 11.49 (1H, s).

m/z ESI M+H$^+$ 585.2.

Example 57

Preparation of 3'-[(4,6-dimethyl-2-oxo-1,2-dihydro-pyridin-3-ylmethyl)-formyl]-5'-[(1-acryloyl-pyrrolidin-3-yl)-ethyl-amino]-4'-methyl-[1,1'-biphenyl]-4-carboxylic acid

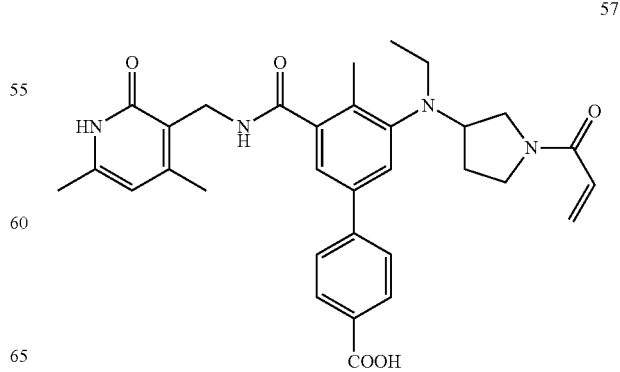

57

153

Step 1: Preparation of tert-butyl 3-({4'-carboxy-5-[(4,6-dimethyl-2-oxo-1,2-dihydro-pyridin-3-ylmethyl)-carbonyl]-4-methyl-biphenyl-3-yl}-ethyl-amino)-pyrrolidine-1-carboxylate

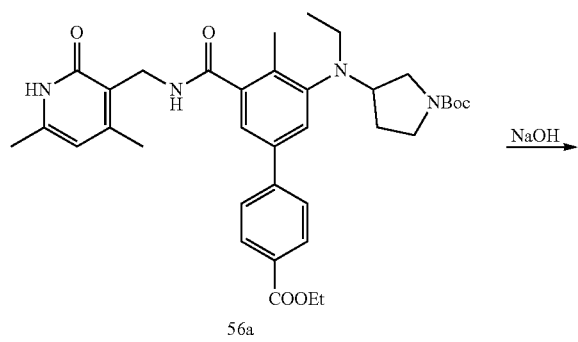
56a

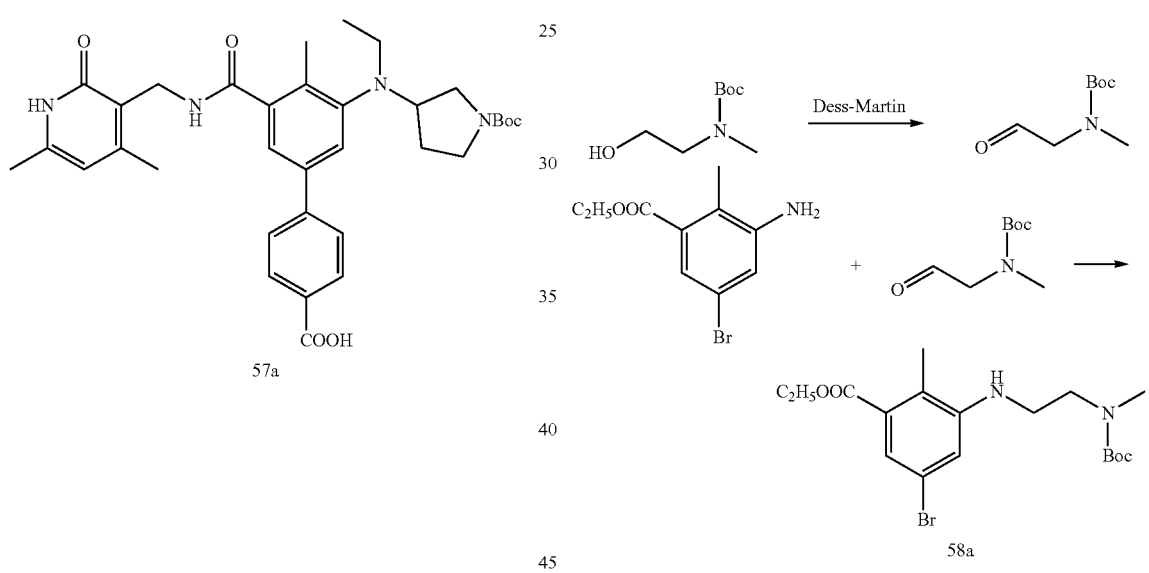
57a

Tert-butyl 3-({4'-ethoxycarbonyl-5-[(4,6-dimethyl-2-oxo-1,2-dihydro-pyridin-3-ylmethyl)-carbamoyl]-4-methyl-biphenyl-3-yl}-ethyl-amino)-pyrrolidine-1-carboxylate 56a (0.33 g, 0.5 mmol) and sodium hydroxide (0.1 g, 2.5 mmol) were dissolved in 3 mL of ethanol and 1 mL of water and stirred overnight. 20 mL of 1 M aqueous solution of citric acid was added, and extracted with ethyl acetate. The ethyl acetate layer was concentrated to give Compound 57a, which was used directly in the next step without purification.

The remaining steps were the same as in Example 56, except that compound 57a was used instead of compound 56a to give Compound 57.

$^1$H-NMR (DMSO-d6) δ: 0.85 (3H, t), 1.65-2.02 (2H, m), 2.11 (3H, s), 2.21 (3H, s), 2.25 (3H, s), 3.01-3.08 (2H, m), 3.26-3.32 (1H, m), 3.50-3.58 (2H, m), 3.68-3.78 (1H, m), 3.91-3.98 (1H, m), 4.29 (2H, d), 5.58-5.67 (1H, m), 5.87 (1H, s), 6.07-6.13 (1H, m), 6.48-6.58 (1H, m), 7.31 (1H, d), 7.56 (1H, d), 7.62 (2H, d), 7.97 (2H, d), 8.27 (1H, t), 11.49 (1H, s).

m/z ESI M+H$^+$ 557.3.

154

Example 58

Preparation of 3-{[2-(acryloyl-methyl-amino)-ethyl]-ethyl-amino}-5-bromo-N-(4,6-dimethyl-2-oxo-1,2-dihydro-pyridin-3-ylmethyl)-2-methyl-benzamide

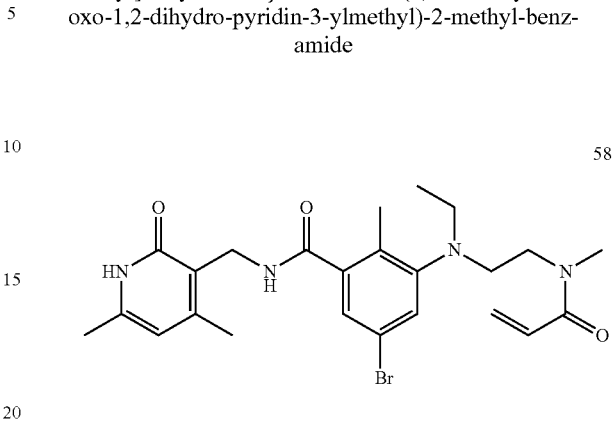
58

Step 1: Preparation of ethyl 5-bromo-3-[2-(Boc-methyl-amino)-ethyl-amino]-2-methyl-benzoate 2-(Boc-methyl-amino)-ethanol (0.19 g, 1 mmol) was dissolved in 4 mL of dichloromethane, and added with Dess-Martin periodinane (0.64 g, 1.5 mmol), and stirred at room temperature for 1 hour. 3 mL of a saturated sodium thiosulfate solution and 5 mL of a saturated sodium bicarbonate solution were added to the reaction mixture, and the mixture was stirred until clarified. Then, it was extracted with 20 mL of dichloromethane, and the dichloromethane layer was concentrated under reduced pressure. The residues were dissolved in 5 mL of acetic acid, and added with ethyl 5-bromo-3-amino-2-methyl-benzoate Ic (0.26 g, 1 mmol). The sodium borohydride (0.22 g, 6 mmol) was added portionwise and then stirred at room temperature for 0.5 hour. The reaction solution was added with water and ethyl acetate. The ethyl acetate layer was washed with aqueous solution of sodium hydroxide. The organic layer was dried over anhydrous sodium sulfate and filtered. The filtrate was concentrated under reduced pressure. The residues were purified by column chromatography (eluent: petroleum ether:ethyl acetate 30:1 to 3:1) to give 0.3 g of title product.

The remaining steps were the same as in Example 1, except that compound 58a was used instead of compound 1d to give Compound 58.

$^1$H-NMR (DMSO-d$_6$) δ: 0.86 (3H, t), 2.08 (3H, d), 2.11 (3H, s), 2.19 (3H, s), 2.83-3.04 (5H, m), 3.06-3.12 (2H, m), 3.40 (2H, t), 4.25 (2H, d), 5.52-5.67 (1H, m), 5.87 (1H, s), 6.00-6.12 (1H, m), 6.40-6.71 (1H, m), 7.06 (1H, d), 7.30 (1H, d), 8.22 (1H, t), 11.50 (1H, s).

m/z ESI M+H$^+$ 503.2.

Example 59

Preparation of N-(4,6-dimethyl-2-oxo-1,2-dihydro-pyridin-3-ylmethyl)-3-[(1-acryloyl-pyrrolidin-3-yl)-(2,2,2-trifluoroethyl)-amino]-2-methyl-5-bromobenzamide

59

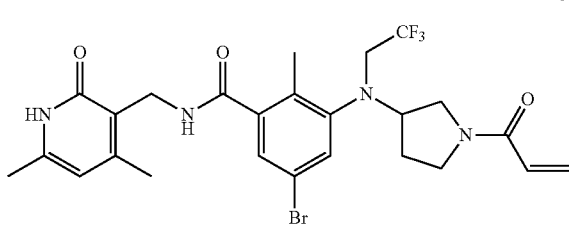

Step 1: Preparation of 9H-fluoren-9-ylmethyl 3-(5-bromo-3-ethoxycarbonyl-2-methyl-phenylamino)-pyrrolidin-1-ylcarboxylate

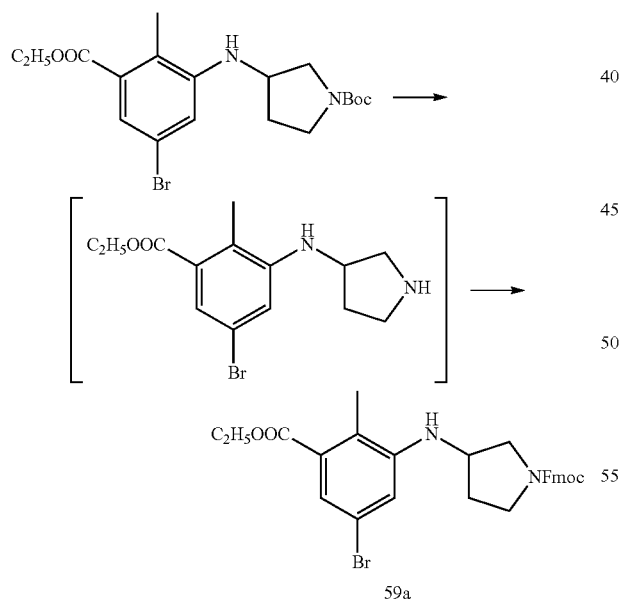

59a

Tert-butyl 3-(5-bromo-3-ethoxycarbonyl-2-methyl-phenylamino)-pyrrolidin-1-ylcarboxylate 1b (1.6 g, 3.75 mmol) was dissolved in 20 mL of dichloromethane, and then added with 2.5 mL of trifluoroacetic acid and refluxed for 20 hours. The reaction mixture was cooled to room temperature and extracted with a saturated solution of sodium bicarbonate. The dichloromethane layer was added with FmocCl (1.06 g, 4.1 mmol) and 1 mL of N-methyl morpholine under ice-water bath, and the mixture was stirred for 0.5 hour. The reaction solution was added with dichloromethane and 1 M of dilute hydrochloric acid. The organic layer was dried over anhydrous sodium sulfate and filtered. The filtrate was concentrated under reduced pressure. The residues were purified by column chromatography (eluent: petroleum ether:ethyl acetate 50:1 to 5:1) to give 1.48 g of title product.

Step 2: Preparation of 9H-fluoren-9-ylmethyl 3-[(5-bromo-3-ethoxycarbonyl-2-methyl-phenyl)-(2,2,2-trifluoroethyl)-amino]-pyrrolidin-1-ylcarboxylate

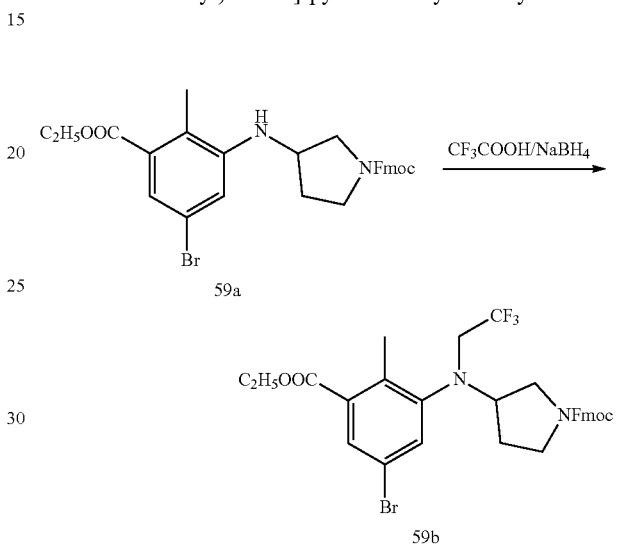

Compound 59a (2.2 g, 4 mmol) was dissolved in 20 mL of trifluoroacetic acid, and added with sodium borohydride (3.7 g, 100 mmol) portionwise over 20 hours. The mixture was stirred for 5 hours after the addition. The reaction solution was added with ethyl acetate and water. The ethyl acetate layer was washed with aqueous solution of sodium hydroxide to remove the residual trifluoroacetic acid, and then dried over anhydrous sodium sulfate and filtered. The filtrate was concentrated under reduced pressure. The residues were purified by column chromatography (eluent: petroleum ether:ethyl acetate 20:1 to 5:1) to give 0.86 g of title product.

Step 3: Preparation of tert-butyl 3-[(5-bromo-3-ethoxycarbonyl-2-methyl-phenyl)-(2,2,2-trifluoro-ethyl)-amino]-pyrrolidin-1-ylcarboxylate

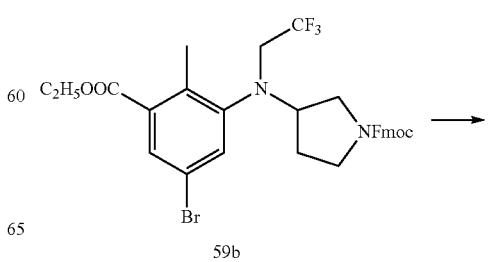

59b

-continued

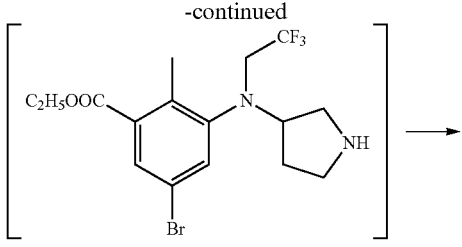

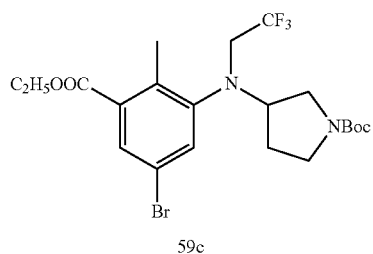
59c

Compound 59b (0.86 g, 1.3 mmol) was dissolved in 2.5 mL of DMF, and added with 0.5 mL of piperidine and stirred for 20 minutes. The reaction solution was added with ethyl acetate and water. The ethyl acetate layer was concentrated under reduced pressure. The residues were dissolved in 25 mL of dichloromethane and added with (Boc)$_2$O (1.75 g, 8 mmol) and stirred for 15 minutes. The mixture was purified by column chromatography (eluent: petroleum ether:ethyl acetate 80:1 to 10:1) to give 0.4 g of title product.

The remaining steps were the same as in Example 1, except that compound 59c was used instead of compound 1e to give Compound 59.

$^1$H-NMR (DMSO-d6) δ: 1.75-2.05 (2H, m), 2.11 (3H, s), 2.15 (3H, s), 2.19 (3H, s), 3.15-3.26 (1H, m), 3.42-3.55 (2H, m), 3.63-3.81 (2H, m), 3.85-3.96 (2H, m), 4.25 (2H, d), 5.62-5.68 (1H, m), 5.87 (1H, s), 6.07-6.13 (1H, m), 6.48-6.58 (1H, m), 7.20 (1H, d), 7.67 (1H, d), 8.27 (1H, t), 11.49 (1H, s).

m/z ESI M+H$^+$ 569.1.

Example 60

Preparation of N-(4,6-dimethyl-2-oxo-1,2-dihydro-pyridin-3-ylmethyl)-3-[(1-acryloyl-pyrrolidin-3-yl)-ethyl-amino]-5-bromo-4-fluoro-2-methyl-benzamide

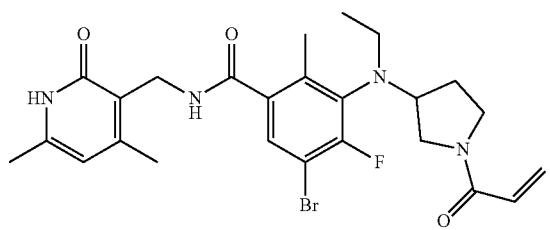

Step 1: Preparation of 5-bromo-4-fluoro-2-methylbenzoic acid (60a)

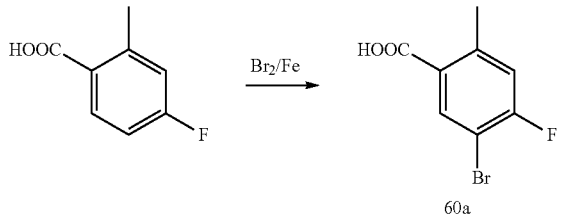
60a

4-Fluoro-2-methylbenzoic acid (10 g, 65 mmol) and iron powder (0.56 g, 10 mmol) were added to 30 mL of bromine and stirred for 30 hours. The reaction solution was poured into 400 ml of water, and then filtered to collect the precipitated solid. The solid was dissolved in 90 ml of methanol, and added with 250 mL of dilute hydrochloric acid dropwise to precipitate a solid. 12.7 g of the crude product 60a (containing the isomer 3-bromo-4-fluoro-2-methylbenzoic acid) was obtained by filtration, which was used directly in the next step without purification.

The remaining steps were the same as in Example 2, except that compound 60a was used instead of 5-fluoro-2-methylbenzoic acid to give Compound 60.

$^1$H-NMR (CDCl$_3$) δ: 0.92 (3H, t), 1.64-2.05 (2H, m), 2.28 (3H, s), 2.33 (3H, s), 2.40 (3H, s), 3.02-3.10 (2H, m), 3.48-4.02 (5H, m), 4.53 (2H, d), 5.61-5.70 (1H, m), 5.99 (1H, s), 6.36-6.44 (2H, m), 7.22 (1H, t), 7.42 (1H, d), 12.01 (1H, s).

m/z ESI M+H$^+$ 533.1.

Example 61

Preparation of N-(4,6-dimethyl-2-oxo-1,2-dihydro-pyridin-3-ylmethyl)-3-[(1-acryloyl-piperidin-4-yl)-ethyl-amino]-5-bromo-4-fluoro-2-methyl-benzamide

61

The preparation method was the same as Example 60, except that 1-Boc-4-piperidone was used instead of 1-Boc-3-pyrrolidone to give Compound 61.

$^1$H-NMR (CDCl$_3$) δ: 0.89 (3H, t), 1.25-1.74 (3H, m), 1.97-2.02 (1H, m), 2.27 (3H, s), 2.33 (3H, s), 2.40 (3H, s), 2.59-2.64 (1H, m), 3.00-3.28 (4H, m), 3.88-4.02 (1H, m), 4.50-4.55 (3H, m), 5.68 (1H, m), 5.99 (1H, s), 6.28 (1H, m), 6.55 (1H, m), 7.20 (1H, t), 7.38 (1H, d), 11.71 (1H, s).

m/z ESI M+H$^+$ 547.1.

Example 62

Preparation of N-(4,6-dimethyl-2-oxo-1,2-dihydro-pyridin-3-ylmethyl)-5-[(1-acryloyl-piperidin-4-yl)-ethyl-amino]-3'-fluoro-4-methyl-4'-(morpholin-4-ylmethyl)-[1,1'-biphenyl]-3-carboxamide

62

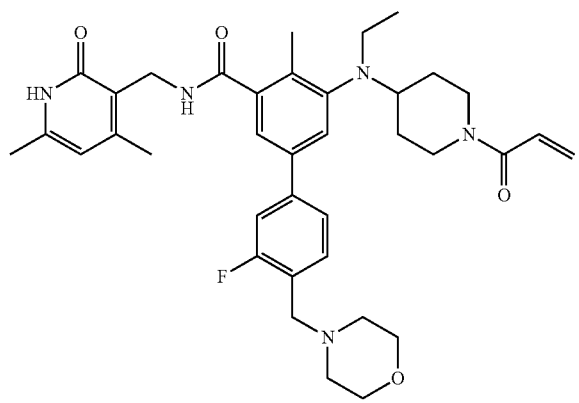

The preparation method was the same as Example 23, except that 1-Boc-4-piperidone was used instead of 1-Boc-3-pyrrolidone to give Compound 62.

$^1$H-NMR (DMSO-d6) δ: 0.83 (3H, t), 1.37-1.49 (2H, m), 1.78 (2H, d), 2.11 (3H, s), 2.22 (3H, s), 2.26 (3H, s), 2.40 (4H, br), 2.65 (1H, t), 2.99-3.13 (4H, m), 3.55 (2H, s), 3.58 (4H, br), 4.01 (1H, d), 4.30 (2H, d), 4.36 (1H, d), 5.63-5.67 (1H, m), 5.87 (1H, s), 6.05-6.10 (1H, m), 6.75-6.82 (1H, m), 7.28 (1H, s), 7.45-7.51 (4H, m), 8.22 (1H, t), 11.49 (1H, s).

m/z ESI M+H$^+$ 644.3.

Example 63

Preparation of N-(4,6-dimethyl-2-oxo-1,2-dihydro-pyridin-3-ylmethyl)-5-[(1-acryloyl-piperidin-4-yl)-ethyl-amino]-4-methyl-4'-(4,4-difluoro-piperidin-1-ylmethyl)-[1,1'-biphenyl]-3-carboxamide

63

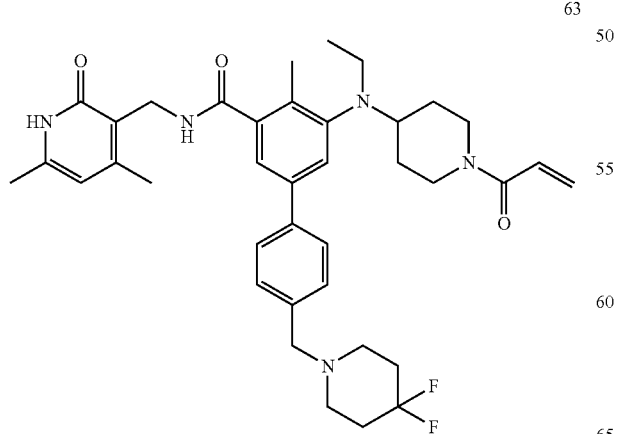

The preparation method was the same as Example 34, except that 4,4-difluoropiperidin was used instead of piperidine to give Compound 63.

$^1$H-NMR (DMSO-d6) δ: 0.81-0.87 (4H, m), 1.21-1.51 (5H, m), 1.78 (2H, t), 1.93-2.01 (4H, m), 2.11 (3H, s), 2.22 (3H, s), 2.26 (3H, s), 2.66 (1H, t), 3.00-3.13 (4 h, m), 3.40-3.47 (1H, m), 3.58 (2H, s), 4.01 (1H, d), 4.28-4.38 (3H, m), 5.63-5.67 (1H, m), 5.87 (1H, s), 6.05-6.10 (1H, m), 6.75-6.82 (1H, m), 7.23 (1H, s), 7.37-7.41 (3H, m), 7.60 (2H, d), 8.22 (1H, t), 11.49 (1H, s).

m/z ESI M+H$^+$ 660.3.

Example 64

Preparation of N-(4,6-dimethyl-2-oxo-1,2-dihydro-pyridin-3-ylmethyl)-5-[(1-acryloyl-piperidin-4-yl)-ethyl-amino]-4-methyl-4'-(4-acetyl-piperazin-1-ylmethyl)-[1,1'-biphenyl]-3-carboxamide

64

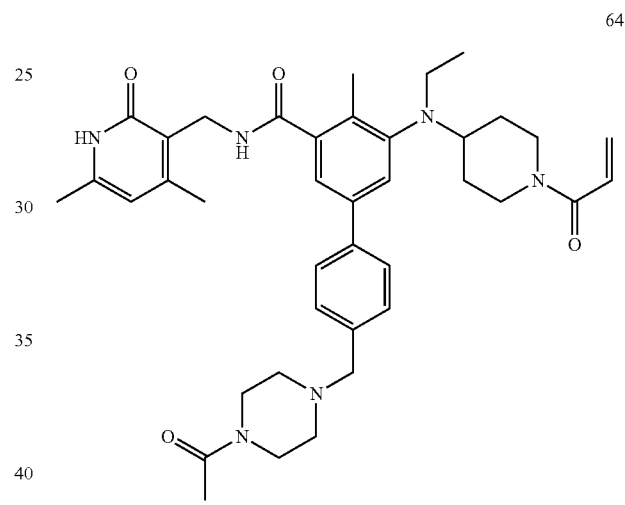

The preparation method was the same as Example 34, except that 4-acetylpiperazine was used instead of piperidine to give Compound 64.

$^1$H-NMR (DMSO-d6) δ: 0.84 (3H, t), 1.39-1.46 (2H, t), 1.98-2.02 (2H, d), 1.99 (3H, s), 2.11 (3H, s), 2.21 (3H, s), 2.25 (3H, s), 2.32 (2H, br), 2.39 (2H, br), 2.66 (1H, t), 2.99-3.10 (4H, m), 3.43 (4H, s), 3.53 (2H, s), 3.99-4.03 (1H, m), 4.29-4.38 (3H, m), 5.63-5.67 (1H, m), 5.87 (1H, s), 6.05-6.10 (1H, m), 6.75-6.82 (1H, m), 7.23 (1H, s), 7.38-7.41 (3H, m), 7.60 (2H, d), 8.21 (1H, t), 11.49 (1H, s).

m/z ESI M+H$^+$ 667.4.

Example 65

Preparation of N-(4,6-dimethyl-2-oxo-1,2-dihydro-pyridin-3-ylmethyl)-5-[(1-acryloyl-piperidin-4-yl)-ethyl-amino]-4-methyl-4'-(4-methoxypiperidin-1-ylmethyl)-[1,1'-biphenyl]-3-carboxamide

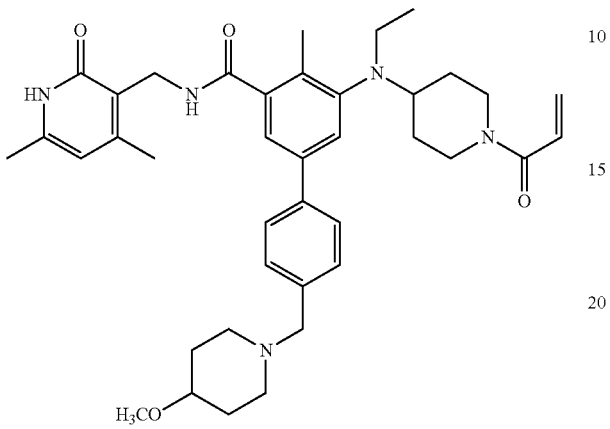

The preparation method was the same as Example 34, except that 4-methoxypiperidine was used instead of piperidine to give Compound 65.

$^1$H-NMR (DMSO-d6) δ: 0.84 (3H, t), 1.35-1.48 (2H, m), 1.60-1.83 (3H, m), 1.91-2.02 (3H, m), 2.11 (3H, s), 2.22 (3H, s), 2.26 (3H, s), 2.65 (1H, t), 2.85-3.22 (8H, m), 3.25 (3H, s), 3.42 (2H, s), 3.99-4.03 (1H, m), 4.24-4.38 (4H, m), 5.63-5.67 (1H, m), 53.89 (1H, s), 6.05-6.12 (1H, m), 6.75-6.82 (1H, m), 7.27 (1H, s), 7.45 (1H, s), 7.62-7.76 (4H, m), 8.22 (1H, t), 11.49 (1H, s).

m/z ESI M+H$^+$ 654.4.

Example 66

Preparation of N-(4,6-dimethyl-2-oxo-1,2-dihydro-pyridin-3-ylmethyl)-5-[(1-acryloyl-piperidin-4-yl)-ethyl-amino]-4-methyl-4'-(4-dimethylamino-piperi-din-1-ylmethyl)-[1,1'-biphenyl]-3-carboxamide

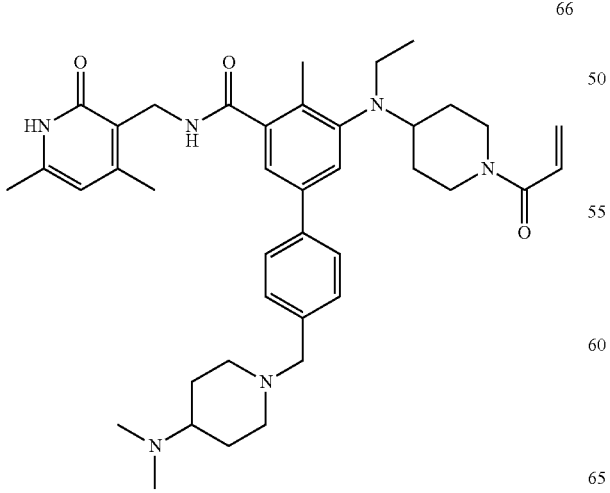

The preparation method was the same as Example 34, except that 4-(dimethylamino) piperidine was used instead of piperidine to give Compound 66.

$^1$H-NMR (DMSO-d6) δ: 0.84 (3H, t), 1.38-1.53 (4H, m), 1.78-1.86 (2H, m), 1.93-2.02 (2H, m), 2.11 (3H, s), 2.22 (3H, s), 2.25 (3H, s), 2.31 (1H, m), 2.44 (6H, s), 2.66 (1H, t), 2.91-3.12 (8H, m), 3.50 (2H, s), 3.97-4.02 (1H, m), 4.28-4.39 (3H, m), 5.63-5.66 (1H, m), 5.87 (1H, s), 6.05-6.10 (1H, m), 6.75-6.82 (1H, m), 7.23 (1H, d), 7.35-7.41 (3H, m), 7.59 (2H, d), 8.19 (1H, t), 11.47 (1H, s).

m/z ESI M+H$^+$ 667.4.

Example 67

Preparation of N-(4,6-dimethyl-2-oxo-1,2-dihydro-pyridin-3-ylmethyl)-5-[(1-acryloyl-piperidin-4-yl)-ethyl-amino]-4-methyl-4'-(4-methylhomopiperazin-1-ylmethyl)-[1,1'-biphenyl]-3-carboxamide

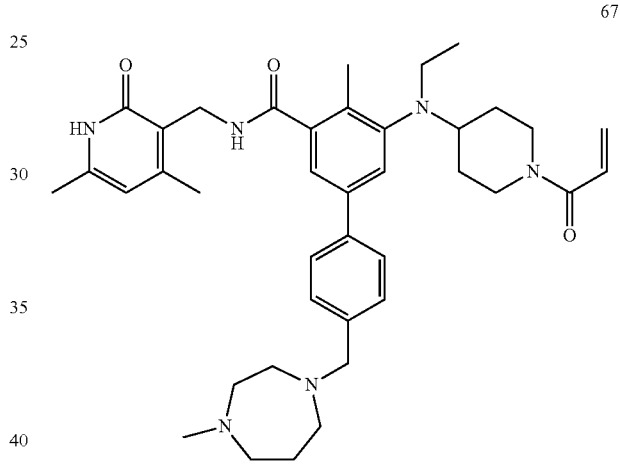

The preparation method was the same as Example 34, except that 4-methylhomopiperazine was used instead of piperidine to give Compound 67.

$^1$H-NMR (DMSO-d6) δ: 0.83 (3H, t), 1.37-1.48 (2H, m), 1.75-1.81 (2H, d), 1.93-2.01 (2H, m), 2.11 (3H, s), 2.21 (3H, s), 2.25 (3H, s), 2.61-2.78 (6H, m), 2.84 (2H, s), 2.99-3.13 (4H, m), 3.20-3.32 (4H, br), 3.72 (2H, s), 4.00 (1H, d), 4.28-4.37 (3H, m), 5.62-5.67 (1H, m), 5.86 (1H, s), 6.04-6.09 (1H, m), 7.22 (1H, s), 7.40-7.45 (3H, m), 7.60 (2H, d), 8.20 (1H, t), 11.47 (1H, s).

m/z ESI M+H$^+$ 653.4.

Example 68

Preparation of N-(4,6-dimethyl-2-oxo-1,2-dihydro-pyridin-3-ylmethyl)-5-[(1-acryloyl-piperidin-4-yl)-ethyl-amino]-4-methyl-4'-(3-oxopiperazin-1-ylmethyl)-[1,1'-biphenyl]-3-carboxamide

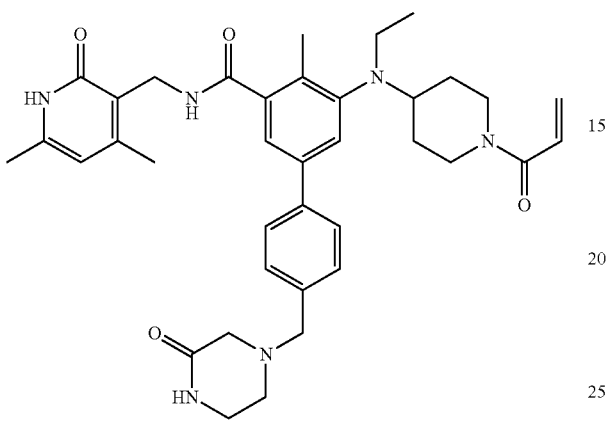

The preparation method was the same as Example 34, except that 3-piperazinone was used instead of piperidine to give Compound 68.

¹H-NMR (DMSO-d6) δ: 0.84 (3H, t), 1.36-1.17 (2H, m), 1.75-1.81 (2H, m), 2.11 (3H, s), 2.22 (3H, s), 2.26 (3H, s), 2.57 (2H, t), 2.66 (1H, t), 2.93 (2H, s), 2.99-3.12 (4H, m), 3.16 (2H, t), 3.58 (2H, s), 3.97-4.03 (1H, m), 4.29-4.40 (3H, m), 5.62-5.66 (1H, m), 5.87 (1H, s), 6.05-6.10 (1H, m), 6.74-6.82 (1H, m), 7.24 (1H, d), 7.38-7.42 (3H, m), 7.61 (2H, d), 7.67 (1H, s), 8.21 (1H, t), 11.48 (1H, s).

m/z ESI M+H⁺ 639.3.

Example 69

Preparation of N-(4,6-dimethyl-2-oxo-1,2-dihydro-pyridin-3-ylmethyl)-5-[(1-acryloyl-piperidin-4-yl)-ethyl-amino]-4-methyl-4'-(4-methylpiperazin-1-ylmethyl)-[1,1'-biphenyl]-3-carboxamide

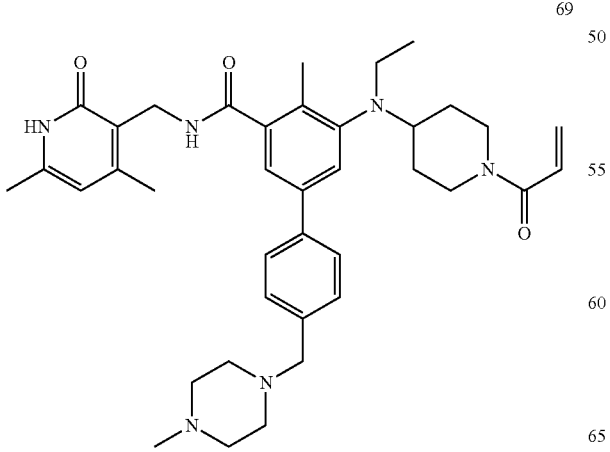

The preparation method was the same as Example 34, except that 4-methylpiperazine was used instead of piperidine to give Compound 69.

¹H-NMR (DMSO-d6) δ: 0.84 (3H, t), 1.39-1.47 (2H, m), 1.75-1.83 (2H, m), 2.11 (3H, s), 2.20 (3H, s), 2.22 (3H, s), 2.25 (3H, s), 2.39 (8H, br), 2.66 (1H, t), 2.99-3.12 (4H, m), 3.49 (2H, s), 4.01 (1H, d), 4.29-4.39 (3H, m), 5.63-5.66 (1H, m), 5.87 (1H, s), 6.05-6.10 (1H, m), 6.70-6.82 (1H, m), 7.23 (1H, d), 7.35-7.41 (3H, m), 7.58 (2H, d), 8.20 (1H, t), 11.47 (1H, s).

m/z ESI M+H⁺ 639.3.

Example 70

Preparation of N-(4,6-dimethyl-2-oxo-1,2-dihydro-pyridin-3-ylmethyl)-5-[(1-acryloyl-piperidin-4-yl)-ethyl-amino]-4-methyl-3'-(morpholin-4-ylmethyl)-[1,1'-biphenyl]-3-carboxamide

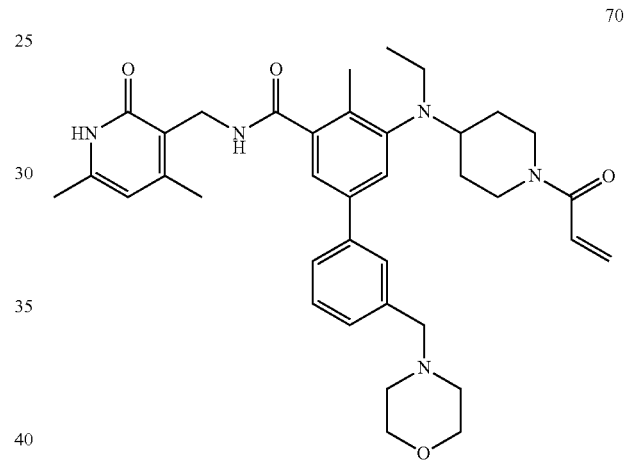

The preparation method was the same as Example 30, except that 1-Boc-4-piperidone was used instead of 1-Boc-3-pyrrolidone to give Compound 70.

¹H-NMR (DMSO-d6) δ: 0.85 (3H, t), 1.37-1.50 (2H, m), 1.75-1.83 (2H, d), 2.11 (3H, s), 2.22 (3H, s), 2.26 (3H, s), 2.39 (4H, br), 2.65 (1H, t), 2.99-3.12 (4H, m), 3.53 (2H, s), 3.58 (4H, br), 4.01 (1H, d), 4.29-4.38 (3H, m), 5.63-5.67 (1H, m), 5.87 (1H, s), 6.05-6.10 (1H, m), 6.75-6.83 (1H, m), 7.22 (1H, s), 7.31 (1H, d), 7.39-7.45 (2H, m), 7.50-7.55 (2H, m), 8.23 (1H, t), 11.49 (1H, s).

m/z ESI M+H⁺ 626.3.

Example 71

Preparation of N-(4,6-dimethyl-2-oxo-1,2-dihydro-pyridin-3-ylmethyl)-5-[(1-acryloyl-piperidin-4-yl)-ethyl-amino]-3'-chloro-4-methyl-4'-(morpholin-4-ylmethyl)-[1,1'-biphenyl]-3-carboxamide

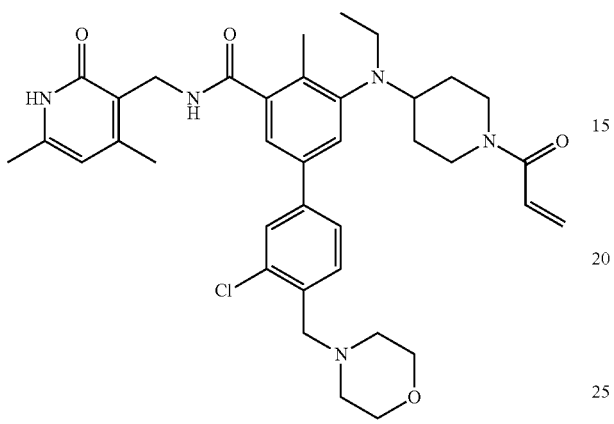

The preparation method was the same as Example 21, except that 1-Boc-4-piperidone was used instead of 1-Boc-3-pyrrolidone to give Compound 71.

$^1$H-NMR (DMSO-d6) δ: 0.84 (3H, t), 1.37-1.48 (2H, m), 1.74-1.82 (2H, d), 2.11 (3H, s), 2.21 (3H, s), 2.25 (3H, s), 2.44 (4H, br), 2.65 (1H, t), 2.99-3.12 (4H, m), 3.59 (6H, br), 4.01 (1H, d), 4.29-4.41 (3H, m), 5.62-5.66 (1H, m), 5.86 (1H, s), 6.04-6.09 (1H, m), 6.74-6.82 (1H, m), 7.25 (1H, s), 7.44 (1H, s), 7.54-7.62 (2H, m), 7.71 (1H, s), 8.22 (1H, t), 11.48 (1H, s).

m/z ESI M+H$^+$ 660.3.

Example 72

Preparation of N-(4,6-dimethyl-2-oxo-1,2-dihydro-pyridin-3-ylmethyl)-5-[(1-acryloyl-piperidin-4-yl)-ethyl-amino]-4-methyl-3'-(piperidin-1-ylmethyl)-[1,1'-biphenyl]-3-carboxamide

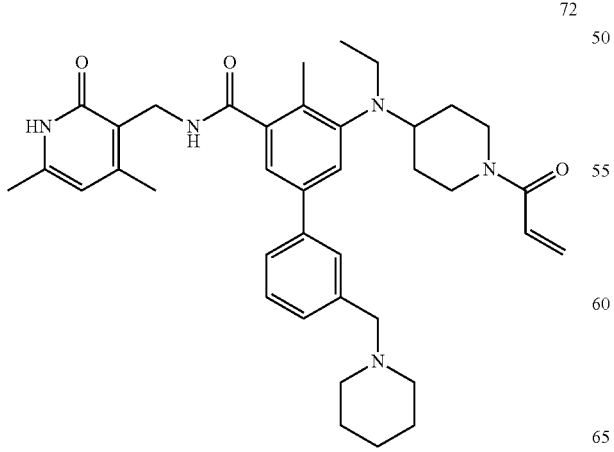

The preparation method was the same as Example 70, except that piperidine was used instead of morpholine to give Compound 72.

$^1$H-NMR (DMSO-d6) δ: 0.85 (3H, t), 1.37-1.50 (2H, m), 1.64-1.85 (8H, d), 2.12 (3H, s), 2.22 (3H, s), 2.26 (3H, s), 2.67 (1H, t), 2.85-3.15 (10H, m), 4.02 (1H, d), 4.29-4.41 (5H, m), 5.63-5.67 (1H, m), 5.88 (1H, s), 6.06-6.10 (1H, m), 6.75-6.83 (1H, m), 7.30 (1H, s), 7.48-7.57 (3H, m), 7.72-7.78 (1H, m), 7.88 (1H, s), 8.21 (1H, t), 9.90 (1H, br), 11.49 (1H, s).

m/z ESI M+H$^+$ 624.3.

Example 73

Preparation of N-(4,6-dimethyl-2-oxo-1,2-dihydro-pyridin-3-ylmethyl)-5-[(1-acryloyl-piperidin-4-yl)-ethyl-amino]-4-methyl-3'-(4-methylpiperazin-1-ylmethyl)-[1,1'-biphenyl]-3-carboxamide

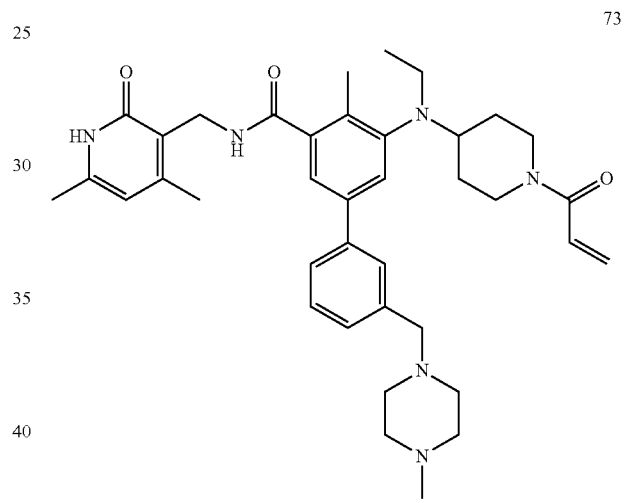

The preparation method was the same as Example 70, except that N-methyl piperazine was used instead of morpholine to give Compound 73.

$^1$H-NMR (DMSO-d6) δ: 0.84 (3H, t), 1.37-1.50 (2H, m), 1.74-1.82 (2H, d), 2.12 (3H, s), 2.20 (3H, s), 2.25 (3H, s), 2.61-3.25 (16H, m), 3.62 (2H, s), 4.01 (1H, d), 4.29-4.42 (3H, m), 5.63-5.67 (1H, m), 5.88 (1H, s), 6.05-6.10 (1H, m), 6.75-6.83 (1H, m), 7.23 (1H, s), 7.32 (1H, d), 7.40-7.48 (2H, m), 7.52-7.59 (2H, d), 8.22 (1H, t), 11.49 (1H, s).

m/z ESI M+H$^+$ 639.4.

Example 74

Preparation of N-(4,6-dimethyl-2-oxo-1,2-dihydro-pyridin-3-ylmethyl)-5-[(1-acryloyl-piperidin-4-yl)-ethyl-amino]-4-methyl-3'-(4-acetylpiperazin-1-ylmethyl)-[1,1'-biphenyl]-3-carboxamide

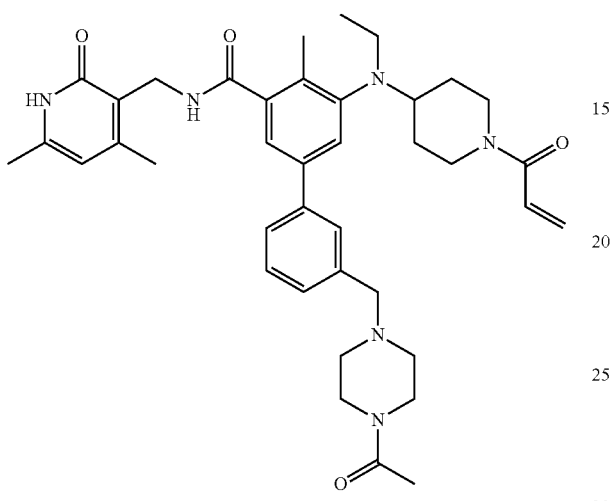

74

The preparation method was the same as Example 70, except that N-acetyl piperazine was used instead of morpholine to give Compound 74.

¹H-NMR (DMSO-d6) δ: 0.84 (3H, t), 1.38-1.48 (2H, m), 1.75-1.82 (2H, d), 1.98 (3H, s), 2.11 (3H, s), 2.22 (3H, s), 2.26 (3H, s), 2.33 (2H, br), 2.40 (2H, br), 2.66 (1H, t), 2.99-3.13 (4H, m), 3.42 (4H, br), 3.58 (2H, s), 4.01 (1H, d), 4.29-4.42 (3H, m), 5.63-5.67 (1H, m), 5.87 (1H, s), 6.05-6.10 (1H, m), 6.75-6.83 (1H, m), 7.22 (1H, s), 7.31 (1H, d), 7.40-7.45 (2H, m), 7.52-7.55 (2H, d), 8.23 (1H, t), 11.48 (1H, s).

m/z ESI M+H⁺ 667.3.

Example 75

Preparation of N-(4,6-dimethyl-2-oxo-1,2-dihydro-pyridin-3-ylmethyl)-5-[(1-acryloyl-piperidin-4-yl)-ethyl-amino]-4-methyl-3'-(4-methylhomopiperazin-1-ylmethyl)-[1,1'-biphenyl]-3-carboxamide

75

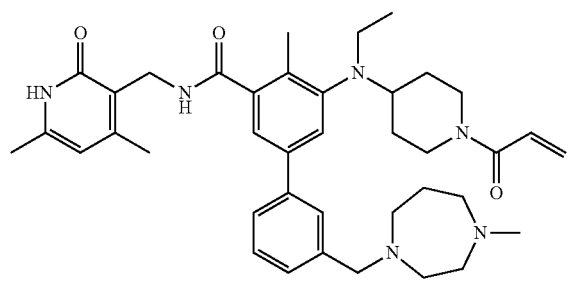

The preparation method was the same as Example 70, except that N-methylhomopiperazine was used instead of morpholine to give Compound 75.

¹H-NMR (DMSO-d6) δ: 0.77 (3H, t), 1.35-1.49 (2H, m), 1.75-1.83 (2H, m), 1.94-2.04 (2H, m), 2.04 (3H, s), 2.11 (3H, s), 2.18 (3H, s), 2.59-2.76 (5H, m), 2.80 (1H, br), 2.99-3.25 (6H, m), 3.70 (2H, s), 3.94 (1H, d), 4.22-4.31 (3H, m), 5.55-5.60 (1H, m), 5.80 (1H, s), 5.98-6.03 (1H, m), 6.67-6.75 (1H, m), 7.16 (1H, s), 7.33-7.61 (5H, m), 8.13 (1H, t), 11.40 (1H, s).

m/z ESI M+H⁺ 653.3.

Example 76

Preparation of N-(4,6-dimethyl-2-oxo-1,2-dihydro-pyridin-3-ylmethyl)-5-[(1-acryloyl-piperidin-4-yl)-ethyl-amino]-4-methyl-4'-(3-methoxy-1-azetidinylmethyl)-[1,1'-biphenyl]-3-carboxamide

76

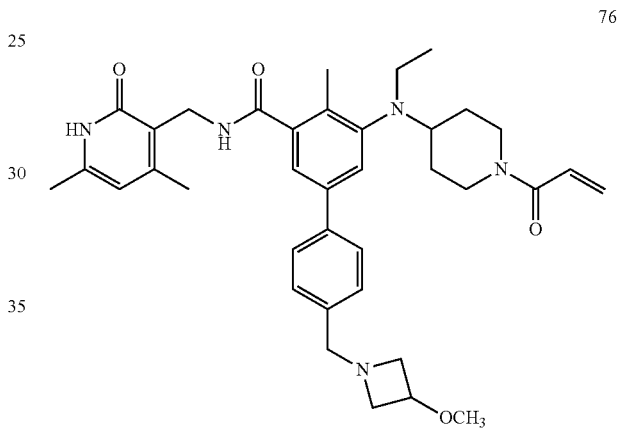

The preparation method was the same as Example 34, except that 3-methoxyazetidine was used instead of piperidine to give Compound 76.

¹H-NMR (DMSO-d6) δ: 0.84 (3H, t), 1.37-1.49 (2H, m), 1.78 (2H, d), 2.11 (3H, s), 2.22 (3H, s), 2.26 (3H, s), 2.67 (1H, t), 2.99-3.13 (4H, m), 3.20 (3H, s), 3.40 (2H, br), 3.80 (2H, br), 3.87-4.13 (4H, m), 4.29-4.38 (3H, m), 5.63-5.66 (1H, m), 5.87 (1H, s), 6.04-6.10 (1H, m), 6.75-6.82 (1H, m), 7.24 (1H, d), 7.41-7.46 (3H, m), 7.63 (2H, d), 8.21 (1H, t), 11.48 (1H, s).

m/z ESI M+H⁺ 626.3.

Example 77

Preparation of N-(4,6-dimethyl-2-oxo-1,2-dihydro-pyridin-3-ylmethyl)-5-[(1-acryloyl-piperidin-4-yl)-ethyl-amino]-4-methyl-4'-[4-(2-methoxyethyloxy)-piperidin-1-ylmethyl]-[1,1'-biphenyl]-3-carboxamide

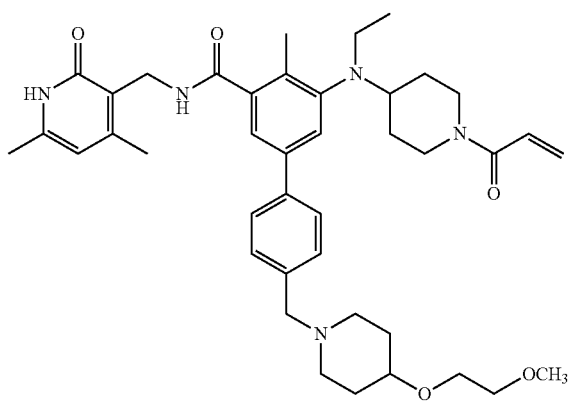

77

The preparation method was the same as Example 34, except that 4-(2-methoxyethoxy) piperidine was used instead of piperidine to give Compound 77.

$^1$H-NMR (DMSO-d6) δ: 0.84 (3H, t), 1.36-1.49 (2H, m), 1.78 (2H, m), 1.93-2.12 (7H, m), 2.22 (3H, s), 2.27 (3H, s), 2.66 (1H, t), 2.89-3.22 (8H, m), 3.24 (3H, s), 3.44 (2H, br), 3.53 (2H, t), 4.01 (1H, d), 4.26-4.38 (5H, m), 5.63-5.67 (1H, m), 5.87 (1H, s), 6.05-6.10 (1H, m), 6.75-6.83 (1H, m), 7.28 (1H, s), 7.45 (1H, s), 7.67-7.75 (4H, m), 8.22 (1H, t), 11.49 (1H, s).

m/z ESI M+H$^+$ 698.5.

Example 78

Preparation of N-(4,6-dimethyl-2-oxo-1,2-dihydro-pyridin-3-ylmethyl)-5-[(1-acryloyl-piperidin-4-yl)-ethyl-amino]-4-methyl-4'-(2-oxa-7-aza-spiro[3.5]nonan-7-ylmethyl)-[1,1'-biphenyl]-3-carboxamide

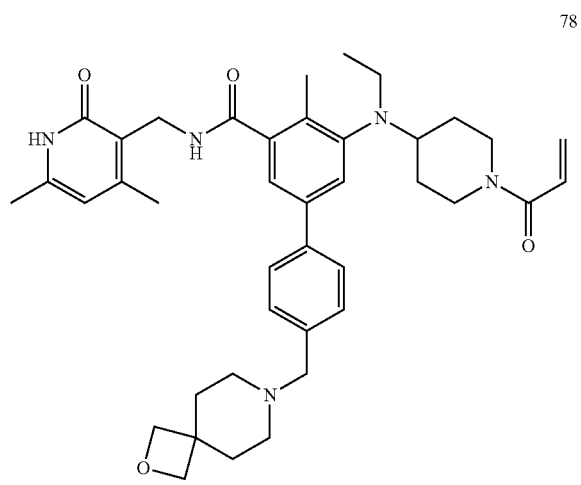 [SMILES: C=CC(=O)N1CCC(N(CC)c2cc(-c3ccc(CN4CCC5(CC4)COC5)cc3)cc(C(=O)NCc3c(C)cc(C)[nH]c3=O)c2C)CC1]

78

The preparation method was the same as Example 34, except that 2-oxa-7-aza-spiro[3,5]nonane was used instead of piperidine to give Compound 78.

$^1$H-NMR (DMSO) δ: 0.83 (3H, t), 1.37-1.17 (2H, m), 1.73-2.04 (6H, m), 2.11 (3H, s), 2.21 (3H, s), 2.25 (3H, s), 2.65 (1H, t), 2.99-3.09 (4H, m), 3.40 (6H, br), 4.01 (1H, d), 4.23-4.42 (7H, m), 5.62-5.66 (1H, m), 5.86 (1H, s), 6.04-6.09 (1H, m), 6.74-6.81 (1H, m), 7.25 (1H, s), 7.43 (1H, s), 7.44 (2H, d), 7.65 (2H, d), 8.20 (1H, t), 11.49 (1H, s).

m/z ESI M+H$^+$ 666.3.

Example 79

Preparation of N-(4,6-dimethyl-2-oxo-1,2-dihydro-pyridin-3-ylmethyl)-5-bromo-3-{ethyl-[1-(4-morpholin-4-yl-but-2-enoyl)-piperidin-4-yl]-amino}-2-methyl-benzamide

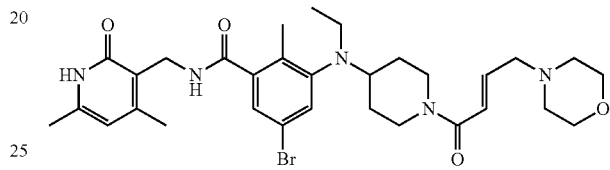

79

The preparation method was the same as Example 14, except that 1-Boc-4-piperidone was used instead of 1-Boc-3-pyrrolidone, and 4-(morpholin-4-yl) crotonic acid hydrochloride was used instead of 4-dimethylamino crotonic acid hydrochloride to give Compound 79.

$^1$H-NMR (DMSO-d6) δ: 0.78 (3H, t), 1.32-1.47 (2H, m), 1.72 (2H, d), 2.11 (3H, s), 2.15 (3H, s), 2.19 (3H, s), 2.37 (4H, br), 2.59 (1H, t), 2.93-3.18 (6H, m), 3.58 (4H, br), 3.95-4.02 (1H, m), 4.25 (2H, d), 4.33-4.36 (1H, m), 5.86 (1H, s), 6.51-6.63 (2H, m), 7.09 (1H, s), 7.31 (1H, s), 8.23 (1H, t), 11.47 (1H, s).

m/z ESI M+H$^+$ 628.1.

Example 80

Preparation of N-(4,6-dimethyl-2-oxo-1,2-dihydro-pyridin-3-ylmethyl)-5-[(1-acryloyl-piperidin-4-yl)-ethyl-amino]-4-methyl-3'-[4-(morpholin-4-yl)piperazin-1-ylmethyl]-biphenyl-3-carboxamide

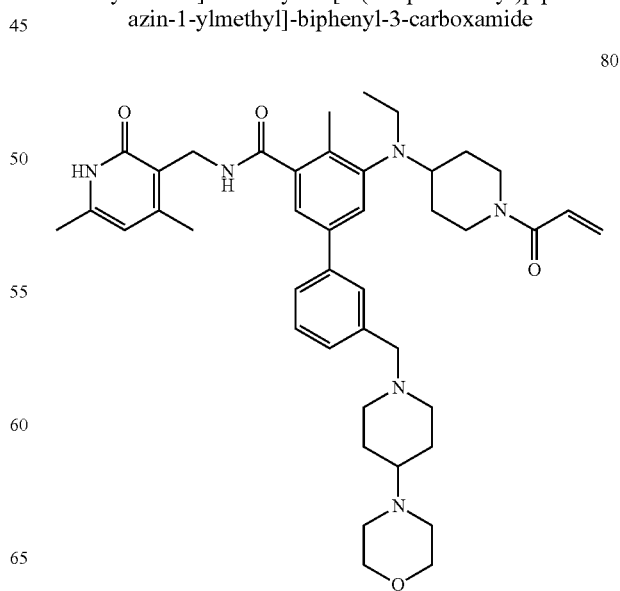

80

The preparation method was the same as Example 70, except that 4-(piperidin-4-yl) morpholine was used instead of morpholine to give Compound 80.

¹H-NMR (DMSO) δ: 0.89 (3H, t), 1.35-1.48 (4H, m), 1.82 (4H, d), 2.16 (3H, s), 2.27 (3H, s), 2.30 (3H, s), 2.42 (4H, br), 2.70 (1H, t), 2.99-3.07 (5H, m), 3.62 (4H, s), 4.06 (1H, d), 4.33-4.42 (3H, m), 5.62-5.65 (1H, m), 5.87 (1H, s), 6.03-6.09 (1H, m), 6.74-6.80 (1H, m), 7.22 (1H, s), 7.30 (1H, s), 7.40-7.57 (4H, m), 8.19 (1H, t), 11.45 (1H, s).

m/z ESI M+H⁺ 709.5.

Example 81

Preparation of N-(4,6-dimethyl-2-oxo-1,2-dihydropyridin-3-ylmethyl)-5-[(1-acryloyl-piperidin-4-yl)-ethyl-amino]-4-methyl-4'-[4-(morpholin-4-yl)piperazin-1-ylmethyl]-[1,1'-biphenyl]-3-carboxamide

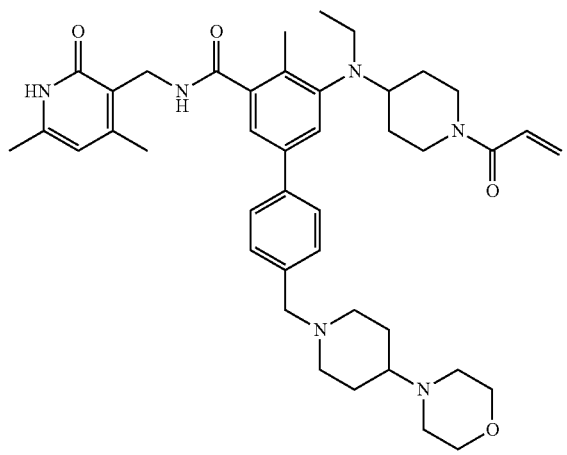

81

The preparation method was the same as Example 34, except that 4-(piperidin-4-yl) morpholine was used instead of piperidine to give Compound 81.

¹H-NMR (DMSO) δ: 0.84 (3H, t), 1.37-1.49 (3H, m), 1.73-1.945 (5H, m), 2.11 (3H, s), 2.22 (3H, s), 2.26 (3H, s), 2.45-2.68 (6H, m), 2.96-3.17 (8H, m), 3.61 (6H, br), 4.01 (1H, d), 4.28-4.39 (3H, m), 5.62-5.67 (1H, m), 5.87 (1H, s), 6.04-6.10 (1H, dd), 6.76-6.83 (1H, m), 7.25 (1H, s), 7.42-7.53 (3H, m), 7.63 (2H, d), 8.22 (1H, t), 11.50 (1H, s).

m/z ESI M+H⁺ 709.5.

Example 82

Preparation of N-(4,6-dimethyl-2-oxo-1,2-dihydropyridin-3-ylmethyl)-5-[(1-acryloyl-piperidin-4-yl)-ethyl-amino]-4-methyl-3'-(4-methoxypiperidin-1-ylmethyl)-[1,1'-biphenyl]-3-carboxamide

82

The preparation method was the same as Example 70, except that 4-methoxypiperidine was used instead of morpholine to give Compound 82.

¹H-NMR (DMSO) δ: 0.85 (3H, t), 1.38-1.47 (3H, m), 1.76-1.97 (5H, m), 2.12 (3H, s), 2.22 (3H, s), 2.26 (3H, s), 2.61-2.71 (2H, m), 2.97-3.20 (7H, m), 3.25 (3H, s), 3.34 (2H, s), 4.02 (1H, d), 4.30-4.39 (4H, m), 5.63-5.67 (1H, m), 5.88 (1H, s), 6.05-6.10 (1H, m), 6.75-6.83 (1H, m), 7.20-7.93 (6H, m), 8.21 (1H, t), 11.47 (1H, s).

m/z ESI M+H⁺ 654.3.

Example 83

Preparation of N-(4,6-dimethyl-2-oxo-1,2-dihydropyridin-3-ylmethyl)-5-[(1-acryloyl-piperidin-4-yl)-ethyl-amino]-4-methyl-4'-(4-oxo-piperidin-1-ylmethyl)-[1,1'-biphenyl]-3-carboxamide

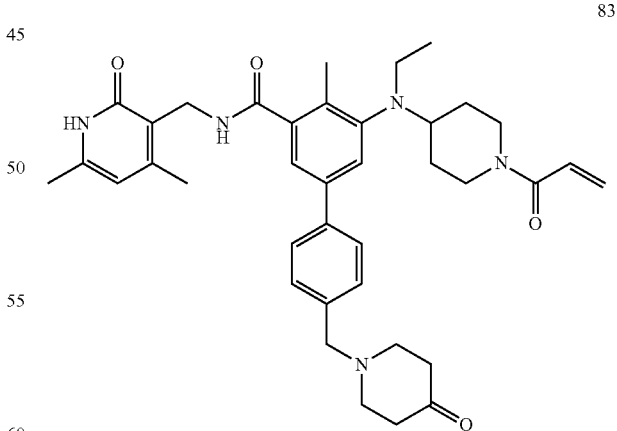

83

The preparation method was the same as Example 70, except that 4-oxopiperidine was used instead of morpholine to give Compound 83.

¹H-NMR (DMSO) δ: 0.85 (3H, t), 1.35-1.48 (2H, m), 1.73-1.83 (2H, m), 2.12 (3H, s), 2.23 (3H, s), 2.26 (3H, s), 2.39 (4H, br), 2.60-2.76 (5H, m), 2.99-3.13 (4H, m), 3.63

(2H, s), 3.98-4.023 (1H, m), 4.26-4.41 (3H, m), 5.61-5.68 (1H, m), 5.88 (1H, s), 6.03-6.13 (1H, m), 6.72-6.83 (1H, m), 7.25 (1H, s), 7.38-7.51 (3H, m), 7.64 (2H, d), 8.23 (1H, t), 11.50 (1H, s).

m/z ESI M+H⁺ 638.3.

Example 84

Preparation of N-(4,6-dimethyl-2-oxo-1,2-dihydro-pyridin-3-ylmethyl)-5-[(1-acryloyl-piperidin-4-yl)-ethyl-amino]-4-methyl-4'-(4-hydroxypiperidin-1-ylmethyl)-[1,1'-biphenyl]-3-carboxamide

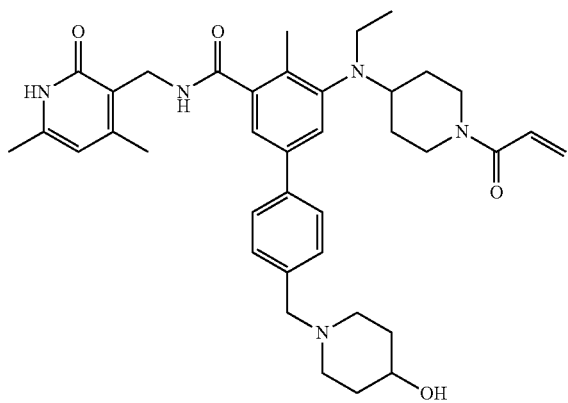

84

The preparation method was the same as Example 34, except that 4-piperidinol was used instead of piperidine to give Compound 84.

¹H-NMR (DMSO) δ: 0.83 (3H, t), 1.37-1.45 (2H, m), 1.58-1.81 (4H, m), 1.86-1.97 (2H, m), 2.11 (3H, s), 2.21 (3H, s), 2.25 (3H, s), 2.65 (1H, t), 2.82-3.18 (8H, m), 3.34 (2H, s), 4.01 (1H, d), 4.28-4.38 (4H, m), 5.62-5.66 (1H, m), 5.87 (1H, s), 6.04-6.09 (1H, m), 6.74-6.82 (1H, m), 7.27 (1H, s), 7.44 (1H, s), 7.60-7.75 (4H, m), 8.21 (1H, t), 11.48 (1H, s).

m/z ESI M+H⁺ 640.3.

Example 85

Preparation of N-(4,6-dimethyl-2-oxo-1,2-dihydro-pyridin-3-ylmethyl)-5-[(1-acryloyl-piperidin-4-yl)-ethyl-amino]-4-methyl-4'-(3-isopropoxy-1-azetidi-nylmethyl)-[1,1'-biphenyl]-3-carboxamide

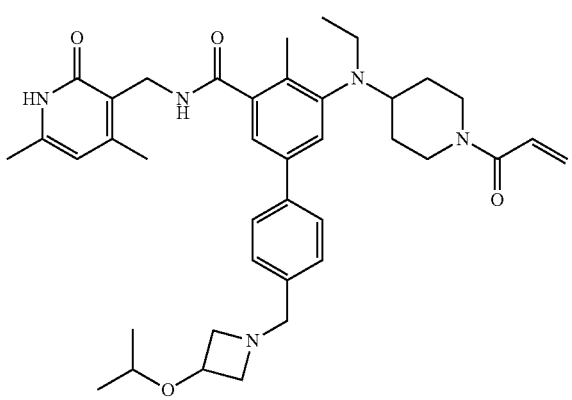

85

The preparation method was the same as Example 34, except that 3-isopropoxy-1-azetidine was used instead of piperidine to give Compound 85.

¹H-NMR (DMSO) δ: 0.84 (3H, t), 1.08 (6H, d), 1.36-1.47 (2H, m), 1.78 (2H, d), 2.12 (3H, s), 2.22 (3H, s), 2.26 (3H, s), 2.65 (1H, t), 2.99-3.12 (4H, m), 3.61-3.72 (2H, m), 4.03-4.41 (9H, m), 5.63-5.67 (1H, m), 5.87 (1H, s), 6.05-6.10 (1H, m), 6.75-6.83 (1H, m), 7.26 (1H, s), 7.43 (1H, s), 7.56 (2H, d), 7.69 (2H, d), 8.23 (1H, t), 11.50 (1H, s).

m/z ESI M+H⁺ 654.3.

Example 86

Preparation of N-(4,6-dimethyl-2-oxo-1,2-dihydro-pyridin-3-ylmethyl)-5-[(1-acryloyl-piperidin-4-yl)-ethyl-amino]-3'-chloro-4-methyl-4'-[4-(morpholin-4-yl)-piperidin-1-ylmethyl]-[1,1'-biphenyl]-3-carboxamide

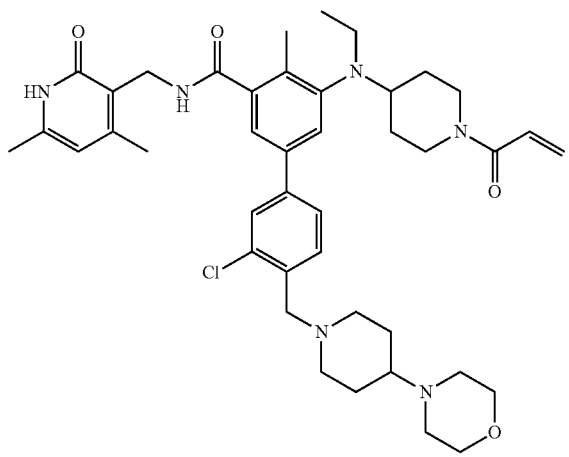

86

The preparation method was the same as Example 21, except that 1-Boc-4-piperidone was used instead of 1-Boc-3-pyrrolidone to give Compound 86.

¹H-NMR (DMSO) δ: 0.84 (3H, t), 1.33-1.49 (4H, m), 1.71-1.82 (4H, m), 1.99-2.09 (2H, m), 2.11 (3H, s), 2.22 (3H, s), 2.26 (3H, s), 2.45 (4H, br), 2.65 (1H, t), 2.90 (2H, d), 2.99-3.13 (5H, m), 3.56 (6H, br), 4.01 (1H, d), 4.29-4.38 (3H, m), 5.63-5.67 (1H, m), 5.87 (1H, s), 6.05-6.10 (1H, m), 6.76-6.83 (1H, m), 7.26 (1H, s), 7.45 (1H, s), 7.54 (1H, d), 7.61 (1H, d), 7.71 (1H, s), 8.25 (1H, t), 11.50 (1H, s).

m/z ESI M+H⁺ 743.3.

Example 87

Preparation of N-(4,6-dimethyl-2-oxo-1,2-dihydro-pyridin-3-ylmethyl)-5-[(1-acryloyl-piperidin-4-yl)-ethyl-amino]-4-methyl-4'-(1-oxa-8-aza-spiro[4.5]decan-8-ylmethyl)-[1,1'-biphenyl]-3-carboxamide

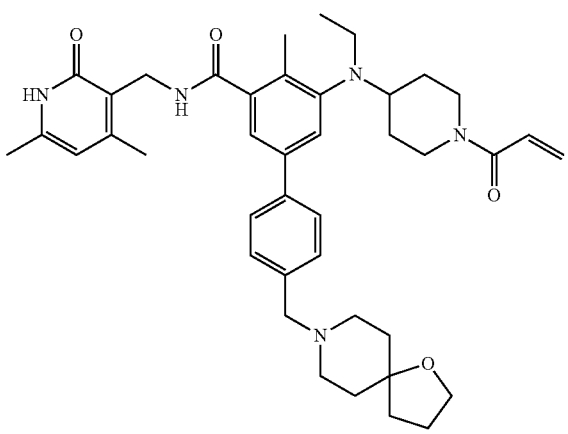

The preparation method was the same as Example 34, except that 1-oxa-8-aza-spiro [4.5] decane was used instead of piperidine to give Compound 87.

¹H-NMR (DMSO) δ: 0.84 (3H, t), 1.36-1.47 (2H, m), 1.63-1.94 (10H, m), 2.11 (3H, s), 2.22 (3H, s), 2.26 (3H, s), 2.65 (1H, t), 2.99-3.43 (9H, m), 3.72 (2H, t), 4.02 (1H, d), 4.29-4.41 (4H, m), 5.64-5.67 (1H, m), 5.87 (1H, s), 6.05-6.10 (1H, s), 6.76-6.83 (1H, m), 7.26 (1H, s), 7.44 (1H, s), 7.61-7.79 (4H, m), 8.24 (1H, t), 11.51 (1H, s).

m/z ESI M+H⁺ 680.3.

Example 88

Preparation of N-(4,6-dimethyl-2-oxo-1,2-dihydro-pyridin-3-ylmethyl)-5-[(1-acryloyl-piperidin-4-yl)-ethyl-amino]-4-methyl-4'-(4-ethoxypiperidin-1-ylmethyl)-[1,1'-biphenyl]-3-carboxamide

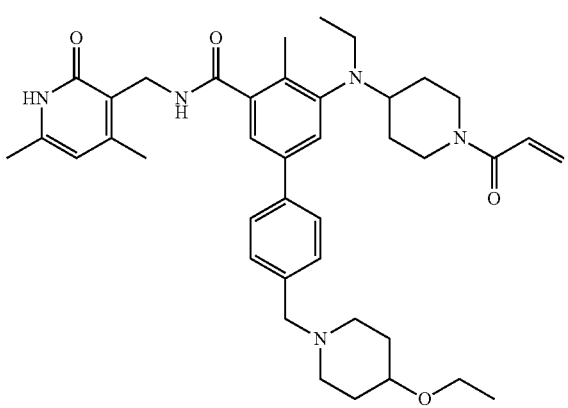

The preparation method was the same as Example 34, except that 4-ethoxypiperidine was used instead of piperidine to give Compound 88.

¹H-NMR (CDCl₃) δ: 0.88 (3H, t), 1.20 (3H, t), 1.48-1.62 (3H, m), 1.78-1.82 (5H, m), 2.13 (3H, s), 2.17-2.32 (2H, m), 2.35 (3H, s), 2.41 (3H, s), 2.69 (1H, t), 2.92-3.11 (6H, m), 3.46 (2H, q), 3.57 (1H, br), 3.88-3.98 (3H, m), 4.50-4.58 (3H, d), 5.64-5.68 (1H, m), 5.91 (1H, s), 6.22-6.27 (1H, s), 6.52-6.59 (1H, m), 7.21 (1H, t), 7.28 (1H, s), 7.30 (1H, s), 7.49 (2H, d), 7.56 (2H, d), 11.67 (1H, s).

m/z ESI M+H⁺ 668.4.

Example 89

Preparation of N-(4,6-dimethyl-2-oxo-1,2-dihydro-pyridin-3-ylmethyl)-5-[(1-acryloyl-piperidin-4-yl)-ethyl-amino]-4-methyl-4'-[4-(tetrahydropyran-4-yl)-piperazin-1-ylmethyl]-[1,1'-biphenyl]-3-carboxamide

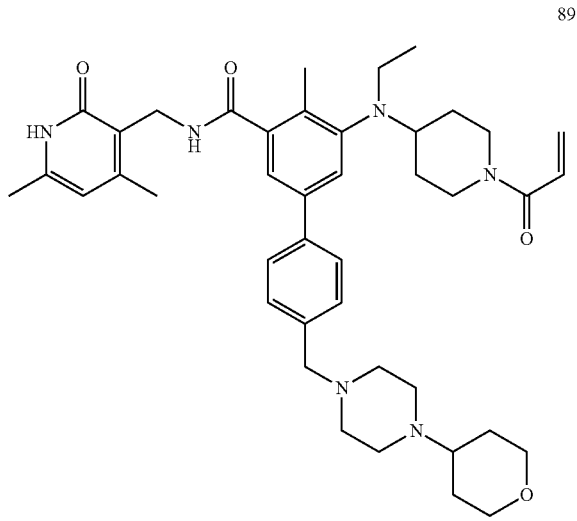 [SMILES: C=CC(=O)N1CCC(N(CC)c2cc(-c3ccc(CN4CCN(C5CCOCC5)CC4)cc3)cc(C(=O)NCc3c(C)cc(C)[nH]c3=O)c2C)CC1]

The preparation method was the same as Example 34, except that 4-(tetrahydropyran-4-yl)-piperazine was used instead of piperidine to give Compound 89.

¹H-NMR (DMSO) δ: 0.83 (3H, t), 1.28-1.48 (3H, m), 1.72-1.95 (5H, m), 2.11 (3H, s), 2.21 (3H, s), 2.26 (3H, s), 2.53-3.20 (13H, m), 3.27 (3H, t), 3.57 (2H, s), 3.92 (2H, d), 4.01 (1H, d), 4.28-4.38 (3H, m), 5.63-5.67 (1H, m), 5.87 (1H, s), 6.05-6.10 (1H, m), 6.75-6.83 (1H, m), 7.23 (1H, s), 7.37-7.45 (3H, m), 7.62 (2H, d), 8.23 (1H, t), 11.51 (1H, s).

m/z ESI M+H⁺ 710.0.

Example 90

Preparation of N-(4,6-dimethyl-2-oxo-1,2-dihydro-pyridin-3-ylmethyl)-5-[(1-acryloyl-piperidin-4-yl)-ethyl-amino]-3'-chloro-4-methyl-4'-(4-methoxypiperidin-4-ylmethyl)-[1,1'-biphenyl]-3-carboxamide

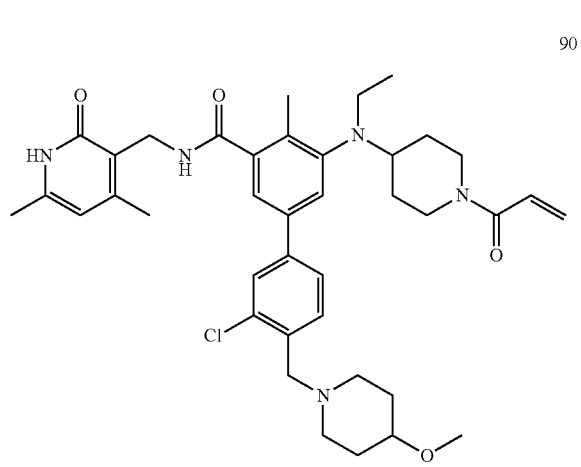 [SMILES: C=CC(=O)N1CCC(N(CC)c2cc(-c3ccc(CN4CCC(OC)CC4)c(F)c3)cc(C(=O)NCc3c(C)cc(C)[nH]c3=O)c2C)CC1]

90

The preparation method was the same as Example 86, except that 4-methoxypiperidine was used instead of 4-(morpholin-4-yl)-piperidine to give Compound 90.

$^1$H-NMR (CDCl$_3$) δ: 0.91 (3H, t), 1.56-1.63 (3H, m), 1.77-1.92 (5H, m), 2.08-2.22 (5H, m), 2.36 (3H, s), 2.42 (3H, s), 2.72 (1H, t), 2.92-3.13 (6H, m), 3.36 (3H, s), 3.36-3.43 (1H, m), 3.92-4.02 (3H, m), 4.52-4.61 (3H, m), 5.66-5.70 (1H, m), 5.95 (1H, s), 6.24-6.30 (1H, m), 6.54-6.61 (1H, m), 7.22 (1H, t), 7.27 (1H, d), 7.30 (1H, d), 7.45 (1H, d), 7.51 (1H, d), 7.83 (1H, br), 11.40 (1H, br).

m/z ESI M+H$^+$ 688.3.

Example 91

Preparation of N-(4,6-dimethyl-2-oxo-1,2-dihydro-pyridin-3-ylmethyl)-5-[(1-acryloyl-piperidin-4-yl)-ethyl-amino]-3'-chloro-4-methyl-4'-(3-methoxypiperidin-4-ylmethyl)-[1,1'-biphenyl]-3-carboxamide

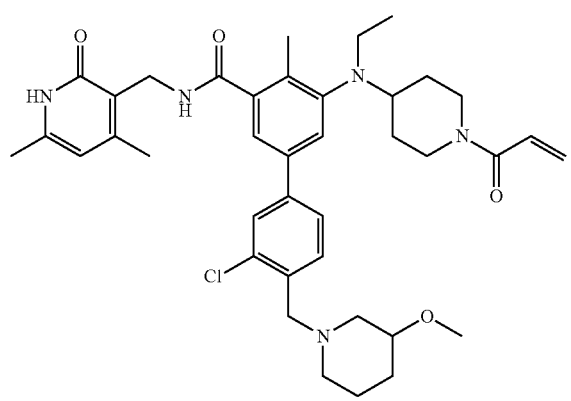

91

The preparation method was the same as Example 86, except that 3-methoxypiperidine was used instead of 4-(morpholin-4-yl)-piperidine to give Compound 91.

$^1$H-NMR (CDCl$_3$) δ: 0.91 (3H, t), 1.53-1.64 (3H, m), 1.79-1.93 (5H, m), 2.02-2.10 (2H, m), 2.20 (3H, s), 2.35 (3H, s), 2.42 (3H, s), 2.72 (1H, t), 2.89-3.18 (6H, m), 3.37 (3H, s), 3.51-3.61 (1H, m), 3.88-4.02 (3H, m), 4.52-4.61 (3H, m), 5.65-5.70 (1H, m), 5.97 (1H, s), 6.24-6.30 (1H, m), 6.54-6.61 (1H, m), 7.20 (1H, t), 7.28 (1H, d), 7.30 (1H, d), 7.44 (1H, d), 7.51 (1H, d), 7.76 (1H, br), 11.45 (1H, br).

m/z ESI M+H$^+$ 688.3.

Example 92

Preparation of N-(4,6-dimethyl-2-oxo-1,2-dihydro-pyridin-3-ylmethyl)-5-[(1-acryloyl-piperidin-4-yl)-ethyl-amino]-4-methyl-4'-(3-methoxypiperidin-4-ylmethyl)-[1,1'-biphenyl]-3-carboxamide

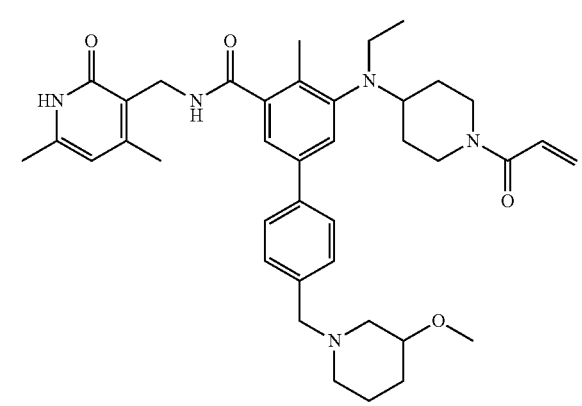

92

The preparation method was the same as Example 34, except that 3-methoxypiperidine was used instead of piperidine to give Compound 92.

$^1$H-NMR (CDCl$_3$) δ: 0.90 (3H, t), 1.51-1.62 (2H, m), 1.74-1.90 (4H, m), 1.95-2.04 (2H, m), 2.06-2.22 (5H, m), 2.36 (3H, s), 2.42 (3H, s), 2.66-2.84 (2H, m), 2.98-3.12 (5H, m), 3.34 (3H, s), 3.41-3.51 (1H, m), 3.68 (2H, br), 3.93 (1H, d), 4.51-4.61 (3H, m), 5.65-5.68 (1H, m), 5.94 (1H, s), 6.23-6.28 (1H, m), 6.52-6.61 (1H, m), 7.15 (1H, t), 7.29 (1H, d), 7.31 (1H, d), 7.39 (2H, d), 7.46 (2H, d), 11.57 (1H, br).

m/z ESI M+H$^+$ 654.4.

Example 93

Preparation of N-(4,6-dimethyl-2-oxo-1,2-dihydro-pyridin-3-ylmethyl)-5-[(1-acryloyl-piperidin-4-yl)-ethyl-amino]-3'-fluoro-4-methyl-4'-(3-methoxypip-eridin-4-ylmethyl)-[1,1'-biphenyl]-3-carboxamide

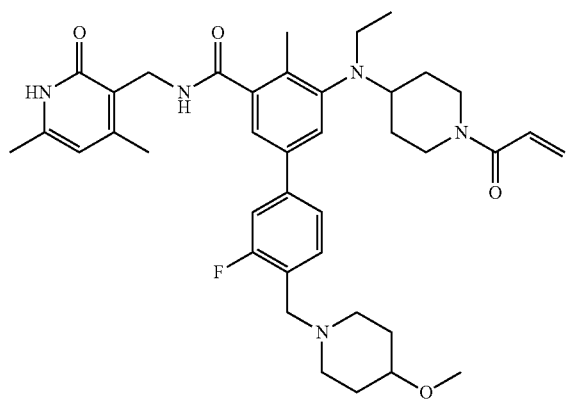

93

The preparation method was the same as Example 90, except that 2-fluoro-4-bromobenzoic acid was used instead of 2-chloro-4-bromobenzoic acid to give Compound 93.

$^1$H-NMR (CDCl$_3$) δ: $^1$H-NMR (DMSO) 0.83 (3H, t), 1.39-1.45 (3H, m), 1.78 (2H, d), 2.11 (3H, s), 2.21 (4H, m), 2.25 (4H, m), 2.30 (4H, m), 2.65 (4H, m), 3.03 (4H, m), 3.31 (4H, m), 4.01 (1H, d), 4.3-4.40 (4H, m), 5.64 (1H, dd), 5.87 (1H, s), 6.07 (1H, dd), 6.78 (1H, dd), 7.13-7.27 (4H, m), 7.43 (1H, m), 7.57 (1H, m), 7.71 (1H, m), 8.20 (1H, s), 10.15 (1H, s), 11.47 (1H, s).

m/z ESI M+H$^+$ 672.8.

Example 94

Preparation of N-(4,6-dimethyl-2-oxo-1,2-dihydro-pyridin-3-ylmethyl)-5-[(1-acryloyl-piperidin-4-yl)-ethyl-amino]-3',4-dimethyl-4'-(3-methoxypiperidin-4-ylmethyl)-[1,1'-biphenyl]-3-carboxamide

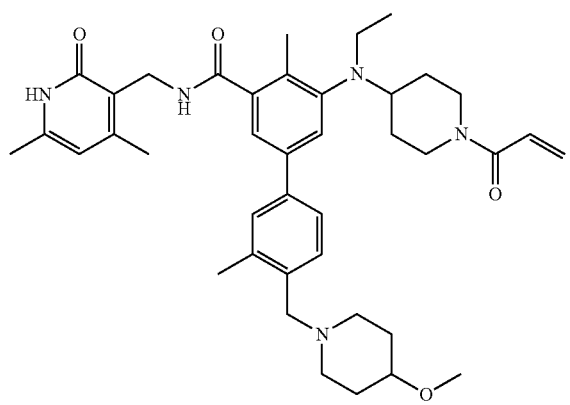

94

The preparation method was the same as Example 90, except that 2-methyl-4-bromobenzoic acid was used instead of 2-chloro-4-bromobenzoic acid to give Compound 94.

$^1$H-NMR (DMSO) δ: 0.83 (3H, t), 1.39-1.45 (3H, m), 1.78 (2H, d), 2.11 (3H, s), 2.21 (4H, m), 2.25 (4H, m), 2.30 (4H, m), 2.65 (4H, m), 3.03 (4H, m), 3.31 (4H, m), 4.01 (1H, d), 4.3-4.40 (4H, m), 5.64 (1H, dd), 5.87 (1H, s), 6.07 (1H, dd), 6.78 (1H, dd), 7.13-7.27 (4H, m), 7.43 (1H, m), 7.57 (1H, m), 7.71 (1H, m), 8.20 (1H, s), 10.15 (1H, s), 11.47 (1H, s).

m/z ESI M+H$^+$ 668.9.

Example 95

Preparation of N-(4,6-dimethyl-2-oxo-1,2-dihydro-pyridin-3-ylmethyl)-5-[(1-acryloyl-piperidin-4-yl)-ethyl-amino]-4-methyl-4'-(3-methoxypiperidin-1-ylmethyl)-[1,1'-biphenyl]-3-carboxamide

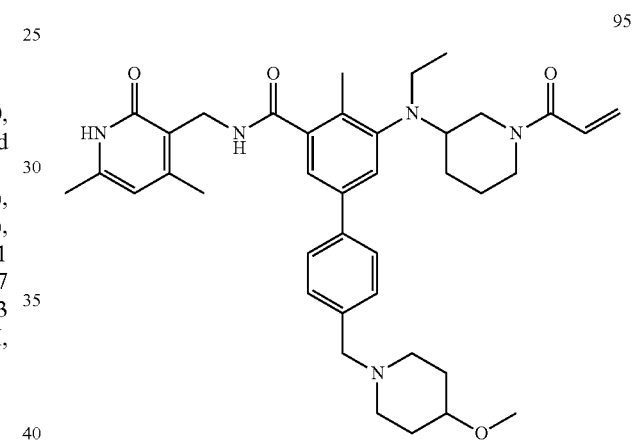

95

The preparation method was the same as Example 65, except that 1-Boc-3-piperidone was used instead of 1-Boc-4-piperidone to give Compound 95.

$^1$H-NMR (DMSO-d6) δ: 0.84 (3H, t), 1.43 (3H, m), 1.78 (2H, m), 2.00 (H, m), 2.11 (3H, s) 2.22 (3H, s), 2.25 (2H, m), 2.31 (3H, s), 2.38 (1H, m), 2.67 (2H, s), 3.08 (4H, m), 3.26 (4H, m), 4.0 (1H, m), 4.32 (4H, m), 5.64 (1H, dd), 5.87 (1H, s), 6.08 (1H, dd), 6.79 (1H, q), 7.17 (2H, dd), 67.26 (2H, d), 7.43 (1H, d), 7.57 (1H, d), 7.71 (1H, m), 8.20 (1H, d), 10.15 (1H, s), 11.48 (1H, s).

m/z ESI M+H$^+$ 654.3.

Example 96

Preparation of 5-((1-(2-cyanoacetyl)piperidin-4-yl)(ethyl)amino)-N-((4,6-dimethyl-2-oxo-1,2-dihydro-pyridin-3-yl)methyl)-4-methyl-4'-(morpholin-4-ylmethyl)biphenyl-3-carboxamide

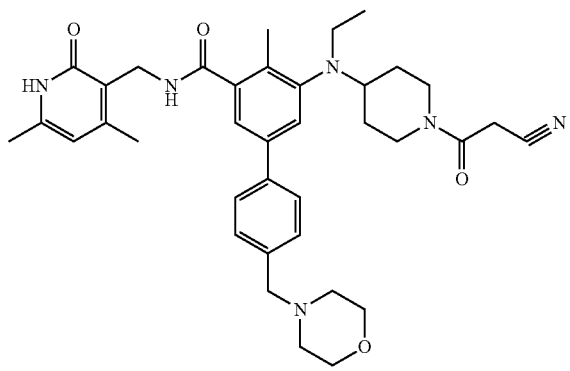

The preparation method was the same as Example 35 with 5-(ethyl-piperidin-4-yl-amino)-4-methyl-4'-morpholin-4-yl-methyl-biphenyl-3-carboxylic acid (4,6-dimethyl-2-oxo-1,2-dihydro-pyridin-3-ylmethyl)-amide as a starting material.

Cyanoacetic acid (70 mg, 0.82 mmol), HATU (311 mg, 0.82 mmol), triethylamine (138 mg, 1.36 mmol), 10 ml of DCM and 2.5 ml of DMF were added to a 100 ml flask, and stirred at room temperature for 30 mins. 5-(Ethyl-piperidin-4-yl-amino)-4-methyl-4'-morpholin-4-ylmethyl-biphenyl-3-carboxylic acid (4,6-dimethyl-2)-oxo-1,2-dihydro-pyridin-3-ylmethyl)-amide (390 mg, 0.68 mmol) was added and stirred at room temperature for 3 hours. The reaction solution was added with 20 ml of sodium bicarbonate solution, and extracted with 20 ml of ethyl acetate for three times. The combined organic phases were dried over anhydrous sodium sulfate, and then purified by column chromatography (DCM/MeOH=20:1) to give Compound 96.

$^1$H-NMR (DMSO) δ: 11.49 (s, 1H), 8.22 (t, 1H), 7.35~7.64 (m, 5H), 7.25 (s, 1H), 5.87 (s, 1H), 4.29 (d, 2H), 4.22 (d, 1H), 4.01 (d, 2H), 3.60~3.63 (m, 7H), 2.97~3.12 (m, 8H), 2.65 (t, 1H), 2.25 (s, 3H), 2.21 (s, 3H), 2.11 (s, 3H), 1.74 (d, 2H), 1.55 (q, 1H), 1.38 (q, 1H), 0.84 (t, 3H).

m/z ESI M+H$^+$ 639.8.

Biological Test

Test Example 1 Determination of in vitro 50% growth inhibition activity (GI 50) of the present compounds on the tumor cell lines expressing wild type and mutant EZH2.

Experimental Materials and Methods

1) Tumor Cell Lines and Cell Culture

Tumor cell line is an effective cell model for studying in vitro tumor growth inhibition.

In the present invention, a representative tumor cell line was selected to determine the cell growth inhibition activity of the present compound. Cell culture conditions and methods were in accordance with the requirements for each cell lines. The cells were subcultured in vitro for less than 3 generations each time, and as required, monoclone purification and identification of cell lines could be carried out.

The cell culture media used were RPMI1640 (Gibco) comprising 5-20% of fetal bovine serum (Gibco), 1% of double-antibiotic and 2 mM of glutamine.

Human B cell non-hodgkin lymphoma Karpas 422 (ATCC) expressing EZH2 Y641N mutant protein was subjected to suspension culture with RPMI 1640 comprising 10% of FBS and 1% of double-antibiotic and 2 mM of glutamine.

Human diffuse large cell B lymphoma lymphocyte Pfeiffer (ATCC) expressing EZH2 A677G mutant protein was subjected to suspension culture with RPMI 1640 comprising 10% of FBS and 1% of double- -antibiotic and 2 mM of glutamine.

Human B cell lymphoma SU-DHL-8(ATCC) expressing wild-type EZH2 was subjected to suspension culture with RPMI 1640 comprising 10% of FBS and 1% of double-antibiotic and 2 mM of glutamine.

2) Drug Treatment

Suspension culture cells were collected by centrifugation (1700 rpm, 3 minutes), and the supernatant was discarded and the cells were counted. According to each cell growth cycle, different concentrations of cells were prepared (1-10× 10$^4$ cells per ml) and added to 96-well plates (Corning) with 100 μl per well, and then incubated overnight at 37° C., 5% CO$_2$. The next day, the test compound was added to the cultured cells (2 wells in parallel). The final concentration of the solvent was less than 1/1,000. The cells were further cultured for 6 to 12 days and assayed by MTT.

The compound of the present invention and the control compound EPZ-6438 were dissolved in DMSO (Sigma) respectively, with the purity of more than 98%. The compound was stored at a concentration of 10 mM at −20° C. and diluted to two-fold or 10-fold series prior to use.

The control compound EPZ-6438 was synthesized according to the patented method of US2012264734, and its structural formula is as follows.

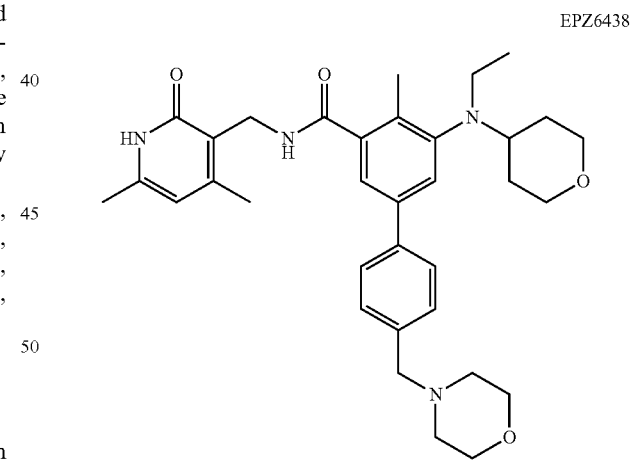

EPZ6438

3) MTT Detection and GI50 Calculation

The MTT test reagent was a Dojindo CCK8 kit and the Microplate Reader was a THERMO MULTISKAN FC instrument.

For the suspension culture cells, CCK8 was directly added to 10% of the final concentration. The cells were continually incubated for 1 to 4 1 to 4 hours. When a dark yellow color could be observed in the solvent control wells, the absorbance value at OD450 nm was measured and the cell growth rate was calculated according to the following formula:

$$\text{Cell Growth Rate (\%)} = 100 \times (T - T_0)/(C - T_0)$$

T=Optical density of drug-treated cell wells−Optical density of blank control wells; $T_0$=Optical density of cell wells before drug treatment−Optical density of blank control wells; C=Optical density of solvent control wells−Optical density of blank control wells.

The drug concentration for a 50% inhibition of cell growth, i.e. GI50 was calculated according to the drug concentration and cell growth rate curve. The experiments were repeated 3 times and a statistical analysis of data was conducted.

Experimental Results

Table 2 summarizes the results of GI50 concentration ranges for the growth inhibitory activity of the present compounds on the tumor cell lines expressing wild-type and different mutant EZH2 in vitro. The smaller the GI50 value is, the more active the compound is. If the concentration of the compound is high for the growth inhibition (GI50) of EZH2 wild-type cells and low for the mutant cells, that is, the ratio of EZH2 wild-type GI50 to EZH2 mutant GI50 is large, then the selectivity of the compound is high.

TABLE 2

GI50(nM)
(***: <1 nM; : 1 nM∼<10 nM; *: 10 nM∼<100 nM; **: 100 nM∼<1000 nM; *: >1000 nM)

| Compounds | Pfeiffer (EZH2 A677G) Drug treatment for 10 days | Karpas-422 (EZH2 Y641N) Drug treatment for 6 days | SU-DHL-8 (EZH2 WT) Drug treatment for 6 days |
|---|---|---|---|
| EPZ-6438 | **** | *** | * |
| 1 | **** | *** | * |
| 2 | *** | *** | * |
| 3 | **** | *** | * |
| 6 | **** | *** | * |
| 9 | *** | * | * |
| 10 | *** | * | * |
| 15 | **** | *** | * |
| 16 | *** | ** | * |
| 18 | **** | *** | * |
| 19 | *** | ** | * |
| 20 | **** | ** | * |
| 21 | **** | ** | * |
| 23 | **** | *** | * |
| 24 | **** | ** | * |
| 30 | **** | *** | * |
| 31 | **** | *** | * |
| 34 | **** | *** | * |
| 35 | **** | *** | * |
| 48 | *** | ** | * |
| 51 | **** | *** | * |
| 52 | **** | *** | * |
| 53 | **** | *** | * |
| 62 | **** | *** | * |
| 65 | ***** | *** | * |
| 70 | **** | *** | * |
| 71 | **** | *** | * |
| 75 | **** | *** | * |
| 76 | **** | *** | * |
| 77 | ***** | *** | * |
| 81 | **** | *** | * |
| 87 | ***** | *** | * |
| 88 | ***** | *** | * |
| 89 | ***** | *** | * |

Conclusion: the results show that the compounds of the present invention have high growth inhibitory activity against EZH2 A677G mutant cells Pfeiffer, and the GI50 value may be up to subnanomolar level (such as compounds 65, 77, 87, 88 and 89). A strong growth inhibition activity against EZH2 Y641N mutant cells Klarpas 422 is also indicated. The EZH2 wild-type cell SU-DHL-8 requires high concentration to show certain growth inhibition activity.

Test Example 2 Determination of the in vivo growth inhibition activity of the present compounds on EZH2 A677G mutant positive-expressing tumor cell line Pfeiffer NOD/SCID mice were subcutaneously inoculated with human diffuse large cell B lymphoma lymphocyte Pfeiffer (ATCC) expressing EZH2 A677G mutant protein to establish a subcutaneous transplantation model of human B cell lymphoma.

Experimental animals: NOD/SCID mice, female, 9 weeks (weeks of age when tumor cell inoculation), average weight 20.3 g, 18 mice, were purchased from Shanghai Lingchang biotechnology co., Ltd. with animal certificate No.: 2002007656. The breeding environment was SPF grade.

Test samples: the present example compounds 34 (purity: 99.03%) and 35 (purity: 97.6%), solid powder, preserved at −20° C.

Cell and Animal Modeling:

Pfeiffer cells were cultured in RPM1640 medium containing 10% of fetal bovine serum. Log-phase Pfeiffer cells were collected and resuspended with PBS to $1 \times 10^8$ cells per ml for subcutaneous inoculation in NOD/SCID mice.

All the mice were treated with Co60 irradiation at a dose of 200 rad the day before the inoculation, and $1 \times 10^7$ Pfeiffer cells were then subcutaneously inoculated at the right back, and the cells were resuspended in 1:1 PBS and Matrigel (0.1 ml/mouse). When the average tumor volume was 134 mm³, the mice were randomly grouped according to tumor size. Tumor volume was calculated as: long diameter×short diameter²/2. The day of tumor cells inoculation was defined as day 0. The test was divided into solvent control group and drug treatment group (compound 34 group and compound 35 group). 6 mice for each group were given orally once a day for a total of 4 weeks. Efficacy was assessed based on relative tumor growth inhibition value (TGI), and safety was assessed based on animal weight change and mortality.

Preparation of test samples: compounds 34 or 35 was weighed and mixed with ultrapure water, and methanesulfonic acid was added for clarification. The PH value was about 1.64 at this moment. 4M NaOH was then added to adjust the PH to 3.5 and bring to volume by ultrapure water, the final concentrations was 20 mg/ml.

Determination standard: TGI (%): TGI=1−T/C (%).

T/C % refers to the relative value-added rate of tumor, that is, the percentage value of relative tumor volume or tumor weight for the treatment group and the control group at a certain point. T and C were the relative tumor volumes (RTV) of the treatment group and the control group at a specific point, respectively. The calculation formula is as follows:

$$T/C\% = T_{RTV}/C_{RTV} * 100\%$$

$T_{RTV}$: mean RTV of the treatment group; $C_{RTV}$: mean RTV of solvent control group; $RTV = V_t/V_0$, $V_0$ was the tumor volume of the animal when grouping, $V_t$ was the tumor volume of the animal after treatment. Statistical analysis: all test results were defined as mean tumor volume±SEM (mean standard error). Tumor volume data of 27 days after the start of treatment were selected for statistical analysis among different groups, and independent sample T test was used to compare whether there were significant differences in tumor volume between the treatment group and the control group. All data were analyzed using SPSS 18.0. $P<0.05$ was considered as significant difference.

TABLE 3

Changes of tumor volume (mm³) in mice over treatment time

| Time (After the start of treatment) | The solvent control group | Compound 34 group (200 mg/kg) | Compound 35 group (200 mg/kg) |
|---|---|---|---|
| Day 0 | 134 ± 10 | 135 ± 10 | 134 ± 9 |
| Day 3 | 320 ± 24 | 298 ± 25 | 324 ± 38 |
| Day 7 | 522 ± 81 | 439 ± 48 | 681 ± 72 |
| Day 10 | 630 ± 74 | 441 ± 56 | 635 ± 88 |
| Day 14 | 995 ± 112 | 381 ± 39 | 710 ± 87 |
| Day 17 | 1394 ± 143 | 472 ± 100 | 751 ± 135 |
| Day 21 | 1631 ± 146 | 477 ± 158 | 801 ± 152 |
| Day 24 | 1783 ± 163 | 570 ± 154 | 1029 ± 193 |
| Day 27 | 1869 ± 178 | 538 ± 199 | 1116 ± 196 |

TABLE 4

TGI and T/C values of each groups on the 27th day after the start of treatment

| Groups | Tumor volume mm³ ($\bar{x}$ ± S) 0 day after the start of treatment | Tumor volume mm³ ($\bar{x}$ ± S) 27 days after the start of treatment | RTV ($\bar{x}$ ± S) | TGI (%) | T/C (%) | P value (Compared to the control group) |
|---|---|---|---|---|---|---|
| The solvent control group | 134 ± 10 | 1869 ± 178 | 14.2 ± 1.3 | — | — | — |
| Compound 34 group (200 mg/kg) | 135 ± 10 | 538 ± 199 | 4.7 ± 2.3 | 67.1 | 32.9 | 0.005 |
| Compound 35 group (200 mg/kg) | 134 ± 9 | 1116 ± 196 | 8.2 ± 1.1 | 42.3 | 57.7 | 0.006 |

TABLE 5

Tumor weights of each groups

| Groups | Tumor weight (mg) ($\bar{x}$ ± S) 27 days after the start of treatment | TGI | T/C (%) | P value (Compared to the control group) |
|---|---|---|---|---|
| The solvent control group | 1130 ± 174 | — | — | — |
| Compound 34 group (200 mg/kg) | 264 ± 113 | 76.6 | 23.4 | 0.002 |
| Compound 35 group (200 mg/kg) | 580 ± 99 | 48.7 | 51.3 | 0.021 |

Conclusion: The results in tables 3, 4 and 5 show that the mean tumor volume of the solvent control group is 1869 mm³ on the 27th day after the start of treatment. On contrary, compound 34 (200 mg/kg) and compound 35 (200 mg/kg) groups have significant anti-tumor effects. On the 27th day after the start of treatment, the average tumor volume is 538 mm³ and 1116 mm³, respectively. The relative tumor growth inhibition value TGI is 67.1% and 42.3%, respectively. The both have statistically significant difference with regard to the solvent control group (p is 0.005 and 0.006 respectively). The results of tumor weight analysis are consistent with those of relative tumor volume analysis.

The mice maintained a stable body weight during the treatment at 200 mg/kg dose for compound 34 and 35, and were well tolerated to the tested drugs.

Test Example 3 the In Vitro Irreversible Inhibition of the Present Invention on the Growth of EZH2 A677G Mutant Positive-Expressing Tumor Cell Line Pfeiffer The test of the compound washout effect on the in vitro growth inhibition of human diffuse large cell B lymphoma lymphocyte Pfeiffer (ATCC) expressing EZH2 A677G mutant protein was performed as follows.

Human diffuse large cell B lymphoma lymphocyte Pfeiffer (ATCC) was subjected to suspension culture with a complete medium (RPMI 1640 comprising 10% of FBS and 1% of double-antibiotic and 2 mM glutamine). Log-phase Pfeiffer cells were centrifuged directly (1700 rpm, 3 min), and the supernatant was discarded and the cells were counted. Cells were prepared with the complete medium ($2 \times 10^4$ cells per ml), inoculated to 96-well plates (Corning), 200 µl per well, and incubated overnight at 37° C., 5% $CO_2$. The next day, different concentrations of the test compound (compound 34) was added to the cultured cells, 4 wells in parallel, and the final concentration of DMSO in the solvent was not more than 1/1000. The cells were further cultured for 12 h. The cells in half of the test wells were then collected by centrifugation (parallel to 2 wells), and washed three times with serum-free cell culture medium, and then resuspended in a same volume of complete cell culture medium (200 µl). It was further cultured together with the untreated cells for 10 days at 37° C., 5% $CO_2$. MTT assay was performed according to Test Example 1. The experiment was repeated once, and the results are shown in table 6.

The control compound EPZ-6438 was prepared by the method in Test Example 1.

TABLE 6

Irreversible inhibition of compound 34 on the in vitro growth of Pfeiffer cells

| Compound | Drug concentration (nM) | Pfeiffer cells growth rate (%) (10 days) Continuous | Pfeiffer cells growth rate (%) (10 days) Washout |
|---|---|---|---|
| Vehical | — | 100% | 100% |
| Compound 34 | 25 | 0% | 0% |
|  | 50 | 0% | 0% |
|  | 100 | 0% | 0% |
| EPZ-6438 | 25 | 0% | 92% |

Table 6 shows that the compound 34 continuous or washout treatment of Pfeiffer cells can effectively inhibit the growth of cells in vitro. The control compound EPZ-6438 can effectively inhibit the growth of cells in vitro when continuous treatment of cell culture medium, but it will not be able to effectively inhibit the growth of cells when washout treatment at tested concentrations (25 nM). The results show that the compound 34 has a potential irreversible inhibitory effect on cell growth in vitro.

Test Example 4 Study of In Vivo Pharmacokinetics of the Present Compounds in Rats Male SD rats (Shanghai Sippr-BK Experimental Animal Co., Ltd) were purchased and kept in Shanghai University of Traditional Chinese Medicine animal center (approved by the ethics committee of Shanghai University of Traditional Chinese Medicine) for 7 days. The rats were randomly divided into 4 groups (~220 g), 3 rats for each group. Animals were administered intravenously (iv) and orally (po). The rats in po group were starved for 12 hours before administration. After administration, blood was collected from the orbital venous plexus at 0 min (before administration), 2 min, 5 min, 15 min, 30 min, 1 h, 2 h, 4 h, 6 h, 8 h and 24 h. About 200 ul of blood was collected at each time point, and were collected in 1.5 ml centrifuge tube containing heparin sodium. The upper blood serum were collected by centrifugation (8000 rpm, 3 min) and stored at −80° C.

Preparation of test samples: 125.0 mg compound 34 or compound 35 was weighed and added with 4 ml ultrapure water, and 25 ul methanesulfonic acid was added with stirring. The mixture was further stirred until clear and transparent (pH ~3.32). 1 ml of the above solution was added with 4 ml of ultra-pure water to obtain 5 mg/ml of compound 34 or compound 35 solution (pH=3.5).

Dose and mode of administration: single oral dose (100 mpk) and single intravenous dose (5 mpk).

Administration volume: 4 ml/kg (orally), 1 ml/kg (intravenously).

The plasma concentration of the compound was determined by LC-MS/MS (AB scexqtrap@4500 LCMS/MS system). Pharmacokinetic parameters were calculated by WinNonlin (a professional software). The experiment was repeated once. The results are shown in table 7.

TABLE 7

Results of the bioavailability of the present compound in rats

| | Compound 34 | Compound 35 |
|---|---|---|
| Solvent | Methanesulfonic acid aqueous solution | Methanesulfonic acid aqueous solution |
| IV | 5 mg/kg | 5 mg/kg |
| PO | 100 mg/kg | 100 mg/kg |
| SD rats | 3 (iv), 3 (po) | 3 (iv), 3 (po) |
| Blood sampling time | 0 min, 2 min, 5 min, 15 min, 30 min, 1 h, 2 h, 4 h, 6 h, 8 h, 24 h | 0 min, 2 min, 5 min, 15 min, 30 min, 1 h, 2 h, 4 h, 6 h, 8 h, 24 h |
| Bioavailability | 48.8% | 39.1% |

Conclusion: Compound 34 and compound 35 show good bioavailability in SD rats.

What is claimed is:

1. A compound of general formula (I) or a pharmaceutically acceptable salt, solvate, metabolite or prodrug thereof,

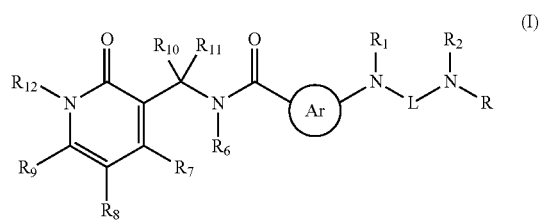

wherein:
R is selected from the group consisting of

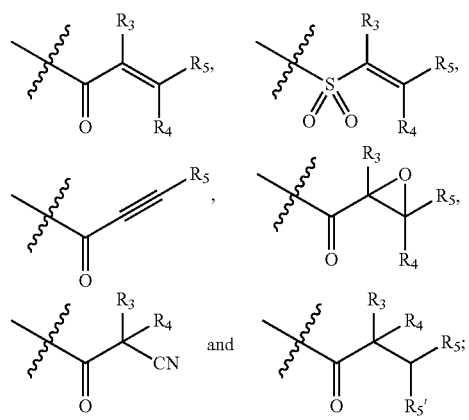

Ar is a phenyl, wherein Ar is optionally further substituted with one or more -Q-T groups;

L is selected from a $C_2$-$C_8$ saturated or unsaturated linear or branched hydrocarbon chain or cyclic structure, wherein any hydrogen atom in L is optionally replaced by a halogen, a cyano group, a hydroxyl group, or a $C_1$-$C_6$ alkoxy group, and any carbon atom in L is optionally replaced by N, O, S; L is optionally further substituted with one or more -Q-T groups;

$R_1$ and $R_2$ are each independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, 4-12 membered heterocyclic, the alkyl, alkenyl, alkynyl, cycloalkyl and heterocyclic groups are optionally further substituted with one or more -Q-T groups; or $R_1$ is optionally attached to any position of L to form a 4-12 membered heterocyclic group containing 0 or 1 additional hetero atom together with the N atom attached to them, the heterocyclic group is optionally further substituted with one or more -Q-T groups; or $R_2$ is optionally attached to any position of L to form a 4-12 membered heterocyclic group containing 0 or 1 additional hetero atom together with the N atom attached to them, the heterocyclic group is optionally further substituted with one or more -Q-T groups; or $R_1$, $R_2$, and L, together with the two N atoms attached to them, form a 4-12 membered heterocyclic group, the heterocyclic group is optionally further substituted with one or more -Q-T groups;

$R_3$ is selected from the group consisting of hydrogen, fluorine, and $R_a$;

$R_4$ and $R_5$ are each independently selected from the group consisting of hydrogen and $R_a$;

$R_5'$ is selected from the group consisting of halogen, —OS(O)$_2$—$C_1$-$C_6$ alkyl or —OS(O)$_2$—$C_3$-$C_6$ cycloalkyl;

$R_a$ is selected from the group consisting of $C_1$-$C_6$ alkyl, $C_2$-$C_6$ alkenyl, $C_2$-$C_6$ alkynyl, $C_3$-$C_6$ cycloalkyl, and 4-12 membered heterocyclic group; the alkyl, alkenyl, alkynyl, cycloalkyl or heterocyclic group is optionally further substituted with one or more -Q-T groups;

$R_6$ and $R_{12}$ are each independently selected from the group consisting of hydrogen, $C_1$-$C_6$ alkyl and $C_3$-$C_6$ cycloalkyl;

$R_7$ and $R_9$ are each independently selected from the group consisting of hydrogen, halogen and $R_b$;

$R_b$ is selected from the group consisting of $C_1$-$C_6$ alkyl, $C_2$-$C_6$ alkenyl, $C_2$-$C_6$ alkynyl, $C_3$-$C_6$ cycloalkyl, and 4-12 membered heterocyclic; the alkyl, alkenyl, alkynyl, cycloalkyl, or heterocyclic group is optionally further substituted with one or more groups selected from the group consisting of halogen, cyano, hydroxy, $C_1$-$C_6$ alkoxy, $C_1$-$C_6$ alkyl-OC(O)—, amino, $C_1$-$C_6$ alkylamino, bis-$C_1$-$C_6$ alkylamino, and a 4-12 membered heterocyclic;

$R_8$, $R_{10}$ and $R_{11}$ are each independently selected from the group consisting of hydrogen, halogen, $C_1$-$C_3$ alkyl and cycloalkyl;

Q is selected from a bond or a $C_1$-$C_6$ alkylene group, the alkylene group is optionally further substituted with one or more groups selected from the group consisting of halogen, cyano, hydroxy, and $C_1$-$C_6$ alkoxy;

T is selected from the group consisting of hydrogen, halogen, cyano, hydroxy, —$NR_hR_i$, —C(O)$R_h$, O$R_h$, —C(O)O—$R_h$, C(O)N$R_hR_i$, —N$R_h$C(O)$R_i$, —N$R_j$C(O)N$R_hR_i$, —N$R_h$C(O)O$R_i$, and $R_k$; or -Q-T group is oxo;

$R_k$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- to 10-membered heteroaryl and aryl, $R_k$ is optionally further substituted with one or more -$Q_1$-$T_1$ groups;

$R_h$, $R_i$ and $R_j$ are each independently selected from the group consisting of hydrogen and $R_1$, and $R_1$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl, $R_1$ is optionally further substituted with one or more -$Q_1$-$T_1$ groups; or $R_h$ and $R_i$, together with the N atom attached to them, form a 4-12 membered heterocyclic group containing 0 or 1 additional hetero atom, the heterocyclic group is optionally further substituted with one or more -$Q_1$-$T_1$ groups;

$Q_1$ is a bond or a $C_1$-$C_6$ alkylene group, the alkylene group is optionally further substituted with one or more groups selected from the group consisting of halogen, cyano, hydroxy, and $C_1$-$C_6$ alkoxy;

$T_1$ is selected from the group consisting of hydrogen, halogen, cyano, hydroxyl, —$NR_mR_n$, —C(O)$R_m$, O$R_m$, —C(O)O$R_m$, —C(O)N$R_mR_n$, —N$R_m$C(O)$R_n$, —$NR_o$C(O) N$R_mR_n$, —N$R_m$C(O)O$R_n$, —O(CH$_2$)$_a$N$R_mR_n$, —(CH$_2$)$_a$N$R_mR_n$, —S(O)$_2$N$R_mR_n$ and $R_p$; or -$Q_1$-$T_1$ group is oxo;

$R_p$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl;

$R_m$, $R_n$ and $R_o$ are each independently selected from the group consisting of hydrogen and $R_q$, $R_q$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl, $R_q$ is optionally further substituted with one or more groups selected from the group consisting of halogen, hydroxy, 5- or 6-membered heteroaryl and aryl, wherein the heteroaryl or aryl group is optionally further substituted with one or more groups selected from the group consisting of $C_1$-$C_6$ alkyl, hydroxy and oxo; or $R_m$ and $R_n$, together with the N atom attached to them, form a 4-12 membered heterocyclic group containing 0 or 1 additional hetero atom, the heterocyclic group is optionally further substituted with one or more groups selected from the group consisting of halogen, hydroxy, oxo, $C_1$-$C_6$ alkyl, —O$R_x$, —N$R_xR_y$, —C(O)$R_x$, and —O(CH$_2$)$_a$O$R_x$;

$R_x$ and $R_y$ are each independently selected from the group consisting of hydrogen and $R_z$, $R_z$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl, $R_q$ is optionally further substituted with one or more groups selected from the group consisting of halogen, hydroxy, 5- or 6-membered heteroaryl and aryl, wherein the heteroaryl or aryl group is optionally further substituted with one or more groups selected from the group consisting of $C_1$-$C_6$ alkyl, hydroxy and oxo; or $R_x$ and $R_y$, together with the N atom attached to them, form a 4-12 membered heterocyclic group containing 0 or 1 additional hetero atom;

a is an integer from 1 to 4.

2. The compound of general formula (I) or the pharmaceutically acceptable salt, solvate, metabolite or prodrug thereof according to claim 1, wherein:

Ar is selected from

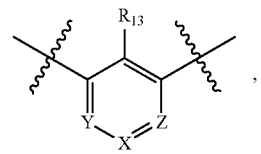

X is selected from $CR_{14}$;
Y is selected from $CR_{15}$;
Z is selected from $CR_{16}$;
$R_{13}$ is selected from the group consisting of hydrogen, halogen, $C_1$-$C_6$ alkyl and $C_3$-$C_6$ cycloalkyl;
$R_{14}$, $R_{15}$, $R_{16}$ are each independently selected from the group -Q-T;
Q is selected from a bond or a $C_1$-$C_6$ alkylene group;
T is selected from the group consisting of hydrogen, halogen, cyano, hydroxyl, —$NR_hR_i$, —C(O)$R_h$, O$R_h$, —C(O)O—$R_h$, C(O)N$R_hR_i$, —N$R_h$C(O)$R_i$, —N$R_j$C(O)N$R_hR_i$, —N$R_h$C(O)O$R_i$ and $R_k$;

$R_k$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5 to 10 membered heteroaryl and aryl, $R_k$ is optionally further substituted with one or more -$Q_1$-$T_1$ groups;

$R_h$, $R_i$ and $R_j$ are each independently selected from the group consisting of hydrogen and $R_1$, $R_1$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl, $R_1$ is optionally further substituted with one or more -$Q_1$-$T_1$ groups; or

191

$R_h$ and $R_i$, together with the N atom attached to them, form a 4-12 membered heterocyclic group containing 0 or 1 additional hetero atom; the heterocyclic group is optionally further substituted with one or more -$Q_1$-$T_1$ groups;

$Q_1$ is a bond or a $C_1$-$C_6$ alkylene group;

$T_1$ is selected from the group consisting of hydrogen, halogen, cyano, hydroxy, —$NR_mR_n$, —$C(O)R_m$, $OR_m$, —$C(O)O$—$R_m$, —$C(O)NR_mR_n$, —$NR_mC(O)R_n$, —$NR_oC(O)NR_mR_n$, —$NR_mC(O)OR_n$, —$O(CH_2)_aNR_mR_n$, —$(CH_2)_aNR_mR_n$, —$S(O)_2NR_mR_n$ and $R_p$;

$R_p$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl, and aryl;

$R_m$, $R_n$, $R_o$ are each independently selected from the group consisting of hydrogen and $R_q$, and $R_q$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl, $R_q$ is optionally further substituted with one or more groups selected from the group consisting of halogen, hydroxy, 5- or 6-membered heteroaryl and aryl, wherein the heteroaryl or aryl group is optionally further substituted with one or more groups selected from the group consisting of $C_1$-$C_6$ alkyl, hydroxy and oxo; or $R_m$ and $R_n$, together with the N atom attached to them, form a 4-12 membered heterocyclic group containing 0 or 1 additional hetero atom; the heterocyclic group is optionally further substituted with one or more groups selected from the group consisting of halogen, hydroxy, oxo, $C_1$-$C_6$ alkyl, —$OR_x$, —$NR_xR_y$, —$C(O)R_x$, and —$O(CH_2)_aOR_x$;

$R_x$ and $R_y$ are each independently selected from the group consisting of hydrogen and $R_z$, and $R_z$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl, $R_q$ is optionally further substituted with one or more groups selected from the group consisting of halogen, hydroxy, 5- or 6-membered heteroaryl and aryl, wherein the heteroaryl or aryl group is optionally further substituted with one or more groups selected from the group consisting of $C_1$-$C_6$ alkyl, hydroxy and oxo; or $R_x$ and $R_y$, together with the N atom attached to them, form a 4-12 membered heterocyclic group containing 0 or 1 additional hetero atom;

a is an integer from 1 to 4.

3. The compound of general formula (I) or the pharmaceutically acceptable salt, solvate, metabolite or prodrug thereof according to claim 1, wherein:

Ar is

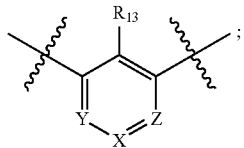

$R_{13}$ is selected from the group consisting of hydrogen, halogen, and $C_1$-$C_6$ alkyl;
X is selected from $CR_{14}$;
Y is selected from $CR_{15}$;
Z is selected from $CR_{16}$;

192

$R_{14}$ is selected from the group -Q-T;
$R_{15}$ and $R_{16}$ are each independently selected from hydrogen or halogen;
Q is selected from a bond or a $C_1$-$C_6$ alkylene group;
T is selected from the group consisting of hydrogen, halogen, cyano, hydroxy, —$NR_hR_i$, —$C(O)R_h$, $OR_h$, —$C(O)O$—$R_h$, —$C(O)NR_hR_i$, —$NR_hC(O)R_i$, —$NR_jC(O)NR_hR_i$, —$NR_hC(O)OR_i$, and $R_k$;

$R_k$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl, and aryl; the heterocyclic, heteroaryl or aryl is optionally further substituted with one or more -$Q_1$-$T_1$ group;

$R_h$, $R_i$, $R_j$ are each independently selected from the group consisting of hydrogen and $R_1$, and $R_1$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl, $R_1$ is optionally further substituted with one or more -$Q_1$-$T_1$ group; or $R_h$ and $R_i$, together with the N atom attached to them, form a 4-12 membered heterocyclic group containing 0 or 1 additional hetero atom; the heterocyclic group is optionally further substituted with one or more -$Q_1$-$T_1$ group;

$Q_1$ is a bond or a $C_1$-$C_6$ alkylene group;

$T_1$ is selected from the group consisting of hydrogen, halogen, cyano, hydroxy, —$NR_mR_n$, —$C(O)R_m$, $OR_m$, —$C(O)O$—$R_m$, —$C(O)NR_mR_n$, —$NR_mC(O)R_n$, —$NR_oC(O)NR_mR_n$, —$NR_mC(O)OR_n$, —$O(CH_2)_aNR_mR_n$, —$(CH_2)_aNR_mR_n$, —$S(O)_2NR_mR_n$ and $R_p$;

$R_p$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl, and aryl;

$R_m$, $R_n$, $R_o$ are each independently selected from the group consisting of hydrogen and $R_q$, and $R_q$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl, $R_q$ is optionally further substituted with one or more groups selected from the group consisting of halogen, hydroxy, 5- or 6-membered heteroaryl and aryl, wherein the heteroaryl or aryl group is optionally further substituted with one or more groups selected from the group consisting of $C_1$-$C_6$ alkyl, hydroxy and oxo; or $R_m$ and $R_n$, together with the N atom attached to them, form a 4-12 membered heterocyclic group containing 0 or 1 additional hetero atom; the heterocyclic group is optionally further substituted with one or more groups selected from the group consisting of halogen, hydroxy, oxo, $C_1$-$C_6$ alkyl, —$OR_x$, —$NR_xR_y$, —$C(O)R_x$, and —$O(CH_2)_aOR_x$;

$R_x$ and $R_y$ are each independently selected from the group consisting of hydrogen and $R_z$, and $R_z$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl, $R_q$ is optionally further substituted with one or more groups selected from the group consisting of halogen, hydroxy, 5- or 6-membered heteroaryl and aryl, wherein the heteroaryl or aryl group is optionally further substituted with one or more groups selected from the group consisting of $C_1$-$C_6$ alkyl, hydroxy and oxo; or $R_x$ and $R_y$, together with the N atom attached to them, form a 4-12 membered heterocyclic group containing 0 or 1 additional hetero atom;

a is an integer from 1 to 4.

4. The compound of general formula (I) or the pharmaceutically acceptable salt, solvate, metabolite or prodrug thereof according to claim 1, wherein:

Q is selected from a bond or a $C_1$-$C_6$ alkylene group;

T is selected from the group consisting of hydrogen, halogen, —$NR_hR_i$, $OR_h$ and $R_k$;

$R_k$ is selected from the group consisting of $C_1$-$C_6$ alkyl, $C_2$-$C_6$ alkenyl, $C_2$-$C_6$ alkynyl, 4-12 membered heterocyclic, 5- to 10-membered heteroaryl and $C_6$-$C_{10}$ aryl; the alkyl, alkenyl, alkynyl, heterocyclyl, heteroaryl or aryl group is optionally further substituted with one or more -$Q_1$-$T_1$ groups;

$R_h$ and $R_i$ are each independently selected from the group consisting of hydrogen and $R_1$, $R_1$ is selected from the group consisting of $C_1$-$C_6$ alkyl, 5- or 6-membered heteroaryl, and $C_6$-$C_{10}$ aryl, and $R_1$ is optionally further substituted by one or more -$Q_1$-$T_1$ groups; or $R_h$ and $R_i$, together with the N atom attached to them, form a 4-12 membered heterocyclic group containing 0 or 1 additional hetero atom; the heterocyclic group is optionally further substituted with one or more -$Q_1$-$T_1$ groups;

$Q_1$ is a bond or a $C_1$-$C_6$ alkylene group;

$T_1$ is selected from the group consisting of hydrogen, halogen, hydroxyl, —$NR_mR_n$, $OR_m$, —$C(O)OR_m$, —$C(O)NR_mR_n$, —$O(CH_2)_aNR_mR_n$, —$(CH_2)_aNR_mR_n$, —$S(O)_2NR_mR_n$ and $R_p$;

$R_p$ is selected from the group consisting of $C_1$-$C_6$ alkyl and 4-12 membered heterocyclic group;

$R_m$ and $R_n$ are each independently selected from the group consisting of hydrogen and $C_1$-$C_6$ alkyl, and the alkyl group is optionally further substituted with one or more groups selected from the group consisting of hydroxy and 5- or 6-membered heteroaryl groups, wherein the heteroaryl group is optionally further substituted with one or more groups selected from the group consisting of $C_1$-$C_6$ alkyl and oxo; or $R_m$ and $R_n$, together with the N atom attached to them, form a 4-12 membered heterocyclic group containing 0 or 1 additional hetero atom; the heterocyclic group is optionally further substituted with one or more groups selected from the group consisting of halogen, hydroxy, oxo, $C_1$-$C_6$ alkyl, —$OR_x$, —$NR_xR_y$, —$C(O)R_x$, and —$O(CH_2)_aOR_x$;

$R_x$ and $R_y$ are each independently selected from the group consisting of hydrogen and $R_z$, and $R_z$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl; $R_q$ is optionally further substituted with one or more groups selected from the group consisting of halogen, hydroxy, 5- or 6-membered heteroaryl and aryl, wherein the heteroaryl or aryl group is optionally further substituted with one or more groups selected from the group consisting of $C_1$-$C_6$ alkyl, hydroxy and oxo; or $R_x$ and $R_y$, together with the N atom attached to them, form a 4-12 membered heterocyclic group containing 0 or 1 additional hetero atom;

a is an integer from 1 to 4.

5. The compound of general formula (I) or the pharmaceutically acceptable salt, solvate, metabolite or prodrug thereof according to claim 1, wherein:

Q is selected from a bond;

T is selected from the group consisting of hydrogen, halogen, —$NR_hR_i$, $OR_h$ and $R_k$;

$R_k$ is selected from the group consisting of $C_1$-$C_6$ alkyl, $C_2$-$C_6$ alkynyl, phenyl, pyrimidinyl, pyridyl, pyrazolyl, imidazolyl, thiazolyl, oxazolyl and thiopheno [3,2-b] thiophene group, the alkyl, alkynyl, phenyl, pyrimidinyl, pyridyl, pyrazolyl, imidazolyl, thiazolyl, oxazolyl or thiopheno[3,2-b]thiophene group is optionally further substituted with one or more -$Q_1$-$T_1$ groups;

$R_h$ and $R_i$ are each independently selected from the group consisting of hydrogen, pyridyl, pyrimidinyl and phenyl; the pyridyl, pyrimidinyl or phenyl group is optionally further substituted with one or more -$Q_1$-$T_1$ groups; or $R_h$ and $R_i$, together with the N atom attached to them, form a 4-12 membered heterocyclic group containing 0 or 1 additional hetero atom; the heterocyclic group is optionally further substituted with one or more -$Q_1$-$T_1$ groups;

$Q_1$ is a bond or a $C_1$-$C_6$ alkylene group;

$T_1$ is selected from the group consisting of hydrogen, halogen, hydroxyl, —$NR_mR_n$, $OR_m$, —$C(O)OR_m$, —$C(O)NR_mR_n$, —$O(CH_2)_aNR_mR_n$, —$(CH_2)_aNR_mR_n$, —$S(O)_2NR_mR_n$ and $R_p$;

$R_p$ is selected from a $C_1$-$C_6$ alkyl group;

$R_m$ and $R_n$ are each independently selected from the group consisting of hydrogen and $C_1$-$C_6$ alkyl, and the alkyl group is optionally further substituted with one or more groups selected from hydroxy and 5- or 6-membered heteroaryl groups, wherein the heteroaryl group is optionally further substituted with one or more groups selected from the group consisting of $C_1$-$C_6$ alkyl and oxo; or $R_m$ and $R_n$, together with the N atom attached to them, form a 4-12 membered heterocyclic group containing 0 or 1 additional hetero atom; the heterocyclic group is optionally further substituted with one or more groups selected from the group consisting of halogen, hydroxy, oxo, $C_1$-$C_6$ alkyl, —$OR_x$, —$NR_xR_y$, —$C(O)R_x$, and —$O(CH_2)_aOR_x$;

$R_x$ and $R_y$ are each independently selected from the group consisting of hydrogen and $R_z$, and $R_z$ is selected from the group consisting of $C_1$-$C_6$ alkyl, $C_2$-$C_6$ alkenyl, $C_2$-$C_6$ alkynyl, $C_3$-$C_6$ cycloalkyl, 4-12 membered heterocyclic, 5- or 6-membered heteroaryl and aryl, $R_q$ is optionally further substituted with one or more groups selected from the group consisting of halogen, hydroxy, 5- or 6-membered heteroaryl and aryl, wherein the heteroaryl or aryl group is optionally further substituted with one or more groups selected from the group consisting of $C_1$-$C_6$ alkyl, hydroxy and oxo; or $R_x$ and $R_y$, together with the N atom attached to them, form a 4-12 membered heterocyclic group containing 0 or 1 additional hetero atom;

a is an integer from 1 to 4.

6. The compound of general formula (I) or the pharmaceutically acceptable salt, solvate, metabolite or prodrug thereof according to claim 1, wherein:

Q is selected from a bond;

T is selected from the group consisting of hydrogen, halogen, —$NR_hR_i$, $OR_h$ and $R_k$;

$R_k$ is selected from the group consisting of $C_1$-$C_6$ alkyl, $C_2$-$C_6$ alkynyl, phenyl, pyrimidinyl, pyridyl, pyrazolyl, imidazolyl, thiazolyl, oxazolyl and thiopheno [3,2-b] thiophene group, the alkyl, alkynyl, phenyl, pyrimidinyl, pyridyl, pyrazolyl, imidazolyl, thiazolyl, oxazolyl or thiopheno[3,2-b]thiophene group is optionally further substituted with one or more -Q$_1$-T$_1$ groups;

R$_h$ and R$_i$ are each independently selected from the group consisting of hydrogen, pyridyl, pyrimidinyl and phenyl; the pyridyl, pyrimidinyl or phenyl group is optionally further substituted with one or more -Q$_1$-T$_1$ groups; or R$_h$ and R$_i$, together with the N atom attached to them, form a piperidinyl, piperazinyl, pyrrolidinyl or morpholinyl group, the piperidinyl, piperazinyl, pyrrolidinyl or morpholinyl group is optionally further substituted with one or more -Q$_1$-T$_1$ groups;

Q$_1$ is a bond or a C$_1$-C$_6$ alkylene group;

T$_1$ is selected from the group consisting of hydrogen, halogen, hydroxy, —NR$_m$R$_n$, OR$_m$, —C(O)OR$_m$, —C(O)NR$_m$R$_n$, —O(CH$_2$)$_a$NR$_m$R$_n$, —(CH$_2$)$_a$NR$_m$R$_n$, —S(O)$_2$NR$_m$R$_n$ and R$_p$;

R$_p$ is selected from a C$_1$-C$_6$ alkyl group;

R$_m$ and R$_n$ are each independently selected from the group consisting of hydrogen and C$_1$-C$_6$ alkyl, and the alkyl group is optionally further substituted with one or more groups selected from hydroxy or 5- or 6-membered heteroaryl groups, wherein the heteroaryl group is optionally further substituted with one or more groups selected from the group consisting of C$_1$-C$_6$ alkyl and oxo; or R$_m$ and R$_n$, together with the N atom attached to them, form a 4-12 membered heterocyclic group containing 0 or 1 additional hetero atom; the heterocyclic group is optionally further substituted with one or more groups selected from the group consisting of halogen, hydroxy, oxo, C$_1$-C$_6$ alkyl, —OR$_x$, —NR$_x$R$_y$, —C(O)R$_x$, and —O(CH$_2$)$_a$OR$_x$;

R$_x$ and R$_y$ are each independently selected from the group consisting of hydrogen and R$_z$, and R$_z$ is selected from the group consisting of C$_1$-C$_6$ alkyl, C$_2$-C$_6$ alkenyl, C$_2$-C$_6$ alkynyl, C$_3$-C$_6$ cycloalkyl, 4-12 membered heterocyclic, 5- or 6-membered heteroaryl and aryl, R$_q$ is optionally further substituted with one or more groups selected from the group consisting of halogen, hydroxy, 5- or 6-membered heteroaryl and aryl, wherein the heteroaryl or aryl group is optionally further substituted with one or more groups selected from the group consisting of C$_1$-C$_6$ alkyl, hydroxy and oxo; or R$_x$ and R$_y$, together with the N atom attached to them, form a 4-12 membered heterocyclic group containing 0 or 1 additional hetero atom;

a is an integer from 1 to 4.

7. The compound of general formula (I) or the pharmaceutically acceptable salt, solvate, metabolite or prodrug thereof according to claim 1, wherein:

Q is selected from a bond;

T is selected from the group consisting of hydrogen, halogen, —NR$_h$R$_i$, OR$_h$ and R$_k$;

R$_k$ is selected from the group consisting of C$_1$-C$_6$ alkyl, C$_2$-C$_6$ alkynyl, phenyl, pyrimidinyl, pyridyl, and thiopheno[3,2-b] thiophene group, the alkyl, alkynyl, phenyl, pyrimidinyl, pyridyl or thiopheno[3,2-b] thiophene group is optionally further substituted with one or more -Q$_1$-T$_1$ groups;

R$_h$ and R$_i$ are each independently selected from the group consisting of hydrogen, pyridyl, pyrimidinyl and phenyl; the pyridyl, pyrimidinyl or phenyl group is optionally further substituted with one or more -Q$_1$-T$_1$ groups; or R$_h$ and R$_i$, together with the N atom attached to them, form a piperidinyl, piperazinyl or morpholinyl group, the piperidinyl, piperazinyl or morpholinyl group is optionally further substituted with one or more -Q$_1$-T$_1$ groups;

Q$_1$ is a bond or a C$_1$-C$_6$ alkylene group;

T$_1$ is selected from the group consisting of hydrogen, halogen, hydroxy, —NR$_m$R$_n$, OR$_m$, —C(O)OR$_m$, —C(O)NR$_m$R$_n$, —O(CH$_2$)$_a$NR$_m$R$_n$, —(CH$_2$)$_a$NR$_m$R$_n$, —S(O)$_2$NR$_m$R$_n$ and R$_p$;

R$_p$ is selected from a C$_1$-C$_6$ alkyl group;

R$_m$ and R$_n$ are each independently selected from the group consisting of hydrogen and C$_1$-C$_6$ alkyl, and the alkyl group is optionally further substituted with one or more groups selected from the group consisting of hydroxy, pyridyl and pyrimidinyl, wherein the pyridyl or pyrimidinyl group is optionally further substituted with one or more groups selected from the group consisting of C$_1$-C$_6$ alkyl and oxo; or R$_m$ and R$_n$, together with the N atom attached to them, form a piperidinyl, morpholinyl, pyrrolidinyl, piperazinyl, homopiperazinyl, azetidinyl and azaspirocyclyl group; the piperidinyl, morpholinyl, pyrrolidinyl, piperazinyl, homopiperazinyl, azetidinyl or azaspirocyclyl group is optionally further substituted with one or more groups selected from the group consisting of halogen, oxo, C$_1$-C$_6$ alkyl, —OR$_x$, —NR$_x$R$_y$, —C(O)R$_x$, and —O(CH$_2$)$_a$OR$_x$;

R$_x$ and R$_y$ are each independently selected from the group consisting of hydrogen and R$_z$, and R$_z$ is selected from the group consisting of C$_1$-C$_6$ alkyl and C$_3$-C$_6$ cycloalkyl, R$_q$ is optionally further substituted with one or more groups selected from the group consisting of halogen and hydroxy; or R$_x$ and R$_y$, together with the N atom attached to them, form a 4-12 membered heterocyclic group containing 0 or 1 additional hetero atom;

a is an integer from 1 to 4.

8. The compound of general formula (I) or the pharmaceutically acceptable salt, solvate, metabolite or prodrug thereof according to claim 1, wherein the compound is a compound of formula (IIA), formula (IIB), formula (IIC), formula (IID), formula (IIE) or formula (IIF) or a pharmaceutically acceptable salt, solvate, metabolite or prodrug thereof,

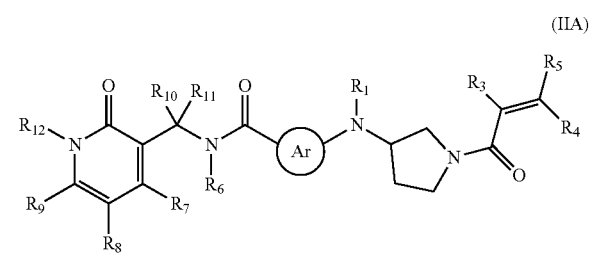

(IIA)

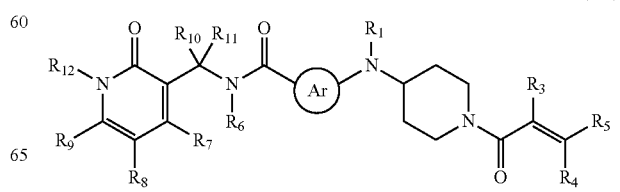

(IIB)

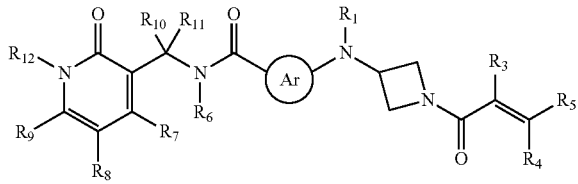

(IIC)

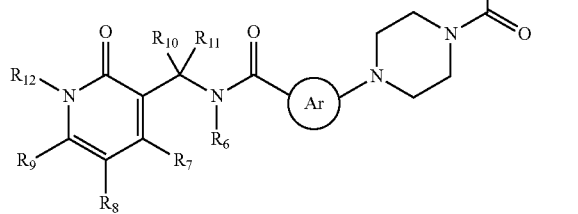

(IID)

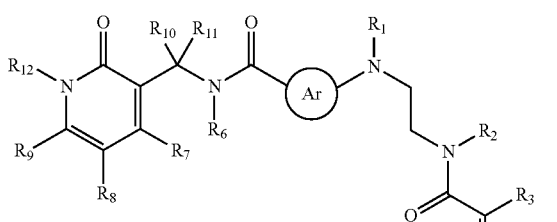

(IIE)

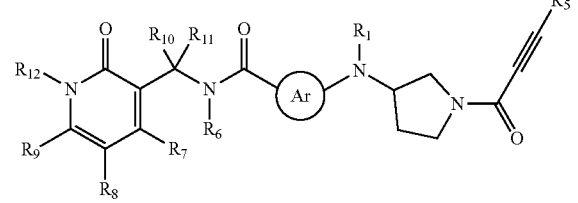

(IIF)

wherein, $R_1$ to $R_{12}$ and Ar are as defined in claim 1.

9. The compound of general formula (I) or the pharmaceutically acceptable salt, solvate, metabolite or prodrug thereof according to claim 8, wherein:
$R_1$ and $R_2$ are selected from the group consisting of hydrogen, $C_1$-$C_6$ alkyl, $C_3$-$C_6$ cycloalkyl, and 4-12 membered heterocyclic;
$R_3$ and $R_4$ are selected from hydrogen;
$R_5$ is selected from the group consisting of hydrogen and $C_1$-$C_6$ alkyl, the alkyl is optionally further substituted with one or more -Q-T groups;
$R_6$ and $R_{12}$ are selected from hydrogen;
$R_7$ and $R_9$ are selected from the group consisting of hydrogen and $C_1$-$C_6$ alkyl;
$R_8$, $R_{10}$ and $R_{11}$ are selected from hydrogen;
-Q-T is a —$NR_hR_i$ group;
$R_h$ and $R_i$ are each independently selected from hydrogen and $C_1$-$C_6$ alkyl; or
$R_h$ and $R_i$, together with the N atom attached to them, form a 4-12 membered heterocyclic group containing 0 or 1 additional hetero atom;

Ar is selected from a 5- or 6-membered aryl or heteroaryl group, and a fused ring formed from a 5- or 6-membered aryl or heteroaryl group, wherein Ar is optionally further substituted with one or more -Q-T groups.

10. The compound of general formula (I) or the pharmaceutically acceptable salt, solvate, metabolite or prodrug thereof according to claim 8, wherein:
Ar is a phenyl group, which is optionally further substituted with one or more -Q-T groups;
$R_1$ and $R_2$ are selected from the group consisting of hydrogen, $C_1$-$C_6$ alkyl, $C_3$-$C_6$ cycloalkyl, and 4-12 membered heterocyclic;
$R_3$ and $R_4$ are selected from hydrogen;
$R_5$ is selected from the group consisting of hydrogen and $C_1$-$C_6$ alkyl, the alkyl is optionally further substituted with one or more -Q-T groups;
$R_6$ and $R_{12}$ are selected from hydrogen;
$R_7$ and $R_9$ are selected from the group consisting of hydrogen and $C_1$-$C_6$ alkyl;
$R_8$, $R_{10}$ and $R_{11}$ are selected from hydrogen;
-Q-T is -phenyl, the phenyl is optionally further substituted with one or more -$Q_1$-$T_1$ groups;
$Q_1$ is a bond or a $C_1$-$C_6$ alkylene group;
$T_1$ is selected from the group consisting of hydrogen, halogen, hydroxyl, —$NR_mR_n$, $OR_m$, —$C(O)OR_m$, —$C(O)NR_mR_n$, —$O(CH_2)_aNR_mR_n$, and —$S(O)_2NR_mR_n$; or
-$Q_1$-$T_1$ is oxo;
$R_m$ and $R_n$ are each independently selected from the group consisting of hydrogen and $R_q$, $R_q$ is selected from $C_1$-$C_6$ alkyl, and $R_q$ is optionally further substituted with one or more groups selected from halogen, hydroxy, and 5- or 6-membered heteroaryl, wherein the heteroaryl or aryl group is optionally further substituted with one or more groups selected from the group consisting of $C_1$-$C_6$ alkyl, hydroxy and oxo; or
$R_m$ and $R_n$, together with the N atom attached to them, form a 4-12 membered heterocyclic group containing 0 or 1 additional hetero atom; the heterocyclic group is optionally further substituted with one or more groups selected from the group consisting of halogen, hydroxy, oxo, $C_1$-$C_6$ alkyl, —$OR_x$, —$NR_xR_y$, —$C(O)R_x$, and —$O(CH_2)_aOR_x$;
$R_x$ and $R_y$ are each independently selected from the group consisting of hydrogen and $R_z$, and $R_z$ is selected from the group consisting of $C_1$-$C_6$ alkyl and $C_3$-$C_6$ cycloalkyl; or
$R_x$ and $R_y$, together with the N atom attached to them, form a 4-12 membered heterocyclic group containing 0 or 1 additional hetero atom;
a is an integer from 1 to 4.

11. The compound of general formula (I) or the pharmaceutically acceptable salt, solvate, metabolite or prodrug thereof according to claim 1, wherein the compound is selected from the group consisting of:

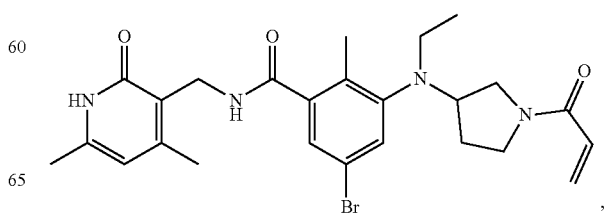

-continued

201
-continued
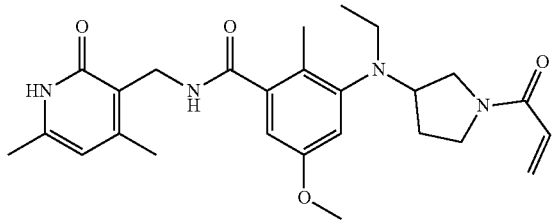
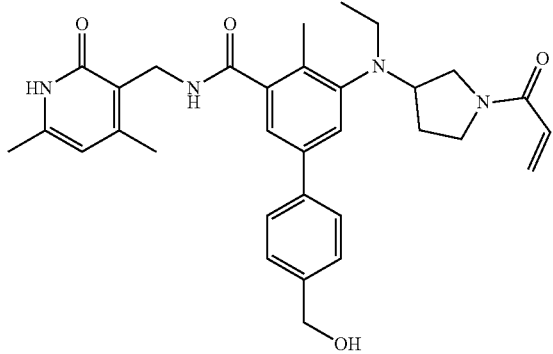
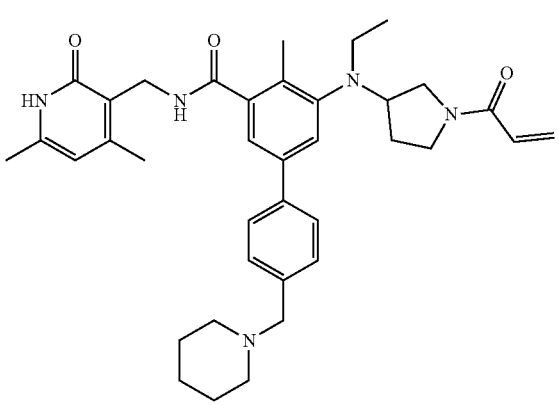
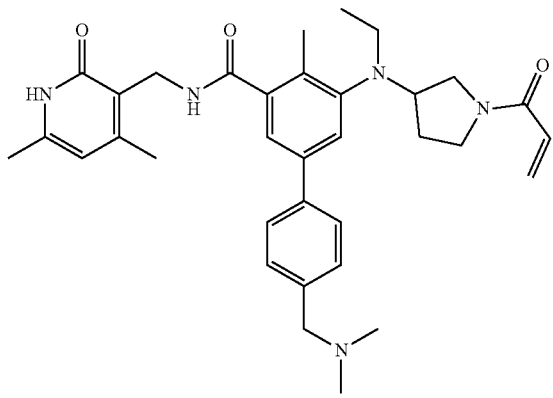
202
-continued
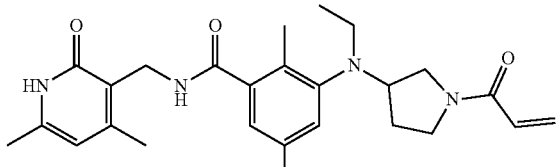
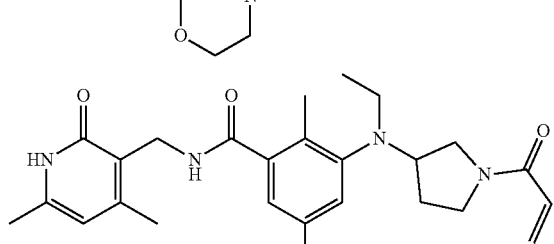
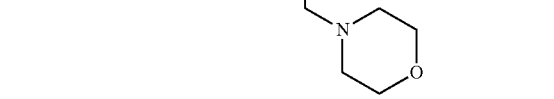
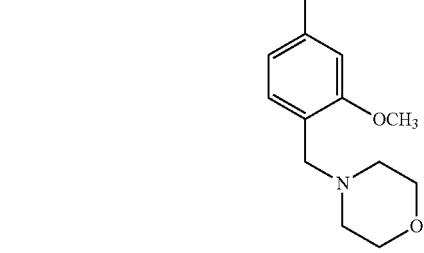
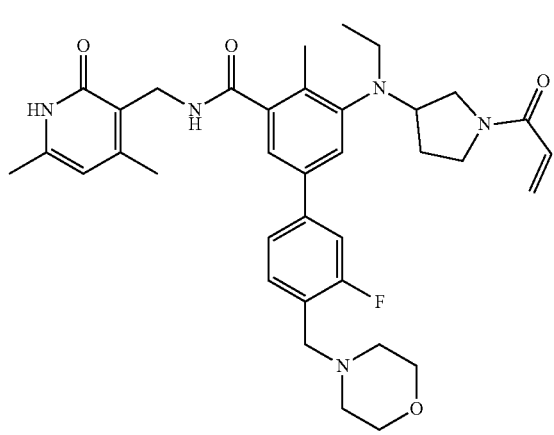

203
-continued
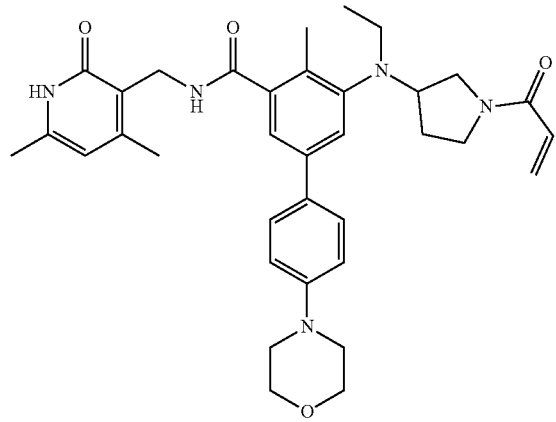
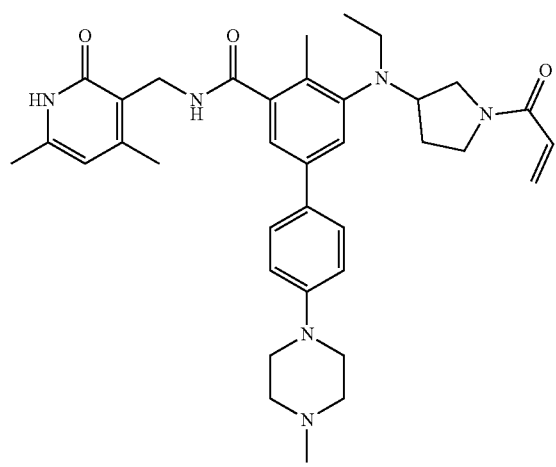
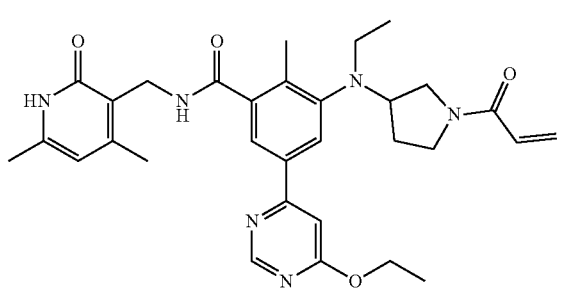
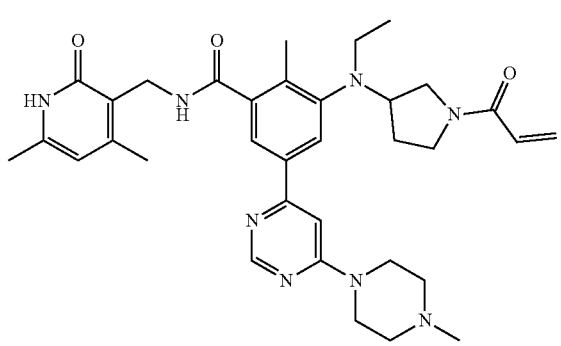
204
-continued
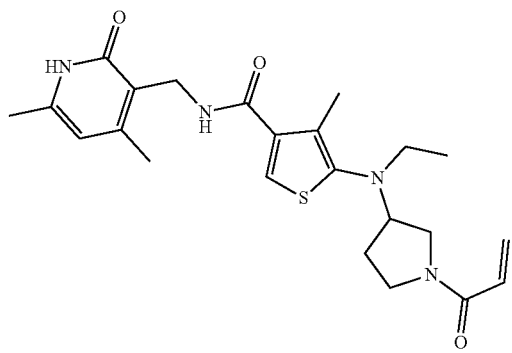
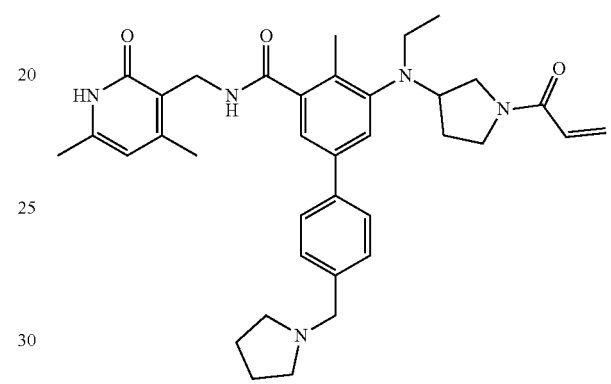
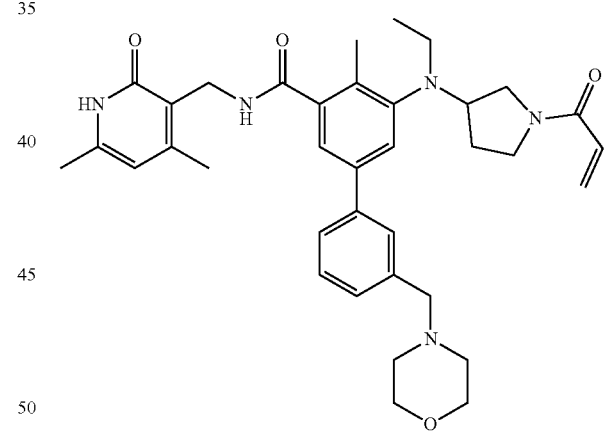
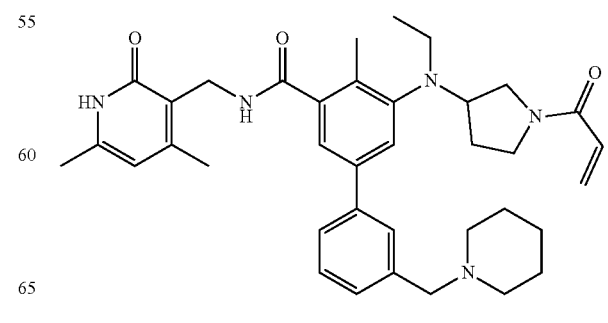

205
-continued
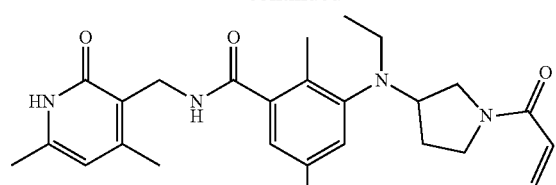
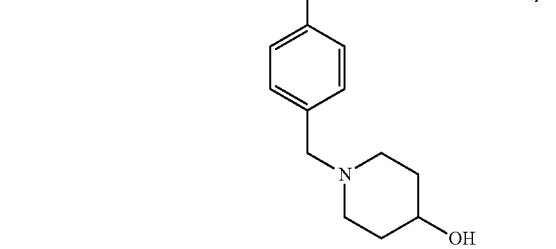
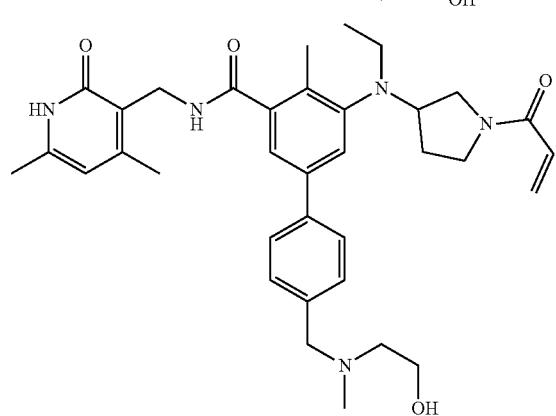
206
-continued
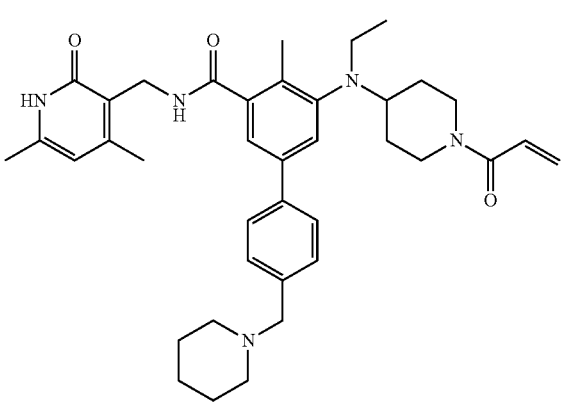
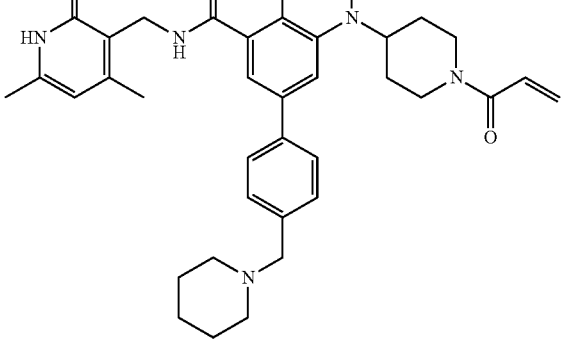
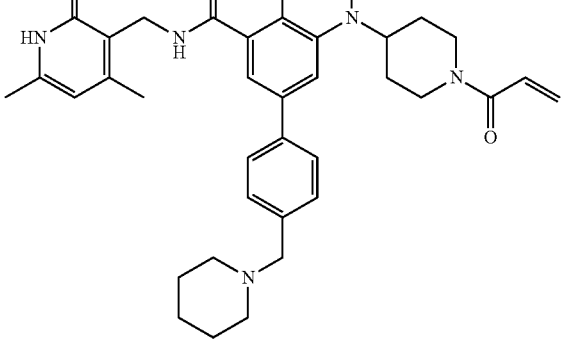

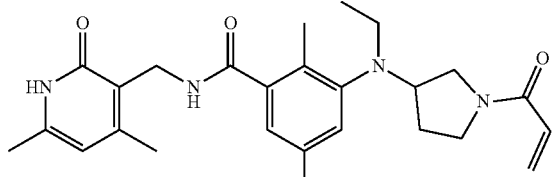
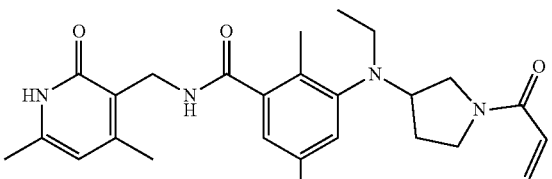
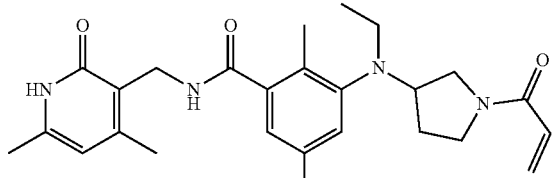
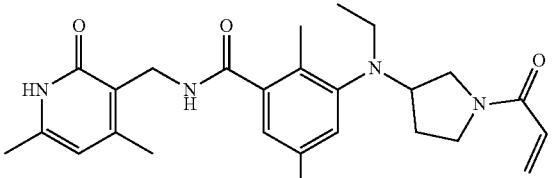
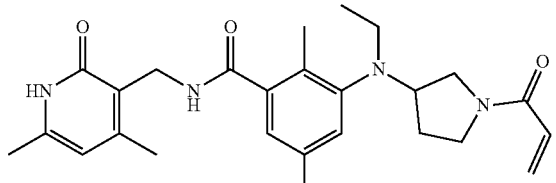
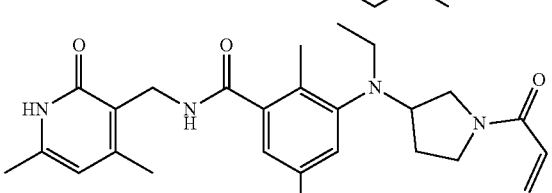
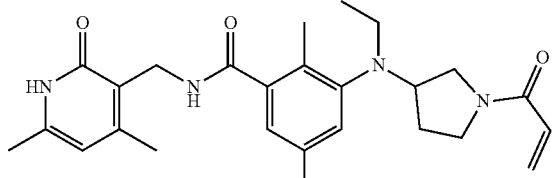

209
-continued
210
-continued
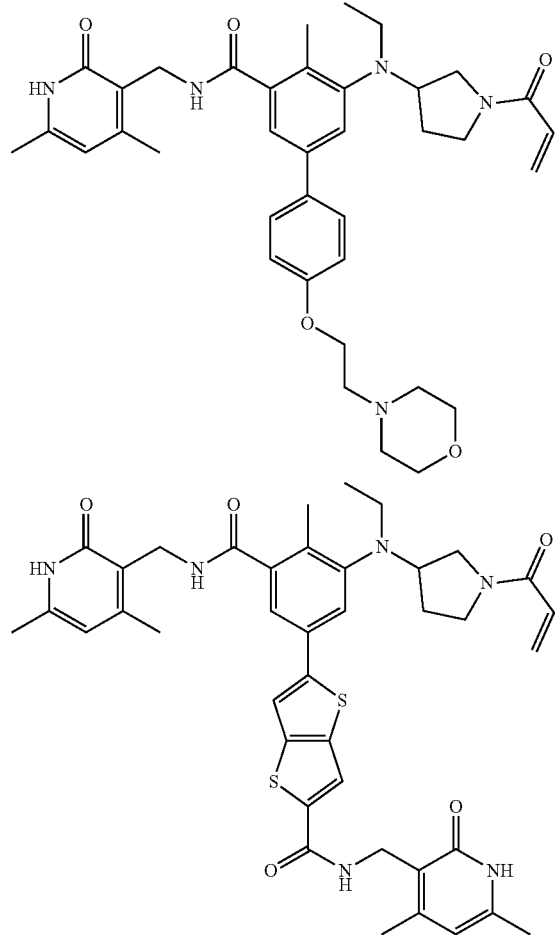
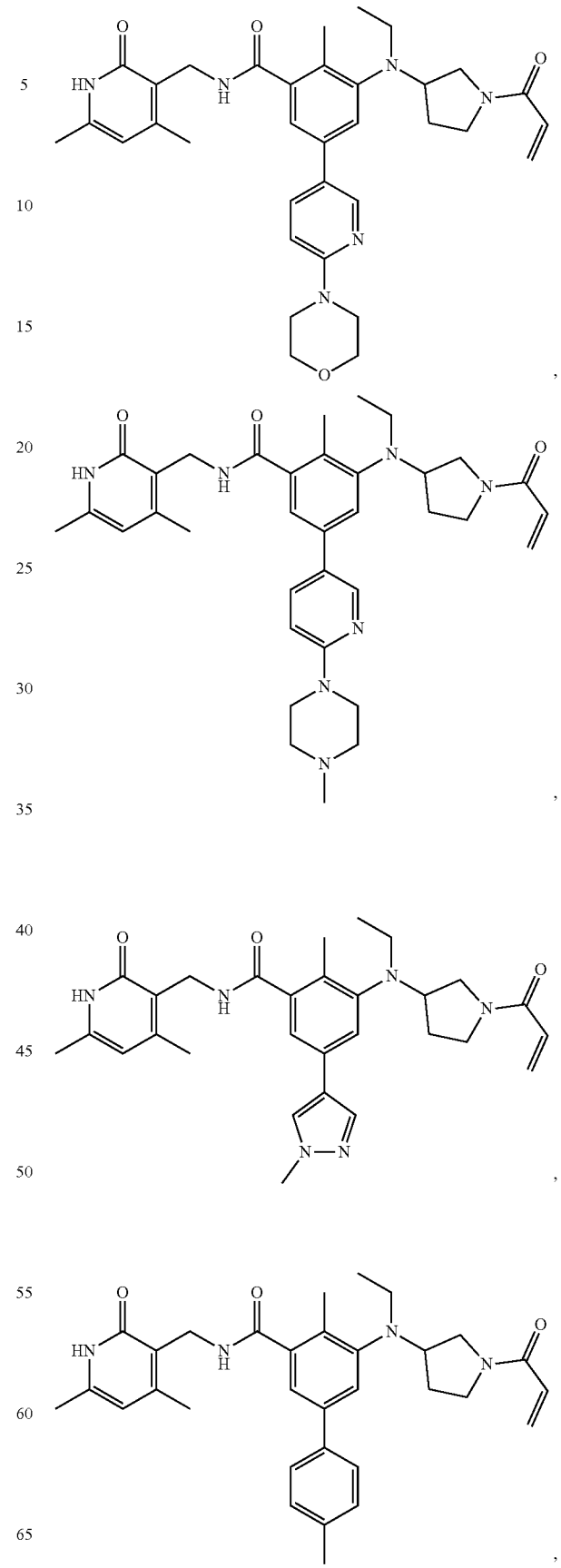

211
-continued
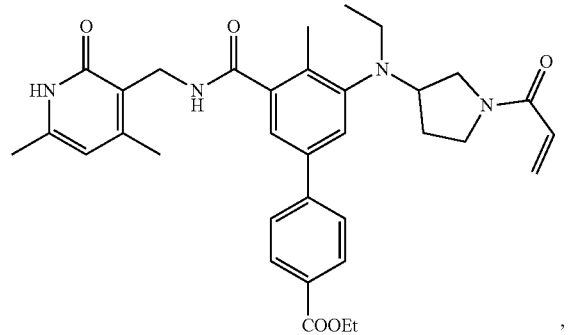
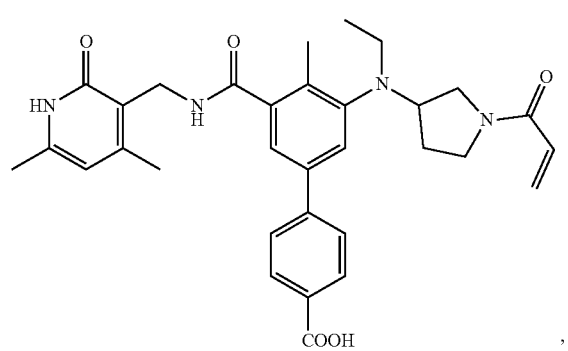
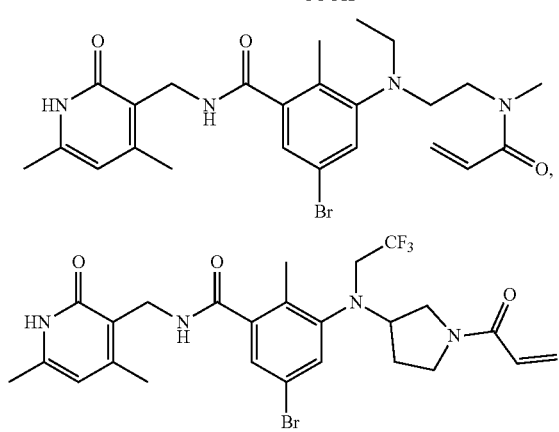
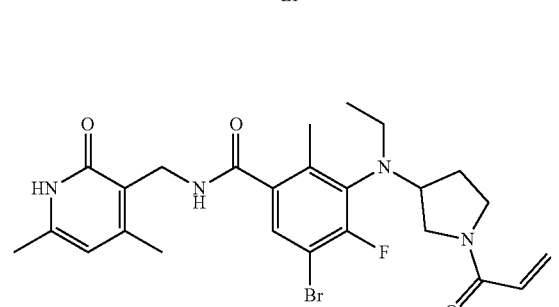
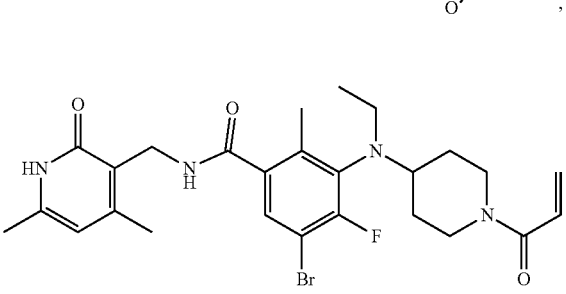
212
-continued
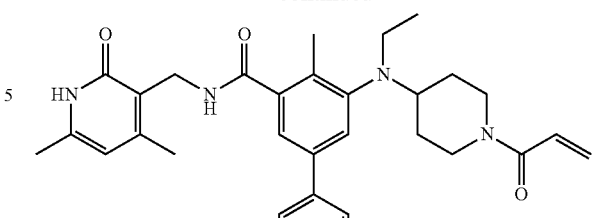
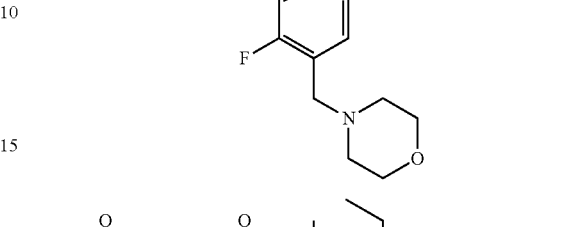
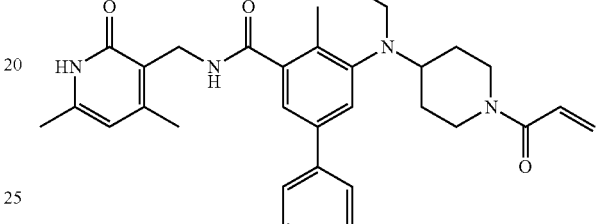
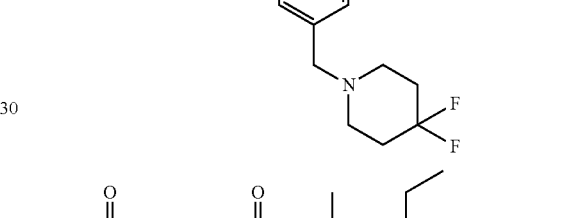
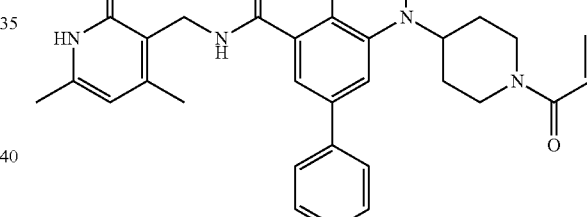
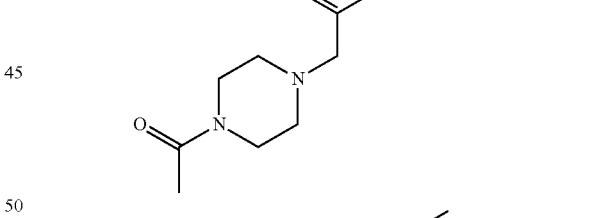
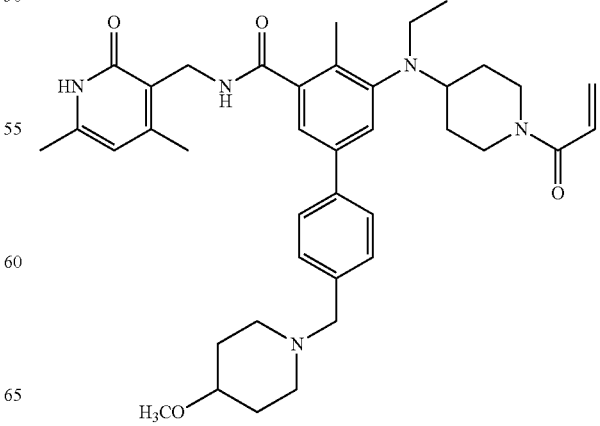

213
-continued
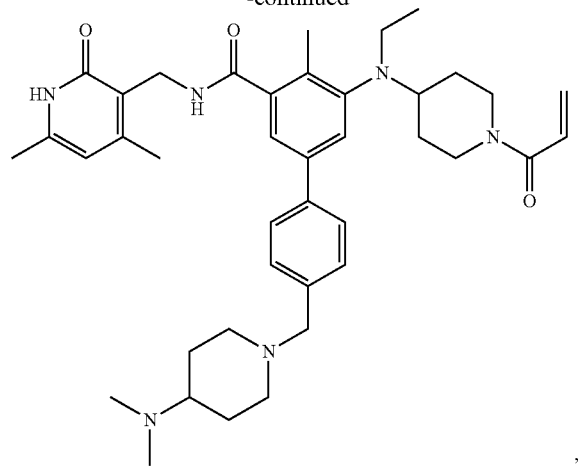
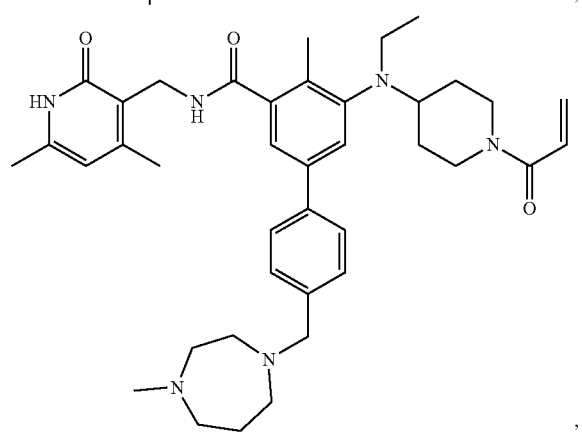
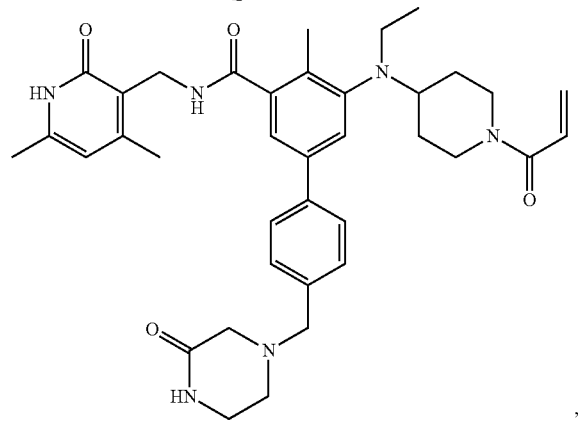
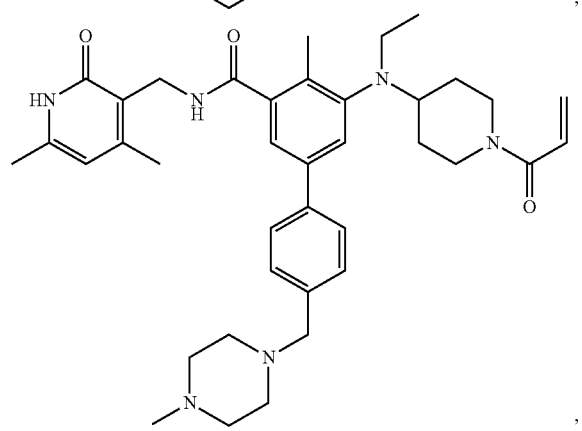
214
-continued
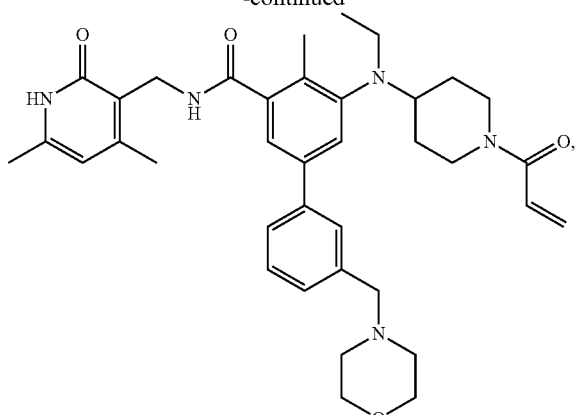
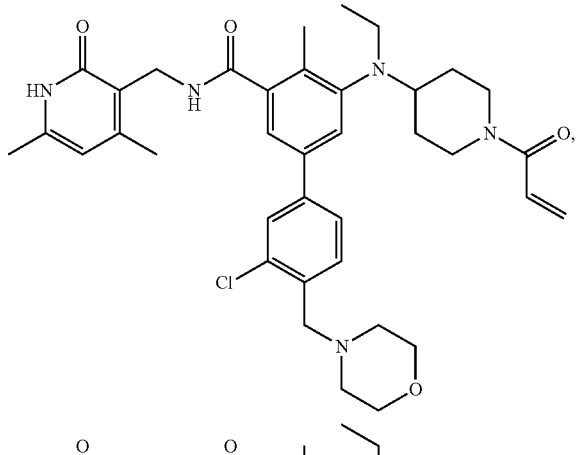
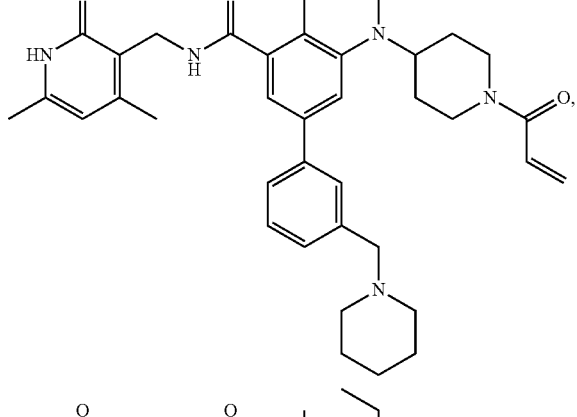

215
-continued
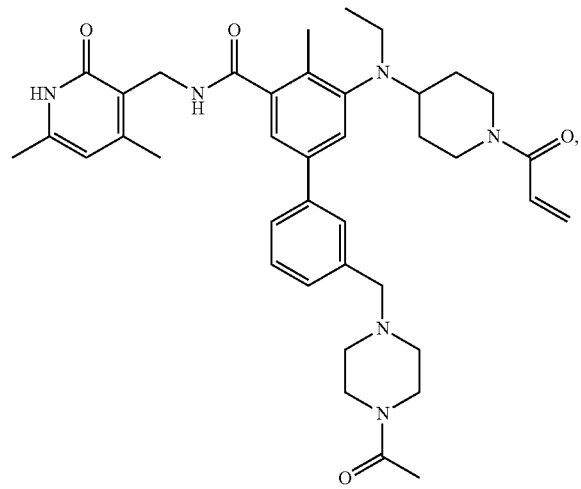
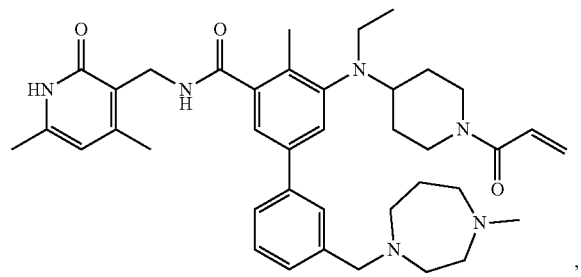
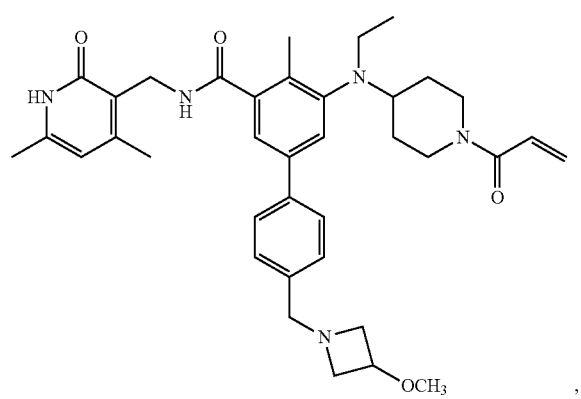
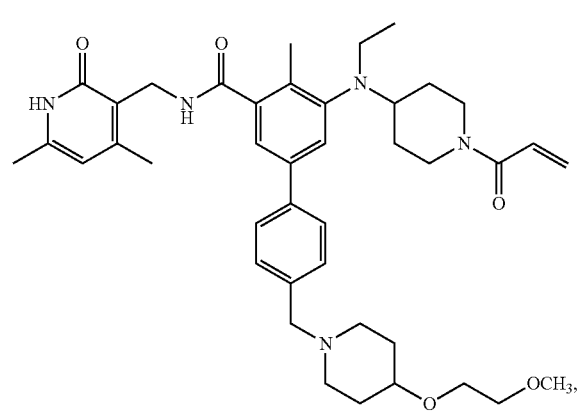
216
-continued
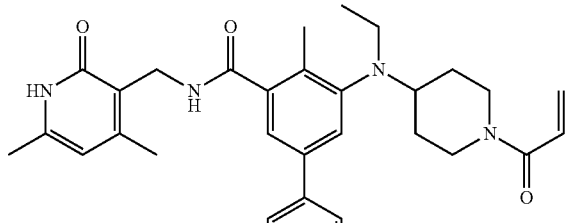
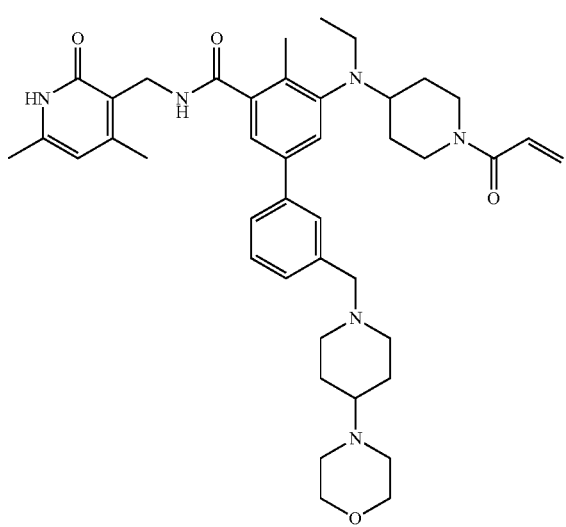
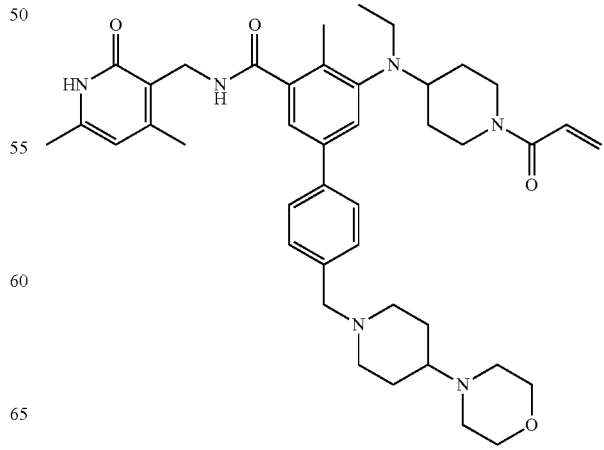

217
-continued
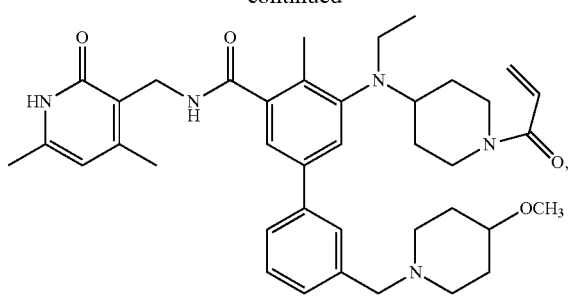
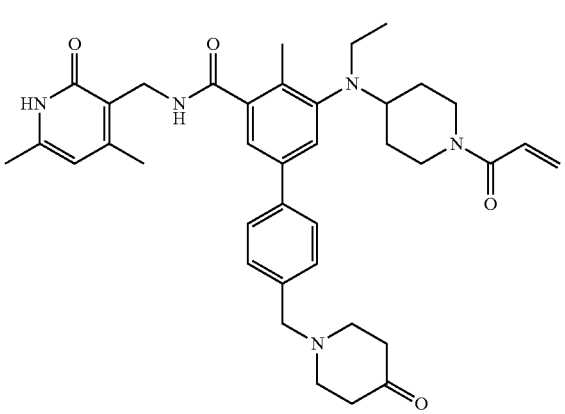
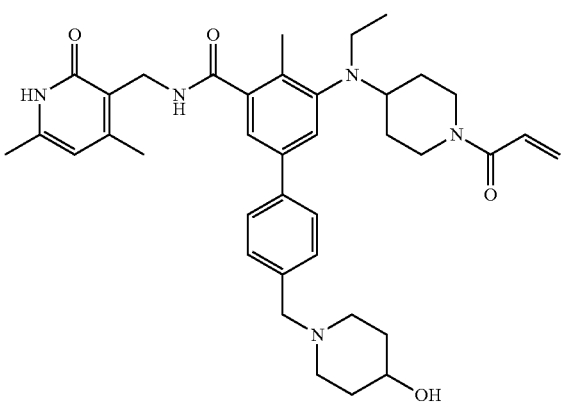
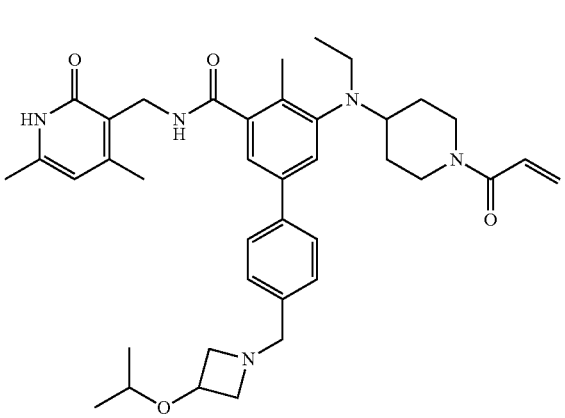
218
-continued
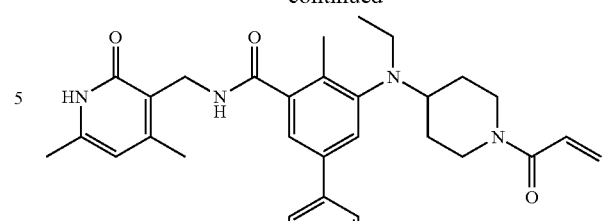
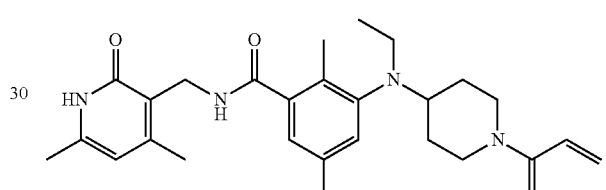
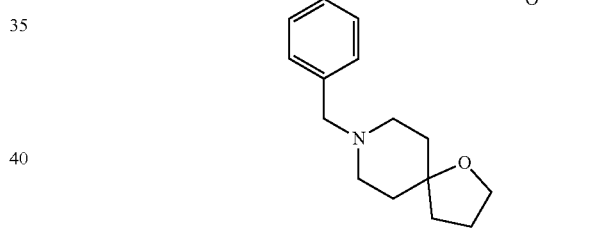
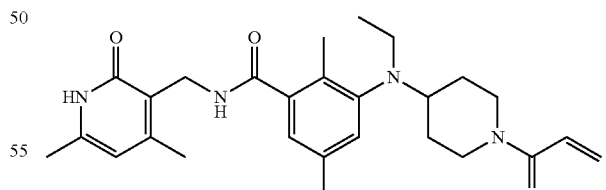
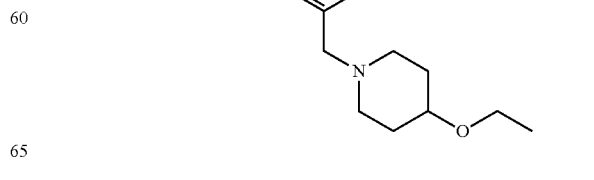

219
-continued
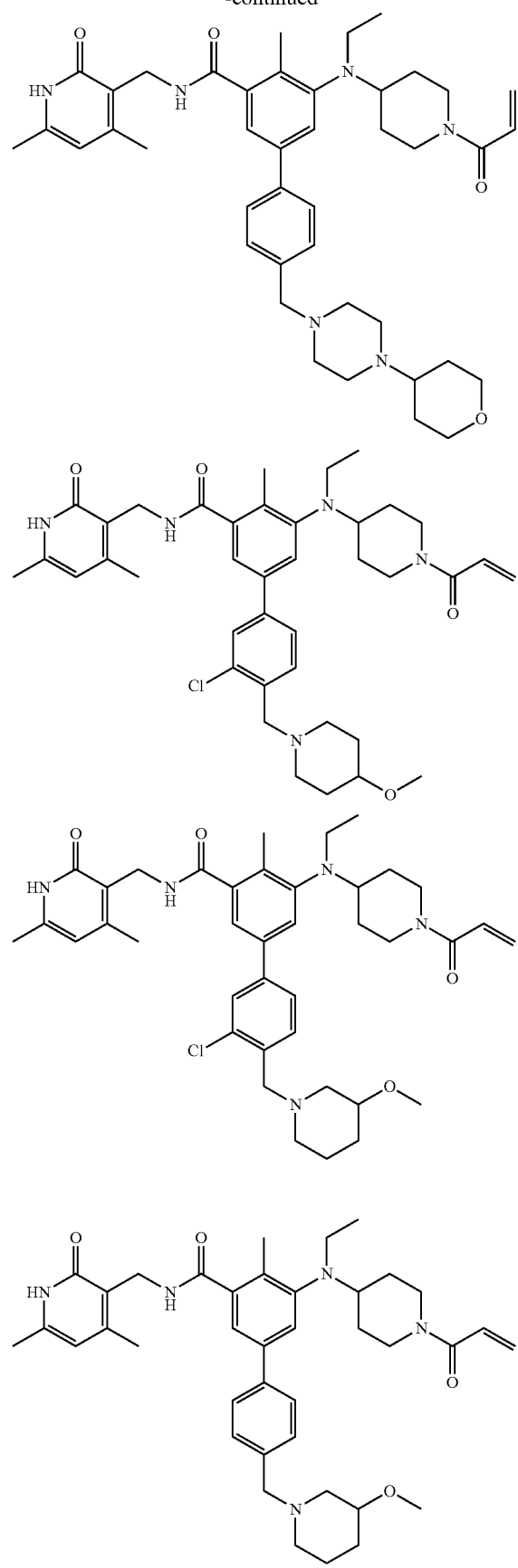
220
-continued
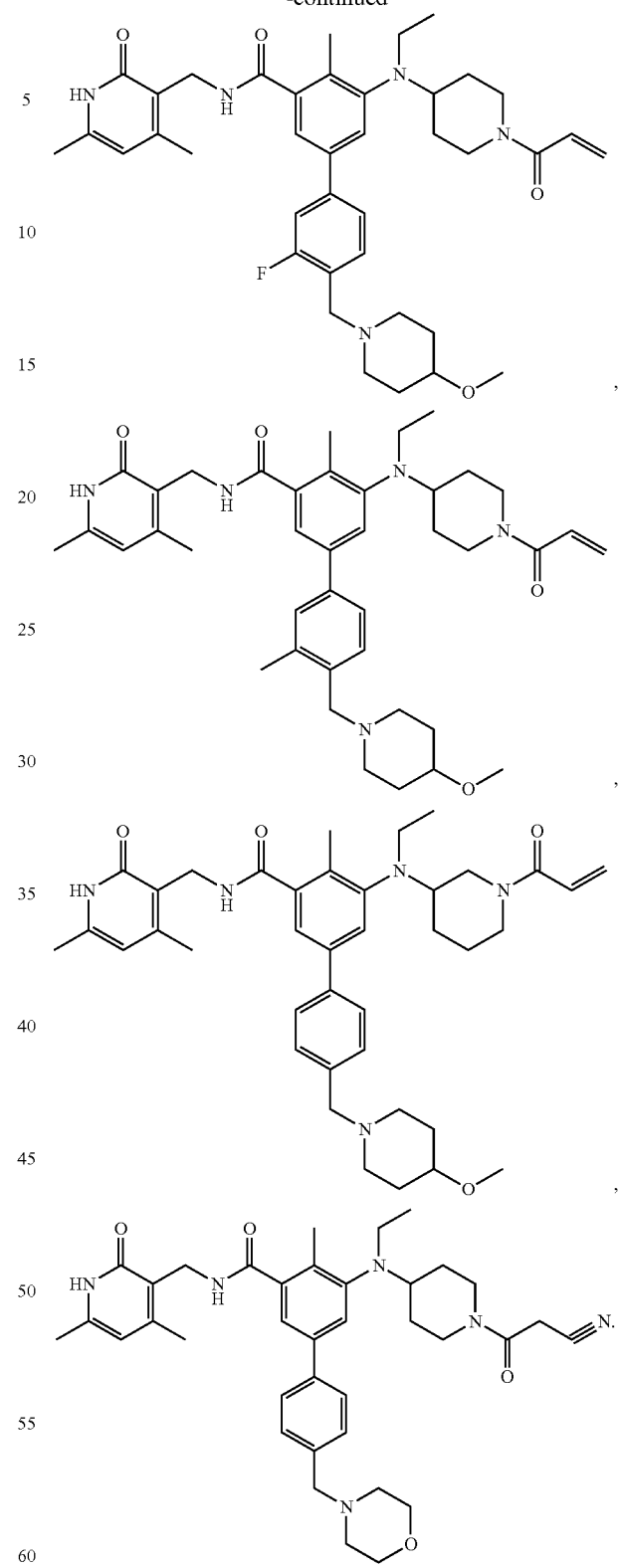
12. A deuterated compound of the compound of general formula (I) or the pharmaceutically acceptable salt, solvate, metabolite or prodrug thereof according to claim 1, wherein one or more of the H atoms in the compound of general formula (I) is independently replaced by a D atom.

13. The deuterated compound of the compound of general formula (I) or the pharmaceutically acceptable salt, solvate, metabolite or prodrug thereof according to claim 12, wherein the compound is selected from the group consisting of:

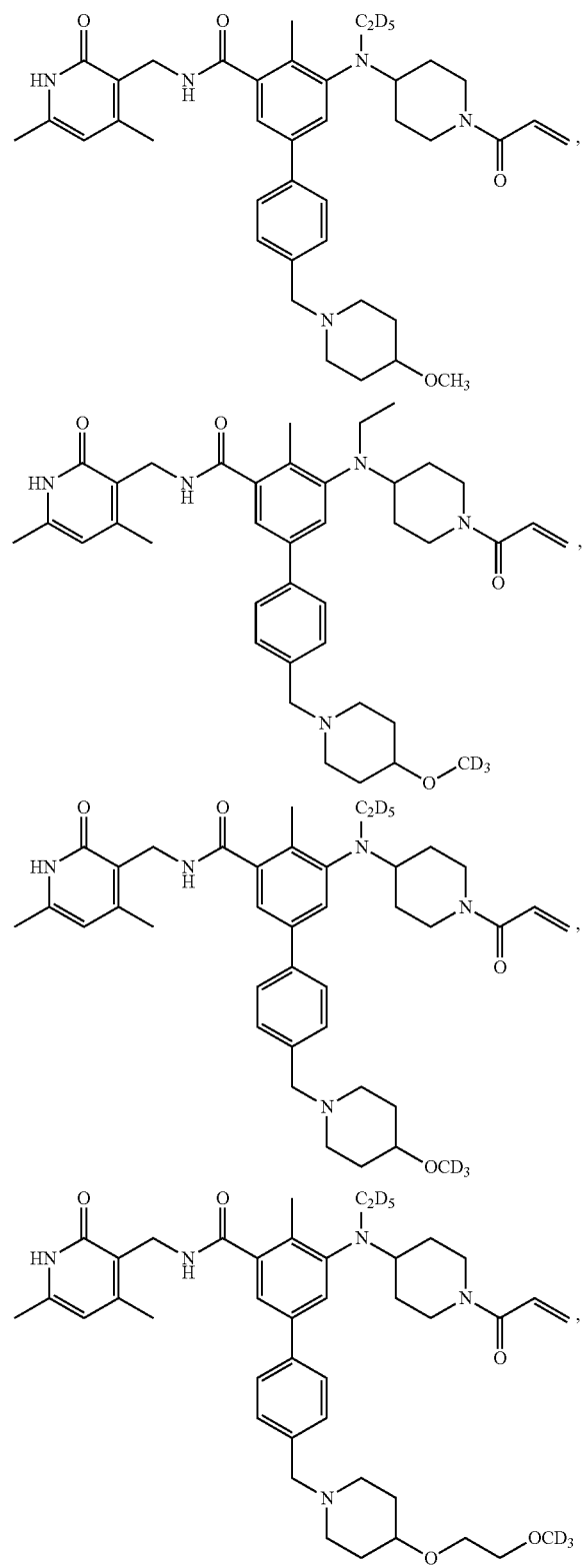

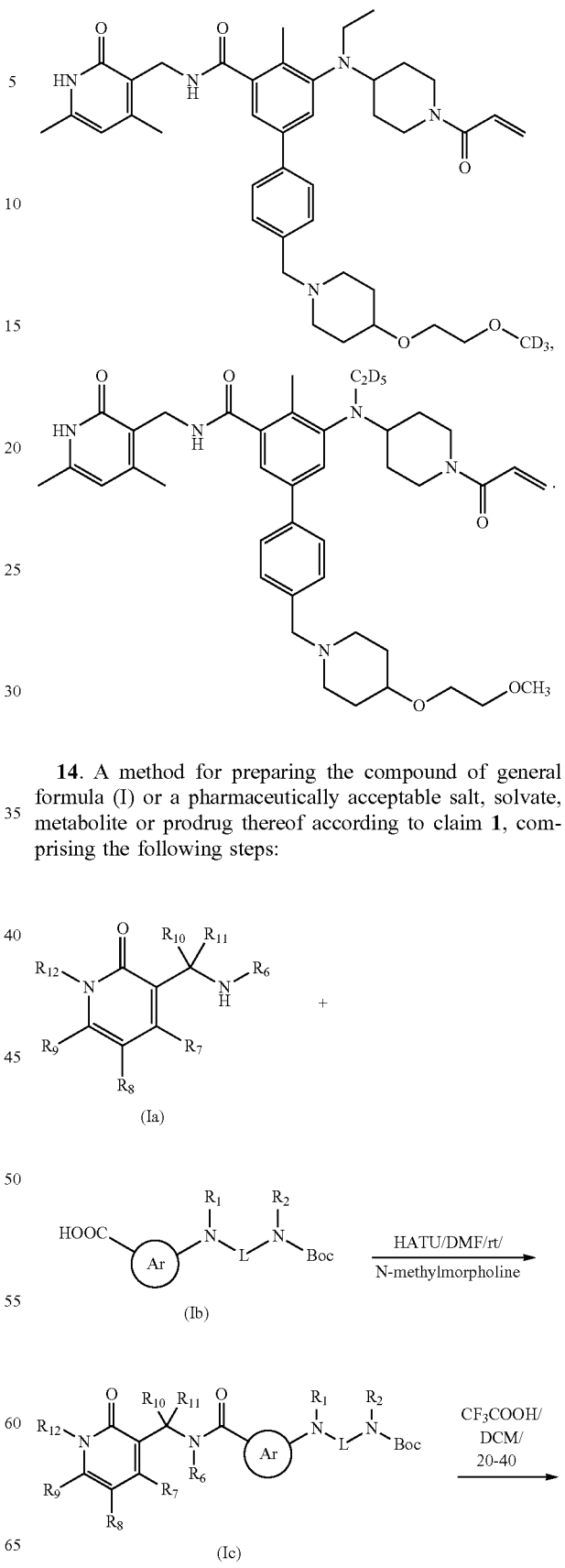

14. A method for preparing the compound of general formula (I) or a pharmaceutically acceptable salt, solvate, metabolite or prodrug thereof according to claim 1, comprising the following steps:

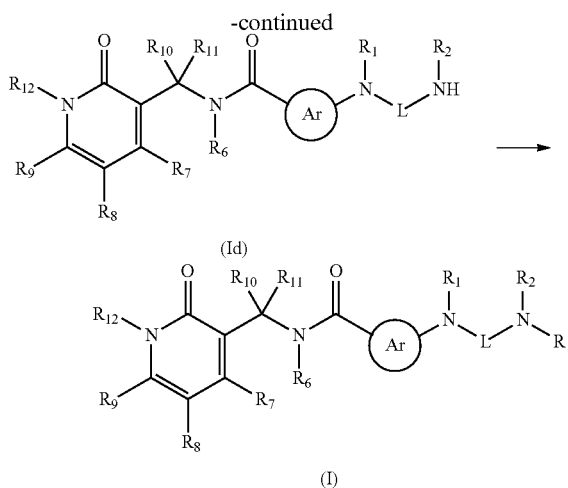

Step 1): Compound (Ia) and compound (Ib) are subjected to a condensation reaction in the presence of a condensing agent such as HATU to obtain a compound (Ic);

Step 2): Compound (Ic) is hydrolyzed under acidic conditions to obtain a compound (Id);

Step 3): Compound (Id) is reacted with the corresponding R to obtain a compound of general formula (I);

wherein, the reaction of R with an amino group is a condensation reaction of a carboxylic acid form of R with an amine condensing agent such as HATU, or an ammonolysis reaction of an acid chloride, an acid anhydride or a mixed acid anhydride of R with an amino group.

15. A pharmaceutical composition comprising the compound of general formula (I), or a pharmaceutically acceptable salt, solvate, metabolite or prodrug thereof according to claim 1, or the deuterated compound of the compound of general formula (I), or a pharmaceutically acceptable salt, solvate, metabolite or prodrug thereof, and one or more pharmaceutically acceptable carriers.

16. A method of treating a disease associated with histone methyltransferase EZH2, the method comprising administering to a patient in need thereof a compound of general formula (I) or a pharmaceutically acceptable salt, solvate, metabolite or prodrug thereof according to claim 1, or a deuterated compound of the compound of general formula (I) or a pharmaceutically acceptable salt, solvate, metabolite or prodrug thereof, or a pharmaceutical composition comprising the compound of general formula (I) wherein the disease associated with histone methyltransferase EZH2 is selected from the group consisting of cancer, diabetes, inflammation, and cardiovascular diseases.

17. The method according to claim 16, wherein the disease associated with histone methyltransferase EZH2 is cancer, and the cancer is selected from the group consisting of lung cancer, stomach cancer, liver cancer, breast cancer, nasopharyngeal carcinoma, pancreatic cancer, ovarian cancer, cervical cancer, colorectal cancer, glioma, melanoma, prostate cancer, kidney cancer, esophageal cancer, mesothelioma, head and neck cancer, bladder cancer, salivary gland carcinoma, anaplastic large cell lymphoma, leukemia, lymphoma, non-hodgkin's lymphoma and multiple myeloma.

* * * * *